(12) United States Patent
Kim et al.

(10) Patent No.: US 9,068,010 B2
(45) Date of Patent: Jun. 30, 2015

(54) **CLONING AND BASE SEQUENCE DETERMINATION OF NOVEL ITURIN BIOSYNTHESIS GENE FROM ANTAGONISTIC MICROORGANISM *BACILLUS SUBTILIS* AND CHARACTERISTICS OF THE GENE**

(75) Inventors: Sung Uk Kim, Daejeon (KR); Ingyu Hwang, Seoul (KR); Byoung-Keun Park, Gyeongsangnam-do (KR); Seungeun Kim, Daejeon (KR); Jae Sun Moon, Daejeon (KR); Ho Yong Park, Daejeon (KR); Kwang Hee Son, Daejeon (KR); Tae Sook Jeong, Daejeon (KR)

(73) Assignee: Korea Research Institute of Bioscience and Biotechnology (KR)

( * ) Notice: Subject to any disclaimer, the term of this patent is extended or adjusted under 35 U.S.C. 154(b) by 0 days.

(21) Appl. No.: 13/699,104

(22) PCT Filed: Oct. 26, 2011

(86) PCT No.: PCT/KR2011/008027
§ 371 (c)(1),
(2), (4) Date: Mar. 8, 2013

(87) PCT Pub. No.: WO2012/060572
PCT Pub. Date: May 10, 2012

(65) Prior Publication Data
US 2013/0165635 A1 Jun. 27, 2013

(30) Foreign Application Priority Data
Nov. 5, 2010 (KR) .................. 10-2010-0109724

(51) Int. Cl.
*C07K 14/32* (2006.01)
*C12N 9/00* (2006.01)
*C12P 21/02* (2006.01)
*C12N 15/52* (2006.01)

(52) U.S. Cl.
CPC . *C07K 14/32* (2013.01); *C12N 9/00* (2013.01); *C12P 21/02* (2013.01); *C12N 15/52* (2013.01)

(58) Field of Classification Search
None
See application file for complete search history.

(56) References Cited

PUBLICATIONS

Koumoutsi et al., Structural and functional characterization of gene clusters directing nonribosomal synthesis of bioactive cyclic lipopeptides in *Bacillus amyloliquefaciens* strain., J Bacteriol. (Feb. 2004), vol. 186(4), pp. 1084-1096.*
GenBank AJ575642.1 (last viewed on Aug. 22, 2014).*
Yao, et. al., Cloning, Sequencing, and Characterization of the Genetic Region Relevant to Biosynthesis of the Lipopeptides Iturin A and Surfactin in *Bacillus subtilis, Current Microbiology*, Oct. 2003, Vo. 47(4), pp. 272-277.
Chen, et. al., Comparative analysis of the complete genome sequence of the plant growth-promoting bacterium *Bacillus amyloliquefaciens* FZB42, *Nature Biotechnology*, Sep. 2007, vol. 25, No. 9, pp. 1007-1014.
Grover, et. al., Molecular and Biochemical Approaches for Characterization of Antifungal Trait of a Potent Biocontrol Agent *Bacillus subtilis* RP24, *Current Microbiology*, 2010, vol. 60(2), pp. 99-106/.
Tsuge, et. al., Cloning, Sequencing, and Characterization of the Iturin A Operon, *Journal of Bacteriology*, Nov. 2001, vol. 183, No. 21, pp. 6265-6273.
Pyoung II, et. al., Production of Biosurfactant Lipopeptides Iturin A, Fengycin, and Surfactin A from *Bacillus subtilis* CMB32 for Control of Colletotrichum gloeosporioides, *Journal of Microbiology and Biotechnology*, Sep. 26, 2009, vol. 20(1), pp. 138-145.

* cited by examiner

*Primary Examiner* — Alexander Kim
(74) *Attorney, Agent, or Firm* — Sheridan Ross P.C.

(57) ABSTRACT

The present invention relates to novel iturin biosynthesis genes, and uses thereof. More specifically, the present invention provides novel iturin biosynthesis genes, wherein the iturin biosynthesis genes were cloned from *Bacillus subtilis* subsp. *krictiensis* ATCC 55079, the base sequence was determined after checking whether the cloned genes are iturin biosynthesis genes or not, and it was ascertained that the identified genes are novel genes different from the reported gene by comparing the base sequences with that of the reported gene, and uses thereof.

6 Claims, 24 Drawing Sheets

```
  1 ttgatgaaacagacagcgctcgtaaccggagcaagcggcggaatcggacaa  51
  1  L  M  K  Q  T  A  L  V  T  G  A  S  G  G  I  G  Q   17

52 agtataagtgaagtcctcgcaaaaaacggatatgacgtccttttgcattat 102
 18  S  I  S  E  V  L  A  K  N  G  Y  D  V  L  L  H  Y   35

103 cattctaataaggaggccgcaaacaggcttgcggaaaggctgagcgcatca 154
 36  H  S  N  K  E  A  A  N  R  L  A  E  R  L  S  A  S   53

155 ttcggcgtaaaagcctccgctatccaggctgatctgtcctcaccggatggc 206
 54  F  G  V  K  A  S  A  I  Q  A  D  L  S  S  P  D  G   71

207 gcggagacattcagccgttccgttaagcagcctgtggacgctctgatatta 258
 72  A  E  T  F  S  R  S  V  K  Q  P  V  D  A  L  I  L   89

259 aacagcggcaaaagtcatttcggcctgattacggacgttacggatgacacg 310
 90  N  S  G  K  S  H  F  G  L  I  T  D  V  T  D  D  T  107

311 gcgcgggagatggtgcagctgcatgtgacgagtccgtttcttttggtgcgt 362
108  A  R  E  M  V  Q  L  H  V  T  S  P  F  L  L  V  R  125

363 aatctggtgcccggcatgatccggaaaaaatgcggggggcatcgtcgcgatc 414
126  N  L  V  P  G  M  I  R  K  K  C  G  G  I  V  A  I  143

415 ggttccgtctggcgagaaagcttg                             438
144  G  S  V  W  R  E  S  L                             151
```

Fig. 4

1 : 3-oxoacyl-(acyl-carrier protein) reductase (*Cuphea lanceolata*)

2 : 3-ketoacyl-acyl carrier protein reductase (*Bacillus subtilis*)

3 : 3-oxoacyl-acyl carrier protein reductase (*Salmonella typhimurium*)

4 : 3-oxoacyl-acyl carrier protein reductase (*Deinococcus radiodurans*)

5 : Wild type *Bacillus subtilis*

Fig. 5
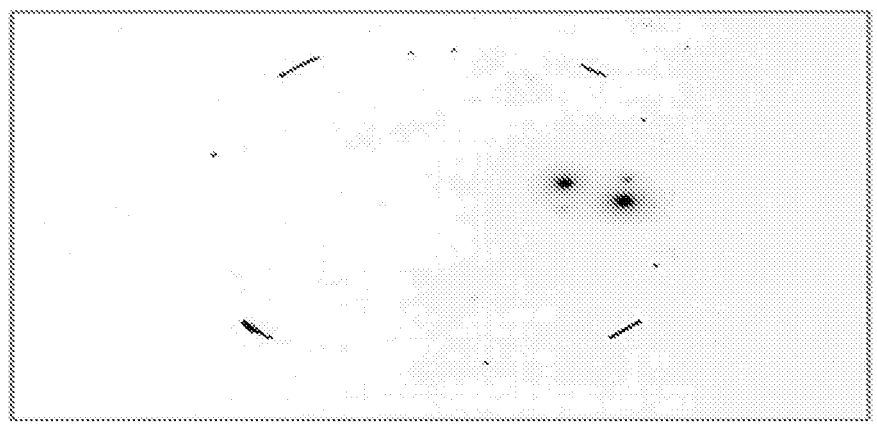
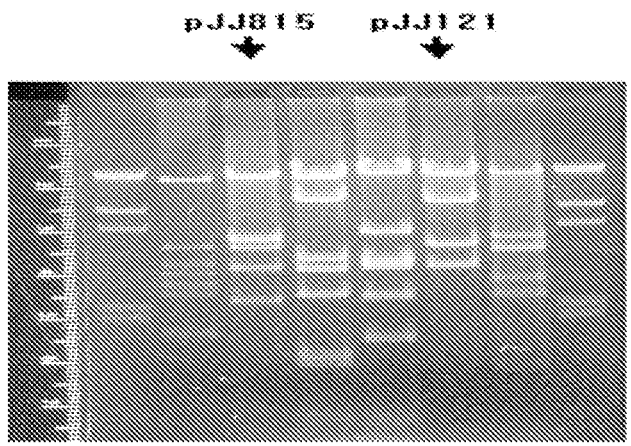
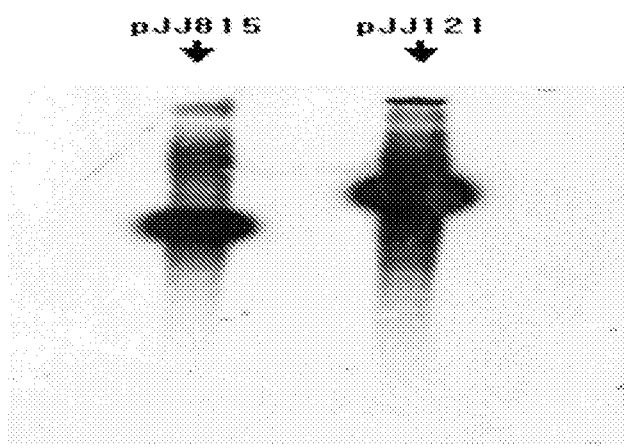

Fig. 7
A. pJJ121E2      B. pJJ121E3      C. pJJ815E2
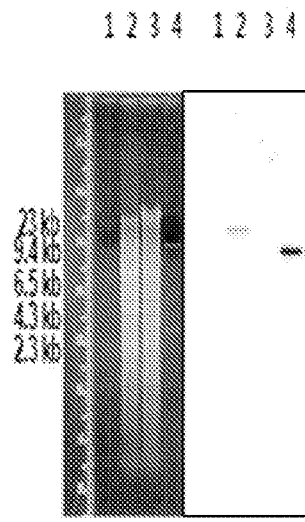 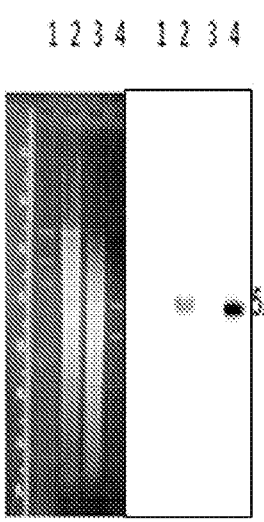 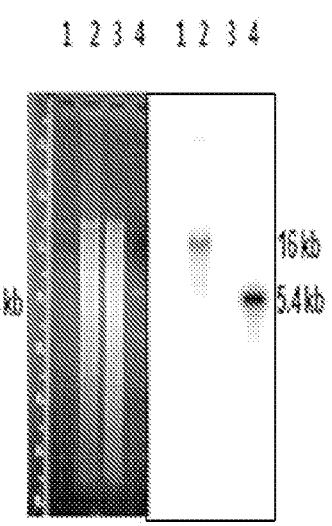
D. pJJ815E4      E. pJJ815E5      F. pJJ815E6
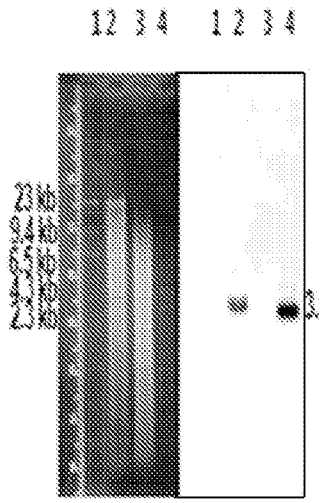  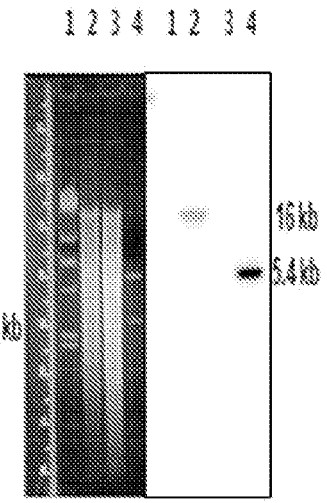

Fig. 8
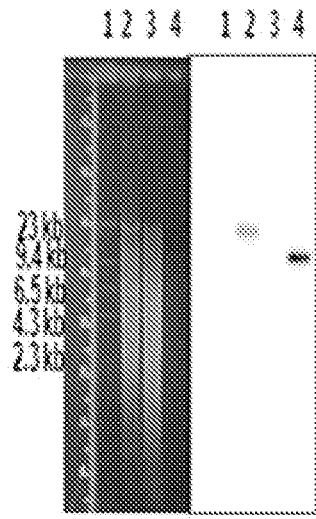
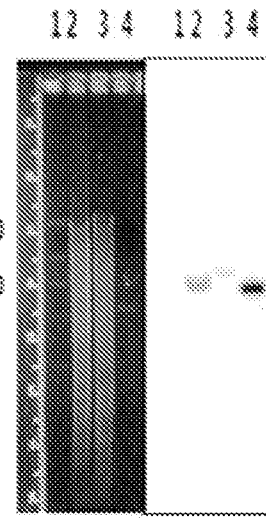
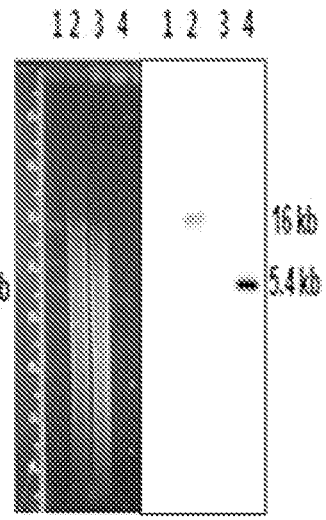
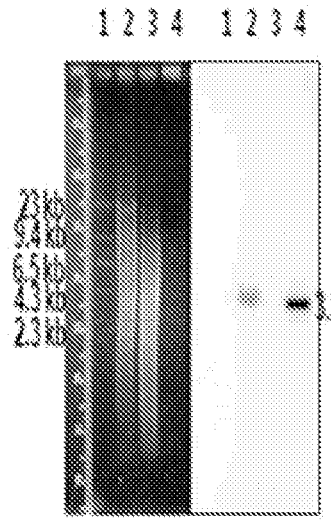
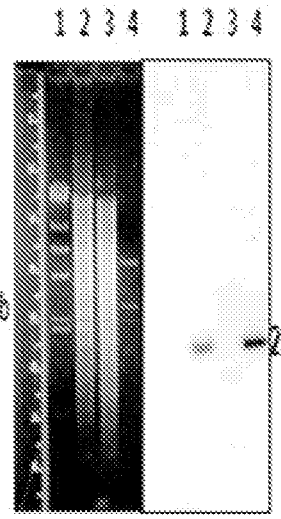
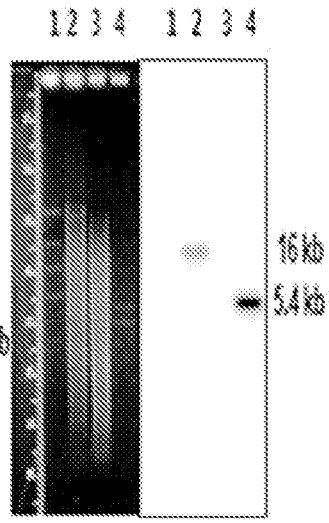

M. grisea	T. mentagrophytes	F. oxysporum

SEQUENCE LISTING

```
<160> NUMBER OF SEQ ID NOS: 49

<210> SEQ ID NO 1
<211> LENGTH: 34830
<212> TYPE: DNA
<213> ORGANISM: Bacillus subtilis

<400> SEQUENCE: 1
cagcttgcat gcctgcaggt cgactctaga ggatcccacc tggctgaacg gctatcaaaa      60
acgctacgtg ttttgtgtat atcaatcgag atgaagaaga tgaaaaagat ttgaaacgga     120
tcaggaaaaa agtttttatt ggtaccagaa tgtaattgaa acaaacggta aaagtttata     180
aaagttccct gagagaaata tgattctctc agggatttct tttacattgc gtctgcatca     240
attatatacg tatccgcatg aagatcggat atttcggcag gcactgaata acaggtaagg     300
ctgtatcggc ctttcggaat attaaagaaa agccgctttg acatcacgct ttcaatctca     360
```

```
attccatctt ttacagcctc aaagggaaca gtcgcttttt tctcatagga tagtaccggt    420
tcacttgtgt taagcctgag gacgataaat gccctcgtat ttctccttgc ttcgaatgaa    480
acagctccgt cagcttccgc atatccttt tcaatggctt catcggtcca atcgataaca    540
ggcggttctg aatctttttg gaagattgta aattgatgat acgaaatggc cagttcttgc    600
ggtttccatg atttattcaa tgcgctgttc ctcctgtttt tttacttgat tttaaataat    660
actctcgttc cgtcgggatc attggtaagc tggtgtccga cccaagagcc ggctccgcgg    720
ttgtctgccg gagaaatata ttctacggag gcattgtttc cgccctgttt acaaaccgcc    780
atcggccatt catccctatc gtatcccgtt ttgacaggca catgtttaag agattgctca    840
cgccgcttat gtactccgtc tctgtcaatg gtgcatatgc tggaatgccc ttcttttatc    900
gcgtccttaa tatgctttgc tgtttccgga tatcgatcgg acggaaatag gattactttg    960
tcgtaatcac tcttctgaac ggtctgctcg ttatctgaga aaagatcacc cttgatcagg   1020
gccgcgactg ctccggcaat gatgataaga acaagcagca gtgcttttaa tgttttcaag   1080
agtatcaatc acctccagtt ttaaattgct gtaaagctgg tccaagaata aagcagaatc   1140
ggccggctgt aaagctgtta aaatatattt ctcagccgca attcagctga atatctgtaa   1200
aaccatccgc acaaatcaat tttattcatt aaatatccga tcagaaagtg ttttttgccg   1260
tttccctatt cagaaatgaa cggttgcggc cgtatcgtca attgacttat tatagcgata   1320
agctcaccgg caggatatct tcgtctgcga gtgtccgacc cgaaaacctt ggcctgcatg   1380
accgtgcgca acaagacgat aaaaagacgg ccatctgata agaaggccgt cagtaaatca   1440
ttccagattc gcatgctttg taaacatgtc tgctgaattc agttcttttt tctccatgat   1500
ttttagaata accgcatcgt aaaacagcag aagagtttgt tcgaataaag aacccatcgg   1560
ctgaatcgtc tttctgtctc cgccggtctc ttccttagga gagccgggaa tcgttatcgt   1620
aagatccgca agtttgccga gacttgaatc ggggttaatc gttaatgcag tgatgatgcc   1680
gttaaggctt ttggcttttt cagccgtatg aagcagactt tttgtttcgc ctgagcctga   1740
gccgatgatg acgagaccgc cttcttggag gggaggggta agcgtctcac cgacgatgta   1800
agcgttcagg ccgatgtgca tcatcctcat ggcgaacgct ttagccataa agccggaacg   1860
ccccgctccg gacgtgaaga tttgatctgc cgataaaatc tcatctgcaa gcttgtcagc   1920
ttcactgtcg gctattaatg ctgcggtgcg ggatatttca ttgagtattt catgtaagta   1980
ttcagtcgtt ttcatgatcc ttgtgaaatc agctgtttca ttttagcagc agcatccgct   2040
ttattgtcag ctcccgtaat gcctccgccg acaatgatta aatctgggtt ttgtttgatg   2100
gcttcaggaa gcgtatcaag tttaatgcct ccggcaattg cggttttagc gctcttgacc   2160
gcttttttaa tcgccgtcag ttcctcgaat gaattctttc cttctgcttg aagatcataa   2220
cctgtgtgaa cacaaatata atcaacaccg agttggtcaa tttcttttgc ccgtgtttca   2280
aggtttttta cgttaatcat gtcgacgaga attttttttct gctgtttttt tgcttcggca   2340
accgcccctt tgatcgttga gtcgtctgtc gctcctaaaa cggtgatgat gtcggcgccc   2400
gcttctgccg ctttcatgat ctcgtagccg cctgcatcca tgattttaag atcggcaagc   2460
actttcaggt gaggaaaggc tgatttcatt tcctgtacgg ctttcaggcc ttcattaatg   2520
acaacgggag tgccgatttc tacaacatct atatattgtt cgacctcttt cacaagttca   2580
attgcttccg ggatattcac taagtctaat gccagctgta attccacttt atatccactc   2640 ctcttttttca tgtatttaca ttctatagag tgccccgcat gttgagaagt acgcactttg   2700
```

```
aagtctaata gttactttga ggatactgtc cccgcaggca atgcgctgtg tttcagcaaa    2760
actgcgtggt agtataaact gatgaaagtt gtgtaaaaaa gtaagcgtgt atgaatagat    2820
gatgaacgta caaaaagtaa gaggaaggag aatggcccgt gagccgaatg gatgagaaaa    2880
cgtttaattg cgaaaaggaa ttgacgcttg ccgtgatagg cgggaagtgg aaaatgctga    2940
ttatgtggca cctggggaaa gaaggaacaa agcggtttaa tgagctgaaa gctttaattc    3000
cggatattac gcacaaaatt cttgtgaatc agctcaggga gctggagcag gatctgatcg    3060
ttcacaggga gtttacccct gtcgtccctc cgaaagtgga gtactcatta acagagcaag    3120
gagagaccct tatgccgatt ttggacgcca tgtataagtg gggaaaagaa tatatggaat    3180
taatcaacat tgataaaact gcaataaagg aatcttttg aagcgctcta tgtaaaatag    3240
agtgcttttt ttgcggttta atgaaatcat attgcgaacg attaaatctc ctgtttcggt    3300
tcttgcgctg ttttttcccc atcatctcat atatgaaaac tattttcatt ctgccataac    3360
tggatattcg agagatttat actatagttt aaagatttt aatttacat aaataatatt    3420 tttaaaaata aattgcggga tgccgcaaaa taccctctgg aattgtcgga attttttcg    3480 gtgtgccgaa tgaaactttt cacccatttt tcggtgataa aacaataat ttcatataaa    3540 gtgaacgtaa gtagatatat agtaattcat gaagaaatag gtaaaccctg ttgcttacaa    3600
acattggatt cttgtcttga tttctcataa atttgagccg catttcggac tgtgcgggtg    3660
agtggattgc ggatttcggc ggtgattgaa tcggatcgt tttggaggta agtggttctt    3720
ttggcttgat aatgagttag ggacattgag ggaggctgtt tctaagggag aattgacaat    3780
tttatcttaa aaaggggagg cgcacacata tggaaataac tttttatcct ttaacaaatg    3840
ctcaaaaacg tatctggtat acagaaaaat tctatccgaa cacaagtatt tcaaatcttg    3900
ccgggttcgg gaaactcatt tctgacgacg gcgtacaggc tcattacgtt gagaaagcga    3960
tacaggaatt cgtccggcgg tatgagtcga tgagaatccg tctgcggctt gatgatgagg    4020
gggagcccgt tcaatatgtg agcgattacc gtccgctgac tatcgaacat acagacatca    4080
ggcaagccgg ctgctctgcg gaagagctgt caaaatgggg acgtgacgag gcaagcaagc    4140
ctctggcatt atatgatcag gatttattcc gttttttccgt gtataccatc agcgaaaatg    4200
aggtctggtt ttacgttaat gtgcatcaca ttatttcaga cgggatttcc atgacgattc    4260
tgggcaatgc gattactgat atttatttgg agctttcggg cggagcaagt atggaacaga    4320
cggagattcc tccttatcga gcatgtgctg actgagcagg aatatgtgca gtcgaagcgg    4380
ttaaaaagga tcgggatttt tggaacgggc agttcgagac cgtgccggag cttgtgtccc    4440
tgaaacggag ccaggcagat gcgggtcttg atgcgaaacg gttttctcaa gaaattcctc    4500
acgacttata tggccgcatt cattcattct gcgaggagca taagtcagc gtactatctc    4560 tgttccaatc agctttgatc acttatctct acaaagtgac cggccgggat gacgttgtta    4620
cgggtacgtt tatgggaaac cggacaaatg cgaaagaaaa gcagatgctc gggatgttcg    4680
tatctacggt tcctgtgcgg acaagcgttg acggaggaca gtcgttcttg gaattcgtta    4740
aaggccggat gaaggatctg atgaaaattc tccgccacca aaagtatccg tataacctgc    4800
ttgtcaatga tttgcgcgct tcgaaaagtt cgctgagcag attgtttacg gtggctctgg    4860
agtaccaggt gatgcagtgg cagaaaaaag agaatctgtc cttcctgaca gaccctattt    4920
tcagcggaag cggtacaaat gatatttcga ttcatgtgaa ggaacgatgg gacactggga    4980
aattgacgat tgatttgac tatcgcagcg acatattcaa gggagaggag attgtatctg    5040
tttctgaacg tttgatcacg ctgattgaag atgcgatttc atctcctgat cgcataattg    5100
```

```
atgagcttac tcttctttct gaatccgaga agagcggct gttgacacgg gcctcaggca    5160
atccggtgaa ttaccgcggg gagatgacga taccggggcc gtttgaagag aaagtgaagt    5220
cactgtctga caaaccggcg gtggtgtatg aaggccgaac attgtcctat cgcacattgc    5280
atgaacagtc aggccgaatt gccggacgtc ttcttaatgc cgggatatca gccgattctc    5340
ctgtcgcggt gctgcttggc cgttctgagc gtgttattgc ggcaatattg gaattttga    5400 aagcgggcgg cgcctatgtg ccgatagatc ctgactttcc ggcggatcgg attcagtaca    5460
ttttggagga cagcggagcg aaggctgttc tgacagaggc cggaatacag gcgcctgcag    5520
cggatgccga acgattgat tttgacgagg ctgttcagtt tgaaacggct gcggacggtg    5580
tcagtacaca atcagaccgg ctggcttaca tcatctacac gtcaggtaca acggggcggc    5640
cgaaaggcgt gatgattgag caccggcaag ttcatcatct ggtgcaatca ctgcagcagg    5700
agatttatca atgcggtgag cagacattaa aatggcgct tttggctccg tttcattttg    5760
atgcgtccgt caaacagatt tttgcctcgc ttcttttggg acagacgctt tatatcgtgc    5820
cgaaaacgac tgtaacgaat ggctcggcac tgctggacta ttatcgtcaa aaccggattg    5880
aagccactga cggaaccccct gcgcatctgc agatgatggt tgcggcggga gatgtcagcg    5940
gaattgaatt gcgccacatg ctcattgggg gagagggcct gtccgccgct gttgctgaac    6000
agctgatgaa cctctttcat caatcgggca gggcgccgcg tctgacgaat gtctacgggc    6060
cgacagaaac gtgcgtagat gcgtccgtgc atcaggtgtc agccgataac ggaatgaatc    6120
aacaggcggc gtacgttccg atcggaaaac cgctcggcaa cgcccgtctg tatatattgg    6180
ataagcacca gaggcttcag cccgacggga cggccggtga gctgtatatc gcgggtgacg    6240
gtgtaggccg cggctattta aatcttccgg atttgaccgc agagaagttt ttgcaagatc    6300
cgtttaacgg aagcggccgc atgtaccgca cgggtgatat ggcgcgctgg ctgccggacg    6360
ggacgatcga atatatcggc cgtgaagatg atcaggtgaa agtccgcggc taccgtattg    6420
agctgggaga aattgaaacg gtgctcagaa aagctccggg ggcggcgcag gccgtcgtgc    6480
tggcacggcc ggatcagcag ggcagcttag atgtttgcgc atatatcgtt caggaaaaag    6540
gaaccgagtt tcaccctgcc gagtacaggg agtatgtgtc caagcacctt cctgattaca    6600
tggtgcccgc ttactttaca aaaacggacg aaattccgct cacgccgagc gggaaggcgg    6660
accgcaaaaa gctgtttgcg cttgatgtgc aggctgtcag ctcatccgaa tatgccgcgc    6720
cgagaaacga acggaggaa acgctcaccg tcatctggca ggaagtcctc ggaatggaca    6780
aggcgggcat ttatgatcat ttcttcgagt caggcggtca ttcattaaag gcaatgacgc    6840
ttctgacgaa aattcataag caaatgggcg ttgaaattcc gctgcaatac ttgtttgagc    6900
atccgacgat tgcggcgctt gccgattatg cggaaaaccg aaacgaagga ccggcattca    6960
gggcgattga gccggctgag aagcaggcga gctatccgct ttcgctcgct cagcagcgga    7020
cttatatcgc gagccaattt gaagatgcgg gagtcggata taacatgccg gctgcggccg    7080
tgattgaggg cgctttagac cttgaaaagc tcgagcgtgc atttctgcc ttaatcagca    7140 ggcatgaagc gctcagaaca tcgtttcaat cggaggacgg cacgccgaga caggtggttc    7200
acgaacatgt tccgtttcat attgaaatgc tcgaagcgcg cggaagaacg aatgaacagg    7260
tcatgaagga ctttgtgcgc cgttttgatt tatctgaggc gccgctgttc agaatcggcc    7320
tgcaaacgct cggtcacaat cgccatatgc tgctgtttga tatgcatcac ctgatttctg    7380
acggggtgtc tatttccatc atgctgaagg aactggctga catctacggc ggaaatcagc    7440
```

```
tgcctgaatt gcgcattcaa tataaagatt atgccgtatg gcaggcggaa cgggcgaaag    7500
aaggctacaa gaaggagcgg gcgtactgga agaagtctt cagcggcgaa ctgccggtgc    7560
ttcagctgct ccctgattat ccgcggccgc aaatgcaaag ctttgaaggt gaccgcgtgt    7620
ccgccaagct gccgaaaatg ctgcgggaac ggctgcagaa gcttgccgag aaaaacggag    7680 ccaccctta catggtgctg ttatcggcat actatacgct gctttctaag tattcgggac     7740
aggaagacat catcgtggga acaccgtcag cgggaagaaa tcactctgat accgaggggc    7800
ttatcgggat gtttgtcaac acgcttgcgc tgcgaagctc cgtgaagcag gatcagacat    7860
ttgccggctt gttaggtcat gtgcgcaaac aggtgctgga gcgtttcc catcaggatt     7920 atccgtttga gtggctgacc gaggagctga acgtgccccg ggacatgagc aggcatccga    7980
tatttgacac gatgttcagt ctgcaaaatg cttcggacgg aattccggag atcgcaacc     8040 tgacgctgtc tcttcatgaa accaacttca atatcgctaa attcgatctg acaatgcagg    8100
cccgggaaac agcggaaggc attgcgctcg atttggatta ttgcacgaag ctgtttaagc    8160
gctcaactgc ggatcgcatg cttgcgcact atgtccgtct gctggagagt gcggcagctc    8220
agccggatgc gaaaatcagc gaatatgatc tgctttctga acgggaggct ttgaaccaat    8280
tacagcggtt caatccggag cgcacggcat acccgaaaga gcaaacgatc gtgcagatct    8340
ttgaagaaca ggcccgaaag aaccctgacc ggacggctct tcagttcgaa ggggaaactc    8400
tgtcgtatca gcagctgaat gaacgcgcca acaggcttgc gcggcatatt ctttcggtcg    8460
gaggcggcgg gaaaaccgcg gctgttttat gtgaacggtc aatggacatg attgtttcca    8520
ttatggctgt gttaaaagcg gggtccgcct atgtgccgat tgatcctgag catccggttc    8580
agcggattca gcatttcttc cgcgacagcg gggcgaaagt gctcctgact cagcaaagcc    8640
tcaagccgct tgcggaaaag gccggttttc aaggcgccat tgtgcttgct gatgatgagg    8700
cgagctatga aaaggactct cgcaatccag cattgccgtt tgactccagc acaattgcca    8760
atcttactta tacatcaggc acgacgggaa cgccgaaagg gaacatcgtc acacatgcca    8820
acattttgcg gacggtaaaa aacacgaact atttgaccgt ttctgaagag gacacagtgc    8880
tcggtctgtc aaactacgtc tttgacgctt ttatgtttga tatgttcggt tcgctgttaa    8940
acggtgcaaa gcttgtgatc gtcccgaaag atacggtgct ggacatgtcg cgcctgtccc    9000
gtgtgatcaa acgggagaac gtcagcattc tgatgattac gacggccctg ttccacctgc    9060
ttgttgatat ggagccgtcc tgtctgacga cgcttcggaa aatcatgttc gggggcgaaa    9120
gagcgtctgt agaacatgtc aaaaaggcgc tggcggcagt cgggaaagga agactgcttc    9180
atatgtacgg tccgtcggaa agcacggtgt ttgcgacata ccatccggtg gatgtcattg    9240
aagaggatac gctctccgtt ccgatcggta accggtcag caatacgaa gtctttatta      9300 tgaactcagc cggacgcatt cagccggcgg gtatcgcggg agagctgtgc gtcagcgggg    9360
aaggtctcgt agaaggctac tacaaccgtc ctgaactgac ggaagaaaaa tttgtaaagc    9420 atccgttta ggaaggtgaa cggatgtata aaacgggcga cttggccaga tggcttccga    9480
atggcgatat cgagtttatc ggacgcatcg accatcaggt gaaaatccgc ggtcagcgga    9540
ttgagcttgg cgaaattgag catcagcttc aaagccatga tcagattcag gaatgcatag    9600
tgctcgctgt ggatcagggc gcgggtgaca aacttctttg cgcgtatttt gtcggcctca    9660
gggaaatatc ttcccgggag ctgagggagc atacggcgaa ggatcttccg gcttatatga    9720
ttccgtccgt ctttattcaa ttggatgaac tgcctcttac agggaacgga aaaatcgaca    9780
ggcgggcgct gccgatgccg gatgtgaccg cagcgaatgc cgtgtcatat acggcgccgc    9840
```

```
gcaatgaaac agaaaaaaaa ctggcggata tttgggctga ggtgctgcaa atggaacggg    9900
tcggcgtcca tgatcagttc tttgagatcg ggggccactc gttagcgggg atgaaactgc    9960
tggcccttat ccagaagaca ttcggcgtgc agcttacctt aaaggacctg ttcacttctc   10020
cgacggctgc tgggctggcg cagctgattg aaggggctga gcggaaggcg gctgagagca   10080
tcgcaccggc tgccgagcgg gaaacgtatc cggtttcttc accgcagaag cggatgttcg   10140
tgcttcagca gctggaaggc gctgaaacaa gctataacat gccgtctgtg ctccgcttaa   10200
aaggaaagct tgatgcagaa aagctgaaat ccgtcatgaa acagctgaca gaacgccatg   10260
aagccttcag aacgacattt gacataaagg atggagaaac ggttcagcgt atatgggcgg   10320
aagcttatat cgacatggaa tattatgaag cctctgaaga agatgctgaa cagattattc   10380
agagctttat ccggccgttc cgtctggatc agcttcctct cgtcagaacg gggctggtca   10440
agctggctga acatgaccac ctgctgctgt tgatatgca ccatatcatt tcggacggcg   10500
cttcagtcgg cgtgctgata gatgaactgt cccgcttgta tggcggcgaa acgcttgagc   10560
cgctgcggat tcattataaa gactatgcgg tatggcagca gaaatttatt caatcagagc   10620
agtaccgcaa gcaggaggag cattggcttc gggagcttga cggcgagctt ccggtattga   10680
cgctgccggc tgattacagc cgtccggccg tgcaaacctt tgaaggagac aagctggtct   10740
tttctctgac tgaggaacag acgtcggctc ttcgcagtct tgcgaaacaa acggattcta   10800
ccatgtacat ggtgctcctg cgtcgtaca gcgcctttct ctcaaaactg agcggacagc   10860
atgacatcat tgtcggctcg ccggctgcgg gacggtcaca tgcggatctc gcaaacgtca   10920
tcggtgtttt tgtgaataca ctcgcgctgc gtacgtatcc ggaagcggac aaaacgttca   10980
cggactatct taagaagtg aaacaaaccg ctttacatgc atttgacgcg caggattatc   11040
cgcttgaaga ccttctgcaa aaggttgagg tgcagcgtga tacgagccga atccgctgt   11100
ttgatgcggt attctcaatg caaaatgcaa atgctgaaga tctggtcatg aaggaattg   11160
agctgaagca ccatccgttt gacagaaaaa cagccaagtt tgacctgacg ctgacggctg   11220
aggacacaga cgaaggctta acgtttgtgc ttgaatataa caccgcgctg tttaaaccgg   11280
aaacagcaga gacgtggaag cattattggc ttcaactgtt aaaagccgca acggaaaatc   11340
cggctgcgaa gctttctgag cttttccttg gtaatgaaac agaaaaacaa gccctccttg   11400
acgcatggaa aggaaaaaca ctctctgtgc cgcaggacaa aacggttcac cgtctctttg   11460
aagaaacagc cgcccgctac gcgaatcggc cggccgcggc atataacggc gcgaaatgga   11520
cgtacggcga gctgaacgca agggcgaacc ggatcgcgcg cattctcata gactgcggcg   11580
tcacggctga cgaacgtgtc ggcattttga cgaaaccgtc cttggaaatg ccgcgggcg   11640
tactcggcgt cctgaaagcg ggcgcggcat ttgtgccgat tgaccccgac tacccacaag   11700
agcggatcag ctacattctg caggacagcg gcgccaagct ccttctcaca caggaagcgc   11760
tggacgtgcc ggatggctac acaggagaaa cgatcctgct tgacggcgga cgctccattc   11820
tgagcctgcc gcttgatgaa aacgatgaag cgaacccgca gactgaaaca acggcggatc   11880
atctcgctta tatgatttac acgtcaggaa cgaccggaca gccgaagggt gtcatggtcg   11940
aacaccatgc gctggtgaac ctgtgcttct ggcatcacga cgcattcgcc atgacggcgg   12000
atgataaaag cgccaaatac gcgggcttcg gttttgacgc ctccatctgg gagatgttcc   12060
cgacatggac catcggcgcg gaacttcacg tcattgacga agcgatccgg ctggatatca   12120
cccgcttaaa tcactatttc gaggagcacg gcgtgaccat caccttcctg ccgacgcagc   12180
```

```
tggccgaaca atttatggag ctggaaaata cctctctccg catgcttctc gtcggcggcg   12240
acaagctgaa gcgggcggtg aaacagccgt acacgatcgt caacaactac ggcccgacgg   12300
aaaacaccgt cgtcgcgaca agcggcgtca tcaatcctga ggaaggatcg ctttcgatcg   12360
gacgggcgat tgccaatacg agagcttata ttctcggcga cggcgatcag gtgcagccgg   12420
aaggcattgc cggtgaattg tgcgtggccg ccgcggtct ggcacgcgga tacctgaacc    12480
gtgaagaaga cggcgaag cggtttaccg cagatccgtt cgtgcccggc gagcgcatgt    12540
accggaccgg cgacctcgtc aaatggaacg cgcagagcgg catcgaatac atcggccgta   12600
tcgaccagca ggtcaaagtg cggggctacc ggatcgagct ttcagaaatc gaagtccgcc   12660
tcgcccagct tgcggatgtt catgacgcag cggtgacggc ggtggaagac aaagcaggca   12720
atgccgcgct ttgcgcctat gtcgcgcctc agcaggacga tattgaagcg ctcaaagccg   12780
cgctgaaaga cacgcttccg gactacatgg tgccggcgtt ctgggtggag atggacgagc   12840
ttccggtcac cgcaaacgga aagattgaca aaaaagccct gccggaaccg gacattgaag   12900
cgggaagcgc cgcttacaaa gcgccggaaa cggagatgga cgctgctt tccgacattt     12960 gggaggaagt gctcggtctt gatcagatcg gcgtaagcga taatttcttc acgctcggcg   13020
gcgactcaat caaaggcatc caaatggcga gccgcctgaa ccagcacggc tacaagctgg   13080
agatgaaaga tctcttccag cacccgacca tcgaagagct cgtctcttat gtggagcgga   13140
cggaaggcaa gcaggccgac cagggacctg tcgaaggcaa agcggagtta acgccgatcc   13200
agcgctggtt ctttgagaaa aacttcacgg acaaacacca ctggaaccaa tccgtcatgc   13260
ttcacgcgaa agacggcttt gatccggaga taacagaaaa acattacat gtcctgacgg     13320 tgcaccatga tgcgctccgg atgatttatc gtgaacaaaa accgtactac agagggcttg   13380
aggatgcgtc tgttgaactg aacgtctttg agctgaacgg acctgctgaa gatcatgaga   13440
accgtatcga acgggaagca gaccgtcttc aaagcagtat tcactggaa acaggacatc     13500 tgctgaaggc cgggctcttc cgggccgaag atggagacca ccttcttctc gcaatccatc   13560
atttagtcgt ggatggtgta tcttggcgga ttttactgga ggacttcacg tccgtttata   13620
cgcagctgaa gcaaggcaat gaaccggcgc tgcctccgaa aacacattca ttcgccgaat   13680
ttgctgagag aatcaaagag tacgcaaata cgaaggcgtt tctgaaagaa gcggattact   13740
ggagggagct tgaggagaaa gaggtatgca ctcagcttcc gaaagacagg cagtctggcg   13800
atcagcgcat gagacatacg agaacggtca gtttctctct gacgcctgaa caaactgaac   13860
agctgacgac gaacgtacat gaagcctacc atacggaaat gaacgacatc ctgctcacgg   13920
cgctcggact ggcgctgaaa gagtggacgg gtgaagacac gatcggcgtt catttggaag   13980
gccacgggcg cgaagacatt cttgacgggc tgaatatcac ccggacggtc ggatggttta   14040
cgagcatgta tccgatgatc cttgagatga agcacgccga cgatctttca tatcagctga   14100
aacaaatgaa agaagacatc agacacatcc cgaacaaagg agtcggctac ggcattctgc   14160
gttatgtaac ggcgcctgag cataaagagg gtctttcatt tgagattgat ccggatatca   14220
gctttaacta cttaggccag tttaatgaga tgtcggattc cggcttattt acaagatccg   14280
ggatgccgtc aggacaatcg ctgagccctg acacagagaa gccgaatgcg cttgatattg   14340
tcggatttat agaaaatggg cagatgacga tgacgtttgc ctatcattct ctcgaatttc   14400
atgaaaaaac cattcaatcg ttcagtgaca gctttaaagg gcacctcttg aaaatcatag   14460
atcactgcct ggcccaagac ggacctgagc ttacgcctag cgatcttggc gatgatgatc   14520
tgacgcttga tgaacttgat aaattaatgg aaattctcta acagaaaaga cagaggtgac   14580
```

```
atatgagcaa aaaatcgatt caaaaggtgt atgcactcac accgatgcag gagggaatgc   14640
tgtatcatgc gctgcttgat ccgcattctt cctcctactt cacacaatta gagcttagga   14700
ttcacggaag ctttcagctt gagcttttttg aaaaaagtgt caatgagctg attcggacat   14760
atgacatcct gcgtacggta ttcgtgcacc agcagcttca aaaaccgcgc caagtcgtat   14820
tagcagagcg gaagacgaag gtgcactatg aagatatcag tcaattagat gaagcgcgcc   14880
aaaccgaata tattgaacgc tataaacgcg atgtgcagca gcagggcttt catctggcga   14940
aggatattct ctttaaagcg gcggtgttca ggctcagtga aaggaactg tatctcgtct   15000 ggagcaatca tcatatcgtc atggacggct ggagtatggg cgttttgatg aaaagcctgt   15060
ttcaaaacta tgaagcgctt cgtgccggcc ggcccgccgg gggaagccag ggcaaacctt   15120
actctgacta tatcaaatgg ctcggaggca gggattatga ggaggcggaa caatattgga   15180
gcagccgcct ggcggatttc gaacagccga gcctgctccc gggccgtctg gcaccagaaa   15240
agaaagacta ccaaaatgaa gaatattctt ttgtctggga tgaagagctg gtcgcgcaga   15300
ttcagcagac cgccaaccgg catcaagtca cggggcctaa cctgtttcag gccgtttggg   15360
gtgcggtgct cagcaaatac aactatacag acgatgtggt gttcggcacc gtcgtatcag   15420
gccgtccttc agaaatcaac ggcattgaaa cgatggcggg gctgttcatc aatacgattc   15480
ccgtcagaat caagattgac aaagatgcag ccttttctga cgtgatggcg gcagttcaga   15540
aaaacgccgt ggaagccgag cgctatgatt atgtgccgct ctatgacatt caaaagcgct   15600
ccgctctgga cggcagcctc ttgaatcatt tggtcgcgtt tgaaaactat ccgctggaca   15660
aagagctgga aaacgggggc atggaggaaa gactcggctt ttccattaaa gttgaacatg   15720
cttttgagca gacgagcttt gatttcaatc tcatcgtgta ccgggaaaaa cgtggactg   15780 tcaaaatcaa atacaacgga gcggctttcg ctcatgatgc catcgaacga acggcgcatc   15840
atctgacctg catgatgaaa gcggcggtcg gaacgcctga tgcgcccgtg cgggaactcg   15900
gccttgtttc aggcgaagaa gagcggcaga ttgttgagat attcaatgat acaaaaacgg   15960
cgcttccgga agaggaggcc gttcaccgtt tgtttgaagc acaggcaaac cggacgcctg   16020
caagcatcgc gataaaagaa gcgggacgcg aatggaccta ccgtgaagtg aacgaagcgg   16080
ccaaccgcct ggcgagacac tttgtgaaga gcgggctgga aaaaggccgg accgccgcta   16140
ttatgaacga ccggtctgcg gaaaccgtta tcggaatgct tgccgtccta aaagcaggcg   16200
gcgcctatgt gccgattgat ccggcttttc cggaggaccg tctccgcttt atggcggaag   16260
acagctcgat tcggcttgtg ctgacagttc aggactatca agaacaagcg gcacattgc   16320 aagtcccgat tgtcatgctg gatgaaagcg aggatgaaac gctaagcgga acagacttga   16380
atcttccggc cggcggcaac gacttggcgt atatcatgta tacatcccggg tcgaccggaa   16440 aaccgaaagg cgtcatgatt gaacacagaa atatcatcag gctcgtcaaa cattcgaatt   16500
acgtgccggt tcatgaagaa gaccggatgg cgcaaacggg agccgtcagc tttgatgccg   16560
gaaccttcga agtcttcggc gcattgctga acggagcggc attgcacccg gtgaaaaaag   16620
agacgctgct tgacgccgga cgattcgccc aatttctgaa agagcagcgg atcacgacca   16680
tgtggctgac gtctccgctg tttaatcagc ttgcccaaaa ggatgccggc atgtttaaca   16740
cgctccggca cctcatcatc ggcggtgatg cgcttgtgcc gcatatcgtc agcaaagtga   16800
ggaaggcatc accggagctg tcgctttgga acggctacgg gccgacggag aatacgacgt   16860
tttcgacgag ttttctcatt gatcaggact acgacggttc gatcccgatc gggaagccga   16920
```

```
tcggaaattc cactgcgtac attatggacg aaaaccgcaa cctccagccg atcggcgcgc  16980
ccggggagct gtgcgtcggc ggaagcggag tggcaagagg ctatgtgaat ctgcctgaat  17040
taacggagaa gcagtttgtc cgcgatccgt tcagaccgga tgaaatgata taccggacgg  17100
gggacttggc gaagtggctt ccggacggca cgatcgagtt tctcggcaga attgacaacc  17160
aagtaaaggt ccgcggtttc agaatcgagc tcggcgaaat tgaggcgaaa atcagccagg  17220
cggagaatgt gacggaatct gcggctgtga tccggaaaaa taaagcggat gaaaatgaaa  17280
tctgcgctta ctttaccgca gaccaagccc tttcgccgga agacctgcgc aaaacgcttt  17340
cggaatcact tccggaatac atgattcccg cgcacttcat ccagatgaat cagtttccgc  17400
tgacggcgaa cggaaagatt gataaaaaag cgctgcctga gcctcaggct gaagccgttc  17460
aaaaagaata cgaagcgccg aaaacggaag cggagcagaa actcgcggac atttgggaag  17520
gtattctcgg tgtaaaagcg ggtgtgactg acaatttctt cacgattggc ggacattctt  17580
taaaagccat gatgatgacc gctaaaatcc aggagcactt tcaaaaagaa gtgccgatta  17640
aagtgttatt tgaaaagccg accattcagg agcttgcgca ttatttggag catgagaccg  17700
aggaggaaca gcagtttgaa ccgatccgac aagcgcctta tcagaagcat tatcctgttt  17760
cctcagcaca gcgcaggatg tatatcctta atcagctcgg acaggccagc acgagctaca  17820
acgtccctgc tgtacttctg ctggaaggat cagtagacaa aaaccgtctt gaagaggcca  17880
tgcaggcatt aatcaaccgt catgagacac tgcgtacgtc gtttgacatg gcagatggag  17940
aagtcgtgca gaccattcat aaaaatgtgt cgtttgagct tgaaaccgcc gagggccggg  18000
aagaagatgc agaagagctg acaaaagcct ttatcaggcc gtttgcgctc aatcgtgcgc  18060
cgctggtccg ttcgaagctg atccggcttg aagaagaccg gcatcttctg ctgattgaca  18120
tgcaccacat tattacggac ggaagctcaa tgggcatttt catcggtgat cttgcgaagc  18180
tttatcaagg cacggagctt gagctgccaa agattcatta taaggatttt tcagtctggc  18240
agcgtgaaaa agcaaatctt gatcagcacg aagcttactg gcttgatacg ttcaaaggcg  18300
atctgccggt gctggatctg ccgcttgatt tcccgcgtcc tgccgagcgc agttttgaag  18360
gggaacgcgt catcttcggg cttgataaac aggtgacggc gcagattaag aagctgctgg  18420
ctgatacgga tacgacgatg tacatgttct tgttagccgc ttttcaagtg ctgctgtcca  18480
aatattcggg gcaggaagac atcatagtcg ggtctccggc ggccggaaga cagcatcctg  18540
atctccaaga cgtgccgggc atgtttgtca acacagttgc gcttcggtcg catcctgccg  18600
gcaaaaaaac gttcaagcaa tttctggatg aagtgaaaac ggcagagcct caagcttttg  18660
agcatcaaag ctatccgctt gaagaattaa ttgaaaaact gccgttaacg agggacacaa  18720
gccggagtcc gctgttcagc gtgttattta atatgcagaa catggagatc ccggccctgc  18780
ggctcggaga tttggagatt tcttcttact ccatgcatca tcatgtcgct aaatttgatc  18840
tttccttaga gcggctgagc gcggagaag aggtcggatt gagctttgat tacgcgaaag  18900
ccttatttgc ggacgaaacc atccgccgct ggagcgctca ttttgtcaat ctgattaaag  18960
cctgcgccga aaatccggat attcagctgg ccgacgcaag cctgctgtcc gctcctgagc  19020
gggaagcgct cctttctgat gaaaacgga cggaagcgga tctgcctgag gcacttttg   19080 tttcgctgtt tgaacggcaa gcgcaaaaaa cgcctgatct cacggcggtt gcgggcggaa  19140
caagtctgac atatcgtgag cttgatgaac gctcgaaccg gtttgcccga caccttcagg  19200
cttgcggaac gggcagtgag gacatcgtgg ccattatgat ggatcgttcg gccgacttga  19260
ttaccgcgat tctcggcgtc atgaaagccg gagcggcatt tctcccgatt gatccggaga  19320
```

```
ctcctgaaga gagaatccgc tactctctcg aagacagcgg aacgaagctt ctggtcgtca   19380
atgagagaaa catgaccgcg gccgccgttt ataaagaaaa aacggtcgta atggaagacg   19440
gagaatggca gaacgaaagc gccgaccggc ttgaaacgga gcccggcgcc gaccggcttg   19500
cctatatcat ttatacctcg ggaacaacgg gcaaaccgaa aggcgtccag ctggagcacc   19560
gcaatctaat caattatgtc acatggttca gccgtgaagc cggtttgacc gaagctgaca   19620
aatccgtgct gctgtcttct tatgcatttg atctcggcta tacggccata ttcccgattc   19680
ttcaggcggg cggcgagctg cacattgtgc cgaaggagac gtacaccgcg cctgatcagc   19740
ttggtgagta tatacagaaa aacggcatta cgtatatgaa actgacgccg tcattgttcc   19800
atatgatcgt caatacagcc cgttttacgt cagaatgccg tttcagcccg cttcgtttag   19860
tggtgctcgg cggagaaaag atcatcacgt ccgatgtccg caagtttcat gacgtatacg   19920
cccataccga ctttatcaat cactacggac cgacggaaac gacgatcggc gccattgcgg   19980
aacggatcaa tatggagtgt cttgatcaat atgagcagcg tcccgtcatc ggccgcccga   20040
tcgcaaatac cggcgcgctt gtattggacg gagcaatgca gctcgttcct ccgggcgcaa   20100
gcggcgagct ttatattacc gggaaggggc ttgccagagg atatcttcac cgtccgcagc   20160
tgacggcgga gaaatttctc tcaaatcctt tttcaccgga cagcctgatg tacaaaacgg   20220
gagatatcgt ccgcaggctt cctgacggga cgattgaatt tatcgccgt gcggatgatc   20280 aggtgaaaat ccggggctac cgcattgaat aaaagaggt tgaaaccgtg ctgttaagcg   20340
taaacggcat tcaggaggcg gtcgttctcg cagtcagcga aggcgggctg ccggaactgt   20400
gcgcgtacta taaagccgac agcgggctga aaggctctga gcttcgcaaa cggctttccg   20460
aaacactgcc gtctcatatg cttccggcct atttcgtgca agtagaccgc attccgctca   20520
cagccaacgg aaaaaccgat aaaaacgccc tcccgaaacc gggcgtcagc caaacggcgc   20580
aaattgcttc agccttgccg gaaacggaat tggaggaaaa gctgtgccgc atttggaaac   20640
agacactcgg tacggatacg ctcggcatcg acgataattt cttcgattac ggcgggcact   20700
ctttaaaagg aatgatgctc ctcgccaata ttcaggctga actggacaaa acggttccgt   20760
taaaagcgct gttcgaacag ccgactgtcc gcctgcttgc cgcatatatc gaaaaatcgg   20820
cggtatctga gggatatcgg atgatcacac cggcagacag tgcagacgcg tacccgttat   20880
catccgccca aaaacggatg tacgtcctga accagcttga ccgggagaca atcagctata   20940
atatgccgtc cgttcttctg atggaaggag aagtcaatat ttcaaagctt caggaagcgc   21000
tcaatcagat gatcaaccgc cacgaatctt tgcggacgtc ctttatcgat aaaaaaggcc   21060
agccgatgca gcagatcgca gaacaggctg acattgacct gcacatcttt gaagcagcgg   21120
acgaggagaa agcggatctt atcattcagg cattcattaa gccgtttgat ctgagcgcgg   21180
ctccgctcat tcgggccgct cttgtcagac tgaatgaaaa gaaacacctg ctgctgctgg   21240
atatgcatca tatcattgcc gacggcgtgt ccagaagcat gctggtcaaa gagctcgctc   21300
acctttacaa aggcggaagt ctgccgtcgc cgaacctgca ctataaagac ttcgccgtct   21360
ggcagaatga acctgagcag gccgaacgga tgaaagacca tgagcgttat tggctctccg   21420
cattttccgg cgagcttcct gaattgaatc tgccgaccga ttttcccgt ccgccggttc   21480 aaagttttaa aggacagtcc gtccgtttca gagcggggcg tgagacggaa aaagcggtgc   21540
gtgaattaat ggaatcatcg ggagcgactc ttcatatggt gcttcacgcc gcgttccatg   21600 tcttttttgag caaaatcacg ggccagcgcg atatcattat cggttcggtg accgccggaa   21660
```

```
gaacgagcgc cgaagttcag gaaatgccgg ggatgtttgt caatacgctt gcgcttcgca    21720
atgaaacgca aaaagagcag accttcgccg ggctgctcga acgggtgaaa caaaccaatc    21780
tcgacgcgct ggcgcatcag gattatccgt ttgaggatct gatcggaaag cttgacctgc    21840
cgagagatat gagccgcaac ccgctgttcc aggtgatggt gacgacagaa gatccggata    21900
aagaaacact ggaactggag aacctgcgca tcactccgta tgagtcaaac caaggcacgg    21960
cgaaattcga tctgacactc ggcggcttta cggatcaaga aggtctcggc cttcagtttg    22020
aatatgcgac tgatctgttt aaaaaagaaa ccattgaaaa gtggagcgcc gggttcctgc    22080
ggattctgaa gcaagcggcg gaaagccegg acagaaagct gcctgagatt tcactgatca    22140
gcgatgctga aaacaagcc ctccttgacg catggaaagg aaaaacactc tctgtgccgc     22200
aggacaaaac ggttcaccgt ctctttgaag aaacggccgc ccgatacgcg aaccggccgg    22260
ccgcggcata taacggcgcg aaatggacgt acggcgagct gaacgcaagg gcgaaccgga    22320
tcgcgcgcat tctcatagac tgcggcgtca cggctgacga acgtgtcggc attttgacga    22380
aaccgtcctt ggaaatggcc gcgggcgtac tcggcgtcct gaaagcgggc gcggcatttg    22440
tgccgattga ccccgactac ccacaagagc ggatcagcta cattctgcag gacagcggcg    22500
ccaagcttct tctcacacag gaagcgctgg acgtgccgga aagctacaaa ggagaaacga    22560
tcctgcttga cggcggacgc tccattctga gcctgccgct tgatgaaaac gatgaagcga    22620
acccgcagac ggaaacaacg gcggatcatc tcgcttatat gatttacacg tcaggaacga    22680
ccggacagcc gaagggtgtc atggtcgaac accatgcgct ggtgaacctg tgcttctggc    22740
atcacgacgc attcgccatg acggcggatg ataaaagcgc caaatacgcg ggcttcggtt    22800
ttgacgcctc catctgggag atgttcccga catggaccat cggcgcggag cttcatgtca    22860
ttgacgaagc gatccggctg gatatcaccc gcttaaatca ctatttcgaa gagcacggcg    22920
taaccatcac cttcctgccg acgcagctgg ccgaacaatt tatggagctg gaaaatacct    22980
ctctccgcat gcttctcgtc ggcggcgaca agctgaagcg ggcggtgaaa cagccgtaca    23040
cgatcgtcaa caactacggc ccgacggaaa acaccgtcgt cgcgacaagc ggcgtcatca    23100
atcctgagga aggatcgctt tcgatcggac gggcgattgc caatacgaga gcttatattc    23160
tcggcgacgg cgatcaggtg cagccggaag gcattgccgg cgaattgtgc gtggccggcc    23220
gcggtctggc acgcggatac ctgaaccgtg aagaagagac ggcgaagcgg tttaccgcag    23280
atccgttcgt gcccggcgag cgcatgtacc ggaccggcga cctcgtcaaa tggaacgcgc    23340
agagcggcat cgaatacatc ggccgtatcg accagcaggt caaagtgcgg ggctaccgga    23400
tcgagctttc agaaatcgaa gtccgcctcg cccagcttgc ggatgttcat gacgcagcgg    23460
tgacggcggt ggaagacaaa gcgggcaatg ccgcgctttg cgcctatgtc gcgcctcggc    23520
aggacgatat tgaagcgctc aaagccgcgc tgaaagacac gctgcctgac tacatggtgc    23580
cggcgttctg ggtggagatg gacgagcttc cggtcaccgc aaacggaaag attgacaaaa    23640
aagccctgcc ggaaccggac attgaagcgg gaagcgccgc ttacaaagcg ccggaaacgg    23700
agatggagac gctgctttcc gacatttggc aggaagtgct cggtcttgat cagatcggcg    23760
taagcgataa tttcttcacc ctcggcgtg actcgatcaa aggcatccaa atggcgagcc     23820
gcctgaacca gcacggctac aagctggaaa tgaaggatct cttccagcac ccgaccatcg    23880
aagagctcgt ctcctatgtg gagcggacgg aaggcaagca ggccgatcag ggacctgtcg    23940
aaggcgaagc ggagttaacg ccgatccagc gctggttctt tgagaaaaac ttcacggaca    24000
aacaccactg gaaccaatcc gtcatgcttc atgcgaaaga cggctttgat ccggacctgg    24060
```

```
tggaaaaaac cctgcaagca ttgattgaac accatgatgc gctccgcatg gtttaccgtg    24120
aagaaaggga aggcatcatt cagacatacc tccctgtcac agaatgcaag gcaagctttg    24180
aaatcgttga tctgtacgga acggacgagg atatgctgaa aagccagatt cagcggcttg    24240
ccgatcatct tcagggcagt cttgatctgg agaacggccc gctgttaaaa gcggagcaat    24300
accggacaga acaaggcgat catctgttaa tcgcggttca ccatctcgtc gtggacgggg    24360
tttcatggag aattctgctt gaggatttcg cttcaggtta taaacaggcg cagcagcaaa    24420
acagcatcgt tctcccgcaa aaacccact cctttaaaga ttgggcggag gcgctgaaca    24480
cgtttgcgca atcagaagag ctgaaaaagc aggcggatta ttgggcgcag gcagatgcgg    24540
aagaactgcg gccgctgccg aaagaccatg atccggacaa acggctcgtc aaacatacgg    24600
cggccgtgaa atgtgaattg actgaggaag aaacggcaca gctgctgaca gatgttcatc    24660
atccgtacgg aacggaaatc aacgacattc tgctcagcgc gctcggctta acgatcggtg    24720
aatggacgga aaacggcaaa gtcggcatca acttagaagg acacggccgg gaagaaatca    24780
taccgaatgt caatatttca cggacggtcg gctggtttac ggcccaatat ccgttgattc    24840
tgcagatcag caaggaagac ggcgtctctt ccgtcattaa aacggtaaaa gagacagtgc    24900
ggcgcgttcc agataaaggt gtaggatacg ggattctccg gtatctgtca tccgatgaaa    24960
cagaaaaagg cgccgcgcct gaaatcagtt ttaactactt ggggcagttt gacaatgaag    25020
tgaaaacgga atggtttgag ccgtctccat atgatatggg acgtcaagtc agcgaagagt    25080
cagaggcgtt atacgcactg agcttcagcg ggatggttac aggcggccgc ttcgtcattt    25140
cctgctcata caatcaggaa gaatatgaaa gaagcaccgt cgaaacacag atgcagcggt    25200
ttaaagacaa tcttttaatg atcatccgcc attgcacggc caaagaggag aaagaattta    25260
cgccgagcga tttcagcgcg caggatcttg agatggatga atgggagac atctttgaca    25320 tgcttgagga gaatttaacg tgacaaaaac agttaacaga aggggggagc ggagcagatg    25380
agccagttca aaaagatca agttcaggac atgtattatt tgtcgccgat gcaggaggga    25440
atgctgtttc atactctcct gaatcccggc caaagctttt acatcgaaca atgacaatg    25500 agagtaaaag gcagcttgaa tatcaaatgc cttgaagaaa gcatgaatgt gatcatggac    25560
cggtacgatg tatttcgtac cgtgttcatt cacgaaaaag taaaaaggcc ggtccaagtc    25620
gtattgaaaa aacggcagtt tcagatagaa gaaatcgatc tgcacacactt aacgggcagc    25680 gagcaagcat ccaaaattaa tgaatacaaa gaacaggata agatcaaggg ctttgatttg    25740
acgcgggata ttccgatgcg ggcagccatc tttaaaaaat cggaagaaag ctttgaatgg    25800
gtgtggagct accaccacat cattttggac ggctggtgct tcggcatcgt cgtgcaggat    25860
ctgtttaagg tatacaatgc cctgcgagaa caaaagccgt acagcctgcc gccggtcaaa    25920
ccgtataaag actatatcaa gtggcttgaa aagcaggata acaagcatc actgcattac    25980 tggcgcgggt acttagaaga ttttgaagga caaacgacat ttgcggagca agaaagaaa    26040 caagagaacg gctatgagcc gaaagagctg ctcttctcac tgccggaggc ggaaacaaaa    26100
gcatttaccg agcttgcaaa atcgcagcat actactttga gtacggcgct gcaggcggtt    26160
tggagtgtat taatcagccg ctaccagcag tccggcgatt tgatcttcgg cacagtcgtt    26220
tccgggcgtc ccgcagaaat caaaggcgtt gaacatatgg tcgggctgtt tatcaatgct    26280
gttccgagcg gggtgaagct gtctgaggat accacattta acggcttgct caagcagctg    26340
caggagcaat cgctggagtc tgagcctcat caatatgtgc cgctctatga catccaaagc    26400
```

```
caggccgatc agccaaagct gattgaccac atcattgtgt ttgaaaatta ccgcttcag    26460 gatgcaaaaa atgaagaaaa cagtgaaaac ggctttgata tggaggacgt ccatgttttt    26520
gagaaatcga attatgatct caacctgatg gcttctccag gtgatgagat gctgattaag    26580
cttgcctata acgggaatgt gtttgatgag gcgtttatcc tacgcttaaa atctcagctt    26640
cttacagcga ttcagcagct catccagaag ccggatcagc ctgtcaatac gatcagactt    26700
gttgatgaaa aggaaagaga gcttctgctt accggcttaa acccgccggc tgagactcat    26760
caggcgaagc ctctgacgga ttggttcaag gaagcggtga atgtaaatcc tgatgcaccg    26820
gcgcttacgt attccggcca gactctttcc tatcgcgaat tagatgagga agcgaaccgt    26880
cttgcgcgcc gtttgcaaaa gcaaggtgcg ggtaaagaca ccgttgtcgc gttgtacacg    26940
aagcgctcgc ttgaactggt gatcggcatt ctcggcgtat taaaagcagg agcggcttat    27000
ctgccggttg atccgaagct gccggaggac cgaatctcgt acatgctgac tgacagtgcg    27060
gcagcctgtc tgctgacaca tcaggagatg aaagaaaaag cggctcagct gccgtataca    27120
ggaacaacac tcatcatcga tgatcaagca cggtttgagg aacaggcaag cgatcctgca    27180
gccgcaattg atcccgatga tccggcgtat attatgtata cgtccggcac aaccggaaag    27240
ccgaagggca atatcaccac tcatgccaat atacaaggat tggtcaagca tgtagactat    27300
atggcatttt ctgaacaaga tacgttctta tctgtttcga attacgcctt tgacgcattt    27360
acttttgatt tctacgcatc aatcctgaat gcggcacggc tcattatcgc agatgaacat    27420
acactgcttg atacagaacg gctcactgat ctgatccggc aggagaatgt caatgtcatg    27480
tttgcgacaa ccgcactttt taatcttctc accgatgcgg gagaggagtg gctgaagggg    27540
ctccgctgtg tgttattcgg gggtgagcgc gcgtctgtgc ctcacgtcag aaaggcgctt    27600
gagatcatgg ggcccggcaa gctgattaat tgctacgggc cgactgaggg aacggtgttt    27660
gcgacagctc acgtcgtgca tgatataccg gattccattt cctcattgcc gatcggaaag    27720
ccgatcagca atgcaagtat ttatattctt aacgggcaaa accagcttca gccgttcgga    27780
gctgtcggtg aactgtgcat cagcggaatg ggtgtatcaa aagggtatct gaaccgtcac    27840
gacctgacga agcaaacgtt tatcccaaat ccgttcaagc cgggagaaac gctttaccgc    27900 acagggggatt tagcacgctg gctgccggat gaacgattga atacgccggg cgtattgacg    27960
accaggtcaa atacgcgtca ccggattgaa cttgaagaaa tcgaaaagca gctgcaggaa    28020
tacccgggtg tgaaagatgc ggtcgttgtt gcagaccgcc atgagtccgg agatgcatca    28080
atcaacgcct atctcgtgaa ccggacgccg ctttcagctg aagacgtaaa gaggcacttg    28140
aaaaaacagc ttcctgctta catggtgccg caaaccttta ctttcttaga agagcttcct    28200
ttaacgacaa acgggaaggt caataaacgg cagctgccga aaccggatca ggctcaggcg    28260
gcgaaagaat ggatcgggcc tcgaaacgcg acggaagaaa cgattgcaca catctggtcc    28320
gagattctcg gcagacagca gatcgggatt catgatgatt tcttcgcgct cggaggccat    28380
tccttaaaag cgatgacggc agcgtcgcgc attaaaaaag agctcggtac ggacatcccg    28440
gtgcagctgt tattcgaagc gacgacaatc gcagacattg ccggttatct gcttcacggt    28500
gaagaaaaag gaatgaaaga tctcaccatc atgaataaaa atcagtctga cacactgttt    28560
gcgttcccgc cggttctcgg ttacgggctg atgtaccagc cgctggcaaa acagctgtcc    28620
ggctatagaa tctgtgcgtt tgattttatc gaggaagaca accgcatcga acgctacaca    28680
gagctgatca atcagctcca gccggaagga ccggtcaagc tgttcggata tcggcaggc    28740 tgcacgctcg ccttttgaaac ggccaaacgg cttgaagccg aaggacgtaa agtggagcgg    28800
```

```
ctgatcatgg ttgattccta taaaaaacaa ggcgtcagcg acttggaagg ccgcaccgta    28860
gaaagcgatg tccaggcgct gatgaaggta aaccgggata acgaagcgct gaatgacgaa    28920
gccgtcaaag aaggtctcgc caaaaaaaca aacgcgtttt attcttattt cgtgcatacc    28980
gtcagcaccg gcacggtcaa tgcggatata gatctattaa cgtcagaacc ggactttgcg    29040
atgccgccgt ggctcgcttc gtgggaggaa gccacgacag gtgaataccg tgtgaaaaaa    29100
ggctgcggca gtcacgcaga aatgctacag ggagaatgtc tcgaaaggaa tgcggcatat    29160
ttgctcgaat tcctaaggaa ggaacatccg aagctgacag cttcacgata gaaaaggagg    29220
aagcccgcca atggtccagc tcttttaaatc gttcgatacc acggaaaaaa cgcagcttat    29280 ctgtttttccg ttcgcaggag gctattccgc atcattccgc ccgctccaca cctatcttca    29340
aggtgagtgt gagatgcttg ccgcggaacc gccgggacag ggaacaaatc aaatgtccgc    29400
cgttgaggat tttgaacagc ttgtcagttt atacaagcag gagttgaatc tccatcctga    29460
ccgcccgttt gtcctgttcg gccacagtat gggaggcatg gtcgctttca ggctggcgca    29520
aaagctggag cgggagggga tttacccgca ggccgtgatc atctcagcca ttcagccgcc    29580
gcatgttgaa aggaaaaaag tgtctcatct tgatgatgaa aaatttctcg cccatattat    29640
cgagctgggc ggaatgccgc aggagttagt ggagaataag gaggtcatgt cattttttcct    29700 gccttctttc aggtccgact accgcgcgct tgaaagcttc cgtccgtctg attctcacat    29760
gattcaatca cccgtccata tttttaacgg gcggaaagat aaaaaatgta tcaaagatgc    29820
ggacggatgg aaaaaatggg ccgacaatcc cgtatttcat gagttttcgg acggccacat    29880
gttcatatta agtgaaactg aaaaagtggc ggaacgaata tatgagatta ttaacaggag    29940
cactgcaggc caattgttat aggatatgac agacagcatt cgctgtctgt tttttgtaac    30000
aaaatctgcc cgtgagtttt ctcatttatc aaaaatttta tgttatgatt tgatggaata    30060
taattttgaa gggattgtcg tacatgaatg atgcagcaaa agagctgaac agaacattat    30120
cggaagaaaa cccgcacgtg cttcatatgc tttctgattt gggcagagag ttgttttatc    30180
cgaaaggggt gctgacacaa tcggcggaag cgaaagccaa ggccgaaaag tataatgcca    30240
cgatcgggat tgccacctca caaggcgagt ccatgcactt ttcccatatt caagagacac    30300
tgtccgccta taaccccgat gatatctacg attatgctcc gccgcaggga aaagagccgc    30360
tcagacagga atggctgaaa aaaatgcgtc tcgaaaatcc ttcattagcc ggcaaagaca    30420
tcagcacgcc gatcgtgaca aacgctttaa cacacgggct gagcattgcc gccgacttgt    30480
tcgtcaatga aggggatgcg ctgcttctgc cggataaata ttgggggaaat tacaatttta    30540 tttttcggtgt ccggcgcaag gcatccattg agacgtaccc gcttttttcag caggatgggc    30600 gttttaatgc ggcggggctg tccgagctgc tgaaaaagca ggaagaaaag gcgattgtcg    30660
tgctgaattt cccgaataat ccgacaggct atacgccggg ggaagaggaa gcgtcagaaa    30720
tcgtcagtgt gatcctggag gcggcggagg ccggcaaaga gattgtcgtg ctcgtagacg    30780
atgcgtatta caatctgttt tacgatgaaa cggccattca ggaatccatc ttcagcaaac    30840
tcgcccaagt gcacgaccgg gtgctttgcg taaaaataga cggcgcgacg aaggaaaatt    30900
atgcgtgggg cttccgcgtc ggttttatta cgtacagcac aaaaagcgaa aaagcgctgc    30960
gcgtgctcga ggaaaaaaca aaagggatta tcagggggaac gatttcaagc gccccgcatc    31020
cgtcccaaac gttatgctg cgggcgatgc agtcaccgga atacgagaaa gaaaaatcgc    31080
tgaaatataa tatcatgaaa aaacgggctg acaaagtgaa agccgttctt gcagaaaaca    31140
```

```
agcactatga agacgtatgg acgccttatc cgtttaactc gggttatttc atgtgtgtcc   31200
ggctgagaga cataaacgcc ggtgaattaa gagtgtcatt gcttgaaaag agaggaatcg   31260
ggacgatatc cattaatgaa accgatttgc gaatcgcatt ttcatgtgtt gaagaagaat   31320
acatcgcgga tctgttcgaa gaaatttatc aagaagcaaa gcagctgcag aaacaggcgg   31380
aaatatcagg ctgacaaaaa aaggaggggg ataccctcct ttttctatgc ttacagcagc   31440
tcttcatacg ttttcatctc aatcccgtca caaaaatcgg gatgcgccgc acaaacggcc   31500
agcttatatt cctcgtccgc atcatatgtg cggatgaaac aaggttcatg tccgtccggg   31560
agctcaatgg acacatggcc gtcgtctttg aggcggacgc tgaatgaatc aagcggaagg   31620
gaaagcccct ttccggcctg cttgataaag ctttcttttca tcgaccacag gtggtaaaaa   31680
taatcggtct gctgatcggg gtgtttcgct tgcagatcac tgtattccgt cggcgaaaaa   31740
aaacgtttgg cgatatcaat cgtgccgggc ttcattttttt caatatctat gccgatcggt   31800
tttgaatcaa cggcacacac gatccagcgc ccggagtggg aaatgttaaa gtgcatgtcc   31860
ggaagcgcgg ggatgtacgg cttccgtat tcctggacgc tgaatgaaat cccggccgga   31920
tcaagtccgt aagccttcgc cgcagcggtg cggatcagca tgtcgccgat caaggtgcgg   31980
tgagcatcct ccttatggta aaagcgccgg cattttttccc gcttttcggc ggacacggcc   32040
gccatcatcc gatcctcttc ccctgcagaa agcgggcggt ccatatatac tccgtaaatc   32100
ttcatgtcca gatcctccgt ctgaaaatat tgtcaaaacc atcctaccat atcagacgaa   32160
agctgtccga aaataaaaaa acaaaaccgt ttcggctttg tttttaatga acggacgttg   32220
cccgccggga gatcgcgtat gttaacagtt tagaggactg cggcaaagaa aaacgcagaa   32280
tcagccccgt caaaacagcc gtaataatgg ttccggcgcc gatcggtccg cccatcaccc   32340
aggctgcggc aagaatcgtc agctcaatgc cgttccgcac ccattgcacg ttccagcccg   32400
ttttttcaga tatcagcatc atcagagagt cccgggggcc cgcgccgagc cctgctgata   32460
cgtaaatacc gacgccgcag ccgatcagca gcaatccgat agaaaaaaac acggccgcta   32520
aggaaaaagc gtgcgcctca ggaagcagaa acgagaagaa atcaataaac attcccatca   32580
gcaccatgtt taagatagcg ccgattttcg ggagtgtcct cgtgaacagg caggttaaag   32640
ccacgatgac cgcgccgacc aagatggacc attggccgac agatagcccg aaatgctgaa   32700
aaagcccata atgaaaggca tcccaagggt tgatgccgag agcttttcct ttaatggtta   32760 acgataccccc gaaagacaaa atcaacagac cggcaaaata aaacgtccag cgcatcaaga   32820
attcccgctt caaagaggtc ccttctttca taacattcat taattgtcat tgtagcataa   32880
ccgcccaaaa aagaagaag cgaaatcagt gtttcgcttc ttctccggct actacaaagg   32940
attcagtata cgatttaaaa accgctgcgt gcgttcttct ttcggcgcgg aaaaaatctg   33000
ggccggcggt ccttgttcca caatgacgcc gccgtcaatg aagatgactt catcggccac   33060
ttcctgcgcg aatttgattt catgggtgac gacgaccatc gtccagcctt cgttcgccag   33120
atccttaatc actttgagca cctcgccgac cagctccgga tcaagtgctg acgtcggttc   33180
gtcaaacagc atcagctcgg gctgaatcgc aagcgcgcgg gcgatgccga cccgctgctg   33240
ctgaccgccg gaaagctgga acggatataa atccattttg tctttcagtc cgacttttttc   33300 cagaagctct atcgcttctt ttctgacttg ctccttgtcg cgcttttgca cttgaacggg   33360
tccttccatg acgttttcaa gcgccgtgcg gtgaggaaac agatgatacg cctgaaagac   33420
catgcctgat ttgcgcgcga ggcggagaat atcagcctgc ttcactttttt tggagaaatc   33480 tattgaaaaa tcggagaatg ccagctcgcc gcgattgggg atctcaagcg cgttcagaca   33540
```

```
gcgcagaagc gtcgtttttc ctgaaccgga cggtcccaga atggcgatga ctttcccttt    33600
ttctatctcc atatctatct tttttaaaat ttcattctgt ccgaatgatt tatttaatcc    33660
tttgacggaa agcatatcga aacctcctta tttggccaca taacggtcga gacgccgttc    33720
gatcacatgc tgtacgattg acagcaagaa gcagatgatc aatagataa aggcggcttc     33780 aatatagatg accaagattt gatcaaggtt ttgcgcgccg atttcctgcg cttttctgaa    33840
cagctccgcg acgagaatct gtgacgcgag agatgtatcc ttgatcaggc tgataaatgt    33900
atttgataat ggcggaatgg acacgcgaaa cgcctgcggc aggatcacgc ggaacaatgt    33960 cttcgatag gtcatgccga tcgtataacc ggcttcccat tgcccttcg gcacggatga      34020 aatagatgcc cggatgattt cagaagcata ggcgcccacg tttaatgaaa acgcgatgac    34080
tgcgcttggg aaagggtcca gcgtaatatt aaatgtcggg aacagataaa aaatgatgaa    34140
caattgaacg agaagaggag tgccgcgcac cgctgatacg tatacgctga cacccatct     34200 caatggtttc atatttgaca ttctggcgag cgccgtaatc agcgcgatga tcattccgaa    34260
aataaaggaa agaatggtaa ggggaatcga gtaatagatt cccccggaaa gaatcggcca    34320
gaatgactgc tgcaccaaat cccacggaat ggctgttgca atcacgggtt ccggcatgtt    34380
acttagaaac atcttcgccg aaccattttt tcgctatttt agaaagagtc ccgtcctctt    34440
tcatttcttt taacgctttg ttgacgtgag tcacaagttc gccgcttcct tttcggaatg    34500
cgaaatatgt ctgctgcggc tggcctgctt caaacgcgat tttcacgttt ttattgccgg    34560 acgttttaa gtagttcagt acggcaagct tatcgttgta agtcagatca gcgcggccct     34620
gctgaatgag ctgaagggat tgcgccatgc cttcaacgcc ttcaatttc gcgccggctt     34680 ctttcgctaa tttattgtaa ttgcttgtta atgactgagc cgctgttttt cctttgacat    34740
cagcctcttt cgcaatcgtg ctgtcttttt tcgtcacgac gactgcattt gacgttgtgt    34800
atttatcaga aaaatcatat tggttctcac                                     34830

<210> SEQ ID NO 2
<211> LENGTH: 420
<212> TYPE: DNA
<213> ORGANISM: Bacillus subtilis

<400> SEQUENCE: 2
gatgaacgta caaaaagtaa gaggaaggag aatggcccgt gagccgaatg gatgagaaaa      60
cgtttaattg cgaaaaggaa ttgacgcttg ccgtgatagg cgggaagtgg aaaatgctga    120
ttatgtggca cctggggaaa gaaggaacaa agcggtttaa tgagctgaaa gctttaattc    180
cggatattac gcacaaaatt cttgtgaatc agctcaggga gctggagcag gatctgatcg    240
ttcacaggga agtttaccct gtcgtccctc cgaaagtgga gtactcatta acagagcaag    300
gagagaccct tatgccgatt ttggacgcca tgtataagtg gggaaaagaa tatatggaat    360
taatcaacat tgataaaact gcaataaagg aatcttttg aagcgctcta tgtaaaatag    420

<210> SEQ ID NO 3
<211> LENGTH: 10500
<212> TYPE: DNA
<213> ORGANISM: Bacillus subtilis

<400> SEQUENCE: 3
tttatcttaa aaaggggagg cgcacacata tggaaataac ttttatcct ttaacaaatg       60 ctcaaaaacg tatctggtat acagaaaaat tctatccgaa cacaagtatt tcaaatcttg    120
```

```
ccgggttcgg gaaactcatt tctgacgacg gcgtacaggc tcattacgtt gagaaagcga    180
tacaggaatt cgtccggcgg tatgagtcga tgagaatccg tctgcggctt gatgatgagg    240
gggagcccgt tcaatatgtg agcgattacc gtccgctgac tatcgaacat acagacatca    300
ggcaagccgg ctgctctgcg gaagagctgt caaaatgggg acgtgacgag gcaagcaagc    360
ctctggcatt atatgatcag gatttattcc gttttccgt gtataccatc agcgaaaatg     420
aggtctggtt ttacgttaat gtgcatcaca ttatttcaga cgggatttcc atgacgattc    480
tgggcaatgc gattactgat atttatttgg agctttcggg cggagcaagt atggaacaga    540
cggagattcc tccttatcga gcatgtgctg actgagcagg aatatgtgca gtcgaagcgg    600
cgggtacgtt tatgggaaac cggacaaatg cgaaagaaaa gcagatgctc gggatgttcg    660
tatctacggt tcctgtgcgg acaagcgttg acggaggaca gtcgttcttg gaattcgtta    720
aaggccggat gaaggatctg atgaaaattc tccgccacca aaagtatccg tataacctgc    780
ttgtcaatga tttgcgcgct tcgaaaagtt cgctgagcag attgtttacg gtggctctgg    840
agtaccaggt gatgcagtgg cagaaaaaag agaatctgtc cttcctgaca gaccctattt    900
tcagcggaag cggtacaaat gatatttcga ttcatgtgaa ggaacgatgg gacactggga    960
aattgacgat tgattttgac tatcgcagcg acatattcaa gggagaggag attgtatctg   1020
tttctgaacg tttgatcacg ctgattgaag atgcgatttc atctcctgat cgcataattg   1080
atgagcttac tcttctttct gaatccgaga agagcggct gttgacacgg gcctcaggca    1140
atccggtgaa ttaccgcggg gagatgacga taccggggct gtttgaagag aaagtgaagt   1200
cactgtctga caaaccggcg gtggtgtatg aaggccgaac attgtcctat cgcacattgc   1260
atgaacagtc aggccgaatt gccggacgtc ttcttaatgc cgggatatca gccgattctc   1320
ctgtcgcggt gctgcttggc cgttctgagc gtgttattgc ggcaatattg gaattttga    1380
aagcgggcgg cgcctatgtg ccgatagatc ctgactttcc ggcggatcgg attcagtaca   1440
ttttggagga cagcggagcg aaggctgttc tgacagaggc cggaatacag gcgcctgcag   1500
cggatgccga acggattgat tttgacgagg ctgttcagtt tgaaacggct gcggacggtg   1560
tcagtacaca atcagaccgg ctggcttaca tcatctacac gtcaggtaca acggggcggc   1620
cgaaaggcgt gatgattgag caccggcaag ttcatcatct ggtgcaatca ctgcagcagg   1680
agatttatca atgcggtgag cagacattaa gaatggcgct tttggctccg tttcattttg   1740
atgcgtccgt caaacagatt tttgcctcgc ttcttttggg acagacgctt tatatcgtgc   1800
cgaaaacgac tgtaacgaat ggctcggcac tgctggacta ttatcgtcaa accggattg    1860
aagccactga cggaacccct gcgcatctgc agatgatggt tgcggcggga gatgtcagcg   1920
gaattgaatt gcgccacatg ctcattgggg gagagggcct gtccgccgct gttgctgaac   1980
agctgatgaa cctctttcat caatcgggca gggcgccgcg tctgacgaat gtctacgggc   2040
cgacagaaac gtgcgtagat gcgtccgtgc atcaggtgtc agccgataac ggaatgaatc   2100
aacaggcggc gtacgttccg atcggaaaac cgctcggcaa cgcccgtctg tatatattgg   2160
ataagcacca gaggcttcag cccgacggga cggccggtga gctgtatatc gcgggtgacg   2220
gtgtaggccg cggctatttt aatcttccgg atttgaccgc agagaagttt ttgcaagatc   2280
cgtttaacgg aagcggccgc atgtaccgca cgggtgatat ggcgcgctgg ctgccggacg   2340
ggacgatcga atatatcggc cgtgaagatg atcaggtgaa agtccgcggc taccgtattg   2400
agctgggaga aattgaaacg gtgctcagaa aagctccggg ggcggcgcag gccgtcgtgc   2460
tggcacggcc ggatcagcag ggcagcttag atgtttgcgc atatatcgtt caggaaaaag   2520
```

-continued

```
gaaccgagtt tcaccctgcc gagtacaggg agtatgtgtc caagcacctt cctgattaca    2580
tggtgcccgc ttactttaca aaaacggacg aaattccgct cacgccgagc gggaaggcgg    2640
accgcaaaaa gctgtttgcg cttgatgtgc aggctgtcag ctcatccgaa tatgccgcgc    2700
cgagaaacga aacggaggaa acgctcaccg tcatctggca ggaagtcctc ggaatggaca    2760
aggcgggcat ttatgatcat ttcttcgagt caggcggtca ttcattaaag gcaatgacgc    2820
ttctgacgaa aattcataag caaatgggcg ttgaaattcc gctgcaatac ttgtttgagc    2880
atccgacgat tgcggcgctt gccgattatg cggaaaaccg aaacgaagga ccggcattca    2940
gggcgattga gccggctgag aagcaggcga gctatccgct ttcgctcgct cagcagcgga    3000
cttatatcgc gagccaattt gaagatgcgg gagtcggata aacatgccg gctgcggccg    3060 tgattgaggg cgctttagac cttgaaaagc tcgagcgtgc attttctgcc ttaatcagca    3120
ggcatgaagc gctcagaaca tcgtttcaat cggaggacgg cacgccgaga caggtggttc    3180
acgaacatgt tccgtttcat attgaaatgc tcgaagcgcg cggaagaacg aatgaacagg    3240
tcatgaagga ctttgtgcgc cgttttgatt tatctgaggc gccgctgttc agaatcggcc    3300
tgcaaacgct cggtcacaat cgccatatgc tgctgtttga tatgcatcac ctgatttctg    3360
acggggtgtc tatttccatc atgctgaagg aactggctga catctacggc ggaaatcagc    3420
tgcctgaatt gcgcattcaa tataaagatt atgccgtatg gcaggcggaa cgggcgaaag    3480
aaggctacaa gaaggagcgg gcgtactgga agaagtctt cagcggcgaa ctgccggtgc    3540
ccgccaagct gccgaaaatg ctgcgggaac ggctgcagaa gcttgccgag aaaaacggag    3600
ccacccttta catggtgctg ttatcggcat actatacgct gctttctaag tattcgggac    3660
aggaagacat catcgtggga acaccgtcag cggaagaaaa tcactctgat accgaggggc    3720 ttatcggat gttttgtcaac acgcttgcgc tgcgaagctc cgtgaagcag gatcagacat    3780
ttgccggctt gttaggtcat gtgcgcaaac aggtgctgga cgcgttttcc catcaggatt    3840
atccgtttga gtggctgacc gaggagctga acgtgccccg ggacatgagc aggcatccga    3900
tatttgacac gatgttcagt ctgcaaaatg cttcggacgg aattccggag atcggcaacc    3960
tgacgctgtc tcttcatgaa accaacttca atatcgctaa attcgatctg acaatgcagg    4020
cccgggaaac agcggaaggc attgcgctcg atttggatta ttgcacgaag ctgtttaagc    4080
gctcaactgc ggatcgcatg cttgcgcact atgtccgtct gctggagagt gcggcagctc    4140
agccggatgc gaaaatcagc gaatatgatc tgctttctga acgggaggct ttgaaccaat    4200
tacagcggtt caatccggag cgcacggcat acccgaaaga gcaaacgatc gtgcagatct    4260
ttgaagaaca ggcccgaaag aaccctgacc ggacggctct tcagttcgaa ggggaaactc    4320
tgtcgtatca gcagctgaat gaacgcgcca acaggcttgc gcggcatatt ctttcggtcg    4380
gaggcggcgg gaaaaccgcg gctgtttat gtgaacggtc aatggacatg attgtttcca    4440
ttatggctgt gttaaaagcg gggtccgcct atgtgccgat tgatcctgag catccggttc    4500
agcggattca gcatttcttc cgcgacagcg gggcgaaagt gctcctgact cagcaaagcc    4560
tcaagccgct tgcggaaaag gccggttttc aaggcgccat tgtgcttgct gatgatgagg    4620
cgagctatga aaaggactct cgcaatccag cattgccgtt tgactccagc acaattgcca    4680
atcttactta tacatcaggc acgacgggaa cgccgaaagg gaacatcgtc acacatgcca    4740
acattttgcg gacggtaaaa aacacgaact atttgaccgt ttctgaagag gacacagtgc    4800
tcggtctgtc aaactacgtc tttgacgctt ttatgtttga tatgttcggt tcgctgttaa    4860
```

```
acggtgcaaa gcttgtgatc gtcccgaaag atacggtgct ggacatgtcg cgcctgtccc    4920
gtgtgatcaa acgggagaac gtcagcattc tgatgattac gacggccctg ttccacctgc    4980
ttgttgatat ggagccgtcc tgtctgacga cgcttcggaa aatcatgttc gggggcgaaa    5040
gagcgtctgt agaacatgtc aaaaaggcgc tggcggcagt cgggaaagga agactgcttc    5100
atatgtacgg tccgtcggaa agcacggtgt ttgcgacata ccatccggtg gatgtcattg    5160
aagaggatac gctctccgtt ccgatcggta accggtcag caatacgaa gtctttatta      5220
tgaactcagc cggacgcatt cagccggcgg gtatcgcggg agagctgtgc gtcagcgggg    5280
aaggtctcgt agaaggctac tacaaccgtc ctgaactgac ggaagaaaaa tttgtaaagc    5340
atccgtttaa ggaaggtgaa cggatgtata aaacgggcga cttggccaga tggcttccga    5400
atggcgatat cgagtttatc ggacgcatcg accatcaggt gaaaatccgc ggtcagcgga    5460
ttgagcttgg cgaaattgag catcagcttc aaagccatga tcagattcag gaatgcatag    5520
tgctcgctgt ggatcagggc gcgggtgaca aacttctttg cgcgtatttt gtcggcctca    5580
gggaaatatc ttcccgggag ctgagggagc atacggcgaa ggatcttccg gcttatatga    5640
ttccgtccgt ctttattcaa ttggatgaac tgcctcttac agggaacgga aaaatcgaca    5700
ggcgggcgct gccgatgccg gatgtgaccg cagcgaatgc cgtgtcatat acggcgccgc    5760
gcaatgaaac agaaaaaaaa ctggcggata tttgggctga ggtgctgcaa atggaacggg    5820
tcggcgtcca tgatcagttc tttgagatcg ggggccactc gttagcgggg atgaaactgc    5880
tggcccttat ccagaagaca ttcggcgtgc agcttacctt aaaggacctg ttcacttctc    5940
cgacggctgc tgggctggcg cagctgattg aaggggctga gcggaaggcg gctgagagca    6000
tcgcaccggc tgccgagcgg gaaacgtatc cggtttcttc accgcagaag cggatgttcg    6060
tgcttcagca gctggaaggc gctgaaacaa gctataacat gccgtctgtg ctccgcttaa    6120
aaggaaagct tgatgcagaa aagctgaaat ccgtcatgaa acagctgaca gaacgccatg    6180
aagccttcag aacgacattt gacataaagg atggagaaac ggttcagcgt atatgggcgg    6240
aagcttatat cgacatggaa tattatgaag cctctgaaga agatgctgaa cagattattc    6300
agagctttat ccgccgttc cgtctggatc agcttcctct cgtcagaacg gggctggtca    6360
agctggctga acatgaccac ctgctgctgt ttgatatgca ccatatcatt tcggacggcg    6420
cttcagtcgg cgtgctgata gatgaactgt cccgcttgta tggcggcgaa acgcttgagc    6480
cgctgcggat tcattataaa gactatgcgg tatggcagca gaaatttatt caatcagagc    6540
agtaccgcaa gcaggaggag cattggcttc gggagcttga cggcgagctt ccggtattga    6600
cgctgccggc tgattacagc cgtccggccg tgcaaacctt tgaaggagac aagctggtct    6660
tttctctgac tgaggaacag acgtcggctc ttcgcagtct tgcgaaacaa acggattcta    6720
ccatgtacat ggtgctcctg cgtcgtaca gcgcctttct ctcaaaactg agcggacagc     6780
atgacatcat tgtcggctcg ccggctgcgg gacggtcaca tgcggatctc gcaaacgtca    6840
tcggtgtttt tgtgaataca ctcgcgctgc gtacgtatcc ggaagcggac aaaacgttca    6900
cggactatct taaagaagtg aaacaaaccg ctttacatgc atttgacgcg caggattatc    6960
cgcttgaaga ccttctgcaa aaggttgagg tgcagcgtga tacgagccga aatccgctgt    7020
ttgatgcggt attctcaatg caaaatgcaa atgctgaaga tctggtcatg aaggaattg     7080
agctgaagca ccatccgttt gacagaaaaa cagccaagtt tgacctgacg ctgacggctg    7140
aggacacaga cgaaggctta acgtttgtgc ttgaatataa caccgcgctg tttaaaccgg    7200
aaacagcaga gacgtggaag cattattggc ttcaactgtt aaaagccgca acggaaaatc    7260
```

-continued

```
cggctgcgaa gctttctgag ctttccttgg tgaatgaaac agaaaaacaa gccctccttg    7320
acgcatggaa aggaaaaaca ctctctgtgc cgcaggacaa aacggttcac cgtctctttg    7380
aagaaacagc cgcccgctac gcgaatcggc cggccgcggc atataacggc gcgaaatgga    7440
cgtacggcga gctgaacgca agggcgaacc ggatcgcgcg cattctcata gactgcggcg    7500
tcacggctga cgaacgtgtc ggcattttga cgaaaccgtc cttggaaatg ccgcgggcg    7560 tactcggcgt cctgaaagcg ggcgcggcat ttgtgccgat tgaccccgac tacccacaag    7620
agcggatcag ctacattctg caggacagcg gcgccaagct ccttctcaca caggaagcgc    7680
tggacgtgcc ggatggctac acaggagaaa cgatcctgct tgacggcgga cgctccattc    7740
tgagcctgcc gcttgatgaa acgatgaag cgaacccgca gactgaaaca acggcggatc    7800
atctcgctta tatgatttac acgtcaggaa cgaccggaca gccgaagggt gtcatggtcg    7860
aacaccatgc gctggtgaac ctgtgcttct ggcatcacga cgcattcgcc atgacggcgg    7920
atgataaaag cgccaaatac gcgggcttcg gttttgacgc ctccatctgg gagatgttcc    7980
cgacatggac catcggcgcg gaacttcacg tcattgacga agcgatccgg ctggatatca    8040
cccgcttaaa tcactatttc gaggagcacg gcgtgaccat caccttcctg ccgacgcagc    8100
tggccgaaca atttatggag ctggaaaata cctctctccg catgcttctc gtcggcggcg    8160
acaagctgaa gcggcggtg aaacagccgt acacgatcgt caacaactac ggcccgacgg    8220
aaaacaccgt cgtcgcgaca agcggcgtca tcaatcctga ggaaggatcg ctttcgatcg    8280
gacgggcgat tgccaatacg agagcttata ttctcggcga cggcgatcag gtgcagccgg    8340
aaggcattgc cggtgaattg tgcgtggccg gccgcggtct ggcacgcgga tacctgaacc    8400
gtgaagaaga gacggcgaag cggtttaccg cagatccgtt cgtgcccggc gagcgcatgt    8460
accggaccgg cgacctcgtc aaatggaacg cgcagagcgg catcgaatac atcggccgta    8520
tcgaccagca ggtcaaagtg cggggctacc ggatcgagct ttcagaaatc gaagtccgcc    8580
tcgcccagct tgcggatgtt catgacgcag cggtgacggc ggtggaagac aaagcaggca    8640
atgccgcgct ttgcgcctat gtcgcgcctc agcaggacga tattgaagcg ctcaaagccg    8700
cgctgaaaga cacgcttccg gactacatgg tgccggcgtt ctgggtggag atggacgagc    8760
ttccggtcac cgcaaacgga aagattgaca aaaagcccct gccggaaccg gacattgaag    8820
cgggaagcgc cgcttacaaa gcgccggaaa cggagatgga gacgctgctt tccgacattt    8880
gggaggaagt gctcggtctt gatcagatcg gcgtaagcga taatttcttc acgctcggcg    8940
gcgactcaat caaaggcatc caaatggcga gccgcctgaa ccagcacggc tacaagctgg    9000
agatgaaaga tctcttccag cacccgacca tcgaagagct cgtctcttat gtggagcgga    9060
cggaaggcaa gcaggccgac cagggacctg tcgaaggcaa agcggagtta acgccgatcc    9120
agcgctggtt cttttgagaaa aacttcacgg acaaacacca ctggaaccaa tccgtcatgc    9180
ttcacgcgaa agacggcttt gatccggaga taacagaaaa acattacat gtcctgacgg    9240 tgcaccatga tgcgctccgg atgatttatc gtgaacaaaa accgtactac agagggcttg    9300
aggatgcgtc tgttgaactg aacgtctttg agctgaacgg acctgctgaa gatcatgaga    9360
accgtatcga acgggaagca gaccgtcttc aaagcagtat ttcactggaa acaggacatc    9420
tgctgaaggc cgggctcttc cgggccgaag atggagacca ccttcttctc gcaatccatc    9480
atttagtcgt ggatggtgta tcttggcgga ttttactgga ggacttcacg tccgtttata    9540
cgcagctgaa gcaaggcaat gaaccggcgc tgcctccgaa aacacattca ttcgccgaat    9600
```

```
ttgctgagag aatcaaagag tacgcaaata cgaaggcgtt tctgaaagaa gcggattact    9660
ggagggagct tgaggagaaa gaggtatgca ctcagcttcc gaaagacagg cagtctggcg    9720
atcagcgcat gagacatacg agaacggtca gtttctctct gacgcctgaa caaactgaac    9780
agctgacgac gaacgtacat gaagcctacc atacggaaat gaacgacatc ctgctcacgg    9840
cgctcggact ggcgctgaaa gagtggacgg gtgaagacac gatcggcgtt catttggaag    9900
gccacgggcg cgaagacatt cttgacgggc tgaatatcac ccggacggtc ggatggttta    9960
cgagcatgta tccgatgatc cttgagatga agcacgccga cgatctttca tatcagctga   10020
aacaaatgaa agaagacatc agacacatcc gaacaaagg agtcggctac ggcattctgc   10080
gttatgtaac ggcgcctgag cataaagagg gtctttcatt tgagattgat ccggatatca   10140
gctttaacta cttaggccag tttaatgaga gtgtcggatc cggcttattt acaagatccg   10200
ggatgccgtc aggacaatcg ctgagccctg acacagagaa gccgaatgcg cttgatattg   10260
tcggatttat agaaaatggg cagatgacga tgacgttgc ctatcattct ctcgaatttc   10320
atgaaaaaac cattcaatcg ttcagtgaca gcttaaagg gcacctcttg aaaatcatag   10380
atcactgcct ggcccaagac ggacctgagc ttacgcctag cgatcttggc gatgatgatc   10440
tgacgcttga tgaacttgat aaattaatgg aaattctcta acagaaaaga cagaggtgac   10500

<210> SEQ ID NO 4
<211> LENGTH: 600
<212> TYPE: DNA
<213> ORGANISM: Bacillus subtilis

<400> SEQUENCE: 4
tttatcttaa aaaggggagg cgcacacata tggaaataac ttttatcct ttaacaaatg     60 ctcaaaaacg tatctggtat acagaaaaat tctatccgaa cacaagtatt tcaaatcttg    120
ccgggttcgg gaaactcatt tctgacgacg gcgtacaggc tcattacgtt gagaaagcga    180
tacaggaatt cgtccggcgg tatgagtcga tgagaatccg tctgcggctt gatgatgagg    240
gggagcccgt tcaatatgtg agcgattacc gtccgctgac tatcgaacat acagacatca    300
ggcaagccgg ctgctctgcg gaaagagctgt caaaatgggg acgtgacgag gcaagcaagc    360
ctctggcatt atatgatcag gatttattcc gttttccgt gtataccatc agcgaaaatg    420
aggtctggtt ttacgttaat gtgcatcaca ttatttcaga cgggatttcc atgacgattc    480
tgggcaatgc gattactgat atttatttgg agctttcggg cggagcaagt atggaacaga    540
cggagattcc tccttatcga gcatgtgctg actgagcagg aatatgtgca gtcgaagcgg    600

<210> SEQ ID NO 5
<211> LENGTH: 9900
<212> TYPE: DNA
<213> ORGANISM: Bacillus subtilis

<400> SEQUENCE: 5
cgggtacgtt tatgggaaac cggacaaatg cgaaagaaaa gcagatgctc gggatgttcg     60
tatctacggt tcctgtgcgg acaagcgttg acggaggaca gtcgttcttg gaattcgtta    120
aaggccggat gaaggatctg atgaaaattc tccgccacca aaagtatccg tataacctgc    180
ttgtcaatga tttgcgcgct tcgaaaagtt cgctgagcag attgtttacg gtggctctgg    240
agtaccaggt gatgcagtgg cagaaaaaag agaatctgtc cttcctgaca gaccctattt    300
tcagcggaag cggtacaaat gatatttcga ttcatgtgaa ggaacgatgg gacactggga    360
aattgacgat tgatttgac tatcgcagcg acatattcaa gggagaggag attgtatctg    420
```

-continued

```
tttctgaacg tttgatcacg ctgattgaag atgcgatttc atctcctgat cgcataattg    480
atgagcttac tcttctttct gaatccgaga aagagcggct gttgacacgg gcctcaggca    540
atccggtgaa ttaccgcggg gagatgacga taccggggct gtttgaagag aaagtgaagt    600
cactgtctga caaaccggcg gtggtgtatg aaggccgaac attgtcctat cgcacattgc    660
atgaacagtc aggccgaatt gccggacgtc ttcttaatgc cgggatatca gccgattctc    720
ctgtcgcggt gctgcttggc cgttctgagc gtgttattgc ggcaatattg gaattttga     780
aagcgggcgg cgcctatgtg ccgatagatc ctgactttcc ggcggatcgg attcagtaca    840
ttttggagga cagcggagcg aaggctgttc tgacagaggc cggaatacag cgcctgcag     900
cggatgccga acggattgat tttgacgagg ctgttcagtt tgaaacggct gcggacggtg    960
tcagtacaca atcagaccgg ctggcttaca tcatctacac gtcaggtaca acggggcggc   1020
cgaaaggcgt gatgattgag caccggcaag ttcatcatct ggtgcaatca ctgcagcagg   1080
agatttatca atgcggtgag cagacattaa gaatggcgct tttggctccg tttcattttg   1140
atgcgtccgt caaacagatt tttgcctcgc ttcttttggg acagacgctt tatatcgtgc   1200
cgaaaacgac tgtaacgaat ggctcggcac tgctggacta ttatcgtcaa aaccggattg   1260
aagccactga cggaacccct gcgcatctgc agatgatggt tgcggcggga gatgtcagcg   1320
gaattgaatt gcgccacatg ctcattgggg gagagggcct gtccgccgct gttgctgaac   1380
agctgatgaa cctctttcat caatcgggca gggcgccgcg tctgacgaat gtctacgggc   1440
cgacagaaac gtgcgtagat gcgtccgtgc atcaggtgtc agccgataac ggaatgaatc   1500
aacaggcggc gtacgttccg atcggaaaac cgctcggcaa cgcccgtctg tatatattgg   1560
ataagcacca gaggcttcag cccgacggga cggccggtga gctgtatatc gcgggtgacg   1620
gtgtaggccg cggctatttta aatcttccgg atttgaccgc agagaagttt ttgcaagatc   1680
cgtttaacgg aagcggccgc atgtaccgca cgggtgatat ggcgcgctgg ctgccggacg   1740
ggacgatcga atatatcggc cgtgaagatg atcaggtgaa agtccgcggc taccgtattg   1800
agctgggaga aattgaaacg gtgctcagaa aagctccggg ggcggcgcag gccgtcgtgc   1860
tggcacggcc ggatcagcag ggcagcttag atgtttgcgc atatatcgtt caggaaaaag   1920
gaaccgagtt tcaccctgcc gagtacaggg agtatgtgtc caagcacctt cctgattaca   1980
tggtgcccgc ttactttaca aaaacggacg aaattccgct cacgccgagc gggaaggcgg   2040
accgcaaaaa gctgtttgcg cttgatgtgc aggctgtcag ctcatccgaa tatgccgcgc   2100
cgagaaacga aacggaggaa acgctcaccg tcatctggca ggaagtcctc ggaatggaca   2160
aggcgggcat ttatgatcat ttcttcgagt caggcggtca ttcattaaag gcaatgacgc   2220
ttctgacgaa aattcataag caaatgggcg ttgaaattcc gctgcaatac ttgtttgagc   2280
atccgacgat tgcggcgctt gccgattatg cggaaaaccg aaacgaagga ccggcattca   2340
gggcgattga gccggctgag aagcaggcga gctatccgct ttcgctcgct cagcagcgga   2400
cttatatcgc gagccaattt gaagatgcgg gagtcggata acatgccg gctgcggccg     2460
tgattgaggg cgctttagac cttgaaaagc tcgagcgtgc attttctgcc ttaatcagca   2520
ggcatgaagc gctcagaaca tcgtttcaat cggaggacgg cacgccgaga caggtggttc   2580
acgaacatgt tccgtttcat attgaaatgc tcgaagcgcg cggaagaacg aatgaacagg   2640
tcatgaagga ctttgtgcgc cgttttgatt tatctgaggc gccgctgttc agaatcggcc   2700
tgcaaacgct cggtcacaat cgccatatgc tgctgtttga tatgcatcac ctgatttctg   2760
```

```
acggggtgtc tatttccatc atgctgaagg aactggctga catctacggc ggaaatcagc    2820
tgcctgaatt gcgcattcaa tataaagatt atgccgtatg gcaggcggaa cgggcgaaag    2880
aaggctacaa gaaggagcgg gcgtactgga agaagtctt cagcggcgaa ctgccggtgc    2940
ccgccaagct gccgaaaatg ctgcgggaac ggctgcagaa gcttgccgag aaaaacggag    3000
ccacccttta catggtgctg ttatcggcat actatacgct gctttctaag tattcgggac    3060
aggaagacat catcgtggga acaccgtcag cgggaagaaa tcactctgat accgaggggc    3120
ttatcgggat gtttgtcaac acgcttgcgc tgcgaagctc cgtgaagcag gatcagacat    3180
ttgccggctt gttaggtcat gtgcgcaaac aggtgctgga cgcgttttcc catcaggatt    3240
atccgtttga gtggctgacc gaggagctga acgtgccccg ggacatgagc aggcatccga    3300
tatttgacac gatgttcagt ctgcaaaatg cttcggacgg aattccggag atcggcaacc    3360
tgacgctgtc tcttcatgaa accaacttca atatcgctaa attcgatctg acaatgcagg    3420
cccgggaaac agcggaaggc attgcgctcg atttggatta ttgcacgaag ctgtttaagc    3480
gctcaactgc ggatcgcatg cttgcgcact atgtccgtct gctggagagt gcggcagctc    3540
agccggatgc gaaaatcagc gaatatgatc tgctttctga acgggaggct ttgaaccaat    3600
tacagcggtt caatccggag cgcacggcat acccgaaaga gcaaacgatc gtgcagatct    3660
ttgaagaaca ggcccgaaag aaccctgacc ggacggctct tcagttcgaa ggggaaactc    3720
tgtcgtatca gcagctgaat gaacgcgcca acaggcttgc gcggcatatt ctttcggtcg    3780
gaggcggcgg gaaaaccgcg gctgttttat gtgaacggtc aatggacatg attgtttcca    3840
ttatggctgt gttaaaagcg gggtccgcct atgtgccgat tgatcctgag catccggttc    3900
agcggattca gcatttcttc cgcgacagcg gggcgaaagt gctcctgact cagcaaagcc    3960
tcaagccgct tgcggaaaag gccggttttc aaggcgccat tgtgcttgct gatgatgagg    4020
cgagctatga aaaggactct cgcaatccag cattgccgtt tgactccagc acaattgcca    4080
atcttactta tacatcaggc acgacgggaa cgccgaaagg gaacatcgtc acacatgcca    4140 acatttgcg gacggtaaaa aacacgaact atttgaccgt ttctgaagag gacacagtgc    4200
tcggtctgtc aaactacgtc tttgacgctt ttatgtttga tatgttcggt tcgctgttaa    4260
acggtgcaaa gcttgtgatc gtcccgaaag atacggtgct ggacatgtcg cgcctgtccc    4320
gtgtgatcaa acgggagaac gtcagcattc tgatgattac gacggccctg ttccacctgc    4380
ttgttgatat ggagccgtcc tgtctgacga cgcttcggaa aatcatgttc gggggcgaaa    4440
gagcgtctgt agaacatgtc aaaaaggcgc tggcggcagt cgggaaagga agactgcttc    4500
atatgtacgg tccgtcggaa agcacggtgt ttgcgacata ccatccggtg gatgtcattg    4560
aagaggatac gctctccgtt ccgatcggta accggtcag caatacgaa gtctttatta    4620 tgaactcagc cggacgcatt cagccggcgg gtatcgcggg agagctgtgc gtcagcgggg    4680
aaggtctcgt agaaggctac tacaaccgtc ctgaactgac ggaagaaaaa tttgtaaagc    4740 atccgttta ggaaggtgaa cggatgtata aaacgggcga cttggccaga tggcttccga    4800
atggcgatat cgagtttatc ggacgcatcg accatcaggt gaaaatccgc ggtcagcgga    4860
ttgagcttgg cgaaattgag catcagcttc aaagccatga tcagattcag gaatgcatag    4920
tgctcgctgt ggatcagggc gcgggtgaca aacttctttg cgcgtatttt gtcggcctca    4980
gggaaatatc ttcccgggag ctgagggagc atacggcgaa ggatcttccg gcttatatga    5040
ttccgtccgt ctttattcaa ttggatgaac tgcctcttac agggaacgga aaaatcgaca    5100
ggcgggcgct gccgatgccg gatgtgaccg cagcgaatgc cgtgtcatat acggcgccgc    5160
```

```
gcaatgaaac agaaaaaaaa ctggcggata tttgggctga ggtgctgcaa atggaacggg   5220
tcggcgtcca tgatcagttc tttgagatcg ggggccactc gttagcgggg atgaaactgc   5280
tggcccttat ccagaagaca ttcggcgtgc agcttacctt aaaggacctg ttcacttctc   5340
cgacggctgc tgggctggcg cagctgattg aaggggctga gcggaaggcg ctgagagca    5400 tcgcaccggc tgccgagcgg gaaacgtatc cggtttcttc accgcagaag cggatgttcg   5460
tgcttcagca gctggaaggc gctgaaacaa gctataacat gccgtctgtg ctccgcttaa   5520
aaggaaagct tgatgcagaa agctgaaat  ccgtcatgaa acagctgaca gaacgccatg   5580
aagccttcag aacgacattt gacataaagg atggagaaac ggttcagcgt atatgggcgg   5640
aagcttatat cgacatggaa tattatgaag cctctgaaga agatgctgaa cagattattc   5700
agagctttat ccggccgttc cgtctggatc agcttcctct cgtcagaacg gggctggtca   5760
agctggctga acatgaccac ctgctgctgt ttgatatgca ccatatcatt tcggacggcg   5820
cttcagtcgg cgtgctgata gatgaactgt cccgcttgta tggcggcgaa acgcttgagc   5880
cgctgcggat tcattataaa gactatgcgg tatggcagca gaaatttatt caatcagagc   5940
agtaccgcaa gcaggaggag cattggcttc gggagcttga cggcgagctt ccggtattga   6000
cgctgccggc tgattacagc cgtccggccg tgcaaacctt tgaaggagac aagctggtct   6060
tttctctgac tgaggaacag acgtcggctc ttcgcagtct tgcgaaacaa acggattcta   6120
ccatgtacat ggtgctcctg cgtcgtaca  gcgcctttct ctcaaaactg agcggacagc   6180
atgacatcat tgtcggctcg ccggctgcgg gacggtcaca tgcggatctc gcaaacgtca   6240
tcggtgtttt tgtgaataca ctcgcgctgc gtacgtatcc ggaagcggac aaaacgttca   6300
cggactatct taagaagtg  aaacaaaccg ctttacatgc atttgacgcg caggattatc   6360
cgcttgaaga ccttctgcaa aaggttgagg tgcagcgtga tacgagccga atccgctgt    6420 ttgatgcggt attctcaatg caaaatgcaa atgctgaaga tctggtcatg aaggaattg    6480 agctgaagca ccatccgttt gacagaaaaa cagccaagtt tgacctgacg ctgacggctg   6540
aggacacaga cgaaggctta acgtttgtgc ttgaatataa caccgcgctg tttaaaccgg   6600
aaacagcaga gacgtggaag cattattggc ttcaactgtt aaaagccgca acggaaaatc   6660
cggctgcgaa gctttctgag ctttccttgg tgaatgaaac agaaaaacaa gccctccttg   6720
acgcatggaa aggaaaaaca ctctctgtgc cgcaggacaa aacggttcac cgtctctttg   6780
aagaaacagc cgcccgctac gcgaatcggc cggccgcggc atataacggc gcgaaatgga   6840
cgtacggcga gctgaacgca agggcgaacc ggatcgcgcg cattctcata gactgcggcg   6900
tcacggctga cgaacgtgtc ggcattttga cgaaaccgtc cttggaaatg ccgcgggcg    6960 tactcggcgt cctgaaagcg ggcgcggcat ttgtgccgat tgaccccgac tacccacaag   7020
agcggatcag ctacattctg caggacagcg gcgccaagct ccttctcaca caggaagcgc   7080
tggacgtgcc ggatggctac acaggagaaa cgatcctgct tgacggcgga cgctccattc   7140
tgagcctgcc gcttgatgaa aacgatgaag cgaacccgca gactgaaaca acggcggatc   7200
atctcgctta tatgatttac acgtcaggaa cgaccggaca gccgaagggt gtcatggtcg   7260
aacaccatgc gctggtgaac ctgtgcttct ggcatcacga cgcattcgcc atgacggcgg   7320
atgataaaag cgccaaatac gcgggcttcg gttttgacgc ctccatctgg gagatgttcc   7380
cgacatggac catcggcgcg gaacttcacg tcattgacga agcgatccgg ctggatatca   7440
cccgcttaaa tcactatttc gaggagcacg gcgtgaccat caccttcctg ccgacgcagc   7500
```

```
tggccgaaca atttatggag ctggaaaata cctctctccg catgcttctc gtcggcggcg    7560
acaagctgaa gcgggcggtg aaacagccgt acacgatcgt caacaactac ggcccgacgg    7620
aaaacaccgt cgtcgcgaca agcggcgtca tcaatcctga ggaaggatcg ctttcgatcg    7680
gacgggcgat tgccaatacg agagcttata ttctcggcga cggcgatcag gtgcagccgg    7740
aaggcattgc cggtgaattg tgcgtggccg ccgcggtct ggcacgcgga tacctgaacc     7800
gtgaagaaga cggcgaag cggtttaccg cagatccgtt cgtgcccggc gagcgcatgt      7860
accggaccgg cgacctcgtc aaatggaacg cgcagagcgg catcgaatac atcggccgta    7920
tcgaccagca ggtcaaagtg cggggctacc ggatcgagct ttcagaaatc gaagtccgcc    7980
tcgcccagct tgcggatgtt catgacgcag cggtgacggc ggtggaagac aaagcaggca    8040
atgccgcgct ttgcgcctat gtcgcgcctc agcaggacga tattgaagcg ctcaaagccg    8100
cgctgaaaga cacgcttccg gactacatgg tgccggcgtt ctgggtggag atggacgagc    8160
ttccggtcac cgcaaacgga agattgaca aaaagccct gccggaaccg gacattgaag      8220
cgggaagcgc cgcttacaaa gcgccggaaa cggagatgga cgctgctt ccgacattt       8280
gggaggaagt gctcggtctt gatcagatcg gcgtaagcga taattcttc acgctcggcg     8340
gcgactcaat caaaggcatc caaatggcga gccgcctgaa ccagcacggc tacaagctgg    8400
agatgaaaga tctcttccag cacccgacca tcgaagagct cgtctcttat gtggagcgga    8460
cggaaggcaa gcaggccgac cagggacctg tcgaaggcaa gcggagtta acgccgatcc     8520
agcgctggtt ctttgagaaa aacttcacgg acaaacacca ctggaaccaa tccgtcatgc    8580
ttcacgcgaa agacggcttt gatccggaga taacagaaaa acattacat gtcctgacgg     8640
tgcaccatga tgcgctccgg atgatttatc gtgaacaaaa accgtactac agagggcttg    8700
aggatgcgtc tgttgaactg aacgtctttg agctgaacgg acctgctgaa gatcatgaga    8760
accgtatcga acgggaagca gaccgtcttc aaagcagtat tcactggaa acaggacatc     8820
tgctgaaggc cgggctcttc cgggccgaag atggagacca ccttcttctc gcaatccatc    8880
atttagtcgt ggatggtgta tcttggcgga ttttactgga ggacttcacg tccgtttata    8940
cgcagctgaa gcaaggcaat gaaccggcgc tgcctccgaa acacattca ttcgccgaat     9000
ttgctgagag aatcaaagag tacgcaaata cgaaggcgtt tctgaaagaa gcggattact    9060
ggagggagct tgaggagaaa gaggtatgca ctcagcttcc gaaagacagg cagtctggcg    9120
atcagcgcat gagacatacg agaacggtca gtttctctct gacgcctgaa caaactgaac    9180
agctgacgac gaacgtacat gaagcctacc atacggaaat gaacgacatc ctgctcacgg    9240
cgctcggact ggcgctgaaa gagtggacgg gtgaagacac gatcggcgtt catttggaag    9300
gccacgggcg cgaagacatt cttgacgggc tgaatatcac ccggacggtc ggatggttta    9360
cgagcatgta tccgatgatc cttgagatga agcacgccga cgatctttca tatcagctga    9420
aacaaatgaa agaagacatc agacacatcc cgaacaaagg agtcggctac ggcattctgc    9480
gttatgtaac ggcgcctgag cataaagagg gtctttcatt tgagattgat ccggatatca    9540
gcttttaacta cttaggccag tttaatgaga tgtcggattc cggcttattt acaagatccg    9600
ggatgccgtc aggacaatcg ctgagccctg acacagagaa gccgaatgcg cttgatattg    9660
tcggatttat agaaaatggg cagatgacga tgacgtttgc ctatcattct ctcgaatttc    9720
atgaaaaaac cattcaatcg ttcagtgaca gctttaaagg gcacctcttg aaaatcatag    9780
atcactgcct ggcccaagac ggacctgagc ttacgcctag cgatcttggc gatgatgatc    9840
tgacgcttga tgaacttgat aaattaatgg aaattctcta acagaaaaga cagaggtgac    9900
```

<210> SEQ ID NO 6
<211> LENGTH: 10800
<212> TYPE: DNA
<213> ORGANISM: Bacillus subtilis

<400> SEQUENCE: 6

```
atatgagcaa aaaatcgatt caaaaggtgt atgcactcac accgatgcag gagggaatgc      60
tgtatcatgc gctgcttgat ccgcattctt cctcctactt cacacaatta gagcttagga     120
ttcacggaag ctttcagctt gagcttttg aaaaagtgt caatgagctg attcggacat       180
atgacatcct gcgtacggta ttcgtgcacc agcagcttca aaaaccgcgc caagtcgtat     240
tagcagagcg gaagacgaag gtgcactatg aagatatcag tcaattagat gaagcgcgcc     300
aaaccgaata tattgaacgc tataaacgcg atgtgcagca gcagggcttt catctggcga     360
aggatattct ctttaaagcg gcggtgttca ggctcagtga aaggaactg tatctcgtct      420
ggagcaatca tcatatcgtc atggacggct ggagtatggg cgttttgatg aaaagcctgt     480
ttcaaaacta tgaagcgctt cgtgccggcc ggcccgccgg gggaagccag ggcaaacctt     540
actctgacta tatcaaatgg ctcggaggca gggattatga ggaggcggaa caatattgga     600
gcagccgcct ggcggatttc gaacagccga gcctgctccc gggccgtctg caccagaaa      660
agaaagacta ccaaaatgaa gaatattctt ttgtctggga tgaagagctg gtcgcgcaga     720
ttcagcagac cgccaaccgg catcaagtca cggggcctaa cctgtttcag gccgtttggg     780
gtgcggtgct cagcaaatac aactatacag acgatgtggt gttcggcacc gtcgtatcag     840
ccgtccttc agaaatcaac ggcattgaaa cgatggcggg gctgttcatc aatacgattc      900
ccgtcagaat caagattgac aaagatgcag ccttttctga cgtgatgcg gcagttcaga      960
aaaacgccgt ggaagccgag cgctatgatt atgtgccgct ctatgacatt caaaagcgct    1020
ccgctctgga cggcagcctc ttgaatcatt tggtcgcgtt tgaaaactat ccgctggaca    1080
aagagctgga aaacgggggc atggaggaaa gactcggctt ttccattaaa gttgaacatg    1140
cttttgagca gacgagcttt gatttcaatc tcatcgtgta ccgggaaaa acgtggactg     1200
tcaaaatcaa atacaacgga gcggctttcg ctcatgatgc catcgaacga acggcgcatc    1260
atctgacctg catgatgaaa gcggcggtcg gaacgcctga tgcgcccgtg cgggaactcg    1320
gccttgttc aggcgaagaa gagcggcaga ttgttgagat attcaatgat acaaaaacgg     1380
cgcttccgga agaggaggcc gttcaccgtt tgtttgaagc acaggcaaac cggacgcctg    1440
caagcatcgc gataaaagaa gcgggacgcg aatggaccta ccgtgaagtg aacgaagcgg    1500
ccaaccgcct ggcgagacac tttgtgaaga gcgggctgga aaaaggccgg accgccgcta    1560
ttatgaacga ccggtctgcg gaaaccgtta tcggaatgct tgccgtccta aaagcaggcg    1620
gcgcctatgt gccgattgat ccggcttttc cggaggaccg tctccgcttt atggcggaag    1680
acagctcgat tcggcttgtg ctgacagttc aggactatca agaacaagcg gcacattgc     1740
aagtcccgat tgtcatgctg gatgaaagcg aggatgaaac gctaagcgga acagacttga    1800
atcttccggc cggcggcaac gacttggcgt atatcatgta tacatccggg tcgaccggaa    1860
aaccgaaagg cgtcatgatt gaacacagaa atatcatcag gctcgtcaaa cattcgaatt    1920
acgtgccggt tcatgaagaa gaccggatgg cgcaaacggg agccgtcagc tttgatgccg    1980
gaaccttcga agtcttcggc gcattgctga acggagcggc attgcacccg gtgaaaaaag    2040
agacgctgct tgacgccgga cgattcgccc aatttctgaa agagcagcgg atcacgacca    2100
```

```
tgtggctgac gtctccgctg tttaatcagc ttgcccaaaa ggatgccggc atgtttaaca    2160
cgctccggca cctcatcatc ggcggtgatg cgcttgtgcc gcatatcgtc agcaaagtga    2220
ggaaggcatc accggagctg tcgctttgga acggctacgg gccgacggag aatacgacgt    2280
tttcgacgag ttttctcatt gatcaggact acgacggttc gatcccgatc gggaagccga    2340
tcggaaattc cactgcgtac attatggacg aaaaccgcaa cctccagccg atcggcgcgc    2400
ccggggagct gtgcgtcggc ggaagcggag tggcaagagg ctatgtgaat ctgcctgaat    2460
taacggagaa gcagtttgtc cgcgatccgt tcagaccgga tgaaatgata taccggacgg    2520
gggacttggc gaagtggctt ccggacggca cgatcgagtt tctcggcaga attgacaacc    2580
aagtaaaggt ccgcggtttc agaatcgagc tcggcgaaat tgaggcgaaa atcagccagg    2640
cggagaatgt gacggaatct gcggctgtga tccggaaaaa taaagcggat gaaaatgaaa    2700
tctgcgctta ctttaccgca gaccaagccc tttcgccgga agacctgcgc aaaacgcttt    2760
cggaatcact tccggaatac atgattcccg cgcacttcat ccagatgaat cagtttccgc    2820
tgacggcgaa cggaaagatt gataaaaaag cgctgcctga gcctcaggct gaagccgttc    2880
aaaaagaata cgaagcgccg aaaacgaagc ggagcagaa actcgcggac atttgggaag    2940
gtattctcgg tgtaaaagcg ggtgtgactg acaatttctt cacgattggc ggacattctt    3000
taaaagccat gatgatgacc gctaaaatcc aggagcactt tcaaaaagaa gtgccgatta    3060
aagtgttatt tgaaaagccg accattcagg agcttgcgca ttatttggag catgagaccg    3120
aggaggaaca gcagtttgaa ccgatccgac aagcgcctta tcagaagcat tatcctgttt    3180
cctcagcaca gcgcaggatg tatatcctta atcagctcgg acaggccagc acgagctaca    3240
acgtccctgc tgtacttctg ctggaaggat cagtagacaa aaaccgtctt gaagaggcca    3300
tgcaggcatt aatcaaccgt catgagacac tgcgtacgtc gtttgacatg gcagatggag    3360
aagtcgtgca gaccattcat aaaaatgtgt cgtttgagct tgaaaccgcc gagggccggg    3420
aagaagatgc agaagagctg acaaaagcct ttatcaggcc gtttgcgctc aatcgtgcgc    3480
cgctggtccg ttcgaagctg atccggcttg aagaagaccg gcatcttctg ctgattgaca    3540
tgcaccacat tattacggac ggaagctcaa tgggcatttt catcggtgat cttgcgaagc    3600
tttatcaagg cacggagctt gagctgccaa agattcatta taaggatttt tcagtctggc    3660
agcgtgaaaa agcaaatctt gatcagcacg aagcttactg gcttgatacg ttcaaaggcg    3720
atctgccggt gctggatctg ccgcttgatt tcccgcgtcc tgccgagcgc agttttgaag    3780
gggaacgcgt catcttcggg cttgataaac aggtgacggc gcagattaag aagctgctgg    3840
ctgatacgga tacgacgatg tacatgttct tgttagccgc ttttcaagtg ctgctgtcca    3900
aatattcggg gcaggaagac atcatagtcg ggtctccggc ggccggaaga cagcatcctg    3960
atctccaaga cgtgccgggc atgtttgtca acacagttgc gcttcggtcg catcctgccg    4020
gcaaaaaaac gttcaagcaa tttctggatg aagtgaaaac ggcgagcctt caagcttttg    4080
agcatcaaag ctatccgctt gaagaattaa ttgaaaaact gccgttaacg agggacacaa    4140
gccggagtcc gctgttcagc gtgttatta atatgcagaa catggagatc ccggccctgc    4200
ggctcggaga tttggagatt tcttcttact ccatgcatca tcatgtcgct aaatttgatc    4260
tttccttaga agcggctgag cgcggagaag aggtcggatt gagctttgat tacgcgaaag    4320
ccttatttgc ggacgaaacc atccgccgct ggagcgctca ttttgtcaat ctgattaaag    4380
cctgcgccga aaatccggat attcagctgg ccgacgcaag cctgctgtcc gctcctgagc    4440
gggaagcgct cctttctgat gaaaaacgga cggaagcgga tctgcctgag ggcacttttg    4500
```

| | | | | | |
|---|---|---|---|---|---|
| tttcgctgtt | tgaacggcaa | gcgcaaaaaa | cgcctgatct | cacgcgcggtt | gcgggcggaa | 4560 |
| caagtctgac | atatcgtgag | cttgatgaac | gctcgaaccg | gtttgcccga | caccttcagg | 4620 |
| cttgcggaac | gggcagtgag | gacatcgtgg | ccattatgat | ggatcgttcg | gccgacttga | 4680 |
| ttaccgcgat | tctcggcgtc | atgaaagccg | gagcggcatt | tctcccgatt | gatccggaga | 4740 |
| ctcctgaaga | gagaatccgc | tactctctcg | aagacagcgg | aacgaagctt | ctggtcgtca | 4800 |
| atgagagaaa | catgaccgcg | gccgccgttt | ataaagaaaa | aacggtcgta | atggaagacg | 4860 |
| gagaatggca | gaacgaaagc | gccgaccggc | ttgaaacgga | gcccggcgcc | gaccggcttg | 4920 |
| cctatatcat | ttatacctcg | ggaacaacgg | gcaaaccgaa | aggcgtccag | ctggagcacc | 4980 |
| gcaatctaat | caattatgtc | acatggttca | gccgtgaagc | cggtttgacc | gaagctgaca | 5040 |
| aatccgtgct | gctgtcttct | tatgcatttg | atctcggcta | tacggccata | ttccgattc | 5100 |
| ttcaggcggg | cggcgagctg | cacattgtgc | cgaaggagac | gtacaccgcg | cctgatcagc | 5160 |
| ttggtgagta | tatacagaaa | aacggcatta | cgtatatgaa | actgacgccg | tcattgttcc | 5220 |
| atatgatcgt | caatacagcc | cgttttacgt | cagaatgccg | tttcagcccg | cttcgtttag | 5280 |
| tggtgctcgg | cggagaaaag | atcatcacgt | ccgatgtccg | caagtttcat | gacgtatacg | 5340 |
| cccataccga | ctttatcaat | cactacggac | cgacggaaac | gacgatcggc | gccattgcgg | 5400 |
| aacggatcaa | tatggagtgt | cttgatcaat | atgagcagcg | tcccgtcatc | ggccgcccga | 5460 |
| tcgcaaatac | cggcgcgctt | gtattggacg | gagcaatgca | gctcgttcct | ccgggcgcaa | 5520 |
| gcggcgagct | ttatattacc | gggaaggggc | ttgccagagg | atatcttcac | cgtccgcagc | 5580 |
| tgacggcgga | gaaatttctc | tcaaatcctt | tttcaccgga | cagcctgatg | tacaaaacgg | 5640 |
| gagatatcgt | ccgcaggctt | cctgacggga | cgattgaatt | tatcggccgt | gcggatgatc | 5700 |
| aggtgaaaat | ccggggctac | cgcattgaat | taaagaggt | tgaaaccgtg | ctgttaagcg | 5760 |
| taaacggcat | tcaggaggcg | gtcgttctcg | cagtcagcga | aggcgggctg | ccggaactgt | 5820 |
| gcgcgtacta | taaagccgac | agcgggctga | aaggctctga | gcttcgcaaa | cggctttccg | 5880 |
| aaacactgcc | gtctcatatg | cttccggcct | atttcgtgca | agtagaccgc | attccgctca | 5940 |
| cagccaacgg | aaaaaccgat | aaaaacgccc | tcccgaaacc | gggcgtcagc | caaacggcgc | 6000 |
| aaattgcttc | agccttgccg | gaaacggaat | tggaggaaaa | gctgtgccgc | atttggaaac | 6060 |
| agacactcgg | tacggatacg | ctcggcatcg | acgataattt | cttcgattac | ggcgggcact | 6120 |
| cttaaaagg | aatgatgctc | ctcgccaata | ttcaggctga | actggacaaa | acggttccgt | 6180 |
| taaaagcgct | gttcgaacag | ccgactgtcc | gcctgcttgc | cgcatatatc | gaaaaatcgg | 6240 |
| cggtatctga | gggatatcgg | atgatcacac | cggcagacag | tgcagacgcg | tacccgttat | 6300 |
| catccgccca | aaaacggatg | tacgtcctga | accagcttga | ccgggagaca | atcagctata | 6360 |
| atatgccgtc | cgttcttctg | atggaaggag | aagtcaatat | ttcaaagctt | caggaagcgc | 6420 |
| tcaatcagat | gatcaaccgc | cacgaatctt | tgccgacgtc | ctttatcgat | aaaaaaggcc | 6480 |
| agccgatgca | gcagatcgca | gaacaggctg | acattgacct | gcacatcttt | gaagcagcgg | 6540 |
| acgaggagaa | agcggatctt | atcattcagg | cattcattaa | gccgtttgat | ctgagcgcgg | 6600 |
| ctccgctcat | tcgggccgct | cttgtcagac | tgaatgaaaa | gaaacacctg | ctgctgctgg | 6660 |
| atatgcatca | tatcattgcc | gacggcgtgt | ccagaagcat | gctggtcaaa | gagctcgctc | 6720 |
| accttttacaa | aggcggaagt | ctgccgtcgc | cgaacctgca | ctataaagac | ttcgccgtct | 6780 |
| ggcagaatga | acctgagcag | gccgaacgga | tgaaagacca | tgagcgttat | tggctctccg | 6840 |

```
cattttccgg cgagcttcct gaattgaatc tgccgaccga tttccccgt ccgccggttc    6900 aaagttttaa aggacagtcc gtccgtttca gagcggggcg tgagacgaa aaagcggtgc    6960 gtgaattaat ggaatcatcg ggagcgactc ttcatatggt gcttcacgcc gcgttccatg   7020 tcttttgag caaatcacg ggccagcgcg atatcattat cggttcggtg accgccggaa    7080
gaacgagcgc cgaagttcag gaaatgccgg ggatgtttgt caatacgctt gcgcttcgca   7140
atgaaacgca aaaagagcag accttcgccg ggctgctcga acgggtgaaa caaaccaatc   7200
tcgacgcgct ggcgcatcag gattatccgt ttgaggatct gatcggaaag cttgacctgc   7260
cgagagatat gagccgcaac ccgctgttcc aggtgatggt gacgacagaa gatccggata   7320
aagaaacact ggaactggag aacctgcgca tcactccgta tgagtcaaac caaggcacgg   7380
cgaaattcga tctgcactc ggcggcttta cggatcaaga aggtctcggc cttcagtttg    7440
aatatgcgac tgatctgttt aaaaaagaaa ccattgaaaa gtggagcgcc gggttcctgc   7500
ggattctgaa gcaagcggcg gaaagcccgg acagaaagct gcctgagatt tcactgatca   7560
gcgatgctga aaaacaagcc ctccttgacg catggaaagg aaaaacactc tctgtgccgc   7620
aggacaaaac ggttcaccgt ctctttgaag aaacggccgc ccgatacgcg aaccggccgg   7680
ccgcggcata taacggcgcg aaatggacgt acggcgagct gaacgcaagg gcgaaccgga   7740
tcgcgcgcat tctcatagac tgcggcgtca cggctgacga acgtgtcggc attttgacga   7800
aaccgtcctt ggaaatggcc gcgggcgtac tcggcgtcct gaaagcgggc gcggcatttg   7860
tgccgattga ccccgactac ccacaagagc ggatcagcta cattctgcag acagcggcg    7920 ccaagcttct tctcacacag gaagcgctgg acgtgccgga aagctacaaa ggagaaacga   7980
tcctgcttga cggcggacgc tccattctga gcctgccgct tgatgaaaac gatgaagcga   8040
acccgcagac ggaaacaacg gcggatcatc tcgcttatat gatttacacg tcaggaacga   8100
ccggacagcc gaagggtgtc atggtcgaac accatgcgct ggtgaacctg tgcttctggc   8160
atcacgacgc attcgccatg acggcggatg ataaaagcgc caaatacgcg ggcttcggtt   8220
ttgacgcctc catctgggag atgttcccga catggaccat cggcgcggag cttcatgtca   8280
ttgacgaagc gatccggctg atatcacccc gcttaaatca ctatttcgaa gagcacggcg   8340
taaccatcac cttcctgccg acgcagctgg ccgaacaatt tatggagctg gaaaataccct  8400 ctctccgcat gcttctcgtc ggcggcgaca agctgaagcg ggcggtgaaa cagccgtaca   8460
cgatcgtcaa caactacggc ccgacggaaa acaccgtcgt cgcgacaagc ggcgtcatca   8520
atcctgagga aggatcgctt tcgatcggac gggcgattgc caatacgaga gcttatattc   8580
tcggcgacgg cgatcaggtg cagccggaag gcattgccgg cgaattgtgc gtggccggcc   8640
gcggtctggc acgcggatac ctgaaccgtg aagaagagac ggcgaagcgg tttaccgcag   8700
atccgttcgt gcccggcgag cgcatgtacc ggaccggcga cctcgtcaaa tggaacgcgc   8760
agagcggcat cgaatacatc ggccgtatcg accagcaggt caaagtgcgg ggctaccgga   8820
tcgagctttc agaaatcgaa gtccgcctcg cccagcttgc ggatgttcat gacgcagcgg   8880
tgacggcggt ggaagacaaa gcgggcaatg ccgcgctttg cgcctatgtc gcgcctcggc   8940
aggacgatat tgaagcgctc aaagccgcgc tgaaagacac gctgcctgac tacatggtgc   9000
cggcgttctg ggtggagatg gacgagcttc cggtcaccgc aaacggaaag attgacaaaa   9060
aagccctgcc ggaaccggac attgaagcgg gaagcgccgc ttacaaagcg ccggaaacgg   9120
agatggagac gctgctttcc gacatttggc aggaagtgct cggtcttgat cagatcggcg   9180
taagcgataa tttcttcacc ctcggcggtg actcgatcaa aggcatccaa atggcgagcc   9240
```

```
gcctgaacca gcacggctac aagctggaaa tgaaggatct cttccagcac ccgaccatcg    9300
aagagctcgt ctcctatgtg gagcggacgg aaggcaagca ggccgatcag ggacctgtcg    9360
aaggcgaagc ggagttaacg ccgatccagc gctggttctt tgagaaaaac ttcacggaca    9420
aacaccactg gaaccaatcc gtcatgcttc atgcgaagaa cggctttgat ccggacctgg    9480
tggaaaaaac cctgcaagca ttgattgaac accatgatgc gctccgcatg gtttaccgtg    9540
aagaaaggga aggcatcatt cagacatacc tccctgtcac agaatgcaag gcaagctttg    9600
aaatcgttga tctgtacgga acggacgagg atatgctgaa agccagatt cagcggcttg     9660 ccgatcatct tcagggcagt cttgatctgg agaacggccc gctgttaaaa gcggagcaat    9720
accggacaga acaaggcgat catctgttaa tcgcggttca ccatctcgtc gtggacgggg    9780
tttcatggag aattctgctt gaggatttcg cttcaggtta taaacaggcg cagcagcaaa    9840
acagcatcgt tctcccgcaa aaacccact cctttaaaga ttgggcggag gcgctgaaca     9900
cgtttgcgca atcagaagag ctgaaaaagc aggcggatta ttgggcgcag gcagatgcgg    9960
aagaactgcg gccgctgccg aaagaccatg atccggacaa acggctcgtc aaacatacgg    10020
cggccgtgaa atgtgaattg actgaggaag aaacggcaca gctgctgaca gatgttcatc    10080
atccgtacgg aacggaaatc aacgacattc tgctcagcgc gctcggctta acgatcggtg    10140
aatggacgga aaacggcaaa gtcggcatca acttagaagg acacggccgg gaagaaatca    10200
taccgaatgt caatatttca cggacggtcg gctggtttac ggcccaatat ccgttgattc    10260
tgcagatcag caaggaagac ggcgtctctt ccgtcattaa aacggtaaaa gagacagtgc    10320
ggcgcgttcc agataaaggt gtaggatacg ggattctccg gtatctgtca tccgatgaaa    10380
cagaaaaagg cgccgcgcct gaaatcagtt ttaactactt ggggcagttt gacaatgaag    10440
tgaaaacgga atggtttgag ccgtctccat atgatatggg acgtcaagtc agcgaagagt    10500
cagaggcgtt atacgcactg agcttcagcg ggatggttac aggcggccgc ttcgtcattt    10560
cctgctcata caatcaggaa gaatatgaaa gaagcaccgt cgaaacacag atgcagcggt    10620
ttaaagacaa tcttttaatg atcatccgcc attgcacggc caaagaggag aaagaattta    10680
cgccgagcga tttcagcgcg caggatcttg agatggatga aatgggagac atctttgaca    10740
tgcttgagga gaatttaacg tgacaaaaac agttaacaga agggggagc ggagcagatg     10800
```

<210> SEQ ID NO 7
<211> LENGTH: 3900
<212> TYPE: DNA
<213> ORGANISM: Bacillus subtilis

<400> SEQUENCE: 7

```
tgcttgagga gaatttaacg tgacaaaaac agttaacaga agggggagc ggagcagatg      60 agccagttca aaaagatca agttcaggac atgtattatt tgtcgccgat gcaggaggga    120
atgctgtttc atactctcct gaatcccggc caaagctttt acatcgaaca atgacaatg    180 agagtaaaag gcagcttgaa tatcaaatgc cttgaagaaa gcatgaatgt gatcatggac    240
cggtacgatg tatttcgtac cgtgttcatt cacgaaaaag taaaaaggcc ggtccaagtc    300
gtattgaaaa aacggcagtt tcagatagaa gaaatcgatc tgcacacactt aacgggcagc    360 gagcaagcat ccaaaattaa tgaatacaaa gaacaggata agatcaaggg ctttgattttg   420 acgcgggata ttccgatgcg ggcagccatc tttaaaaaat cggaagaaag ctttgaatgg    480
gtgtggagct accaccacat cattttggac ggctggtgct tcggcatcgt cgtgcaggat    540
```

```
ctgtttaagg tatacaatgc cctgcgagaa caaaagccgt acagcctgcc gccggtcaaa    600
ccgtataaag actatatcaa gtggcttgaa aagcaggata acaagcatc  actgcattac    660 tggcgcgggt acttagaaga ttttgaagga caaacgacat ttgcggagca agaaagaaa     720 caagagaacg gctatgagcc gaaagagctg ctcttctcac tgccggaggc ggaaacaaaa    780
gcatttaccg agcttgcaaa atcgcagcat actactttga gtacggcgct gcaggcggtt    840
tggagtgtat taatcagccg ctaccagcag tccggcgatt tgatcttcgg cacagtcgtt    900
tccgggcgtc ccgcagaaat caaaggcgtt gaacatatgg tcgggctgtt tatcaatgct    960
gttccgaggc gggtgaagct gtctgaggat accacattta acggcttgct caagcagctg    1020
caggagcaat cgctggagtc tgagcctcat caatatgtgc cgctctatga catccaaagc    1080
caggccgatc agccaaagct gattgaccac atcattgtgt ttgaaaatta tccgcttcag    1140
gatgcaaaaa atgaagaaaa cagtgaaaac ggctttgata tggaggacgt ccatgttttt    1200
gagaaatcga attatgatct caacctgatg gcttctccag gtgatgagat gctgattaag    1260
cttgcctata acgggaatgt gtttgatgag gcgtttatcc tacgcttaaa atctcagctt    1320
cttacagcga ttcagcagct catccagaag ccggatcagc ctgtcaatac gatcagactt    1380
gttgatgaaa aggaaagaga gcttctgctt accggcttaa acccgccggc tgagactcat    1440
caggcgaagc ctctgacgga ttggttcaag aagcggtga  atgtaaatcc tgatgcaccg    1500
gcgcttacgt attccggcca gactctttcc tatcgcgaat tagatgagga agcgaaccgt    1560
cttgcgcgcc gtttgcaaaa gcaaggtgcg ggtaaagaca ccgttgtcgc gttgtacacg    1620
aagcgctcgc ttgaactggt gatcggcatt ctcggcgtat taaaagcagg agcggcttat    1680
ctgccggttg atccgaagct gccggaggac cgaatctcgt acatgctgac tgacagtgcg    1740
gcagcctgtc tgctgacaca tcaggagatg aaagaaaaag cggctcagct gccgtataca    1800
ggaacaacac tcatcatcga tgatcaagca cggtttgagg aacaggcaag cgatcctgca    1860
gccgcaattg atcccgatga tccggcgtat attatgtata cgtccggcac aaccggaaag    1920
ccgaagggca atatcaccac tcatgccaat atacaaggat tggtcaagca tgtagactat    1980
atggcatttt ctgaacaaga tacgttctta tctgtttcga attacgcctt tgacgcattt    2040
acttttgatt tctacgcatc aatcctgaat gcggcacggc tcattatcgc agatgaacat    2100
acactgcttg atacagaacg gctcactgat ctgatccggc aggagaatgt caatgtcatg    2160
tttgcgacaa ccgcactttt taatcttctc accgatgcgg gagaggagtg gctgaagggg    2220
ctccgctgtg tgttattcgg gggtgagcgc cgtgtctgtg ctcacgtcag aaaggcgctt    2280
gagatcatgg ggcccggcaa gctgattaat tgctacgggc cgactgaggg aacggtgttt    2340
gcgacagctc acgtcgtgca tgatataccg gattccattt cctcattgcc gatcggaaag    2400
ccgatcagca atgcaagtat ttatattctt aacgggcaaa accagcttca gccgttcgga    2460
gctgtcggtg aactgtgcat cagcggaatg ggtgtatcaa aagggtatct gaaccgtcac    2520
gacctgacga agcaaacgtt tatcccaaat ccgttcaagc cgggagaaac gctttaccgc    2580 acagggatt  tagcacgctg gctgccggat gaacgattga atacgccggg cgtattgacg    2640
accaggtcaa atacgcgtca ccggattgaa cttgaagaaa tcgaaaagca gctgcaggaa    2700
tacccgggtg tgaaagatgc ggtcgttgtt gcagaccgcc atgagtccgg agatgcatca    2760
atcaacgcct atccgtgaa  ccggacgccg ctttcagctg aagacgtaaa gaggcacttg    2820
aaaaaacagc ttcctgctta catggtgccg caaacctttg ctttcttaga agagcttcct    2880
ttaacgacaa acgggaaggt caataaacgg cagctgccga aaccggatca ggctcaggcg    2940
```

-continued

| | |
|---|---|
| gcgaaagaat ggatcgggcc tcgaaacgcg acggaagaaa cgattgcaca catctggtcc | 3000 |
| gagattctcg gcagacagca gatcgggatt catgatgatt tcttcgcgct cggaggccat | 3060 |
| tccttaaaag cgatgacggc agcgtcgcgc attaaaaaag agctcggtac ggacatcccg | 3120 |
| gtgcagctgt tattcgaagc gacgacaatc gcagacattg ccggttatct gcttcacggt | 3180 |
| gaagaaaaag gaatgaaaga tctcaccatc atgaataaaa atcagtctga cacactgttt | 3240 |
| gcgttcccgc cggttctcgg ttacgggctg atgtaccagc cgctggcaaa acagctgtcc | 3300 |
| ggctatagaa tctgtgcgtt tgattttatc gaggaagaca accgcatcga acgctacaca | 3360 |
| gagctgatca atcagctcca gccggaagga ccggtcaagc tgttcggata ctcggcaggc | 3420 |
| tgcacgctcg cctttgaaac ggccaaacgg cttgaagccg aaggacgtaa agtggagcgg | 3480 |
| ctgatcatgt tgattccta taaaaaacaa ggcgtcagcg acttggaagg ccgcaccgta | 3540 |
| gaaagcgatg tccaggcgct gatgaaggta aaccgggata cgaagcgct gaatgacgaa | 3600 |
| gccgtcaaag aaggtctcgc caaaaaaaca acgcgtttt attcttattt cgtgcatacc | 3660 |
| gtcagcaccg gcacggtcaa tgcggatata gatctattaa cgtcagaacc ggactttgcg | 3720 |
| atgccgccgt ggctcgcttc gtgggaggaa gccacgacag gtgaataccg tgtgaaaaaa | 3780 |
| ggctgcggca gtcacgcaga aatgctacag ggagaatgtc tcgaaaggaa tgcggcatat | 3840 |
| ttgctcgaat tcctaaggaa ggaacatccg aagctgacag cttcacgata gaaaaggagg | 3900 |

<210> SEQ ID NO 8
<211> LENGTH: 780
<212> TYPE: DNA
<213> ORGANISM: Bacillus subtilis

<400> SEQUENCE: 8

| | |
|---|---|
| aagcccgcca atggtccagc tctttaaatc gttcgatacc acggaaaaaa cgcagcttat | 60 |
| ctgttttccg ttcgcaggag gctattccgc atcattccgc ccgctccaca cctatcttca | 120 |
| aggtgagtgt gagatgcttg ccgcggaacc gccgggcacac ggaacaaatc aaatgtccgc | 180 |
| cgttgaggat tttgaacagc ttgtcagttt atacaagcag gagttgaatc tccatcctga | 240 |
| ccgcccgttt gtcctgttcg gccacagtat gggaggcatg gtcgctttca ggctggcgca | 300 |
| aaagctggag cgggagggga tttacccgca ggccgtgatc atctcagcca ttcagccgcc | 360 |
| gcatgttgaa aggaaaaaag tgtctcatct tgatgatgaa aaatttctcg cccatattat | 420 |
| cgagctgggc ggaatgccgc aggagttagt ggagaataag gaggtcatgt cattttttcct | 480 |
| gccttctttc aggtccgact accgcgcgct tgaaagcttc cgtccgtctg attctcacat | 540 |
| gattcaatca cccgtccata tttttaacgg gcggaaagat aaaaaatgta tcaaagatgc | 600 |
| ggacggatgg aaaaaatggg ccgacaatcc cgtatttcat gagttttcgg acggccacat | 660 |
| gttcatatta agtgaaactg aaaaagtggc ggaacgaata tatgagatta ttaacaggag | 720 |
| cactgcaggc caattgttat aggatatgac agacagcatt cgctgtctgt ttttttgtaac | 780 |

<210> SEQ ID NO 9
<211> LENGTH: 1380
<212> TYPE: DNA
<213> ORGANISM: Bacillus subtilis

<400> SEQUENCE: 9

| | |
|---|---|
| taattttgaa gggattgtcg tacatgaatg atgcagcaaa agagctgaac agaacattat | 60 |
| cggaagaaaa cccgcacgtg cttcatatgc tttctgattt gggcagagag ttgttttatc | 120 |

```
cgaaaggggt gctgacacaa tcggcggaag cgaaagccaa ggccggaaag tataatgcca    180
cgatcgggat tgccacctca caaggcgagt ccatgcactt ttcccatatt caagagacac    240
tgtccgccta taaccccgat gatatctacg attatgctcc gccgcaggga aagagccgc     300 tcagacagga atggctgaaa aaatgcgtc tcgaaaatcc ttcattagcc ggcaaagaca     360
tcagcacgcc gatcgtgaca aacgctttaa cacacgggct gagcattgcc gccgacttgt    420
tcgtcaatga aggggatgcg ctgcttctgc cggataaata ttggggaaat tacaatttta    480
ttttcggtgt ccggcgcaag gcatccattg agacgtaccc gcttttcag caggatgggc     540 gttttaatgc ggcggggctg tccgagctgc tgaaaaagca ggaagaaaag gcgattgtcg    600
tgctgaattt cccgaataat ccgacaggct atacgccggg ggaagaggaa gcgtcagaaa    660
tcgtcagtgt gatcctggag gcggcggagg ccggcaaaga gattgtcgtg ctcgtagacg    720
atgcgtatta caatctgttt tacgatgaaa cggccattca ggaatccatc ttcagcaaac    780
tcgcccaagt gcacgaccgg gtgctttgcg taaaaataga cggcgcgacg aaggaaaatt    840
atgcgtgggg cttccgcgtc ggttttatta cgtacagcac aaaaagcgaa aaagcgctgc    900
gcgtgctcga ggaaaaaaca aaagggatta tcagggaaac gatttcaagc gccccgcatc    960
cgtcccaaac gtttatgctg cgggcgatgc agtcaccgga atacgagaaa gaaaaatcgc   1020
tgaaatataa tatcatgaaa aaacgggctg acaaagtgaa agccgttctt gcagaaaaca   1080
agcactatga gacgtatgg acgccttatc cgtttaactc gggttatttc atgtgtgtcc    1140
ggctgagaga cataaacgcc ggtgaattaa gagtgtcatt gcttgaaaag agaggaatcg   1200
ggacgatatc cattaatgaa accgatttgc gaatcgcatt tcatgtgtt gaagaagaat    1260 acatcgcgga tctgttcgaa gaaatttatc aagaagcaaa gcagctgcag aaacaggcgg   1320
aaatatcagg ctgacaaaaa aaggaggggg atacccctcct ttttctatgc ttacagcagc   1380
```

<210> SEQ ID NO 10
<211> LENGTH: 117
<212> TYPE: PRT
<213> ORGANISM: Bacillus subtilis

<400> SEQUENCE: 10

Met Asp Glu Lys Thr Phe Asn Cys Glu Lys Glu Leu Thr Leu Ala Val
1               5                   10                  15

Ile Gly Gly Lys Trp Lys Met Leu Ile Met Trp His Leu Gly Lys Glu
            20                  25                  30

Gly Thr Lys Arg Phe Asn Glu Leu Lys Ala Leu Ile Pro Asp Ile Thr
        35                  40                  45

His Lys Ile Leu Val Asn Gln Leu Arg Glu Leu Glu Gln Asp Leu Ile
    50                  55                  60

Val His Arg Glu Val Tyr Pro Val Val Pro Lys Val Glu Tyr Ser
65                  70                  75                  80

Leu Thr Glu Gln Gly Glu Thr Leu Met Pro Ile Leu Asp Ala Met Tyr
                85                  90                  95

Lys Trp Gly Lys Glu Tyr Met Glu Leu Ile Asn Ile Asp Lys Thr Ala
            100                 105                 110

Ile Lys Glu Ser Phe
        115

<210> SEQ ID NO 11
<211> LENGTH: 3470
<212> TYPE: PRT
<213> ORGANISM: Bacillus subtilis

<400> SEQUENCE: 11

```
Met Glu Ile Thr Phe Tyr Pro Leu Thr Asn Ala Gln Lys Arg Ile Trp
1               5                   10                  15

Tyr Thr Glu Lys Phe Tyr Pro Asn Thr Ser Ile Ser Asn Leu Ala Gly
            20                  25                  30

Phe Gly Lys Leu Ile Ser Asp Asp Gly Val Gln Ala His Tyr Val Glu
        35                  40                  45

Lys Ala Ile Gln Glu Phe Val Arg Arg Tyr Glu Ser Met Arg Ile Arg
50                  55                  60

Leu Arg Leu Asp Asp Glu Gly Glu Pro Val Gln Tyr Val Ser Asp Tyr
65                  70                  75                  80

Arg Pro Leu Thr Ile Glu His Thr Asp Ile Arg Gln Ala Gly Cys Ser
                85                  90                  95

Ala Glu Glu Leu Ser Lys Trp Gly Arg Asp Glu Ala Ser Lys Pro Leu
            100                 105                 110

Ala Leu Tyr Asp Gln Asp Leu Phe Arg Phe Ser Val Tyr Thr Ile Ser
        115                 120                 125

Glu Asn Glu Val Trp Phe Tyr Val Asn Val His His Ile Ile Ser Asp
130                 135                 140

Gly Ile Ser Met Thr Ile Leu Gly Asn Ala Ile Thr Asp Ile Tyr Leu
145                 150                 155                 160

Glu Leu Ser Gly Gly Ala Ser Met Glu Gln Thr Glu Ile Pro Pro Tyr
                165                 170                 175

Arg Ala Cys Ala Asp Met Gly Asn Arg Thr Asn Ala Lys Glu Lys Gln
            180                 185                 190

Met Leu Gly Met Phe Val Ser Thr Val Pro Val Arg Thr Ser Val Asp
        195                 200                 205

Gly Gly Gln Ser Phe Leu Glu Phe Val Lys Gly Arg Met Lys Asp Leu
210                 215                 220

Met Lys Ile Leu Arg His Gln Lys Tyr Pro Tyr Asn Leu Leu Val Asn
225                 230                 235                 240

Asp Leu Arg Ala Ser Lys Ser Ser Leu Ser Arg Leu Phe Thr Val Ala
                245                 250                 255

Leu Glu Tyr Gln Val Met Gln Trp Gln Lys Lys Glu Asn Leu Ser Phe
            260                 265                 270

Leu Thr Asp Pro Ile Phe Ser Gly Ser Gly Thr Asn Asp Ile Ser Ile
        275                 280                 285

His Val Lys Glu Arg Trp Asp Thr Gly Lys Leu Thr Ile Asp Phe Asp
290                 295                 300

Tyr Arg Ser Asp Ile Phe Lys Gly Glu Glu Ile Val Ser Val Ser Glu
305                 310                 315                 320

Arg Leu Ile Thr Leu Ile Glu Asp Ala Ile Ser Ser Pro Asp Arg Ile
                325                 330                 335

Ile Asp Glu Leu Thr Leu Leu Ser Glu Glu Lys Glu Arg Leu Leu
            340                 345                 350

Thr Arg Ala Ser Gly Asn Pro Val Asn Tyr Arg Gly Glu Met Thr Ile
        355                 360                 365

Pro Gly Leu Phe Glu Glu Lys Val Lys Ser Leu Ser Asp Lys Pro Ala
370                 375                 380

Val Val Tyr Glu Gly Arg Thr Leu Ser Tyr Arg Thr Leu His Glu Gln
385                 390                 395                 400

Ser Gly Arg Ile Ala Gly Arg Leu Leu Asn Ala Gly Ile Ser Ala Asp
```

```
            405                 410                 415
Ser Pro Val Ala Val Leu Leu Gly Arg Ser Glu Arg Val Ile Ala Ala
                420                 425                 430

Ile Leu Gly Ile Leu Lys Ala Gly Gly Ala Tyr Val Pro Ile Asp Pro
            435                 440                 445

Asp Phe Pro Ala Asp Arg Ile Gln Tyr Ile Leu Glu Asp Ser Gly Ala
        450                 455                 460

Lys Ala Val Leu Thr Glu Ala Gly Ile Gln Ala Pro Ala Ala Asp Ala
465                 470                 475                 480

Glu Arg Ile Asp Phe Asp Glu Ala Val Gln Phe Glu Thr Ala Ala Asp
                485                 490                 495

Gly Val Ser Thr Gln Ser Asp Arg Leu Ala Tyr Ile Ile Tyr Thr Ser
            500                 505                 510

Gly Thr Thr Gly Arg Pro Lys Gly Val Met Ile Glu His Arg Gln Val
        515                 520                 525

His His Leu Val Gln Ser Leu Gln Gln Glu Ile Tyr Gln Cys Gly Glu
    530                 535                 540

Gln Thr Leu Arg Met Ala Leu Leu Ala Pro Phe His Phe Asp Ala Ser
545                 550                 555                 560

Val Lys Gln Ile Phe Ala Ser Leu Leu Leu Gly Gln Thr Leu Tyr Ile
                565                 570                 575

Val Pro Lys Thr Thr Val Thr Asn Gly Ser Ala Leu Leu Asp Tyr Tyr
            580                 585                 590

Arg Gln Asn Arg Ile Glu Ala Thr Asp Gly Thr Pro Ala His Leu Gln
        595                 600                 605

Met Met Val Ala Ala Gly Asp Val Ser Gly Ile Glu Leu Arg His Met
    610                 615                 620

Leu Ile Gly Gly Glu Gly Leu Ser Ala Ala Val Ala Glu Gln Leu Met
625                 630                 635                 640

Asn Leu Phe His Gln Ser Gly Arg Ala Pro Arg Leu Thr Asn Val Tyr
                645                 650                 655

Gly Pro Thr Glu Thr Cys Val Asp Ala Ser Val His Gln Val Ser Ala
            660                 665                 670

Asp Asn Gly Met Asn Gln Gln Ala Ala Tyr Val Pro Ile Gly Lys Pro
        675                 680                 685

Leu Gly Asn Ala Arg Leu Tyr Ile Leu Asp Lys His Gln Arg Leu Gln
    690                 695                 700

Pro Asp Gly Thr Ala Gly Glu Leu Tyr Ile Ala Gly Asp Gly Val Gly
705                 710                 715                 720

Arg Gly Tyr Leu Asn Leu Pro Asp Leu Thr Ala Glu Lys Phe Leu Gln
                725                 730                 735

Asp Pro Phe Asn Gly Ser Gly Arg Met Tyr Arg Thr Gly Asp Met Ala
            740                 745                 750

Arg Trp Leu Pro Asp Gly Thr Ile Glu Tyr Ile Gly Arg Glu Asp Asp
        755                 760                 765

Gln Val Lys Val Arg Gly Tyr Arg Ile Glu Leu Gly Glu Ile Glu Thr
    770                 775                 780

Val Leu Arg Lys Ala Pro Gly Ala Ala Gln Ala Val Leu Ala Arg
785                 790                 795                 800

Pro Asp Gln Gln Gly Ser Leu Asp Val Cys Ala Tyr Ile Val Gln Glu
                805                 810                 815

Lys Gly Thr Glu Phe His Pro Ala Glu Tyr Arg Glu Tyr Val Ser Lys
            820                 825                 830
```

-continued

His Leu Pro Asp Tyr Met Val Pro Ala Tyr Phe Thr Lys Thr Asp Glu
        835                 840                 845

Ile Pro Leu Thr Pro Ser Gly Lys Ala Asp Arg Lys Lys Leu Phe Ala
850                 855                 860

Leu Asp Val Gln Ala Val Ser Ser Ser Glu Tyr Ala Ala Pro Arg Asn
865                 870                 875                 880

Glu Thr Glu Glu Thr Leu Thr Val Ile Trp Gln Glu Val Leu Gly Met
                885                 890                 895

Asp Lys Ala Gly Ile Tyr Asp His Phe Phe Glu Ser Gly Gly His Ser
                900                 905                 910

Leu Lys Ala Met Thr Leu Leu Thr Lys Ile His Lys Gln Met Gly Val
                915                 920                 925

Glu Ile Pro Leu Gln Tyr Leu Phe Glu His Pro Thr Ile Ala Ala Leu
        930                 935                 940

Ala Asp Tyr Ala Glu Asn Arg Asn Glu Gly Pro Ala Phe Arg Ala Ile
945                 950                 955                 960

Glu Pro Ala Glu Lys Gln Ala Ser Tyr Pro Leu Ser Leu Ala Gln Gln
                965                 970                 975

Arg Thr Tyr Ile Ala Ser Gln Phe Glu Asp Ala Gly Val Gly Tyr Asn
                980                 985                 990

Met Pro Ala Ala Val Ile Glu Gly Ala Leu Asp Leu Glu Lys Leu
        995                 1000                1005

Glu Arg Ala Phe Ser Ala Leu Ile Ser Arg His Glu Ala Leu Arg
        1010                1015                1020

Thr Ser Phe Gln Ser Glu Asp Gly Thr Pro Arg Gln Val Val His
        1025                1030                1035

Glu His Val Pro Phe His Ile Glu Met Leu Glu Ala Arg Gly Arg
        1040                1045                1050

Thr Asn Glu Gln Val Met Lys Asp Phe Val Arg Arg Phe Asp Leu
        1055                1060                1065

Ser Glu Ala Pro Leu Phe Arg Ile Gly Leu Gln Thr Leu Gly His
        1070                1075                1080

Asn Arg His Met Leu Leu Phe Asp Met His His Leu Ile Ser Asp
        1085                1090                1095

Gly Val Ser Ile Ser Ile Met Leu Lys Glu Leu Ala Asp Ile Tyr
        1100                1105                1110

Gly Gly Asn Gln Leu Pro Glu Leu Arg Ile Gln Tyr Lys Asp Tyr
        1115                1120                1125

Ala Val Trp Gln Ala Glu Arg Ala Lys Glu Gly Tyr Lys Lys Glu
        1130                1135                1140

Arg Ala Tyr Trp Lys Glu Val Phe Ser Gly Glu Leu Pro Val Leu
        1145                1150                1155

Gln Leu Leu Pro Asp Tyr Pro Arg Pro Gln Met Gln Ser Phe Glu
        1160                1165                1170

Gly Asp Arg Val Ser Ala Lys Leu Pro Lys Met Leu Arg Glu Arg
        1175                1180                1185

Leu Gln Lys Leu Ala Glu Lys Asn Gly Ala Thr Leu Tyr Met Val
        1190                1195                1200

Leu Leu Ser Ala Tyr Tyr Thr Leu Leu Ser Lys Tyr Ser Gly Gln
        1205                1210                1215

Glu Asp Ile Ile Val Gly Thr Pro Ser Ala Gly Arg Asn His Ser
        1220                1225                1230

```
Asp Thr Glu Gly Leu Ile Gly Met Phe Val Asn Thr Leu Ala Leu
1235                1240                1245

Arg Ser Ser Val Lys Gln Asp Gln Thr Phe Ala Gly Leu Leu Gly
1250                1255                1260

His Val Arg Lys Gln Val Leu Asp Ala Phe Ser His Gln Asp Tyr
1265                1270                1275

Pro Phe Glu Trp Leu Thr Glu Glu Leu Asn Val Pro Arg Asp Met
1280                1285                1290

Ser Arg His Pro Ile Phe Asp Thr Met Phe Ser Leu Gln Asn Ala
1295                1300                1305

Ser Asp Gly Ile Pro Glu Ile Gly Asn Leu Thr Leu Ser Leu His
1310                1315                1320

Glu Thr Asn Phe Asn Ile Ala Lys Phe Asp Leu Thr Met Gln Ala
1325                1330                1335

Arg Glu Thr Ala Glu Gly Ile Ala Leu Asp Leu Asp Tyr Cys Thr
1340                1345                1350

Lys Leu Phe Lys Arg Ser Thr Ala Asp Arg Met Leu Ala His Tyr
1355                1360                1365

Val Arg Leu Leu Glu Ser Ala Ala Ala Gln Pro Asp Ala Lys Ile
1370                1375                1380

Ser Glu Tyr Asp Leu Leu Ser Glu Arg Glu Ala Leu Asn Gln Leu
1385                1390                1395

Gln Arg Phe Asn Pro Glu Arg Thr Ala Tyr Pro Lys Glu Gln Thr
1400                1405                1410

Ile Val Gln Ile Phe Glu Glu Gln Ala Arg Lys Asn Pro Asp Arg
1415                1420                1425

Thr Ala Leu Gln Phe Glu Gly Glu Thr Leu Ser Tyr Gln Gln Leu
1430                1435                1440

Asn Glu Arg Ala Asn Arg Leu Ala Arg His Ile Leu Ser Val Gly
1445                1450                1455

Gly Gly Gly Lys Thr Ala Ala Val Leu Cys Glu Arg Ser Met Asp
1460                1465                1470

Met Ile Val Ser Ile Met Ala Val Leu Lys Ala Gly Ser Ala Tyr
1475                1480                1485

Val Pro Ile Asp Pro Glu His Pro Val Gln Arg Ile Gln His Phe
1490                1495                1500

Phe Arg Asp Ser Gly Ala Lys Val Leu Leu Thr Gln Gln Ser Leu
1505                1510                1515

Lys Pro Leu Ala Glu Lys Ala Gly Phe Gln Gly Ala Ile Val Leu
1520                1525                1530

Ala Asp Asp Glu Ala Ser Tyr Glu Lys Asp Ser Arg Asn Pro Ala
1535                1540                1545

Leu Pro Phe Asp Ser Ser Thr Ile Ala Asn Leu Thr Tyr Thr Ser
1550                1555                1560

Gly Thr Thr Gly Thr Pro Lys Gly Asn Ile Val Thr His Ala Asn
1565                1570                1575

Ile Leu Arg Thr Val Lys Asn Thr Asn Tyr Leu Thr Val Ser Glu
1580                1585                1590

Glu Asp Thr Val Leu Gly Leu Ser Asn Tyr Val Phe Asp Ala Phe
1595                1600                1605

Met Phe Asp Met Phe Gly Ser Leu Leu Asn Gly Ala Lys Leu Val
1610                1615                1620

Ile Val Pro Lys Asp Thr Val Leu Asp Met Ser Arg Leu Ser Arg
```

```
            1625                1630                1635

Val Ile Lys Arg Glu Asn Val Ser Ile Leu Met Ile Thr Thr Ala
        1640                1645                1650

Leu Phe His Leu Leu Val Asp Met Glu Pro Ser Cys Leu Thr Thr
        1655                1660                1665

Leu Arg Lys Ile Met Phe Gly Gly Glu Arg Ala Ser Val Glu His
        1670                1675                1680

Val Lys Lys Ala Leu Ala Ala Val Gly Lys Gly Arg Leu Leu His
        1685                1690                1695

Met Tyr Gly Pro Ser Glu Ser Thr Val Phe Ala Thr Tyr His Pro
        1700                1705                1710

Val Asp Val Ile Glu Glu Asp Thr Leu Ser Val Pro Ile Gly Lys
        1715                1720                1725

Pro Val Ser Asn Thr Glu Val Phe Ile Met Asn Ser Ala Gly Arg
        1730                1735                1740

Ile Gln Pro Ala Gly Ile Ala Gly Glu Leu Cys Val Ser Gly Glu
        1745                1750                1755

Gly Leu Val Glu Gly Tyr Tyr Asn Arg Pro Glu Leu Thr Glu Glu
        1760                1765                1770

Lys Phe Val Lys His Pro Phe Lys Glu Gly Glu Arg Met Tyr Lys
        1775                1780                1785

Thr Gly Asp Leu Ala Arg Trp Leu Pro Asn Gly Asp Ile Glu Phe
        1790                1795                1800

Ile Gly Arg Ile Asp His Gln Val Lys Ile Arg Gly Gln Arg Ile
        1805                1810                1815

Glu Leu Gly Glu Ile Glu His Gln Leu Gln Ser His Asp Gln Ile
        1820                1825                1830

Gln Glu Cys Ile Val Leu Ala Val Asp Gln Gly Ala Gly Asp Lys
        1835                1840                1845

Leu Leu Cys Ala Tyr Phe Val Gly Leu Arg Glu Ile Ser Ser Arg
        1850                1855                1860

Glu Leu Arg Glu His Thr Ala Lys Asp Leu Pro Ala Tyr Met Ile
        1865                1870                1875

Pro Ser Val Phe Ile Gln Leu Asp Glu Leu Pro Leu Thr Gly Asn
        1880                1885                1890

Gly Lys Ile Asp Arg Arg Ala Leu Pro Met Pro Asp Val Thr Ala
        1895                1900                1905

Ala Asn Ala Val Ser Tyr Thr Ala Pro Arg Asn Glu Thr Glu Lys
        1910                1915                1920

Lys Leu Ala Asp Ile Trp Ala Glu Val Leu Gln Met Glu Arg Val
        1925                1930                1935

Gly Val His Asp Gln Phe Phe Glu Ile Gly Gly His Ser Leu Ala
        1940                1945                1950

Gly Met Lys Leu Leu Ala Leu Ile Gln Lys Thr Phe Gly Val Gln
        1955                1960                1965

Leu Thr Leu Lys Asp Leu Phe Thr Ser Pro Thr Ala Ala Gly Leu
        1970                1975                1980

Ala Gln Leu Ile Glu Gly Ala Glu Arg Lys Ala Ala Glu Ser Ile
        1985                1990                1995

Ala Pro Ala Ala Glu Arg Glu Thr Tyr Pro Val Ser Ser Pro Gln
        2000                2005                2010

Lys Arg Met Phe Val Leu Gln Gln Leu Glu Gly Ala Glu Thr Ser
        2015                2020                2025
```

-continued

```
Tyr Asn Met Pro Ser Val Leu Arg Leu Lys Gly Lys Leu Asp Ala
        2030                2035                2040

Glu Lys Leu Lys Ser Val Met Lys Gln Leu Thr Glu Arg His Glu
        2045                2050                2055

Ala Phe Arg Thr Thr Phe Asp Ile Lys Asp Gly Glu Thr Val Gln
        2060                2065                2070

Arg Ile Trp Ala Glu Ala Tyr Ile Asp Met Glu Tyr Tyr Glu Ala
        2075                2080                2085

Ser Glu Glu Asp Ala Glu Gln Ile Ile Gln Ser Phe Ile Arg Pro
        2090                2095                2100

Phe Arg Leu Asp Gln Leu Pro Leu Val Arg Thr Gly Leu Val Lys
        2105                2110                2115

Leu Ala Glu His Asp His Leu Leu Leu Phe Asp Met His His Ile
        2120                2125                2130

Ile Ser Asp Gly Ala Ser Val Gly Val Leu Ile Asp Glu Leu Ser
        2135                2140                2145

Arg Leu Tyr Gly Gly Glu Thr Leu Glu Pro Leu Arg Ile His Tyr
        2150                2155                2160

Lys Asp Tyr Ala Val Trp Gln Gln Lys Phe Ile Gln Ser Glu Gln
        2165                2170                2175

Tyr Arg Lys Gln Glu Glu His Trp Leu Arg Glu Leu Asp Gly Glu
        2180                2185                2190

Leu Pro Val Leu Thr Leu Pro Ala Asp Tyr Ser Arg Pro Ala Val
        2195                2200                2205

Gln Thr Phe Glu Gly Asp Lys Leu Val Phe Ser Leu Thr Glu Glu
        2210                2215                2220

Gln Thr Ser Ala Leu Arg Ser Leu Ala Lys Gln Thr Asp Ser Thr
        2225                2230                2235

Met Tyr Met Val Leu Leu Ala Ser Tyr Ser Ala Phe Leu Ser Lys
        2240                2245                2250

Leu Ser Gly Gln His Asp Ile Ile Val Gly Ser Pro Ala Ala Gly
        2255                2260                2265

Arg Ser His Ala Asp Leu Ala Asn Val Ile Gly Val Phe Val Asn
        2270                2275                2280

Thr Leu Ala Leu Arg Thr Tyr Pro Glu Ala Asp Lys Thr Phe Thr
        2285                2290                2295

Asp Tyr Leu Lys Glu Val Lys Gln Thr Ala Leu His Ala Phe Asp
        2300                2305                2310

Ala Gln Asp Tyr Pro Leu Glu Asp Leu Leu Gln Lys Val Glu Val
        2315                2320                2325

Gln Arg Asp Thr Ser Arg Asn Pro Leu Phe Asp Ala Val Phe Ser
        2330                2335                2340

Met Gln Asn Ala Asn Ala Glu Asp Leu Val Met Glu Gly Ile Glu
        2345                2350                2355

Leu Lys His His Pro Phe Asp Arg Lys Thr Ala Lys Phe Asp Leu
        2360                2365                2370

Thr Leu Thr Ala Glu Asp Thr Asp Glu Gly Leu Thr Phe Val Leu
        2375                2380                2385

Glu Tyr Asn Thr Ala Leu Phe Lys Pro Glu Thr Ala Glu Thr Trp
        2390                2395                2400

Lys His Tyr Trp Leu Gln Leu Leu Lys Ala Ala Thr Glu Asn Pro
        2405                2410                2415
```

-continued

```
Ala Ala Lys Leu Ser Glu Leu Ser Leu Val Asn Glu Thr Glu Lys
2420                2425                2430

Gln Ala Leu Leu Asp Ala Trp Lys Gly Lys Thr Leu Ser Val Pro
2435                2440                2445

Gln Asp Lys Thr Val His Arg Leu Phe Glu Glu Thr Ala Ala Arg
2450                2455                2460

Tyr Ala Asn Arg Pro Ala Ala Tyr Asn Gly Ala Lys Trp Thr
2465                2470                2475

Tyr Gly Glu Leu Asn Ala Arg Ala Asn Arg Ile Ala Arg Ile Leu
2480                2485                2490

Ile Asp Cys Gly Val Thr Ala Asp Glu Arg Val Gly Ile Leu Thr
2495                2500                2505

Lys Pro Ser Leu Glu Met Ala Ala Gly Val Leu Gly Val Leu Lys
2510                2515                2520

Ala Gly Ala Ala Phe Val Pro Ile Asp Pro Asp Tyr Pro Gln Glu
2525                2530                2535

Arg Ile Ser Tyr Ile Leu Gln Asp Ser Gly Ala Lys Leu Leu Leu
2540                2545                2550

Thr Gln Glu Ala Leu Asp Val Pro Asp Gly Tyr Thr Gly Glu Thr
2555                2560                2565

Ile Leu Leu Asp Gly Gly Arg Ser Ile Leu Ser Leu Pro Leu Asp
2570                2575                2580

Glu Asn Asp Glu Ala Asn Pro Gln Thr Glu Thr Thr Ala Asp His
2585                2590                2595

Leu Ala Tyr Met Ile Tyr Thr Ser Gly Thr Thr Gly Gln Pro Lys
2600                2605                2610

Gly Val Met Val Glu His His Ala Leu Val Asn Leu Cys Phe Trp
2615                2620                2625

His His Asp Ala Phe Ala Met Thr Ala Asp Asp Lys Ser Ala Lys
2630                2635                2640

Tyr Ala Gly Phe Gly Phe Asp Ala Ser Ile Trp Glu Met Phe Pro
2645                2650                2655

Thr Trp Thr Ile Gly Ala Glu Leu His Val Ile Asp Glu Ala Ile
2660                2665                2670

Arg Leu Asp Ile Thr Arg Leu Asn His Tyr Phe Glu Glu His Gly
2675                2680                2685

Val Thr Ile Thr Phe Leu Pro Thr Gln Leu Ala Glu Gln Phe Met
2690                2695                2700

Glu Leu Glu Asn Thr Ser Leu Arg Met Leu Leu Val Gly Gly Asp
2705                2710                2715

Lys Leu Lys Arg Ala Val Lys Gln Pro Tyr Thr Ile Val Asn Asn
2720                2725                2730

Tyr Gly Pro Thr Glu Asn Thr Val Val Ala Thr Ser Gly Val Ile
2735                2740                2745

Asn Pro Glu Glu Gly Ser Leu Ser Ile Gly Arg Ala Ile Ala Asn
2750                2755                2760

Thr Arg Ala Tyr Ile Leu Gly Asp Gly Asp Gln Val Gln Pro Glu
2765                2770                2775

Gly Ile Ala Gly Glu Leu Cys Val Ala Gly Arg Gly Leu Ala Arg
2780                2785                2790

Gly Tyr Leu Asn Arg Glu Glu Glu Thr Ala Lys Arg Phe Thr Ala
2795                2800                2805

Asp Pro Phe Val Pro Gly Glu Arg Met Tyr Arg Thr Gly Asp Leu
```

```
                2810                2815                2820
Val Lys Trp Asn Ala Gln Ser Gly Ile Glu Tyr Ile Gly Arg Ile
    2825                2830                2835
Asp Gln Gln Val Lys Val Arg Gly Tyr Arg Ile Glu Leu Ser Glu
    2840                2845                2850
Ile Glu Val Arg Leu Ala Gln Leu Ala Asp Val His Asp Ala Ala
    2855                2860                2865
Val Thr Ala Val Glu Asp Lys Ala Gly Asn Ala Ala Leu Cys Ala
    2870                2875                2880
Tyr Val Ala Pro Gln Gln Asp Asp Ile Glu Ala Leu Lys Ala Ala
    2885                2890                2895
Leu Lys Asp Thr Leu Pro Asp Tyr Met Val Pro Ala Phe Trp Val
    2900                2905                2910
Glu Met Asp Glu Leu Pro Val Thr Ala Asn Gly Lys Ile Asp Lys
    2915                2920                2925
Lys Ala Leu Pro Glu Pro Asp Ile Glu Ala Gly Ser Ala Ala Tyr
    2930                2935                2940
Lys Ala Pro Glu Thr Glu Met Glu Thr Leu Leu Ser Asp Ile Trp
    2945                2950                2955
Glu Glu Val Leu Gly Leu Asp Gln Ile Gly Val Ser Asp Asn Phe
    2960                2965                2970
Phe Thr Leu Gly Gly Asp Ser Ile Lys Gly Ile Gln Met Ala Ser
    2975                2980                2985
Arg Leu Asn Gln His Gly Tyr Lys Leu Glu Met Lys Asp Leu Phe
    2990                2995                3000
Gln His Pro Thr Ile Glu Glu Leu Val Ser Tyr Val Glu Arg Thr
    3005                3010                3015
Glu Gly Lys Gln Ala Asp Gln Gly Pro Val Glu Gly Lys Ala Glu
    3020                3025                3030
Leu Thr Pro Ile Gln Arg Trp Phe Phe Glu Lys Asn Phe Thr Asp
    3035                3040                3045
Lys His His Trp Asn Gln Ser Val Met Leu His Ala Lys Asp Gly
    3050                3055                3060
Phe Asp Pro Glu Ile Thr Glu Lys Thr Leu His Val Leu Thr Val
    3065                3070                3075
His His Asp Ala Leu Arg Met Ile Tyr Arg Glu Gln Lys Pro Tyr
    3080                3085                3090
Tyr Arg Gly Leu Glu Asp Ala Ser Val Glu Leu Asn Val Phe Glu
    3095                3100                3105
Leu Asn Gly Pro Ala Glu Asp His Glu Asn Arg Ile Glu Arg Glu
    3110                3115                3120
Ala Asp Arg Leu Gln Ser Ser Ile Ser Leu Glu Thr Gly His Leu
    3125                3130                3135
Leu Lys Ala Gly Leu Phe Arg Ala Glu Asp Gly Asp His Leu Leu
    3140                3145                3150
Leu Ala Ile His His Leu Val Val Asp Gly Val Ser Trp Arg Ile
    3155                3160                3165
Leu Leu Glu Asp Phe Thr Ser Val Tyr Thr Gln Leu Lys Gln Gly
    3170                3175                3180
Asn Glu Pro Ala Leu Pro Pro Lys Thr His Ser Phe Ala Glu Phe
    3185                3190                3195
Ala Glu Arg Ile Lys Glu Tyr Ala Asn Thr Lys Ala Phe Leu Lys
    3200                3205                3210
```

```
Glu Ala Asp Tyr Trp Arg Glu Leu Glu Lys Glu Val Cys Thr
    3215                3220                3225

Gln Leu Pro Lys Asp Arg Gln Ser Gly Asp Gln Arg Met Arg His
    3230                3235                3240

Thr Arg Thr Val Ser Phe Ser Leu Thr Pro Glu Gln Thr Glu Gln
    3245                3250                3255

Leu Thr Thr Asn Val His Glu Ala Tyr His Thr Glu Met Asn Asp
    3260                3265                3270

Ile Leu Leu Thr Ala Leu Gly Leu Ala Leu Lys Glu Trp Thr Gly
    3275                3280                3285

Glu Asp Thr Ile Gly Val His Leu Glu Gly His Gly Arg Glu Asp
    3290                3295                3300

Ile Leu Asp Gly Leu Asn Ile Thr Arg Thr Val Gly Trp Phe Thr
    3305                3310                3315

Ser Met Tyr Pro Met Ile Leu Glu Met Lys His Ala Asp Asp Leu
    3320                3325                3330

Ser Tyr Gln Leu Lys Gln Met Lys Glu Asp Ile Arg His Ile Pro
    3335                3340                3345

Asn Lys Gly Val Gly Tyr Gly Ile Leu Arg Tyr Val Thr Ala Pro
    3350                3355                3360

Glu His Lys Glu Gly Leu Ser Phe Glu Ile Asp Pro Asp Ile Ser
    3365                3370                3375

Phe Asn Tyr Leu Gly Gln Phe Asn Glu Met Ser Asp Ser Gly Leu
    3380                3385                3390

Phe Thr Arg Ser Gly Met Pro Ser Gly Gln Ser Leu Ser Pro Asp
    3395                3400                3405

Thr Glu Lys Pro Asn Ala Leu Asp Ile Val Gly Phe Ile Glu Asn
    3410                3415                3420

Gly Gln Met Thr Met Thr Phe Ala Tyr His Ser Leu Glu Phe His
    3425                3430                3435

Glu Lys Thr Ile Gln Ser Phe Ser Asp Ser Phe Lys Gly His Leu
    3440                3445                3450

Leu Lys Ile Ile Leu Thr Leu Asp Glu Leu Asp Lys Leu Met Glu
    3455                3460                3465

Ile Leu
    3470

<210> SEQ ID NO 12
<211> LENGTH: 181
<212> TYPE: PRT
<213> ORGANISM: Bacillus subtilis

<400> SEQUENCE: 12

Met Glu Ile Thr Phe Tyr Pro Leu Thr Asn Ala Gln Lys Arg Ile Trp
1               5                   10                  15

Tyr Thr Glu Lys Phe Tyr Pro Asn Thr Ser Ile Ser Asn Leu Ala Gly
            20                  25                  30

Phe Gly Lys Leu Ile Ser Asp Asp Gly Val Gln Ala His Tyr Val Glu
        35                  40                  45

Lys Ala Ile Gln Glu Phe Val Arg Arg Tyr Glu Ser Met Arg Ile Arg
    50                  55                  60

Leu Arg Leu Asp Asp Glu Gly Glu Pro Val Gln Tyr Val Ser Asp Tyr
65                  70                  75                  80

Arg Pro Leu Thr Ile Glu His Thr Asp Ile Arg Gln Ala Gly Cys Ser
```

```
            85                  90                  95
Ala Glu Glu Leu Ser Lys Trp Gly Arg Asp Glu Ala Ser Lys Pro Leu
            100                 105                 110

Ala Leu Tyr Asp Gln Asp Leu Phe Arg Phe Ser Val Tyr Thr Ile Ser
            115                 120                 125

Glu Asn Glu Val Trp Phe Tyr Val Asn Val His His Ile Ile Ser Asp
        130                 135                 140

Gly Ile Ser Met Thr Ile Leu Gly Asn Ala Ile Thr Asp Ile Tyr Leu
145                 150                 155                 160

Glu Leu Ser Gly Gly Ala Ser Met Glu Gln Thr Glu Ile Pro Pro Tyr
                165                 170                 175

Arg Ala Cys Ala Asp
            180

<210> SEQ ID NO 13
<211> LENGTH: 3289
<212> TYPE: PRT
<213> ORGANISM: Bacillus subtilis

<400> SEQUENCE: 13

Met Gly Asn Arg Thr Asn Ala Lys Glu Lys Gln Met Leu Gly Met Phe
1               5                   10                  15

Val Ser Thr Val Pro Val Arg Thr Ser Val Asp Gly Gly Gln Ser Phe
            20                  25                  30

Leu Glu Phe Val Lys Gly Arg Met Lys Asp Leu Met Lys Ile Leu Arg
        35                  40                  45

His Gln Lys Tyr Pro Tyr Asn Leu Leu Val Asn Asp Leu Arg Ala Ser
    50                  55                  60

Lys Ser Ser Leu Ser Arg Leu Phe Thr Val Ala Leu Glu Tyr Gln Val
65                  70                  75                  80

Met Gln Trp Gln Lys Lys Glu Asn Leu Ser Phe Leu Thr Asp Pro Ile
            85                  90                  95

Phe Ser Gly Ser Gly Thr Asn Asp Ile Ser Ile His Val Lys Glu Arg
            100                 105                 110

Trp Asp Thr Gly Lys Leu Thr Ile Asp Phe Asp Tyr Arg Ser Asp Ile
            115                 120                 125

Phe Lys Gly Glu Glu Ile Val Ser Val Ser Glu Arg Leu Ile Thr Leu
        130                 135                 140

Ile Glu Asp Ala Ile Ser Ser Pro Asp Arg Ile Ile Asp Glu Leu Thr
145                 150                 155                 160

Leu Leu Ser Glu Ser Glu Lys Glu Arg Leu Leu Thr Arg Ala Ser Gly
                165                 170                 175

Asn Pro Val Asn Tyr Arg Gly Glu Met Thr Ile Pro Gly Leu Phe Glu
            180                 185                 190

Glu Lys Val Lys Ser Leu Ser Asp Lys Pro Ala Val Val Tyr Glu Gly
            195                 200                 205

Arg Thr Leu Ser Tyr Arg Thr Leu His Glu Gln Ser Gly Arg Ile Ala
        210                 215                 220

Gly Arg Leu Leu Asn Ala Gly Ile Ser Ala Asp Ser Pro Val Ala Val
225                 230                 235                 240

Leu Leu Gly Arg Ser Glu Arg Val Ile Ala Ala Ile Leu Gly Ile Leu
                245                 250                 255

Lys Ala Gly Gly Ala Tyr Val Pro Ile Asp Pro Asp Phe Pro Ala Asp
            260                 265                 270
```

-continued

Arg Ile Gln Tyr Ile Leu Glu Asp Ser Gly Ala Lys Ala Val Leu Thr
            275                 280                 285

Glu Ala Gly Ile Gln Ala Pro Ala Ala Asp Ala Glu Arg Ile Asp Phe
        290                 295                 300

Asp Glu Ala Val Gln Phe Glu Thr Ala Ala Asp Gly Val Ser Thr Gln
305                 310                 315                 320

Ser Asp Arg Leu Ala Tyr Ile Ile Tyr Thr Ser Gly Thr Thr Gly Arg
                325                 330                 335

Pro Lys Gly Val Met Ile Glu His Arg Gln Val His His Leu Val Gln
            340                 345                 350

Ser Leu Gln Gln Glu Ile Tyr Gln Cys Gly Glu Gln Thr Leu Arg Met
        355                 360                 365

Ala Leu Leu Ala Pro Phe His Phe Asp Ala Ser Val Lys Gln Ile Phe
    370                 375                 380

Ala Ser Leu Leu Leu Gly Gln Thr Leu Tyr Ile Val Pro Lys Thr Thr
385                 390                 395                 400

Val Thr Asn Gly Ser Ala Leu Leu Asp Tyr Tyr Arg Gln Asn Arg Ile
                405                 410                 415

Glu Ala Thr Asp Gly Thr Pro Ala His Leu Gln Met Met Val Ala Ala
            420                 425                 430

Gly Asp Val Ser Gly Ile Glu Leu Arg His Met Leu Ile Gly Gly Glu
        435                 440                 445

Gly Leu Ser Ala Ala Val Ala Glu Gln Leu Met Asn Leu Phe His Gln
    450                 455                 460

Ser Gly Arg Ala Pro Arg Leu Thr Asn Val Tyr Gly Pro Thr Glu Thr
465                 470                 475                 480

Cys Val Asp Ala Ser Val His Gln Val Ser Ala Asp Asn Gly Met Asn
                485                 490                 495

Gln Gln Ala Ala Tyr Val Pro Ile Gly Lys Pro Leu Gly Asn Ala Arg
            500                 505                 510

Leu Tyr Ile Leu Asp Lys His Gln Arg Leu Gln Pro Asp Gly Thr Ala
        515                 520                 525

Gly Glu Leu Tyr Ile Ala Gly Asp Gly Val Gly Arg Gly Tyr Leu Asn
    530                 535                 540

Leu Pro Asp Leu Thr Ala Glu Lys Phe Leu Gln Asp Pro Phe Asn Gly
545                 550                 555                 560

Ser Gly Arg Met Tyr Arg Thr Gly Asp Met Ala Arg Trp Leu Pro Asp
                565                 570                 575

Gly Thr Ile Glu Tyr Ile Gly Arg Glu Asp Asp Gln Val Lys Val Arg
            580                 585                 590

Gly Tyr Arg Ile Glu Leu Gly Glu Ile Glu Thr Val Leu Arg Lys Ala
        595                 600                 605

Pro Gly Ala Ala Gln Ala Val Val Leu Ala Arg Pro Asp Gln Gln Gly
    610                 615                 620

Ser Leu Asp Val Cys Ala Tyr Ile Val Gln Glu Lys Gly Thr Glu Phe
625                 630                 635                 640

His Pro Ala Glu Tyr Arg Glu Tyr Val Ser Lys His Leu Pro Asp Tyr
                645                 650                 655

Met Val Pro Ala Tyr Phe Thr Lys Thr Asp Glu Ile Pro Leu Thr Pro
            660                 665                 670

Ser Gly Lys Ala Asp Arg Lys Lys Leu Phe Ala Leu Asp Val Gln Ala
        675                 680                 685

Val Ser Ser Ser Glu Tyr Ala Ala Pro Arg Asn Glu Thr Glu Glu Thr

-continued

```
                690                 695                 700
Leu Thr Val Ile Trp Gln Glu Val Leu Gly Met Asp Lys Ala Gly Ile
705                 710                 715                 720
Tyr Asp His Phe Phe Glu Ser Gly His Ser Leu Lys Ala Met Thr
                725                 730                 735
Leu Leu Thr Lys Ile His Lys Gln Met Gly Val Glu Ile Pro Leu Gln
                740                 745                 750
Tyr Leu Phe Glu His Pro Thr Ile Ala Ala Leu Ala Asp Tyr Ala Glu
                755                 760                 765
Asn Arg Asn Glu Gly Pro Ala Phe Arg Ala Ile Glu Pro Ala Glu Lys
                770                 775                 780
Gln Ala Ser Tyr Pro Leu Ser Leu Ala Gln Gln Arg Thr Tyr Ile Ala
785                 790                 795                 800
Ser Gln Phe Glu Asp Ala Gly Val Gly Tyr Asn Met Pro Ala Ala Ala
                805                 810                 815
Val Ile Glu Gly Ala Leu Asp Leu Glu Lys Leu Glu Arg Ala Phe Ser
                820                 825                 830
Ala Leu Ile Ser Arg His Glu Ala Leu Arg Thr Ser Phe Gln Ser Glu
                835                 840                 845
Asp Gly Thr Pro Arg Gln Val Val His Glu His Val Pro Phe His Ile
                850                 855                 860
Glu Met Leu Glu Ala Arg Gly Arg Thr Asn Glu Gln Val Met Lys Asp
865                 870                 875                 880
Phe Val Arg Arg Phe Asp Leu Ser Glu Ala Pro Leu Phe Arg Ile Gly
                885                 890                 895
Leu Gln Thr Leu Gly His Asn Arg His Met Leu Leu Phe Asp Met His
                900                 905                 910
His Leu Ile Ser Asp Gly Val Ser Ile Ser Ile Met Leu Lys Glu Leu
                915                 920                 925
Ala Asp Ile Tyr Gly Gly Asn Gln Leu Pro Glu Leu Arg Ile Gln Tyr
                930                 935                 940
Lys Asp Tyr Ala Val Trp Gln Ala Glu Arg Ala Lys Glu Gly Tyr Lys
945                 950                 955                 960
Lys Glu Arg Ala Tyr Trp Lys Glu Val Phe Ser Gly Glu Leu Pro Val
                965                 970                 975
Leu Gln Leu Leu Pro Asp Tyr Pro Arg Pro Gln Met Gly Ser Phe Glu
                980                 985                 990
Gly Asp Arg Val Ser Ala Lys Leu Pro Lys Met Leu Arg Glu Arg Leu
                995                 1000                1005
Gln Lys Leu Ala Glu Lys Asn Gly Ala Thr Leu Tyr Met Val Leu
        1010                1015                1020
Leu Ser Ala Tyr Tyr Thr Leu Leu Ser Lys Tyr Ser Gly Gln Glu
        1025                1030                1035
Asp Ile Ile Val Gly Thr Pro Ser Ala Gly Arg Asn His Ser Asp
        1040                1045                1050
Thr Glu Gly Leu Ile Gly Met Phe Val Asn Thr Leu Ala Leu Arg
        1055                1060                1065
Ser Ser Val Lys Gln Asp Gln Thr Phe Ala Gly Leu Leu Gly His
        1070                1075                1080
Val Arg Lys Gln Val Leu Asp Ala Phe Ser His Gln Asp Tyr Pro
        1085                1090                1095
Phe Glu Trp Leu Thr Glu Glu Leu Asn Val Pro Arg Asp Met Ser
        1100                1105                1110
```

```
Arg His Pro Ile Phe Asp Thr Met Phe Ser Leu Gln Asn Ala Ser
1115                1120                1125

Asp Gly Ile Pro Glu Ile Gly Asn Leu Thr Leu Ser Leu His Glu
1130                1135                1140

Thr Asn Phe Asn Ile Ala Lys Phe Asp Leu Thr Met Gln Ala Arg
1145                1150                1155

Glu Thr Ala Glu Gly Ile Ala Leu Asp Leu Asp Tyr Cys Thr Lys
1160                1165                1170

Leu Phe Lys Arg Ser Thr Ala Asp Arg Met Leu Ala His Tyr Val
1175                1180                1185

Arg Leu Leu Glu Ser Ala Ala Ala Gln Pro Asp Ala Lys Ile Ser
1190                1195                1200

Glu Tyr Asp Leu Leu Ser Glu Arg Glu Ala Leu Asn Gln Leu Gln
1205                1210                1215

Arg Phe Asn Pro Glu Arg Thr Ala Tyr Pro Lys Glu Gln Thr Ile
1220                1225                1230

Val Gln Ile Phe Glu Glu Gln Ala Arg Lys Asn Pro Asp Arg Thr
1235                1240                1245

Ala Leu Gln Phe Glu Gly Glu Thr Leu Ser Tyr Gln Gln Leu Asn
1250                1255                1260

Glu Arg Ala Asn Arg Leu Ala Arg His Ile Leu Ser Val Gly Gly
1265                1270                1275

Gly Gly Lys Thr Ala Ala Val Leu Cys Glu Arg Ser Met Asp Met
1280                1285                1290

Ile Val Ser Ile Met Ala Val Leu Lys Ala Gly Ser Ala Tyr Val
1295                1300                1305

Pro Ile Asp Pro Glu His Pro Val Gln Arg Ile Gln His Phe Phe
1310                1315                1320

Arg Asp Ser Gly Ala Lys Val Leu Leu Thr Gln Gln Ser Leu Lys
1325                1330                1335

Pro Leu Ala Glu Lys Ala Gly Phe Gln Gly Ala Ile Val Leu Ala
1340                1345                1350

Asp Asp Glu Ala Ser Tyr Glu Lys Asp Ser Arg Asn Pro Ala Leu
1355                1360                1365

Pro Phe Asp Ser Ser Thr Ile Ala Asn Leu Thr Tyr Thr Ser Gly
1370                1375                1380

Thr Thr Gly Thr Pro Lys Gly Asn Ile Val Thr His Ala Asn Ile
1385                1390                1395

Leu Arg Thr Val Lys Asn Thr Asn Tyr Leu Thr Val Ser Glu Glu
1400                1405                1410

Asp Thr Val Leu Gly Leu Ser Asn Tyr Val Phe Asp Ala Phe Met
1415                1420                1425

Phe Asp Met Phe Gly Ser Leu Leu Asn Gly Ala Lys Leu Val Ile
1430                1435                1440

Val Pro Lys Asp Thr Val Leu Asp Met Ser Arg Leu Ser Arg Val
1445                1450                1455

Ile Lys Arg Glu Asn Val Ser Ile Leu Met Ile Thr Thr Ala Leu
1460                1465                1470

Phe His Leu Leu Val Asp Met Glu Pro Ser Cys Leu Thr Thr Leu
1475                1480                1485

Arg Lys Ile Met Phe Gly Gly Glu Arg Ala Ser Val Glu His Val
1490                1495                1500
```

Lys Lys Ala Leu Ala Ala Val Gly Lys Gly Arg Leu Leu His Met
1505                1510                1515

Tyr Gly Pro Ser Glu Ser Thr Val Phe Ala Thr Tyr His Pro Val
1520                1525                1530

Asp Val Ile Glu Glu Asp Thr Leu Ser Val Pro Ile Gly Lys Pro
1535                1540                1545

Val Ser Asn Thr Glu Val Phe Ile Met Asn Ser Ala Gly Arg Ile
1550                1555                1560

Gln Pro Ala Gly Ile Ala Gly Glu Leu Cys Val Ser Gly Glu Gly
1565                1570                1575

Leu Val Glu Gly Tyr Tyr Asn Arg Pro Glu Leu Thr Glu Glu Lys
1580                1585                1590

Phe Val Lys His Pro Phe Lys Glu Gly Glu Arg Met Tyr Lys Thr
1595                1600                1605

Gly Asp Leu Ala Arg Trp Leu Pro Asn Gly Asp Ile Glu Phe Ile
1610                1615                1620

Gly Arg Ile Asp His Gln Val Lys Ile Arg Gly Gln Arg Ile Glu
1625                1630                1635

Leu Gly Glu Ile Glu His Gln Leu Gln Ser His Asp Gln Ile Gln
1640                1645                1650

Glu Cys Ile Val Leu Ala Val Asp Gln Gly Ala Gly Asp Lys Leu
1655                1660                1665

Leu Cys Ala Tyr Phe Val Gly Leu Arg Glu Ile Ser Ser Arg Glu
1670                1675                1680

Leu Arg Glu His Thr Ala Lys Asp Leu Pro Ala Tyr Met Ile Pro
1685                1690                1695

Ser Val Phe Ile Gln Leu Asp Glu Leu Pro Leu Thr Gly Asn Gly
1700                1705                1710

Lys Ile Asp Arg Arg Ala Leu Pro Met Pro Asp Val Thr Ala Ala
1715                1720                1725

Asn Ala Val Ser Tyr Thr Ala Pro Arg Asn Glu Thr Glu Lys Lys
1730                1735                1740

Leu Ala Asp Ile Trp Ala Glu Val Leu Gln Met Glu Arg Val Gly
1745                1750                1755

Val His Asp Gln Phe Phe Glu Ile Gly Gly His Ser Leu Ala Gly
1760                1765                1770

Met Lys Leu Leu Ala Leu Ile Gln Lys Thr Phe Gly Val Gln Leu
1775                1780                1785

Thr Leu Lys Asp Leu Phe Thr Ser Pro Thr Ala Ala Gly Leu Ala
1790                1795                1800

Gln Leu Ile Glu Gly Ala Glu Arg Lys Ala Ala Glu Ser Ile Ala
1805                1810                1815

Pro Ala Ala Glu Arg Glu Thr Tyr Pro Val Ser Ser Pro Gln Lys
1820                1825                1830

Arg Met Phe Val Leu Gln Gln Leu Glu Gly Ala Glu Thr Ser Tyr
1835                1840                1845

Asn Met Pro Ser Val Leu Arg Leu Lys Gly Lys Leu Asp Ala Glu
1850                1855                1860

Lys Leu Lys Ser Val Met Lys Gln Leu Thr Glu Arg His Glu Ala
1865                1870                1875

Phe Arg Thr Thr Phe Asp Ile Lys Asp Gly Glu Thr Val Gln Arg
1880                1885                1890

Ile Trp Ala Glu Ala Tyr Ile Asp Met Glu Tyr Tyr Glu Ala Ser

```
              1895                1900                1905

Glu  Glu  Asp  Ala  Glu  Gln  Ile  Ile  Gln  Ser  Phe  Ile  Arg  Pro  Phe
              1910                1915                1920

Arg  Leu  Asp  Gln  Leu  Pro  Leu  Val  Arg  Thr  Gly  Leu  Val  Lys  Leu
              1925                1930                1935

Ala  Glu  His  Asp  His  Leu  Leu  Leu  Phe  Asp  Met  His  His  Ile  Ile
              1940                1945                1950

Ser  Asp  Gly  Ala  Ser  Val  Gly  Val  Leu  Ile  Asp  Glu  Leu  Ser  Arg
              1955                1960                1965

Leu  Tyr  Gly  Gly  Glu  Thr  Leu  Glu  Pro  Leu  Arg  Ile  His  Tyr  Lys
              1970                1975                1980

Asp  Tyr  Ala  Val  Trp  Gln  Gln  Lys  Phe  Ile  Gln  Ser  Glu  Gln  Tyr
              1985                1990                1995

Arg  Lys  Gln  Glu  Glu  His  Trp  Leu  Arg  Glu  Leu  Asp  Gly  Glu  Leu
              2000                2005                2010

Pro  Val  Leu  Thr  Leu  Pro  Ala  Asp  Tyr  Ser  Arg  Pro  Ala  Val  Gln
              2015                2020                2025

Thr  Phe  Glu  Gly  Asp  Lys  Leu  Val  Phe  Ser  Leu  Thr  Glu  Glu  Gln
              2030                2035                2040

Thr  Ser  Ala  Leu  Arg  Ser  Leu  Ala  Lys  Gln  Thr  Asp  Ser  Thr  Met
              2045                2050                2055

Tyr  Met  Val  Leu  Leu  Ala  Ser  Tyr  Ser  Ala  Phe  Leu  Ser  Lys  Leu
              2060                2065                2070

Ser  Gly  Gln  His  Asp  Ile  Ile  Val  Gly  Ser  Pro  Ala  Ala  Gly  Arg
              2075                2080                2085

Ser  His  Ala  Asp  Leu  Ala  Asn  Val  Ile  Gly  Val  Phe  Val  Asn  Thr
              2090                2095                2100

Leu  Ala  Leu  Arg  Thr  Tyr  Pro  Glu  Ala  Asp  Lys  Thr  Phe  Thr  Asp
              2105                2110                2115

Tyr  Leu  Lys  Glu  Val  Lys  Gln  Thr  Ala  Leu  His  Ala  Phe  Asp  Ala
              2120                2125                2130

Gln  Asp  Tyr  Pro  Leu  Glu  Asp  Leu  Leu  Gln  Lys  Val  Glu  Val  Gln
              2135                2140                2145

Arg  Asp  Thr  Ser  Arg  Asn  Pro  Leu  Phe  Asp  Ala  Val  Phe  Ser  Met
              2150                2155                2160

Gln  Asn  Ala  Asn  Ala  Glu  Asp  Leu  Val  Met  Glu  Gly  Ile  Glu  Leu
              2165                2170                2175

Lys  His  His  Pro  Phe  Asp  Arg  Lys  Thr  Ala  Lys  Phe  Asp  Leu  Thr
              2180                2185                2190

Leu  Thr  Ala  Glu  Asp  Thr  Asp  Glu  Gly  Leu  Thr  Phe  Val  Leu  Glu
              2195                2200                2205

Tyr  Asn  Thr  Ala  Leu  Phe  Lys  Pro  Glu  Thr  Ala  Glu  Thr  Trp  Lys
              2210                2215                2220

His  Tyr  Trp  Leu  Gln  Leu  Leu  Lys  Ala  Ala  Thr  Glu  Asn  Pro  Ala
              2225                2230                2235

Ala  Lys  Leu  Ser  Glu  Leu  Ser  Leu  Val  Asn  Glu  Thr  Glu  Lys  Gln
              2240                2245                2250

Ala  Leu  Leu  Asp  Ala  Trp  Lys  Gly  Lys  Thr  Leu  Ser  Val  Pro  Gln
              2255                2260                2265

Asp  Lys  Thr  Val  His  Arg  Leu  Phe  Glu  Glu  Thr  Ala  Ala  Arg  Tyr
              2270                2275                2280

Ala  Asn  Arg  Pro  Ala  Ala  Ala  Tyr  Asn  Gly  Ala  Lys  Trp  Thr  Tyr
              2285                2290                2295
```

```
Gly Glu Leu Asn Ala Arg Ala Asn Arg Ile Ala Arg Ile Leu Ile
    2300            2305               2310

Asp Cys Gly Val Thr Ala Asp Glu Arg Val Gly Ile Leu Thr Lys
    2315            2320               2325

Pro Ser Leu Glu Met Ala Ala Gly Val Leu Gly Val Leu Lys Ala
    2330            2335               2340

Gly Ala Ala Phe Val Pro Ile Asp Pro Asp Tyr Pro Gln Glu Arg
    2345            2350               2355

Ile Ser Tyr Ile Leu Gln Asp Ser Gly Ala Lys Leu Leu Leu Thr
    2360            2365               2370

Gln Glu Ala Leu Asp Val Pro Asp Gly Tyr Thr Gly Glu Thr Ile
    2375            2380               2385

Leu Leu Asp Gly Gly Arg Ser Ile Leu Ser Leu Pro Leu Asp Glu
    2390            2395               2400

Asn Asp Glu Ala Asn Pro Gln Thr Glu Thr Thr Ala Asp His Leu
    2405            2410               2415

Ala Tyr Met Ile Tyr Thr Ser Gly Thr Thr Gly Gln Pro Lys Gly
    2420            2425               2430

Val Met Val Glu His His Ala Leu Val Asn Leu Cys Phe Trp His
    2435            2440               2445

His Asp Ala Phe Ala Met Thr Ala Asp Asp Lys Ser Ala Lys Tyr
    2450            2455               2460

Ala Gly Phe Gly Phe Asp Ala Ser Ile Trp Glu Met Phe Pro Thr
    2465            2470               2475

Trp Thr Ile Gly Ala Glu Leu His Val Ile Asp Glu Ala Ile Arg
    2480            2485               2490

Leu Asp Ile Thr Arg Leu Asn His Tyr Phe Glu Glu His Gly Val
    2495            2500               2505

Thr Ile Thr Phe Leu Pro Thr Gln Leu Ala Glu Gln Phe Met Glu
    2510            2515               2520

Leu Glu Asn Thr Ser Leu Arg Met Leu Leu Val Gly Gly Asp Lys
    2525            2530               2535

Leu Lys Arg Ala Val Lys Gln Pro Tyr Thr Ile Val Asn Asn Tyr
    2540            2545               2550

Gly Pro Thr Glu Asn Thr Val Val Ala Thr Ser Gly Val Ile Asn
    2555            2560               2565

Pro Glu Glu Gly Ser Leu Ser Ile Gly Arg Ala Ile Ala Asn Thr
    2570            2575               2580

Arg Ala Tyr Ile Leu Gly Asp Gly Asp Gln Val Gln Pro Glu Gly
    2585            2590               2595

Ile Ala Gly Glu Leu Cys Val Ala Gly Arg Gly Leu Ala Arg Gly
    2600            2605               2610

Tyr Leu Asn Arg Glu Glu Glu Thr Ala Lys Arg Phe Thr Ala Asp
    2615            2620               2625

Pro Phe Val Pro Gly Glu Arg Met Tyr Arg Thr Gly Asp Leu Val
    2630            2635               2640

Lys Trp Asn Ala Gln Ser Gly Ile Glu Tyr Ile Gly Arg Ile Asp
    2645            2650               2655

Gln Gln Val Lys Val Arg Gly Tyr Arg Ile Glu Leu Ser Glu Ile
    2660            2665               2670

Glu Val Arg Leu Ala Gln Leu Ala Asp Val His Asp Ala Ala Val
    2675            2680               2685
```

-continued

Thr Ala Val Glu Asp Lys Ala Gly Asn Ala Ala Leu Cys Ala Tyr
2690                2695                2700

Val Ala Pro Gln Gln Asp Asp Ile Glu Ala Leu Lys Ala Ala Leu
2705                2710                2715

Lys Asp Thr Leu Pro Asp Tyr Met Val Pro Ala Phe Trp Val Glu
2720                2725                2730

Met Asp Glu Leu Pro Val Thr Ala Asn Gly Lys Ile Asp Lys Lys
2735                2740                2745

Ala Leu Pro Glu Pro Asp Ile Glu Ala Gly Ser Ala Ala Tyr Lys
2750                2755                2760

Ala Pro Glu Thr Glu Met Glu Thr Leu Leu Ser Asp Ile Trp Glu
2765                2770                2775

Glu Val Leu Gly Leu Asp Gln Ile Gly Val Ser Asp Asn Phe Phe
2780                2785                2790

Thr Leu Gly Gly Asp Ser Ile Lys Gly Ile Gln Met Ala Ser Arg
2795                2800                2805

Leu Asn Gln His Gly Tyr Lys Leu Glu Met Lys Asp Leu Phe Gln
2810                2815                2820

His Pro Thr Ile Glu Glu Leu Val Ser Tyr Val Glu Arg Thr Glu
2825                2830                2835

Gly Lys Gln Ala Asp Gln Gly Pro Val Glu Gly Lys Ala Glu Leu
2840                2845                2850

Thr Pro Ile Gln Arg Trp Phe Phe Glu Lys Asn Phe Thr Asp Lys
2855                2860                2865

His His Trp Asn Gln Ser Val Met Leu His Ala Lys Asp Gly Phe
2870                2875                2880

Asp Pro Glu Ile Thr Glu Lys Thr Leu His Val Leu Thr Val His
2885                2890                2895

His Asp Ala Leu Arg Met Ile Tyr Arg Glu Gln Lys Pro Tyr Tyr
2900                2905                2910

Arg Gly Leu Glu Asp Ala Ser Val Glu Leu Asn Val Phe Glu Leu
2915                2920                2925

Asn Gly Pro Ala Glu Asp His Glu Asn Arg Ile Glu Arg Glu Ala
2930                2935                2940

Asp Arg Leu Gln Ser Ser Ile Ser Leu Glu Thr Gly His Leu Leu
2945                2950                2955

Lys Ala Gly Leu Phe Arg Ala Glu Asp Gly Asp His Leu Leu Leu
2960                2965                2970

Ala Ile His His Leu Val Val Asp Gly Val Ser Trp Arg Ile Leu
2975                2980                2985

Leu Glu Asp Phe Thr Ser Val Tyr Thr Gln Leu Lys Gln Gly Asn
2990                2995                3000

Glu Pro Ala Leu Pro Pro Lys Thr His Ser Phe Ala Glu Phe Ala
3005                3010                3015

Glu Arg Ile Lys Glu Tyr Ala Asn Thr Lys Ala Phe Leu Lys Glu
3020                3025                3030

Ala Asp Tyr Trp Arg Glu Leu Glu Glu Lys Glu Val Cys Thr Gln
3035                3040                3045

Leu Pro Lys Asp Arg Gln Ser Gly Asp Gln Arg Met Arg His Thr
3050                3055                3060

Arg Thr Val Ser Phe Ser Leu Thr Pro Glu Gln Thr Glu Gln Leu
3065                3070                3075

Thr Thr Asn Val His Glu Ala Tyr His Thr Glu Met Asn Asp Ile

```
                    3080              3085              3090
Leu Leu Thr Ala Leu Gly Leu Ala Leu Lys Glu Trp Thr Gly Glu
        3095              3100              3105
Asp Thr Ile Gly Val His Leu Glu Gly His Gly Arg Glu Asp Ile
        3110              3115              3120
Leu Asp Gly Leu Asn Ile Thr Arg Thr Val Gly Trp Phe Thr Ser
        3125              3130              3135
Met Tyr Pro Met Ile Leu Glu Met Lys His Ala Asp Asp Leu Ser
        3140              3145              3150
Tyr Gln Leu Lys Gln Met Lys Glu Asp Ile Arg His Ile Pro Asn
        3155              3160              3165
Lys Gly Val Gly Tyr Gly Ile Leu Arg Tyr Val Thr Ala Pro Glu
        3170              3175              3180
His Lys Glu Gly Leu Ser Phe Glu Ile Asp Pro Asp Ile Ser Phe
        3185              3190              3195
Asn Tyr Leu Gly Gln Phe Asn Glu Met Ser Asp Ser Gly Leu Phe
        3200              3205              3210
Thr Arg Ser Gly Met Pro Ser Gly Gln Ser Leu Ser Pro Asp Thr
        3215              3220              3225
Glu Lys Pro Asn Ala Leu Asp Ile Val Gly Phe Ile Glu Asn Gly
        3230              3235              3240
Gln Met Thr Met Thr Phe Ala Tyr His Ser Leu Glu Phe His Glu
        3245              3250              3255
Lys Thr Ile Gln Ser Phe Ser Asp Ser Phe Lys Gly His Leu Leu
        3260              3265              3270
Lys Ile Ile Leu Thr Leu Asp Glu Leu Asp Lys Leu Met Glu Ile
        3275              3280              3285
Leu

<210> SEQ ID NO 14
<211> LENGTH: 3586
<212> TYPE: PRT
<213> ORGANISM: Bacillus subtilis

<400> SEQUENCE: 14

Met Ser Lys Lys Ser Ile Gln Lys Val Tyr Ala Leu Thr Pro Met Gln
1               5                   10                  15
Glu Gly Met Leu Tyr His Ala Leu Leu Asp Pro His Ser Ser Ser Tyr
                20                  25                  30
Phe Thr Gln Leu Glu Leu Arg Ile His Gly Ser Phe Gln Leu Glu Leu
        35                  40                  45
Phe Glu Lys Ser Val Asn Glu Leu Ile Arg Thr Tyr Asp Ile Leu Arg
    50                  55                  60
Thr Val Phe Val His Gln Gln Leu Gln Lys Pro Arg Gln Val Val Leu
65                  70                  75                  80
Ala Glu Arg Lys Thr Lys Val Tyr Glu Asp Ile Ser Gln Leu Asp
                85                  90                  95
Glu Ala Arg Gln Thr Glu Tyr Ile Glu Arg Tyr Lys Arg Asp Val Gln
            100                 105                 110
Gln Gln Gly Phe His Leu Ala Lys Asp Ile Leu Phe Lys Ala Ala Val
        115                 120                 125
Phe Arg Leu Ser Glu Lys Glu Leu Tyr Leu Val Trp Ser Asn His His
    130                 135                 140
Ile Val Met Asp Gly Trp Ser Met Gly Val Leu Met Lys Ser Leu Phe
```

```
            145                 150                 155                 160
        Gln Asn Tyr Glu Ala Leu Arg Ala Gly Arg Pro Ala Gly Gly Ser Gln
                        165                 170                 175
        Gly Lys Pro Tyr Ser Asp Tyr Ile Lys Trp Leu Gly Gly Arg Asp Tyr
                        180                 185                 190
        Glu Glu Ala Glu Gln Tyr Trp Ser Arg Leu Ala Asp Phe Glu Gln
                        195                 200                 205
        Pro Ser Leu Leu Pro Gly Arg Leu Ala Pro Glu Lys Lys Asp Tyr Gln
                        210                 215                 220
        Asn Glu Glu Tyr Ser Phe Val Trp Asp Glu Glu Leu Val Ala Gln Ile
        225                 230                 235                 240
        Gln Gln Thr Ala Asn Arg His Gln Val Thr Gly Pro Asn Leu Phe Gln
                        245                 250                 255
        Ala Val Trp Gly Ala Val Leu Ser Lys Tyr Asn Tyr Thr Asp Asp Val
                        260                 265                 270
        Val Phe Gly Thr Val Ser Gly Arg Pro Ser Glu Ile Asn Gly Ile
                        275                 280                 285
        Glu Thr Met Ala Gly Leu Phe Ile Asn Thr Ile Pro Val Arg Ile Lys
                        290                 295                 300
        Ile Asp Lys Asp Ala Ala Phe Ser Asp Val Met Ala Ala Val Gln Lys
        305                 310                 315                 320
        Asn Ala Val Glu Ala Glu Arg Tyr Asp Tyr Val Pro Leu Tyr Asp Ile
                        325                 330                 335
        Gln Lys Arg Ser Ala Leu Asp Gly Ser Leu Leu Asn His Leu Val Ala
                        340                 345                 350
        Phe Glu Asn Tyr Pro Leu Asp Lys Glu Leu Glu Asn Gly Gly Met Glu
                        355                 360                 365
        Glu Arg Leu Gly Phe Ser Ile Lys Val Glu His Ala Phe Glu Gln Thr
                        370                 375                 380
        Ser Phe Asp Phe Asn Leu Ile Val Tyr Pro Gly Lys Thr Trp Thr Val
        385                 390                 395                 400
        Lys Ile Lys Tyr Asn Gly Ala Ala Phe Ala His Asp Ala Ile Glu Arg
                        405                 410                 415
        Thr Ala His His Leu Thr Cys Met Met Lys Ala Ala Val Gly Thr Pro
                        420                 425                 430
        Asp Ala Pro Val Arg Glu Leu Gly Leu Val Ser Gly Glu Glu Arg
                        435                 440                 445
        Gln Ile Val Glu Ile Phe Asn Asp Thr Lys Thr Ala Leu Pro Glu Glu
                        450                 455                 460
        Glu Ala Val His Arg Leu Phe Glu Ala Gln Ala Asn Arg Thr Pro Ala
        465                 470                 475                 480
        Ser Ile Ala Ile Lys Glu Ala Gly Arg Glu Trp Thr Tyr Arg Glu Val
                        485                 490                 495
        Asn Glu Ala Ala Asn Arg Leu Ala Arg His Phe Val Lys Ser Gly Leu
                        500                 505                 510
        Glu Lys Gly Arg Thr Ala Ala Ile Met Asn Asp Arg Ser Ala Glu Thr
                        515                 520                 525
        Val Ile Gly Met Leu Ala Val Leu Lys Ala Gly Gly Ala Tyr Val Pro
                        530                 535                 540
        Ile Asp Pro Ala Phe Pro Glu Asp Arg Leu Arg Phe Met Ala Glu Asp
        545                 550                 555                 560
        Ser Ser Ile Arg Leu Val Leu Thr Val Gln Asp Tyr Gln Glu Gln Ala
                        565                 570                 575
```

-continued

```
Gly Thr Leu Gln Val Pro Ile Val Met Leu Asp Glu Ser Glu Asp Glu
            580                 585                 590

Thr Leu Ser Gly Thr Asp Leu Asn Leu Pro Ala Gly Gly Asn Asp Leu
        595                 600                 605

Ala Tyr Ile Met Tyr Thr Ser Gly Ser Thr Gly Lys Pro Lys Gly Val
    610                 615                 620

Met Ile Glu His Arg Asn Ile Ile Arg Leu Val Lys His Ser Asn Tyr
625                 630                 635                 640

Val Pro Val His Glu Glu Asp Arg Met Ala Gln Thr Gly Ala Val Ser
                645                 650                 655

Phe Asp Ala Gly Thr Phe Glu Val Phe Gly Ala Leu Leu Asn Gly Ala
            660                 665                 670

Ala Leu His Pro Val Lys Lys Glu Thr Leu Leu Asp Ala Gly Arg Phe
        675                 680                 685

Ala Gln Phe Leu Lys Glu Gln Arg Ile Thr Thr Met Trp Leu Thr Ser
    690                 695                 700

Pro Leu Phe Asn Gln Leu Ala Gln Lys Asp Ala Gly Met Phe Asn Thr
705                 710                 715                 720

Leu Arg His Leu Ile Ile Gly Gly Asp Ala Leu Val Pro His Ile Val
                725                 730                 735

Ser Lys Val Arg Lys Ala Ser Pro Glu Leu Ser Leu Trp Asn Gly Tyr
            740                 745                 750

Gly Pro Thr Glu Asn Thr Thr Phe Ser Thr Ser Phe Leu Ile Asp Gln
        755                 760                 765

Asp Tyr Asp Gly Ser Ile Pro Ile Gly Lys Pro Ile Gly Asn Ser Thr
    770                 775                 780

Ala Tyr Ile Met Asp Glu Asn Arg Asn Leu Gln Pro Ile Gly Ala Pro
785                 790                 795                 800

Gly Glu Leu Cys Val Gly Gly Ser Gly Val Ala Arg Gly Tyr Val Asn
                805                 810                 815

Leu Pro Glu Leu Thr Glu Lys Gln Phe Val Arg Asp Pro Phe Arg Pro
            820                 825                 830

Asp Glu Met Ile Tyr Arg Thr Gly Asp Leu Ala Lys Trp Leu Pro Asp
        835                 840                 845

Gly Thr Ile Glu Phe Leu Gly Arg Ile Asp Asn Gln Val Lys Val Arg
    850                 855                 860

Gly Phe Arg Ile Glu Leu Gly Glu Ile Glu Ala Lys Ile Ser Gln Ala
865                 870                 875                 880

Glu Asn Val Thr Glu Ser Ala Ala Val Ile Arg Lys Asn Lys Ala Asp
                885                 890                 895

Glu Asn Glu Ile Cys Ala Tyr Phe Thr Ala Asp Gln Ala Leu Ser Pro
            900                 905                 910

Glu Asp Leu Arg Lys Thr Leu Ser Glu Ser Leu Pro Glu Tyr Met Ile
        915                 920                 925

Pro Ala His Phe Ile Gln Met Asn Gln Phe Pro Leu Thr Ala Asn Gly
    930                 935                 940

Lys Ile Asp Lys Lys Ala Leu Pro Glu Pro Gln Ala Glu Ala Val Gln
945                 950                 955                 960

Lys Glu Tyr Glu Ala Pro Lys Thr Glu Ala Glu Gln Lys Leu Ala Asp
                965                 970                 975

Ile Trp Glu Gly Ile Leu Gly Val Lys Ala Gly Val Thr Asp Asn Phe
            980                 985                 990
```

```
Phe Thr Ile Gly Gly His Ser Leu Lys Ala Met Met Met Thr Ala Lys
            995                 1000                1005

Ile Gln Glu His Phe Gln Lys Glu Val Pro Ile Lys Val Leu Phe
    1010                1015                1020

Glu Lys Pro Thr Ile Gln Glu Leu Ala His Tyr Leu Glu His Glu
    1025                1030                1035

Thr Glu Glu Glu Gln Gln Phe Glu Pro Ile Arg Gln Ala Pro Tyr
    1040                1045                1050

Gln Lys His Tyr Pro Val Ser Ser Ala Gln Arg Arg Met Tyr Ile
    1055                1060                1065

Leu Asn Gln Leu Gly Gln Ala Ser Thr Ser Tyr Asn Val Pro Ala
    1070                1075                1080

Val Leu Leu Leu Glu Gly Ser Val Asp Lys Asn Arg Leu Glu Glu
    1085                1090                1095

Ala Met Gln Ala Leu Ile Asn Arg His Glu Thr Leu Arg Thr Ser
    1100                1105                1110

Phe Asp Met Ala Asp Gly Glu Val Val Gln Thr Ile His Lys Asn
    1115                1120                1125

Val Ser Phe Glu Leu Glu Thr Ala Glu Gly Arg Glu Glu Asp Ala
    1130                1135                1140

Glu Glu Leu Thr Lys Ala Phe Ile Arg Pro Phe Ala Leu Asn Arg
    1145                1150                1155

Ala Pro Leu Val Arg Ser Lys Leu Ile Arg Leu Glu Glu Asp Arg
    1160                1165                1170

His Leu Leu Leu Ile Asp Met His His Ile Ile Thr Asp Gly Ser
    1175                1180                1185

Ser Met Gly Ile Phe Ile Gly Asp Leu Ala Lys Leu Tyr Gln Gly
    1190                1195                1200

Thr Glu Leu Glu Leu Pro Lys Ile His Tyr Lys Asp Phe Ser Val
    1205                1210                1215

Trp Gln Arg Glu Lys Ala Asn Leu Asp Gln His Glu Ala Tyr Trp
    1220                1225                1230

Leu Asp Thr Phe Lys Gly Asp Leu Pro Val Leu Asp Leu Pro Leu
    1235                1240                1245

Asp Phe Pro Arg Pro Ala Glu Arg Ser Phe Glu Gly Glu Arg Val
    1250                1255                1260

Ile Phe Gly Leu Asp Lys Gln Val Thr Ala Gln Ile Lys Lys Leu
    1265                1270                1275

Leu Ala Asp Thr Asp Thr Thr Met Tyr Met Phe Leu Leu Ala Ala
    1280                1285                1290

Phe Gln Val Leu Leu Ser Lys Tyr Ser Gly Gln Glu Asp Ile Ile
    1295                1300                1305

Val Gly Ser Pro Ala Ala Gly Arg Gln His Pro Asp Leu Gln Asp
    1310                1315                1320

Val Pro Gly Met Phe Val Asn Thr Val Ala Leu Arg Ser His Pro
    1325                1330                1335

Ala Gly Lys Lys Thr Phe Lys Gln Phe Leu Asp Glu Val Lys Thr
    1340                1345                1350

Ala Ser Leu Gln Ala Phe Glu His Gln Ser Tyr Pro Leu Glu Glu
    1355                1360                1365

Leu Ile Glu Lys Leu Pro Leu Thr Arg Asp Thr Ser Arg Ser Pro
    1370                1375                1380

Leu Phe Ser Val Leu Phe Asn Met Gln Asn Met Glu Ile Pro Ala
```

-continued

```
            1385                1390                1395

Leu Arg Leu Gly Asp Leu Glu Ile Ser Ser Tyr Ser Met His His
        1400                1405                1410

His Val Ala Lys Phe Asp Leu Ser Leu Glu Ala Ala Glu Arg Gly
        1415                1420                1425

Glu Glu Val Gly Leu Ser Phe Asp Tyr Ala Lys Ala Leu Phe Ala
        1430                1435                1440

Asp Glu Thr Ile Arg Arg Trp Ser Ala His Phe Val Asn Leu Ile
        1445                1450                1455

Lys Ala Cys Ala Glu Asn Pro Asp Ile Gln Leu Ala Asp Ala Ser
        1460                1465                1470

Leu Leu Ser Ala Pro Glu Arg Glu Ala Leu Leu Ser Asp Glu Lys
        1475                1480                1485

Arg Thr Glu Ala Asp Leu Pro Glu Gly Thr Phe Val Ser Leu Phe
        1490                1495                1500

Glu Arg Gln Ala Gln Lys Thr Pro Asp Leu Thr Ala Val Ala Gly
        1505                1510                1515

Gly Thr Ser Leu Thr Tyr Arg Glu Leu Asp Glu Arg Ser Asn Arg
        1520                1525                1530

Phe Ala Arg His Leu Gln Ala Cys Gly Thr Gly Ser Glu Asp Ile
        1535                1540                1545

Val Ala Ile Met Met Asp Arg Ser Ala Asp Leu Ile Thr Ala Ile
        1550                1555                1560

Leu Gly Val Met Lys Ala Gly Ala Ala Phe Leu Pro Ile Asp Pro
        1565                1570                1575

Glu Thr Pro Glu Glu Arg Ile Arg Tyr Ser Leu Glu Asp Ser Gly
        1580                1585                1590

Thr Lys Leu Leu Val Val Asn Glu Arg Asn Met Thr Ala Ala Ala
        1595                1600                1605

Val Tyr Lys Glu Lys Thr Val Val Met Glu Asp Gly Glu Trp Gln
        1610                1615                1620

Asn Glu Ser Ala Asp Arg Leu Glu Thr Glu Pro Gly Ala Asp Arg
        1625                1630                1635

Leu Ala Tyr Ile Ile Tyr Thr Ser Gly Thr Thr Gly Lys Pro Lys
        1640                1645                1650

Gly Val Gln Leu Glu His Arg Asn Leu Ile Asn Tyr Val Thr Trp
        1655                1660                1665

Phe Ser Arg Glu Ala Gly Leu Thr Glu Ala Asp Lys Ser Val Leu
        1670                1675                1680

Leu Ser Ser Tyr Ala Phe Asp Leu Gly Tyr Thr Ala Ile Phe Pro
        1685                1690                1695

Ile Leu Gln Ala Gly Gly Glu Leu His Ile Val Pro Lys Glu Thr
        1700                1705                1710

Tyr Thr Ala Pro Asp Gln Leu Gly Glu Tyr Ile Gln Lys Asn Gly
        1715                1720                1725

Ile Thr Tyr Met Lys Leu Thr Pro Ser Leu Phe His Met Ile Val
        1730                1735                1740

Asn Thr Ala Arg Phe Thr Ser Glu Cys Arg Phe Ser Pro Leu Arg
        1745                1750                1755

Leu Val Val Leu Gly Gly Glu Lys Ile Ile Thr Ser Asp Val Arg
        1760                1765                1770

Lys Phe His Asp Val Tyr Ala His Thr Asp Phe Ile Asn His Tyr
        1775                1780                1785
```

```
Gly Pro Thr Glu Thr Thr Ile Gly Ala Ile Ala Glu Arg Ile Asn
    1790            1795                1800

Met Glu Cys Leu Asp Gln Tyr Glu Gln Arg Pro Val Ile Gly Arg
    1805            1810                1815

Pro Ile Ala Asn Thr Gly Ala Leu Val Leu Asp Gly Ala Met Gln
    1820            1825                1830

Leu Val Pro Pro Gly Ala Ser Gly Glu Leu Tyr Ile Thr Gly Lys
    1835            1840                1845

Gly Leu Ala Arg Gly Tyr Leu His Arg Pro Gln Leu Thr Ala Glu
    1850            1855                1860

Lys Phe Leu Ser Asn Pro Phe Ser Pro Asp Ser Leu Met Tyr Lys
    1865            1870                1875

Thr Gly Asp Ile Val Arg Arg Leu Pro Asp Gly Thr Ile Glu Phe
    1880            1885                1890

Ile Gly Arg Ala Asp Asp Gln Val Lys Ile Arg Gly Tyr Arg Ile
    1895            1900                1905

Glu Leu Lys Glu Val Glu Thr Val Leu Leu Ser Val Asn Gly Ile
    1910            1915                1920

Gln Glu Ala Val Val Leu Ala Val Ser Glu Gly Gly Leu Pro Glu
    1925            1930                1935

Leu Cys Ala Tyr Tyr Lys Ala Asp Ser Gly Leu Lys Gly Ser Glu
    1940            1945                1950

Leu Arg Lys Arg Leu Ser Glu Thr Leu Pro Ser His Met Leu Pro
    1955            1960                1965

Ala Tyr Phe Val Gln Val Asp Arg Ile Pro Leu Thr Ala Asn Gly
    1970            1975                1980

Lys Thr Asp Lys Asn Ala Leu Pro Lys Pro Gly Val Ser Gln Thr
    1985            1990                1995

Ala Gln Ile Ala Ser Ala Leu Pro Glu Thr Glu Leu Glu Glu Lys
    2000            2005                2010

Leu Cys Arg Ile Trp Lys Gln Thr Leu Gly Thr Asp Thr Leu Gly
    2015            2020                2025

Ile Asp Asp Asn Phe Phe Asp Tyr Gly Gly His Ser Leu Lys Gly
    2030            2035                2040

Met Met Leu Leu Ala Asn Ile Gln Ala Glu Leu Asp Lys Thr Val
    2045            2050                2055

Pro Leu Lys Ala Leu Phe Glu Gln Pro Thr Val Arg Leu Leu Ala
    2060            2065                2070

Ala Tyr Ile Glu Lys Ser Ala Val Ser Glu Gly Tyr Arg Met Ile
    2075            2080                2085

Thr Pro Ala Asp Ser Ala Asp Ala Tyr Pro Leu Ser Ser Ala Gln
    2090            2095                2100

Lys Arg Met Tyr Val Leu Asn Gln Leu Asp Arg Glu Thr Ile Ser
    2105            2110                2115

Tyr Asn Met Pro Ser Val Leu Leu Met Glu Gly Glu Val Asn Ile
    2120            2125                2130

Ser Lys Leu Gln Glu Ala Leu Asn Gln Met Ile Asn Arg His Glu
    2135            2140                2145

Ser Leu Arg Thr Ser Phe Ile Asp Lys Lys Gly Gln Pro Met Gln
    2150            2155                2160

Gln Ile Ala Glu Gln Ala Asp Ile Asp Leu His Ile Phe Glu Ala
    2165            2170                2175
```

```
Ala Asp Glu Glu Lys Ala Asp Leu Ile Ile Gln Ala Phe Ile Lys
2180                2185                2190

Pro Phe Asp Leu Ser Ala Ala Pro Leu Ile Arg Ala Ala Leu Val
2195                2200                2205

Arg Leu Asn Glu Lys Lys His Leu Leu Leu Leu Asp Met His His
2210                2215                2220

Ile Ile Ala Asp Gly Val Ser Arg Ser Met Leu Val Lys Glu Leu
2225                2230                2235

Ala His Leu Tyr Lys Gly Gly Ser Leu Pro Ser Pro Asn Leu His
2240                2245                2250

Tyr Lys Asp Phe Ala Val Trp Gln Asn Glu Pro Glu Gln Ala Glu
2255                2260                2265

Arg Met Lys Asp His Glu Arg Tyr Trp Leu Ser Ala Phe Ser Gly
2270                2275                2280

Glu Leu Pro Glu Leu Asn Leu Pro Thr Asp Phe Pro Arg Pro Pro
2285                2290                2295

Val Gln Ser Phe Lys Gly Gln Ser Val Arg Phe Arg Ala Gly Arg
2300                2305                2310

Glu Thr Glu Lys Ala Val Arg Glu Leu Met Glu Ser Ser Gly Ala
2315                2320                2325

Thr Leu His Met Val Leu His Ala Ala Phe His Val Phe Leu Ser
2330                2335                2340

Lys Ile Thr Gly Gln Arg Asp Ile Ile Ile Gly Ser Val Thr Ala
2345                2350                2355

Gly Arg Thr Ser Ala Glu Val Gln Glu Met Pro Gly Met Phe Val
2360                2365                2370

Asn Thr Leu Ala Leu Arg Asn Glu Thr Gln Lys Glu Gln Thr Phe
2375                2380                2385

Ala Gly Leu Leu Glu Arg Val Lys Gln Thr Asn Leu Asp Ala Leu
2390                2395                2400

Ala His Gln Asp Tyr Pro Phe Glu Asp Leu Ile Gly Lys Leu Asp
2405                2410                2415

Leu Pro Arg Asp Met Ser Arg Asn Pro Leu Phe Gln Val Met Val
2420                2425                2430

Thr Thr Glu Asp Pro Asp Lys Glu Thr Leu Glu Leu Glu Asn Leu
2435                2440                2445

Arg Ile Thr Pro Tyr Glu Ser Asn Gln Gly Thr Ala Lys Phe Asp
2450                2455                2460

Leu Thr Leu Gly Gly Phe Thr Asp Gln Glu Gly Leu Gly Leu Gln
2465                2470                2475

Phe Glu Tyr Ala Thr Asp Leu Phe Lys Lys Glu Thr Ile Glu Lys
2480                2485                2490

Trp Ser Ala Gly Phe Leu Arg Ile Leu Lys Gln Ala Ala Glu Ser
2495                2500                2505

Pro Asp Arg Lys Leu Pro Glu Ile Ser Leu Ile Ser Asp Ala Glu
2510                2515                2520

Lys Gln Ala Leu Leu Asp Ala Trp Lys Gly Lys Thr Leu Ser Val
2525                2530                2535

Pro Gln Asp Lys Thr Val His Arg Leu Phe Glu Glu Thr Ala Ala
2540                2545                2550

Arg Tyr Ala Asn Arg Pro Ala Ala Tyr Asn Gly Ala Lys Trp
2555                2560                2565

Thr Tyr Gly Glu Leu Asn Ala Arg Ala Asn Arg Ile Ala Arg Ile
```

```
            2570              2575              2580

Leu Ile Asp Cys Gly Val Thr Ala Asp Glu Arg Val Gly Ile Leu
    2585              2590              2595

Thr Lys Pro Ser Leu Glu Met Ala Ala Gly Val Leu Gly Val Leu
    2600              2605              2610

Lys Ala Gly Ala Ala Phe Val Pro Ile Asp Pro Asp Tyr Pro Gln
    2615              2620              2625

Glu Arg Ile Ser Tyr Ile Leu Gln Asp Ser Gly Ala Lys Leu Leu
    2630              2635              2640

Leu Thr Gln Glu Ala Leu Asp Val Pro Glu Ser Tyr Lys Gly Glu
    2645              2650              2655

Thr Ile Leu Leu Asp Gly Gly Arg Ser Ile Leu Ser Leu Pro Leu
    2660              2665              2670

Asp Glu Asn Asp Glu Ala Asn Pro Gln Thr Glu Thr Thr Ala Asp
    2675              2680              2685

His Leu Ala Tyr Met Ile Tyr Thr Ser Gly Thr Thr Gly Gln Pro
    2690              2695              2700

Lys Gly Val Met Val Glu His His Ala Leu Val Asn Leu Cys Phe
    2705              2710              2715

Trp His His Asp Ala Phe Ala Met Thr Ala Asp Asp Lys Ser Ala
    2720              2725              2730

Lys Tyr Ala Gly Phe Gly Phe Asp Ala Ser Ile Trp Glu Met Phe
    2735              2740              2745

Pro Thr Trp Thr Ile Gly Ala Glu Leu His Val Ile Asp Glu Ala
    2750              2755              2760

Ile Arg Leu Asp Ile Thr Arg Leu Asn His Tyr Phe Glu Glu His
    2765              2770              2775

Gly Val Thr Ile Thr Phe Leu Pro Thr Gln Leu Ala Glu Gln Phe
    2780              2785              2790

Met Glu Leu Glu Asn Thr Ser Leu Arg Met Leu Leu Val Gly Gly
    2795              2800              2805

Asp Lys Leu Lys Arg Ala Val Lys Gln Pro Tyr Thr Ile Val Asn
    2810              2815              2820

Asn Tyr Gly Pro Thr Glu Asn Thr Val Val Ala Thr Ser Gly Val
    2825              2830              2835

Ile Asn Pro Glu Glu Gly Ser Leu Ser Ile Gly Arg Ala Ile Ala
    2840              2845              2850

Asn Thr Arg Ala Tyr Ile Leu Gly Asp Gly Asp Gln Val Gln Pro
    2855              2860              2865

Glu Gly Ile Ala Gly Glu Leu Cys Val Ala Gly Arg Gly Leu Ala
    2870              2875              2880

Arg Gly Tyr Leu Asn Arg Glu Glu Thr Ala Lys Arg Phe Thr
    2885              2890              2895

Ala Asp Pro Phe Val Pro Gly Glu Arg Met Tyr Arg Thr Gly Asp
    2900              2905              2910

Leu Val Lys Trp Asn Ala Gln Ser Gly Ile Glu Tyr Ile Gly Arg
    2915              2920              2925

Ile Asp Gln Gln Val Lys Val Arg Gly Tyr Arg Ile Glu Leu Ser
    2930              2935              2940

Glu Ile Glu Val Arg Leu Ala Gln Leu Ala Asp Val His Asp Ala
    2945              2950              2955

Ala Val Thr Ala Val Glu Asp Lys Ala Gly Asn Ala Ala Leu Cys
    2960              2965              2970
```

```
Ala Tyr Val Ala Pro Arg Gln Asp Ile Glu Ala Leu Lys Ala
            2975            2980            2985

Ala Leu Lys Asp Thr Leu Pro Asp Tyr Met Val Pro Ala Phe Trp
            2990            2995            3000

Val Glu Met Asp Glu Leu Pro Val Thr Ala Asn Gly Lys Ile Asp
            3005            3010            3015

Lys Lys Ala Leu Pro Glu Pro Asp Ile Glu Ala Gly Ser Ala Ala
            3020            3025            3030

Tyr Lys Ala Pro Glu Thr Glu Met Glu Thr Leu Leu Ser Asp Ile
            3035            3040            3045

Trp Gln Glu Val Leu Gly Leu Asp Gln Ile Gly Val Ser Asp Asn
            3050            3055            3060

Phe Phe Thr Leu Gly Gly Asp Ser Ile Lys Gly Ile Gln Met Ala
            3065            3070            3075

Ser Arg Leu Asn Gln His Gly Tyr Lys Leu Glu Met Lys Asp Leu
            3080            3085            3090

Phe Gln His Pro Thr Ile Glu Glu Leu Val Ser Tyr Val Glu Arg
            3095            3100            3105

Thr Glu Gly Lys Gln Ala Asp Gln Gly Pro Val Glu Gly Glu Ala
            3110            3115            3120

Glu Leu Thr Pro Ile Gln Arg Trp Phe Phe Glu Lys Asn Phe Thr
            3125            3130            3135

Asp Lys His His Trp Asn Gln Ser Val Met Leu His Ala Lys Asp
            3140            3145            3150

Gly Phe Asp Pro Asp Leu Val Glu Lys Thr Leu Gln Ala Leu Ile
            3155            3160            3165

Glu His His Asp Ala Leu Arg Met Val Tyr Arg Glu Glu Arg Glu
            3170            3175            3180

Gly Ile Ile Gln Thr Tyr Leu Pro Val Thr Glu Cys Lys Ala Ser
            3185            3190            3195

Phe Glu Ile Val Asp Leu Tyr Gly Thr Asp Glu Asp Met Leu Lys
            3200            3205            3210

Ser Gln Ile Gln Arg Leu Ala Asp His Leu Gln Gly Ser Leu Asp
            3215            3220            3225

Leu Glu Asn Gly Pro Leu Leu Lys Ala Glu Gln Tyr Arg Thr Glu
            3230            3235            3240

Gln Gly Asp His Leu Leu Ile Ala Val His His Leu Val Val Asp
            3245            3250            3255

Gly Val Ser Trp Arg Ile Leu Leu Glu Asp Phe Ala Ser Gly Tyr
            3260            3265            3270

Lys Gln Ala Gln Gln Gln Asn Ser Ile Val Leu Pro Gln Lys Thr
            3275            3280            3285

His Ser Phe Lys Asp Trp Ala Glu Ala Leu Asn Thr Phe Ala Gln
            3290            3295            3300

Ser Glu Glu Leu Lys Lys Gln Ala Asp Tyr Trp Ala Gln Ala Asp
            3305            3310            3315

Ala Glu Glu Leu Arg Pro Leu Pro Lys Asp His Asp Pro Asp Lys
            3320            3325            3330

Arg Leu Val Lys His Thr Ala Ala Val Lys Cys Glu Leu Thr Glu
            3335            3340            3345

Glu Glu Thr Ala Gln Leu Leu Thr Asp Val His His Pro Tyr Gly
            3350            3355            3360
```

```
Thr Glu Ile Asn Asp Ile Leu Leu Ser Ala Leu Gly Leu Thr Ile
    3365                3370                3375

Gly Glu Trp Thr Glu Asn Gly Lys Val Gly Ile Asn Leu Glu Gly
3380                3385                3390

His Gly Arg Glu Glu Ile Ile Pro Asn Val Asn Ile Ser Arg Thr
    3395                3400                3405

Val Gly Trp Phe Thr Ala Gln Tyr Pro Leu Ile Leu Gln Ile Ser
    3410                3415                3420

Lys Glu Asp Gly Val Ser Ser Val Ile Lys Thr Val Lys Glu Thr
    3425                3430                3435

Val Arg Arg Val Pro Asp Lys Gly Val Gly Tyr Gly Ile Leu Arg
    3440                3445                3450

Tyr Leu Ser Ser Asp Glu Thr Glu Lys Gly Ala Ala Pro Glu Ile
    3455                3460                3465

Ser Phe Asn Tyr Leu Gly Gln Phe Asp Asn Glu Val Lys Thr Glu
    3470                3475                3480

Trp Phe Glu Pro Ser Pro Tyr Asp Met Gly Arg Gln Val Ser Glu
    3485                3490                3495

Glu Ser Glu Ala Leu Tyr Ala Leu Ser Phe Ser Gly Met Val Thr
    3500                3505                3510

Gly Gly Arg Phe Val Ile Ser Cys Ser Tyr Asn Gln Glu Glu Tyr
    3515                3520                3525

Glu Arg Ser Thr Val Glu Thr Gln Met Gln Arg Phe Lys Asp Asn
    3530                3535                3540

Leu Leu Met Ile Ile Arg His Cys Thr Ala Lys Glu Glu Lys Glu
    3545                3550                3555

Phe Thr Pro Ser Asp Phe Ser Ala Gln Asp Leu Glu Met Asp Glu
    3560                3565                3570

Met Gly Asp Ile Phe Asp Met Leu Glu Glu Asn Leu Thr
    3575                3580                3585

<210> SEQ ID NO 15
<211> LENGTH: 1277
<212> TYPE: PRT
<213> ORGANISM: Bacillus subtilis

<400> SEQUENCE: 15

Met Ser Gln Phe Lys Lys Asp Gln Val Gln Asp Met Tyr Tyr Leu Ser
1               5                   10                  15

Pro Met Gln Glu Gly Met Leu Phe His Thr Leu Leu Asn Pro Gly Gln
                20                  25                  30

Ser Phe Tyr Ile Glu Gln Met Thr Met Arg Val Lys Gly Ser Leu Asn
            35                  40                  45

Ile Lys Cys Leu Glu Glu Ser Met Asn Val Ile Met Asp Arg Tyr Asp
        50                  55                  60

Val Phe Arg Thr Val Phe Ile His Glu Lys Val Lys Arg Pro Val Gln
65                  70                  75                  80

Val Val Leu Lys Lys Arg Gln Phe Gln Ile Glu Glu Ile Asp Leu Thr
                85                  90                  95

His Leu Thr Gly Ser Glu Gln Ala Ser Lys Ile Asn Glu Tyr Lys Glu
            100                 105                 110

Gln Asp Lys Ile Lys Gly Phe Asp Leu Thr Arg Asp Ile Pro Met Arg
        115                 120                 125

Ala Ala Ile Phe Lys Lys Ser Glu Glu Ser Phe Glu Trp Val Trp Ser
    130                 135                 140
```

```
Tyr His His Ile Ile Leu Asp Gly Trp Cys Phe Gly Ile Val Val Gln
145                 150                 155                 160

Asp Leu Phe Lys Val Tyr Asn Ala Leu Arg Glu Gln Lys Pro Tyr Ser
            165                 170                 175

Leu Pro Pro Val Lys Pro Tyr Lys Asp Tyr Ile Lys Trp Leu Glu Lys
            180                 185                 190

Gln Asp Lys Gln Ala Ser Leu His Tyr Trp Arg Gly Tyr Leu Glu Asp
            195                 200                 205

Phe Glu Gly Gln Thr Thr Phe Ala Glu Gln Arg Lys Lys Gln Glu Asn
210                 215                 220

Gly Tyr Glu Pro Lys Glu Leu Leu Phe Ser Leu Pro Glu Ala Glu Thr
225                 230                 235                 240

Lys Ala Phe Thr Glu Leu Ala Lys Ser Gln His Thr Thr Leu Ser Thr
            245                 250                 255

Ala Leu Gln Ala Val Trp Ser Val Leu Ile Ser Arg Tyr Gln Gln Ser
            260                 265                 270

Gly Asp Leu Ile Phe Gly Thr Val Ser Gly Arg Pro Ala Glu Ile
            275                 280                 285

Lys Gly Val Glu His Met Val Gly Leu Phe Ile Asn Ala Val Pro Arg
290                 295                 300

Arg Val Lys Leu Ser Glu Asp Thr Thr Phe Asn Gly Leu Leu Lys Gln
305                 310                 315                 320

Leu Gln Glu Gln Ser Leu Glu Ser Glu Pro His Gln Tyr Val Pro Leu
            325                 330                 335

Tyr Asp Ile Gln Ser Gln Ala Asp Gln Pro Lys Leu Ile Asp His Ile
            340                 345                 350

Ile Val Phe Glu Asn Tyr Pro Leu Gln Asp Ala Lys Asn Glu Glu Asn
            355                 360                 365

Ser Glu Asn Gly Phe Asp Met Glu Asp Val His Val Phe Glu Lys Ser
370                 375                 380

Asn Tyr Asp Leu Asn Leu Met Ala Ser Pro Gly Asp Glu Met Leu Ile
385                 390                 395                 400

Lys Leu Ala Tyr Asn Gly Asn Val Phe Asp Glu Ala Phe Ile Leu Arg
            405                 410                 415

Leu Lys Ser Gln Leu Leu Thr Ala Ile Gln Gln Leu Ile Gln Lys Pro
            420                 425                 430

Asp Gln Pro Val Asn Thr Ile Arg Leu Val Asp Glu Lys Glu Arg Glu
            435                 440                 445

Leu Leu Leu Thr Gly Leu Asn Pro Pro Ala Glu Thr His Gln Ala Lys
            450                 455                 460

Pro Leu Thr Asp Trp Phe Lys Glu Ala Val Asn Val Asn Pro Asp Ala
465                 470                 475                 480

Pro Ala Leu Thr Tyr Ser Gly Gln Thr Leu Ser Tyr Arg Glu Leu Asp
            485                 490                 495

Glu Glu Ala Asn Arg Leu Ala Arg Arg Leu Gln Lys Gln Gly Ala Gly
            500                 505                 510

Lys Asp Thr Val Val Ala Leu Tyr Thr Lys Arg Ser Leu Glu Leu Val
            515                 520                 525

Ile Gly Ile Leu Gly Val Leu Lys Ala Gly Ala Ala Tyr Leu Pro Val
            530                 535                 540

Asp Pro Lys Leu Pro Glu Asp Arg Ile Ser Tyr Met Leu Thr Asp Ser
545                 550                 555                 560
```

```
Ala Ala Ala Cys Leu Leu Thr His Gln Glu Met Lys Glu Lys Ala Ala
            565                 570                 575

Gln Leu Pro Tyr Thr Gly Thr Thr Leu Ile Ile Asp Asp Gln Ala Arg
        580                 585                 590

Phe Glu Glu Gln Ala Ser Asp Pro Ala Ala Ile Asp Pro Asp Asp
    595                 600                 605

Pro Ala Tyr Ile Met Tyr Thr Ser Gly Thr Thr Gly Lys Pro Lys Gly
    610                 615                 620

Asn Ile Thr Thr His Ala Asn Ile Gln Gly Leu Val Lys His Val Asp
625                 630                 635                 640

Tyr Met Ala Phe Ser Glu Gln Asp Thr Phe Leu Ser Val Ser Asn Tyr
                645                 650                 655

Ala Phe Asp Ala Phe Thr Phe Asp Phe Tyr Ala Ser Ile Leu Asn Ala
            660                 665                 670

Ala Arg Leu Ile Ile Ala Asp Glu His Thr Leu Leu Asp Thr Glu Arg
        675                 680                 685

Leu Thr Asp Leu Ile Arg Gln Glu Asn Val Asn Val Met Phe Ala Thr
    690                 695                 700

Thr Ala Leu Phe Asn Leu Leu Thr Asp Ala Gly Glu Glu Trp Leu Lys
705                 710                 715                 720

Gly Leu Arg Cys Val Leu Phe Gly Gly Glu Arg Ala Ser Val Pro His
                725                 730                 735

Val Arg Lys Ala Leu Glu Ile Met Gly Pro Gly Lys Leu Ile Asn Cys
            740                 745                 750

Tyr Gly Pro Thr Glu Gly Thr Val Phe Ala Thr Ala His Val Val His
        755                 760                 765

Asp Ile Pro Asp Ser Ile Ser Ser Leu Pro Ile Gly Lys Pro Ile Ser
    770                 775                 780

Asn Ala Ser Ile Tyr Ile Leu Asn Gly Gln Asn Gln Leu Gln Pro Phe
785                 790                 795                 800

Gly Ala Val Gly Glu Leu Cys Ile Ser Gly Met Gly Val Ser Lys Gly
                805                 810                 815

Tyr Leu Asn Arg His Asp Leu Thr Lys Gln Thr Phe Ile Pro Asn Pro
            820                 825                 830

Phe Lys Pro Gly Glu Thr Leu Tyr Arg Thr Gly Asp Leu Ala Arg Trp
        835                 840                 845

Leu Pro Asp Glu Arg Leu Asn Thr Pro Gly Val Leu Thr Thr Arg Ser
    850                 855                 860

Asn Thr Arg His Arg Ile Glu Leu Glu Glu Ile Glu Lys Gln Leu Gln
865                 870                 875                 880

Glu Tyr Pro Gly Val Lys Asp Ala Val Val Val Ala Asp Arg His Glu
                885                 890                 895

Ser Gly Asp Ala Ser Ile Asn Ala Tyr Leu Val Asn Arg Thr Pro Leu
            900                 905                 910

Ser Ala Glu Asp Val Lys Arg His Leu Lys Lys Gln Leu Pro Ala Tyr
        915                 920                 925

Met Val Pro Gln Thr Phe Thr Phe Leu Glu Glu Leu Pro Leu Thr Thr
    930                 935                 940

Asn Gly Lys Val Asn Lys Arg Gln Leu Pro Lys Pro Asp Gln Ala Gln
945                 950                 955                 960

Ala Ala Lys Glu Trp Ile Gly Pro Arg Asn Ala Thr Glu Glu Thr Ile
                965                 970                 975

Ala His Ile Trp Ser Glu Ile Leu Gly Arg Gln Gln Ile Gly Ile His
```

Asp Asp Phe Phe Ala Leu Gly Gly His Ser Leu Lys Ala Met Thr Ala
            980             985                 990
    995                 1000                 1005

Ala Ser Arg Ile Lys Lys Glu Leu Gly Thr Asp Ile Pro Val Gln
    1010                 1015                 1020

Leu Leu Phe Glu Ala Thr Thr Ile Ala Asp Ile Ala Gly Tyr Leu
    1025                 1030                 1035

Leu His Gly Glu Glu Lys Gly Met Lys Asp Leu Thr Ile Met Asn
    1040                 1045                 1050

Lys Asn Gln Ser Asp Thr Leu Phe Ala Phe Pro Pro Val Leu Gly
    1055                 1060                 1065

Tyr Gly Leu Met Tyr Gln Pro Leu Ala Lys Gln Leu Ser Gly Tyr
    1070                 1075                 1080

Arg Ile Cys Ala Phe Asp Phe Ile Glu Glu Asp Asn Arg Ile Glu
    1085                 1090                 1095

Arg Tyr Thr Glu Leu Ile Asn Gln Leu Gln Pro Glu Gly Pro Val
    1100                 1105                 1110

Lys Leu Phe Gly Tyr Ser Ala Gly Cys Thr Leu Ala Phe Glu Thr
    1115                 1120                 1125

Ala Lys Arg Leu Glu Ala Glu Gly Arg Lys Val Glu Arg Leu Ile
    1130                 1135                 1140

Met Val Asp Ser Tyr Lys Lys Gln Gly Val Ser Asp Leu Glu Gly
    1145                 1150                 1155

Arg Thr Val Glu Ser Asp Val Gln Ala Leu Met Lys Val Asn Arg
    1160                 1165                 1170

Asp Asn Glu Ala Leu Asn Asp Glu Ala Val Lys Glu Gly Leu Ala
    1175                 1180                 1185

Lys Lys Thr Asn Ala Phe Tyr Ser Tyr Phe Val His Thr Val Ser
    1190                 1195                 1200

Thr Gly Thr Val Asn Ala Asp Ile Asp Leu Leu Thr Ser Glu Pro
    1205                 1210                 1215

Asp Phe Ala Met Pro Pro Trp Leu Ala Ser Trp Glu Glu Ala Thr
    1220                 1225                 1230

Thr Gly Glu Tyr Arg Val Lys Lys Gly Cys Gly Ser His Ala Glu
    1235                 1240                 1245

Met Leu Gln Gly Glu Cys Leu Glu Arg Asn Ala Ala Tyr Leu Leu
    1250                 1255                 1260

Glu Phe Leu Arg Lys Glu His Pro Lys Leu Thr Ala Ser Arg
    1265                 1270                 1275

<210> SEQ ID NO 16
<211> LENGTH: 243
<212> TYPE: PRT
<213> ORGANISM: Bacillus subtilis

<400> SEQUENCE: 16

Met Val Gln Leu Phe Lys Ser Phe Asp Thr Thr Glu Lys Thr Gln Leu
1               5                   10                  15

Ile Cys Phe Pro Phe Ala Gly Gly Tyr Ser Ala Ser Phe Arg Pro Leu
                20                  25                  30

His Thr Tyr Leu Gln Gly Glu Cys Glu Met Leu Ala Ala Glu Pro Pro
            35                  40                  45

Gly His Gly Thr Asn Gln Met Ser Ala Val Glu Asp Phe Glu Gln Leu
        50                  55                  60

```
Val Ser Leu Tyr Lys Gln Glu Leu Asn Leu His Pro Asp Arg Pro Phe
 65                  70                  75                  80

Val Leu Phe Gly His Ser Met Gly Gly Met Val Ala Phe Arg Leu Ala
                 85                  90                  95

Gln Lys Leu Glu Arg Glu Gly Ile Tyr Pro Gln Ala Val Ile Ile Ser
            100                 105                 110

Ala Ile Gln Pro Pro His Val Glu Arg Lys Val Ser His Leu Asp
        115                 120                 125

Asp Glu Lys Phe Leu Ala His Ile Ile Glu Leu Gly Gly Met Pro Gln
    130                 135                 140

Glu Leu Val Glu Asn Lys Glu Val Met Ser Phe Phe Leu Pro Ser Phe
145                 150                 155                 160

Arg Ser Asp Tyr Arg Ala Leu Glu Ser Phe Arg Pro Ser Asp Ser His
                165                 170                 175

Met Ile Gln Ser Pro Val His Ile Phe Asn Gly Arg Lys Asp Lys Lys
                180                 185                 190

Cys Ile Lys Asp Ala Asp Gly Trp Lys Trp Ala Asp Asn Pro Val
        195                 200                 205

Phe His Glu Phe Ser Asp Gly His Met Phe Ile Leu Ser Glu Thr Glu
210                 215                 220

Lys Val Ala Glu Arg Ile Tyr Glu Ile Ile Asn Arg Ser Thr Ala Gly
225                 230                 235                 240

Gln Leu Leu

<210> SEQ ID NO 17
<211> LENGTH: 436
<212> TYPE: PRT
<213> ORGANISM: Bacillus subtilis

<400> SEQUENCE: 17

Met Asn Asp Ala Ala Lys Glu Leu Asn Arg Thr Leu Ser Glu Glu Asn
1               5                   10                  15

Pro His Val Leu His Met Leu Ser Asp Leu Gly Arg Glu Leu Phe Tyr
                20                  25                  30

Pro Lys Gly Val Leu Thr Gln Ser Ala Glu Ala Lys Ala Lys Ala Gly
            35                  40                  45

Lys Tyr Asn Ala Thr Ile Gly Ile Ala Thr Ser Gln Gly Glu Ser Met
 50                  55                  60

His Phe Ser His Ile Gln Glu Thr Leu Ser Ala Tyr Asn Pro Asp Asp
 65                  70                  75                  80

Ile Tyr Asp Tyr Ala Pro Pro Gln Gly Lys Glu Pro Leu Arg Gln Glu
                 85                  90                  95

Trp Leu Lys Lys Met Arg Leu Glu Asn Pro Ser Leu Ala Gly Lys Asp
            100                 105                 110

Ile Ser Thr Pro Ile Val Thr Asn Ala Leu Thr His Gly Leu Ser Ile
        115                 120                 125

Ala Ala Asp Leu Phe Val Asn Glu Gly Asp Ala Leu Leu Leu Pro Asp
    130                 135                 140

Lys Tyr Trp Gly Asn Tyr Asn Phe Ile Phe Gly Val Arg Arg Lys Ala
145                 150                 155                 160

Ser Ile Glu Thr Tyr Pro Leu Phe Gln Gln Asp Gly Arg Phe Asn Ala
                165                 170                 175

Ala Gly Leu Ser Glu Leu Leu Lys Lys Gln Glu Glu Lys Ala Ile Val
            180                 185                 190
```

```
Val Leu Asn Phe Pro Asn Asn Pro Thr Gly Tyr Thr Pro Gly Glu Glu
            195                 200                 205

Glu Ala Ser Glu Ile Val Ser Val Ile Leu Glu Ala Ala Glu Ala Gly
        210                 215                 220

Lys Glu Ile Val Leu Val Asp Asp Ala Tyr Tyr Asn Leu Phe Tyr
225                 230                 235                 240

Asp Glu Thr Ala Ile Gln Glu Ser Ile Phe Ser Lys Leu Ala Gln Val
                245                 250                 255

His Asp Arg Val Leu Cys Val Lys Ile Asp Gly Ala Thr Lys Glu Asn
            260                 265                 270

Tyr Ala Trp Gly Phe Arg Val Gly Phe Ile Thr Tyr Ser Thr Lys Ser
        275                 280                 285

Glu Lys Ala Leu Arg Val Leu Glu Gly Lys Thr Lys Gly Ile Ile Arg
    290                 295                 300

Gly Thr Ile Ser Ser Ala Pro His Pro Ser Gln Thr Phe Met Leu Arg
305                 310                 315                 320

Ala Met Gln Ser Pro Glu Tyr Glu Lys Glu Lys Ser Leu Lys Tyr Asn
                325                 330                 335

Ile Met Lys Lys Arg Ala Asp Lys Val Lys Ala Val Leu Ala Glu Asn
            340                 345                 350

Lys His Tyr Glu Asp Val Trp Thr Pro Tyr Pro Phe Asn Ser Gly Tyr
        355                 360                 365

Phe Met Cys Val Arg Leu Arg Asp Ile Asn Ala Gly Glu Leu Arg Val
    370                 375                 380

Ser Leu Leu Glu Lys Arg Gly Ile Gly Thr Ile Ser Ile Asn Glu Thr
385                 390                 395                 400

Asp Leu Arg Ile Ala Phe Ser Cys Val Glu Glu Tyr Ile Ala Asp
                405                 410                 415

Leu Phe Glu Glu Ile Tyr Gln Glu Ala Lys Gln Leu Gln Lys Gln Ala
                420                 425                 430

Glu Ile Ser Gly
        435

<210> SEQ ID NO 18
<211> LENGTH: 25
<212> TYPE: DNA
<213> ORGANISM: Artificial Sequence
<220> FEATURE:
<223> OTHER INFORMATION: SrfA1 primer

<400> SEQUENCE: 18
cgggaaagcg ctggggaata accgc                                         25

<210> SEQ ID NO 19
<211> LENGTH: 25
<212> TYPE: DNA
<213> ORGANISM: Artificial Sequence
<220> FEATURE:
<223> OTHER INFORMATION: SrfA2 primer

<400> SEQUENCE: 19
ccttcaaagc tttgaacagg tggtc                                         25

<210> SEQ ID NO 20
<211> LENGTH: 26
<212> TYPE: DNA
<213> ORGANISM: Artificial Sequence
<220> FEATURE:
<223> OTHER INFORMATION: SrfA3 primer
```

```
<400> SEQUENCE: 20
ctcgcttggc ggagattcca tcaaag                                            26

<210> SEQ ID NO 21
<211> LENGTH: 26
<212> TYPE: DNA
<213> ORGANISM: Artificial Sequence
<220> FEATURE:
<223> OTHER INFORMATION: SrfA4 primer

<400> SEQUENCE: 21
gttctgtctc ttcagcagtc agcgag                                            26

<210> SEQ ID NO 22
<211> LENGTH: 24
<212> TYPE: DNA
<213> ORGANISM: Artificial Sequence
<220> FEATURE:
<223> OTHER INFORMATION: SrfA5 primer

<400> SEQUENCE: 22
gcgattgatt atgcgcttgt tgag                                              24

<210> SEQ ID NO 23
<211> LENGTH: 25
<212> TYPE: DNA
<213> ORGANISM: Artificial Sequence
<220> FEATURE:
<223> OTHER INFORMATION: SrfA6 primer

<400> SEQUENCE: 23
tcggcacata cgctgattga actgc                                             25

<210> SEQ ID NO 24
<211> LENGTH: 24
<212> TYPE: DNA
<213> ORGANISM: Artificial Sequence
<220> FEATURE:
<223> OTHER INFORMATION: SrfA7 primer

<400> SEQUENCE: 24
gggtaaagga tcgcctcaat cgtt                                              24

<210> SEQ ID NO 25
<211> LENGTH: 24
<212> TYPE: DNA
<213> ORGANISM: Artificial Sequence
<220> FEATURE:
<223> OTHER INFORMATION: SrfA8 primer

<400> SEQUENCE: 25
cgaaataggc tatctcgcac tcag                                              24

<210> SEQ ID NO 26
<211> LENGTH: 23
<212> TYPE: DNA
<213> ORGANISM: Artificial Sequence
<220> FEATURE:
<223> OTHER INFORMATION: SrfA9 primer

<400> SEQUENCE: 26
ttcagaatag ggcttatcaa gca                                               23

<210> SEQ ID NO 27
```

-continued

```
<211> LENGTH: 25
<212> TYPE: DNA
<213> ORGANISM: Artificial Sequence
<220> FEATURE:
<223> OTHER INFORMATION: SrfA10 primer

<400> SEQUENCE: 27
gctgtgttgc cgcctttatc tttga                                            25

<210> SEQ ID NO 28
<211> LENGTH: 20
<212> TYPE: DNA
<213> ORGANISM: Artificial Sequence
<220> FEATURE:
<223> OTHER INFORMATION: SrfB1 primer

<400> SEQUENCE: 28
atgtctcaga tgcatggagc                                                  20

<210> SEQ ID NO 29
<211> LENGTH: 20
<212> TYPE: DNA
<213> ORGANISM: Artificial Sequence
<220> FEATURE:
<223> OTHER INFORMATION: SrfB2 primer

<400> SEQUENCE: 29
ctggcaacta ataggctgac                                                  20

<210> SEQ ID NO 30
<211> LENGTH: 20
<212> TYPE: DNA
<213> ORGANISM: Artificial Sequence
<220> FEATURE:
<223> OTHER INFORMATION: SrfB3 primer

<400> SEQUENCE: 30
attgaagctt gtgccgcctg                                                  20

<210> SEQ ID NO 31
<211> LENGTH: 20
<212> TYPE: DNA
<213> ORGANISM: Artificial Sequence
<220> FEATURE:
<223> OTHER INFORMATION: SrfB4 primer

<400> SEQUENCE: 31
tcctttaaag ctttgcacag                                                  20

<210> SEQ ID NO 32
<211> LENGTH: 24
<212> TYPE: DNA
<213> ORGANISM: Artificial Sequence
<220> FEATURE:
<223> OTHER INFORMATION: SrfB5 primer

<400> SEQUENCE: 32
gaaacagcag cgattatgaa cgac                                             24

<210> SEQ ID NO 33
<211> LENGTH: 25
<212> TYPE: DNA
<213> ORGANISM: Artificial Sequence
<220> FEATURE:
<223> OTHER INFORMATION: SrfB6 primer

<400> SEQUENCE: 33
```

```
agacatcgag ccagtattcc tcatc                                          25
```

<210> SEQ ID NO 34
<211> LENGTH: 22
<212> TYPE: DNA
<213> ORGANISM: Artificial Sequence
<220> FEATURE:
<223> OTHER INFORMATION: SrfB7 primer

<400> SEQUENCE: 34

```
atttcgagcg gccagctgaa cg                                             22
```

<210> SEQ ID NO 35
<211> LENGTH: 24
<212> TYPE: DNA
<213> ORGANISM: Artificial Sequence
<220> FEATURE:
<223> OTHER INFORMATION: SrfB8 primer

<400> SEQUENCE: 35

```
tttcatccgg cgccgtatag gttt                                           24
```

<210> SEQ ID NO 36
<211> LENGTH: 25
<212> TYPE: DNA
<213> ORGANISM: Artificial Sequence
<220> FEATURE:
<223> OTHER INFORMATION: SrfB9 primer

<400> SEQUENCE: 36

```
gcaaaatttc cggacagcgg gatat                                          25
```

<210> SEQ ID NO 37
<211> LENGTH: 23
<212> TYPE: DNA
<213> ORGANISM: Artificial Sequence
<220> FEATURE:
<223> OTHER INFORMATION: SrfB10 primer

<400> SEQUENCE: 37

```
tcgatccggc cgatgtattc aat                                            23
```

<210> SEQ ID NO 38
<211> LENGTH: 586
<212> TYPE: PRT
<213> ORGANISM: Bacillus subtilis

<400> SEQUENCE: 38

```
Lys Ile Ser Gly Gln Arg Asp Ile Ile Ile Gly Ser Val Thr Ala Gly
1               5                   10                  15

Arg Thr Ser Ala Glu Val Gln Glu Met Pro Gly Met Phe Val Asn Thr
                20                  25                  30

Leu Ala Leu Arg Asn Glu Thr Gln Lys Glu Gln Thr Phe Ala Gly Leu
            35                  40                  45

Leu Glu Gln Val Lys Gln Thr Asn Leu Asp Ala Leu Ala His Gln Asp
        50                  55                  60

Tyr Pro Phe Glu Asp Leu Ile Gly Lys Leu Asp Leu Pro Arg Asp Met
65                  70                  75                  80

Ser Arg Asn Pro Leu Phe Gln Val Met Val Thr Glu Asp Pro Asp
                85                  90                  95

Lys Glu Thr Leu Glu Leu Glu Asn Leu Arg Ile Thr Pro Tyr Glu Ser
                100                 105                 110
```

-continued

```
Asn Gln Gly Thr Ala Lys Phe Asp Leu Thr Leu Gly Gly Phe Thr Asp
        115                 120                 125
Gln Glu Gly Leu Gly Leu Gln Phe Glu Tyr Ala Thr Asp Leu Phe Lys
    130                 135                 140
Lys Glu Thr Ile Glu Lys Trp Ser Ala Gly Phe Leu Arg Ile Leu Lys
145                 150                 155                 160
Gln Ala Ala Glu Ser Pro Asp Arg Lys Leu Pro Glu Ile Ser Leu Ile
                165                 170                 175
Ser Asp Ala Glu Lys Gln Ala Leu Leu Asp Ala Trp Lys Gly Lys Thr
            180                 185                 190
Leu Ser Val Pro Gln Asp Lys Thr Val His Arg Leu Phe Glu Glu Thr
        195                 200                 205
Ala Ala Arg Tyr Ala Asn Arg Pro Ala Ala Tyr Asn Gly Ala Lys
    210                 215                 220
Trp Thr Tyr Gly Glu Leu Asn Ala Arg Ala Asn Arg Ile Ala Arg Ile
225                 230                 235                 240
Leu Ile Asp Cys Gly Val Thr Ala Asp Glu Arg Val Gly Ile Leu Thr
                245                 250                 255
Lys Pro Ser Leu Glu Met Ala Ala Gly Val Leu Gly Val Leu Lys Ala
            260                 265                 270
Gly Ala Ala Phe Val Pro Ile Asp Pro Asp Tyr Pro Gln Glu Arg Ile
        275                 280                 285
Ser Tyr Ile Leu Gln Asp Ser Gly Ala Lys Leu Leu Leu Thr Gln Glu
    290                 295                 300
Ala Leu Asp Val Pro Glu Ser Tyr Lys Gly Glu Thr Ile Leu Leu Asp
305                 310                 315                 320
Gly Gly Arg Ser Ile Leu Ser Leu Pro Leu Asp Glu Asn Asp Glu Ala
                325                 330                 335
Asn Pro Gln Thr Glu Thr Thr Ala Asp His Leu Ala Tyr Met Ile Tyr
            340                 345                 350
Thr Ser Gly Thr Thr Gly Gln Pro Lys Gly Val Met Val Glu His His
        355                 360                 365
Ala Leu Val Asn Leu Cys Phe Trp His His Asp Ala Phe Ala Met Thr
    370                 375                 380
Ala Asp Asp Lys Ser Ala Lys Tyr Ala Gly Phe Gly Phe Asp Ala Ser
385                 390                 395                 400
Ile Trp Glu Met Phe Pro Thr Trp Thr Ile Gly Ala Glu Leu His Val
                405                 410                 415
Ile Asp Glu Ala Ile Arg Leu Asp Ile Thr Arg Leu Asn His Tyr Phe
            420                 425                 430
Glu Glu His Gly Val Thr Ile Thr Phe Leu Pro Thr Gln Leu Ala Glu
        435                 440                 445
Gln Phe Met Glu Leu Glu Asn Thr Ser Leu Arg Met Leu Leu Val Gly
    450                 455                 460
Gly Asp Lys Leu Lys Arg Ala Val Lys Gln Pro Tyr Thr Ile Val Asn
465                 470                 475                 480
Asn Tyr Gly Pro Thr Glu Asn Thr Val Val Ala Thr Ser Gly Val Ile
                485                 490                 495
Asn Pro Glu Glu Gly Ser Leu Ser Ile Gly Arg Ala Ile Ala Asn Thr
            500                 505                 510
Arg Ala Tyr Ile Leu Gly Asp Gly Asp Gln Val Gln Pro Glu Gly Ile
        515                 520                 525
```

```
Ala Gly Glu Leu Cys Val Ala Gly Arg Gly Leu Ala Arg Gly Tyr Leu
530                 535                 540

Asn Arg Glu Glu Glu Thr Ala Lys Arg Phe Thr Ala Asp Pro Phe Val
545                 550                 555                 560

Pro Gly Glu Arg Met Tyr Arg Thr Gly Asp Leu Val Lys Trp Asn Ala
                565                 570                 575

Gln Ser Gly Ile Glu Tyr Ile Gly Arg Ile
            580                 585

<210> SEQ ID NO 39
<211> LENGTH: 656
<212> TYPE: PRT
<213> ORGANISM: Bacillus subtilis

<400> SEQUENCE: 39

Thr Ile Arg Phe Arg Thr Gly Ser Glu Thr Ala Lys Ala Val Glu Lys
1               5                   10                  15

Leu Leu Ala Glu Thr Gly Thr Thr Leu His Met Val Leu His Ala Val
                20                  25                  30

Phe His Val Phe Leu Ser Lys Ile Ser Gly Gln Arg Asp Ile Val Ile
            35                  40                  45

Gly Ser Val Thr Ala Gly Arg Thr Asn Ala Asp Val Gln Asp Met Pro
    50                  55                  60

Gly Met Phe Val Asn Thr Leu Ala Leu Arg Met Glu Ala Lys Glu Gln
65                  70                  75                  80

Gln Thr Phe Ala Glu Leu Leu Glu Leu Ala Lys Gln Thr Asn Leu Ser
                85                  90                  95

Ala Leu Glu His Gln Glu Tyr Pro Phe Glu Asp Leu Val Asn Gln Leu
            100                 105                 110

Asp Leu Pro Arg Asp Met Ser Arg Asn Pro Leu Phe Asn Val Met Val
        115                 120                 125

Thr Thr Glu Asn Pro Asp Lys Glu Gln Leu Thr Leu Gln Asn Leu Ser
130                 135                 140

Ile Ser Pro Tyr Glu Ala His Gln Gly Thr Ser Lys Phe Asp Leu Thr
145                 150                 155                 160

Leu Gly Gly Phe Thr Asp Glu Asn Gly Ile Gly Leu Gln Leu Glu Tyr
                165                 170                 175

Ala Thr Asp Leu Phe Ala Lys Glu Thr Ala Glu Lys Trp Ser Glu Tyr
            180                 185                 190

Val Leu Arg Leu Leu Lys Ala Val Ala Asp Asn Pro Asn Gln Pro Leu
        195                 200                 205

Ser Ser Leu Leu Leu Val Thr Glu Thr Glu Lys Gln Ala Leu Leu Glu
210                 215                 220

Ala Trp Lys Gly Lys Ala Leu Pro Val Pro Thr Asp Lys Thr Val His
225                 230                 235                 240

Gln Leu Phe Glu Glu Thr Val Gln Arg His Lys Asp Arg Pro Ala Val
                245                 250                 255

Thr Tyr Asn Gly Gln Ser Trp Thr Tyr Gly Glu Leu Asn Ala Lys Ala
            260                 265                 270

Asn Arg Leu Ala Arg Ile Leu Met Asp Cys Gly Ile Ser Pro Asp Asp
        275                 280                 285

Arg Val Gly Val Leu Thr Lys Pro Ser Leu Glu Met Ser Ala Ala Val
    290                 295                 300

Leu Gly Val Leu Lys Ala Gly Ala Ala Phe Val Pro Ile Asp Pro Asp
305                 310                 315                 320
```

```
Tyr Pro Asp Gln Arg Ile Glu Tyr Ile Leu Gln Asp Ser Gly Ala Lys
                325                 330                 335

Leu Leu Leu Lys Gln Glu Gly Ile Ser Val Pro Asp Ser Tyr Thr Gly
            340                 345                 350

Asp Val Ile Leu Leu Asp Gly Ser Arg Thr Ile Leu Ser Leu Pro Leu
        355                 360                 365

Asp Glu Asn Asp Glu Gly Asn Pro Glu Thr Ala Val Thr Ala Glu Asn
    370                 375                 380

Leu Ala Tyr Met Ile Tyr Thr Ser Gly Thr Thr Gly Gln Pro Lys Gly
385                 390                 395                 400

Val Met Val Glu His His Ala Leu Val Asn Leu Cys Phe Trp His His
                405                 410                 415

Asp Ala Phe Ser Met Thr Ala Glu Asp Arg Ser Ala Lys Tyr Ala Gly
            420                 425                 430

Phe Gly Phe Asp Ala Ser Ile Trp Glu Met Phe Pro Thr Trp Thr Ile
        435                 440                 445

Gly Ala Glu Leu His Val Ile Asp Glu Ala Ile Arg Leu Asp Ile Val
    450                 455                 460

Arg Leu Asn Asp Tyr Phe Glu Thr Asn Gly Val Thr Ile Thr Phe Leu
465                 470                 475                 480

Pro Thr Gln Leu Ala Glu Gln Phe Met Glu Leu Glu Asn Thr Ser Leu
                485                 490                 495

Arg Val Leu Leu Thr Gly Gly Asp Lys Leu Lys Arg Ala Val Lys Lys
            500                 505                 510

Pro Tyr Thr Leu Val Asn Asn Tyr Gly Pro Thr Glu Asn Thr Val Val
        515                 520                 525

Ala Thr Ser Ala Glu Ile His Pro Glu Glu Gly Ser Leu Ser Ile Gly
    530                 535                 540

Arg Ala Ile Ala Asn Thr Arg Val Tyr Ile Leu Gly Glu Gly Asn Gln
545                 550                 555                 560

Val Gln Pro Glu Gly Val Ala Gly Glu Leu Cys Val Ala Arg Gly
                565                 570                 575

Leu Ala Arg Gly Tyr Leu Asn Arg Glu Asp Glu Thr Ala Lys Arg Phe
            580                 585                 590

Val Ala Asp Pro Phe Val Pro Gly Glu Arg Met Tyr Arg Thr Gly Asp
        595                 600                 605

Leu Val Lys Trp Val Asn Gly Gly Ile Glu Tyr Ile Gly Arg Ile Asp
    610                 615                 620

Gln Gln Val Lys Val Arg Gly Tyr Arg Ile Glu Leu Ser Glu Ile Glu
625                 630                 635                 640

Val Gln Leu Ala Gln Leu Ser Glu Val Gln Asp Ala Ala Val Thr Arg
                645                 650                 655

<210> SEQ ID NO 40
<211> LENGTH: 656
<212> TYPE: PRT
<213> ORGANISM: Bacillus subtilis

<400> SEQUENCE: 40

Thr Ile Arg Phe Arg Thr Gly Ser Glu Thr Ala Lys Ala Val Glu Lys
1               5                   10                  15

Leu Leu Ala Glu Thr Gly Thr Thr Leu His Met Val Leu His Ala Val
            20                  25                  30

Phe His Val Phe Leu Ser Lys Ile Ser Gly Gln Arg Asp Ile Val Ile
```

```
            35                  40                  45
Gly Ser Val Thr Ala Gly Arg Thr Asn Ala Asp Val Gln Asp Met Pro
 50                  55                  60
Gly Met Phe Val Asn Thr Leu Ala Leu Arg Met Glu Ala Lys Glu Gln
 65                  70                  75                  80
Gln Thr Phe Ala Glu Leu Leu Glu Leu Ala Lys Gln Thr Asn Leu Ser
                 85                  90                  95
Ala Leu Glu His Gln Glu Tyr Pro Phe Glu Asp Leu Val Asn Gln Leu
            100                 105                 110
Asp Leu Pro Arg Asp Met Ser Arg Asn Pro Leu Phe Asn Val Met Val
            115                 120                 125
Thr Thr Glu Asn Pro Asp Lys Glu Leu Thr Leu Gln Asn Leu Ser
130                 135                 140
Ile Ser Pro Tyr Glu Ala His Gln Gly Thr Ser Lys Phe Asp Leu Thr
145                 150                 155                 160
Leu Gly Gly Phe Thr Asp Glu Asn Gly Ile Gly Leu Gln Leu Glu Tyr
                165                 170                 175
Ala Thr Asp Leu Phe Ala Lys Glu Thr Ala Glu Lys Trp Ser Glu Tyr
            180                 185                 190
Val Leu Arg Leu Leu Lys Ala Val Ala Asp Asn Pro Asn Gln Pro Leu
            195                 200                 205
Ser Ser Leu Leu Leu Val Thr Glu Thr Glu Lys Gln Ala Leu Leu Glu
210                 215                 220
Ala Trp Lys Gly Lys Ala Leu Pro Val Pro Thr Asp Lys Thr Val His
225                 230                 235                 240
Gln Leu Phe Glu Glu Thr Val Gln Arg His Lys Asp Arg Pro Ala Val
                245                 250                 255
Thr Tyr Asn Gly Gln Ser Trp Thr Tyr Gly Glu Leu Asn Ala Lys Ala
            260                 265                 270
Asn Arg Leu Ala Arg Ile Leu Met Asp Cys Gly Ile Ser Pro Asp Asp
            275                 280                 285
Arg Val Gly Val Leu Thr Lys Pro Ser Leu Glu Met Ser Ala Ala Val
290                 295                 300
Leu Gly Val Leu Lys Ala Gly Ala Ala Phe Val Pro Ile Asp Pro Asp
305                 310                 315                 320
Tyr Pro Asp Gln Arg Ile Glu Tyr Ile Leu Gln Asp Ser Gly Ala Lys
                325                 330                 335
Leu Leu Leu Lys Gln Glu Gly Ile Ser Val Pro Asp Ser Tyr Thr Gly
            340                 345                 350
Asp Val Ile Leu Leu Asp Gly Ser Arg Thr Ile Leu Ser Leu Pro Leu
            355                 360                 365
Asp Glu Asn Asp Glu Gly Asn Pro Glu Thr Ala Val Thr Ala Glu Asn
            370                 375                 380
Leu Ala Tyr Met Ile Tyr Thr Ser Gly Thr Thr Gly Gln Pro Lys Gly
385                 390                 395                 400
Val Met Val Glu Asp His Ala Leu Val Asn Leu Cys Phe Trp Asp His
                405                 410                 415
Asp Ala Phe Ser Met Thr Ala Glu Asp Arg Ser Ala Lys Tyr Ala Gly
            420                 425                 430
Phe Gly Phe Asp Ala Ser Ile Trp Glu Met Phe Pro Thr Trp Thr Ile
            435                 440                 445
Gly Ala Glu Leu His Val Ile Asp Glu Ala Ile Arg Leu Asp Ile Val
450                 455                 460
```

```
Arg Leu Asn Asp Tyr Phe Glu Thr Asn Gly Val Thr Ile Thr Phe Leu
465                 470                 475                 480

Pro Thr Gln Leu Ala Glu Gln Phe Met Glu Leu Glu Asn Thr Ser Leu
                485                 490                 495

Arg Val Leu Leu Thr Gly Gly Asp Lys Leu Lys Arg Ala Val Lys Lys
            500                 505                 510

Pro Tyr Thr Leu Val Asn Asn Tyr Gly Pro Thr Glu Asn Thr Val Val
            515                 520                 525

Ala Thr Ser Ala Glu Ile His Pro Glu Glu Gly Ser Leu Ser Ile Gly
        530                 535                 540

Arg Ala Ile Ala Asn Thr Arg Val Tyr Ile Leu Gly Glu Gly Asn Gln
545                 550                 555                 560

Val Gln Pro Glu Gly Val Ala Gly Glu Leu Cys Val Ala Gly Arg Gly
                565                 570                 575

Leu Ala Arg Gly Tyr Leu Asn Arg Glu Asp Glu Thr Ala Lys Arg Phe
            580                 585                 590

Val Ala Asp Pro Phe Val Pro Gly Glu Arg Met Tyr Arg Thr Gly Asp
        595                 600                 605

Leu Val Lys Trp Val Asn Gly Gly Ile Glu Tyr Ile Gly Arg Ile Asp
    610                 615                 620

Gln Gln Val Lys Val Arg Gly Tyr Arg Ile Glu Leu Ser Glu Ile Glu
625                 630                 635                 640

Val Gln Leu Ala Gln Leu Ser Glu Val Glu Asp Arg Ala Val Thr Arg
                645                 650                 655
```

<210> SEQ ID NO 41
<211> LENGTH: 658
<212> TYPE: PRT
<213> ORGANISM: Bacillus subtilis

<400> SEQUENCE: 41

```
Arg Ile Ala Phe Ser Leu Glu Ala Gly Lys Ala Asp Ala Leu Arg Arg
1               5                   10                  15

Leu Ala Lys Glu Thr Asp Ser Thr Leu Tyr Met Val Leu Leu Ala Ser
            20                  25                  30

Tyr Ser Ala Phe Leu Ser Lys Ile Cys Gly Gln Asp Asp Ile Ile Val
        35                  40                  45

Gly Ser Pro Val Ala Gly Arg Ser Gln Ala Asp Val Ser Arg Val Ile
    50                  55                  60

Gly Met Phe Val Asn Thr Leu Ala Leu Arg Thr Tyr Pro Lys Gly Glu
65                  70                  75                  80

Lys Thr Phe Ala Asp Tyr Leu Asn Glu Val Lys Glu Thr Ala Leu Ser
                85                  90                  95

Ala Phe Asp Ala Gln Asp Tyr Pro Leu Glu Asp Leu Ile Gly Asn Val
            100                 105                 110

Gln Val Gln Arg Asp Thr Ser Ser Asn Pro Leu Phe Asp Ala Val Phe
        115                 120                 125

Ser Met Gln Asn Ala Asn Ile Lys Asp Leu Thr Met Lys Gly Ile Gln
    130                 135                 140

Leu Glu Pro His Pro Phe Glu Arg Lys Thr Ala Lys Phe Asp Leu Thr
145                 150                 155                 160

Leu Thr Ala Asp Glu Thr Asp Gly Gly Leu Thr Phe Val Leu Glu Tyr
                165                 170                 175

Asn Thr Ala Leu Phe Lys Gln Glu Thr Ile Glu Arg Trp Lys Gln Tyr
```

```
            180                 185                 190
Trp Met Glu Leu Leu Asp Ala Val Thr Gly Asn Pro Asn Gln Pro Leu
            195                 200                 205
Ser Ser Leu Ser Leu Val Thr Glu Thr Glu Lys Gln Ala Leu Leu Glu
            210                 215                 220
Ala Trp Lys Gly Lys Ala Leu Pro Val Pro Thr Asp Lys Thr Val His
225                 230                 235                 240
Gln Leu Phe Glu Glu Thr Ala Gln Arg His Lys Asp Arg Pro Ala Val
                245                 250                 255
Thr Tyr Asn Gly Gln Ser Trp Thr Tyr Gly Glu Leu Asn Ala Lys Ala
                260                 265                 270
Asn Arg Leu Ala Arg Ile Leu Met Asp Cys Gly Ile Ser Pro Asp Asp
            275                 280                 285
Arg Val Gly Val Leu Thr Lys Pro Ser Leu Glu Met Ser Ala Ala Val
290                 295                 300
Leu Gly Val Leu Lys Ala Gly Ala Ala Phe Val Pro Ile Asp Pro Asp
305                 310                 315                 320
Tyr Pro Asp Gln Arg Ile Glu Tyr Ile Leu Gln Asp Ser Gly Ala Lys
                325                 330                 335
Leu Leu Leu Lys Gln Glu Gly Ile Ser Val Pro Asp Ser Tyr Thr Gly
            340                 345                 350
Asp Val Ile Leu Leu Asp Gly Ser Arg Thr Ile Leu Ser Leu Pro Leu
            355                 360                 365
Asp Glu Asn Asp Glu Glu Asn Pro Glu Asn Pro Glu Thr Ala Val Thr
        370                 375                 380
Ala Glu Asn Leu Ala Tyr Met Ile Tyr Thr Ser Gly Thr Thr Gly Gln
385                 390                 395                 400
Pro Lys Gly Val Met Val Glu His His Ala Leu Val Asn Leu Cys Phe
                405                 410                 415
Trp His His Asp Ala Phe Ser Met Thr Ala Glu Asp Arg Ser Ala Lys
            420                 425                 430
Tyr Ala Gly Phe Gly Phe Asp Ala Ser Ile Trp Glu Met Phe Pro Thr
            435                 440                 445
Trp Ser Ile Gly Ala Glu Leu His Val Ile Glu Glu Ala Ile Arg Leu
        450                 455                 460
Asp Ile Val Arg Leu Asn Asp Tyr Phe Glu Thr Asn Gly Val Thr Ile
465                 470                 475                 480
Thr Phe Leu Pro Thr Gln Leu Ala Glu Gln Phe Met Glu Leu Glu Asn
                485                 490                 495
Thr Ser Leu Arg Val Leu Leu Thr Gly Gly Asp Lys Leu Lys Arg Ala
            500                 505                 510
Val Lys Lys Pro Tyr Thr Leu Val Asn Asn Tyr Gly Pro Thr Glu Asn
            515                 520                 525
Thr Val Val Ala Thr Ser Ala Glu Ile His Pro Glu Glu Gly Ser Leu
            530                 535                 540
Ser Ile Gly Arg Ala Ile Ala Asn Thr Arg Val Tyr Ile Leu Gly Glu
545                 550                 555                 560
Gly Asn Gln Val Gln Pro Glu Gly Val Ala Gly Glu Leu Cys Val Ala
                565                 570                 575
Gly Arg Gly Leu Ala Arg Gly Tyr Leu Asn Arg Glu Asp Glu Thr Ala
            580                 585                 590
Lys Arg Phe Val Ala Asp Pro Phe Val Pro Gly Glu Arg Met Tyr Arg
            595                 600                 605
```

```
Thr Gly Asp Leu Val Lys Trp Thr Gly Gly Ile Glu Tyr Ile Gly
    610                 615                 620

Arg Ile Asp Gln Gln Val Lys Val Arg Gly Tyr Arg Ile Glu Leu Ser
625                 630                 635                 640

Glu Ile Glu Val Gln Leu Ala Gln Leu Ser Glu Val Gln Asp Ala Ala
                645                 650                 655

Val Thr

<210> SEQ ID NO 42
<211> LENGTH: 657
<212> TYPE: PRT
<213> ORGANISM: Bacillus subtilis

<400> SEQUENCE: 42

Arg Val Arg Phe Lys Ala Ser Lys Asp Ala Ala Leu Lys Ile Arg Arg
1               5                   10                  15

Leu Thr Ala Glu Thr Asn Thr Thr Leu Asn Ile Val Met Leu Ala Val
                20                  25                  30

Phe Asn Leu Phe Leu Ser Arg Leu Ala Gly Gln Lys Asp Ile Val Val
            35                  40                  45

Gly Thr Ala Ala Ala Gly Arg Thr Asn Ala Asp Leu Lys Asp Met Pro
    50                  55                  60

Gly Met Phe Val Asn Ser Leu Ala Leu Lys Asn His Val Pro Asp Gln
65                  70                  75                  80

Ala Ser Phe Ser Glu Phe Leu Glu Glu Val Lys Asn Asn Ser Leu Ala
                85                  90                  95

Ala Leu Asp His Gln Asp Tyr Pro Phe Glu Glu Leu Ile Ala Lys Leu
                100                 105                 110

Asp Leu Pro Arg Asp Met Ser Arg Asn Pro Leu Phe Asn Val Met Leu
            115                 120                 125

Thr Thr Glu Asp Pro Asp Lys Glu Thr Leu Asp Leu Asp Gly Leu Thr
    130                 135                 140

Ile Lys Pro Tyr Glu Ile Ser His Ala Ala Lys Phe Asp Leu Thr
145                 150                 155                 160

Leu Gly Ala Phe Glu Lys Asp His Glu Ile Gly Leu Gln Phe Glu Tyr
                165                 170                 175

Ala Thr Asp Leu Phe Gln Lys Gln Thr Ile Glu Arg Trp Ser Gly Tyr
                180                 185                 190

Leu Leu Asn Leu Leu Glu Ala Val Ala Glu Asn Pro Asp Ala Arg Leu
            195                 200                 205

Ser Glu Leu Ser Leu Leu Asp Glu Ala Glu Lys Arg Arg Ile Val Gln
    210                 215                 220

Asn Trp Asn Glu Thr Lys Leu Asp Val Pro Glu Asp Lys Thr Val His
225                 230                 235                 240

Glu Leu Phe Glu Ala Gln Val Leu Arg Thr Pro Asp Arg Gly Ala Ala
                245                 250                 255

Val Tyr Asn Gly Val Glu Trp Thr Tyr Lys Glu Leu Asn Ala Arg Ala
                260                 265                 270

Asn Arg Leu Ala Arg Leu Leu Ile Glu Lys Gly Ala Arg Pro Glu Gln
            275                 280                 285

Arg Ile Gly Ile Met Val Lys Pro Ser Leu Glu Met Ala Ala Gly Val
    290                 295                 300

Leu Gly Ile Leu Lys Ala Gly Ala Ala Tyr Val Pro Ile Asp Pro Ser
305                 310                 315                 320
```

Tyr Pro Ala Glu Arg Ile Gly Tyr Val Leu Lys Asp Ser Gly Ala Glu
            325                 330                 335

Leu Leu Leu Thr Gln Ser Gly Leu Thr Val Pro Asp Thr Phe Thr Gly
            340                 345                 350

Asp Val Ile Asp Leu Asn Arg Glu Gly Ser Ile Leu Asp Gly Glu Leu
            355                 360                 365

Tyr Pro Glu Asp Asp Met Asn Pro Asp Ser Gln Arg Gln Ser Asp Asn
370                 375                 380

Leu Ala Tyr Leu Ile Tyr Thr Ser Gly Thr Thr Gly Gln Pro Lys Gly
385                 390                 395                 400

Val Met Val Glu His Arg Ser Leu Val Asn Leu Cys Tyr Trp His Asn
            405                 410                 415

Asp Ala Phe Lys Val Thr Glu His Asp Lys Ser Ala Lys Tyr Ala Gly
            420                 425                 430

Phe Gly Phe Asp Ala Ser Val Trp Glu Met Phe Pro Tyr Trp Ile Ala
            435                 440                 445

Gly Ala Glu Leu His Ile Ile Asp Glu Ala Ile Arg Met Asp Ile Thr
            450                 455                 460

Arg Leu Asn Gln Tyr Phe Glu Glu Asn Lys Ile Thr Ile Thr Phe Leu
465                 470                 475                 480

Pro Thr Gln Leu Cys Glu Gln Phe Met Glu Leu Asp Asn Gln Ser Leu
            485                 490                 495

Arg Val Leu Leu Thr Gly Gly Asp Lys Leu Lys Arg Ile Ala Lys Arg
            500                 505                 510

Ser Tyr Thr Leu Val Asn Asn Tyr Gly Pro Thr Glu Asn Thr Val Val
            515                 520                 525

Ala Thr Ser Ala Ala Ile Asp Pro Asp Glu Gly Met Leu Ser Ile Gly
            530                 535                 540

Lys Pro Ile Ala Asn Thr Arg Val Tyr Val Leu Gly Gln Asn Asn Glu
545                 550                 555                 560

Val Gln Pro Val Gly Val Ala Gly Glu Leu Cys Ile Ala Gly Arg Gly
            565                 570                 575

Leu Ala Arg Gly Tyr Leu Asn Lys Pro Glu Glu Thr Ala Lys Arg Phe
            580                 585                 590

Thr Glu Asp Pro Phe Val Pro Gly Glu Arg Met Tyr Arg Thr Gly Asp
            595                 600                 605

Ala Val Lys Trp Leu Glu Asp Gly Arg Leu Glu Tyr Ile Gly Arg Ile
            610                 615                 620

Asp Gln Gln Val Lys Ile Arg Gly Phe Arg Ile Glu Leu Ser Glu Ile
625                 630                 635                 640

Glu Val Gln Leu Ala Arg Leu Ser Glu Val Gln Glu Ala Val Val Thr
            645                 650                 655

Asp

<210> SEQ ID NO 43
<211> LENGTH: 432
<212> TYPE: DNA
<213> ORGANISM: Artificial sequence
<220> FEATURE:
<223> OTHER INFORMATION: 0.4kb PCR product

<400> SEQUENCE: 43
ttgatgaaac agacagcgct cgtaaccgga gcaagcggcg gaatcggaca agtataagt       60 gaagtcctcg caaaaaacgg atatgacgtc cttttgcatt atcattctaa taaggaggcc     120

```
gcaaacaggc ttgcggaaag gctgagcgca tcattcggcg taaaagcctc cgctatccag    180
gctgatctgt cctcaccgga tggcgcggag acaytcagcc gttccgttaa gcagcctgtg    240
gacgctctga tattaaacag cggcaaaagt catttcggcc tgattacgga cgttacggat    300
gacacggcgc gggagatggt gcagctgcat gtgacgagtc cgtttctttt ggtgcgtaat    360
ctggtgcccg gcatgatccg gaaaaatgc ggggcatcg tcgcgatcgg ttccgtctgg    420
cgagaaagct tg                                                         432
```

<210> SEQ ID NO 44
<211> LENGTH: 144
<212> TYPE: PRT
<213> ORGANISM: Artificial sequence
<220> FEATURE:
<223> OTHER INFORMATION: Peptide encoded by the 0.4kb PCR product

<400> SEQUENCE: 44

```
Leu Met Lys Gln Thr Ala Leu Val Thr Gly Ala Ser Gly Gly Ile Gly
1               5                   10                  15

Gln Ser Ile Ser Glu Val Leu Ala Lys Asn Gly Tyr Asp Val Leu Leu
            20                  25                  30

His Tyr His Ser Asn Lys Glu Ala Ala Asn Arg Leu Ala Glu Arg Leu
        35                  40                  45

Ser Ala Ser Phe Gly Val Lys Ala Ser Ala Ile Gln Ala Asp Leu Ser
    50                  55                  60

Ser Pro Asp Gly Ala Glu Thr Phe Ser Arg Ser Val Lys Gln Pro Val
65                  70                  75                  80

Asp Ala Leu Ile Leu Asn Ser Gly Lys Ser His Phe Gly Leu Ile Thr
                85                  90                  95

Asp Val Thr Asp Asp Thr Ala Arg Glu Met Val Gln Leu His Val Thr
            100                 105                 110

Ser Pro Phe Leu Leu Val Arg Asn Leu Val Pro Gly Met Ile Arg Lys
        115                 120                 125

Lys Cys Gly Gly Ile Val Ala Ile Gly Ser Val Trp Arg Glu Ser Leu
    130                 135                 140
```

<210> SEQ ID NO 45
<211> LENGTH: 146
<212> TYPE: PRT
<213> ORGANISM: Cuphea lanceolata

<400> SEQUENCE: 45

```
Val Glu Ser Pro Val Val Ile Val Thr Gly Ala Ser Arg Gly Ile Gly
1               5                   10                  15

Lys Ala Ile Ala Leu Ser Leu Gly Lys Ala Gly Cys Lys Val Leu Val
            20                  25                  30

Asn Tyr Ala Arg Ser Ser Lys Glu Ala Glu Glu Val Ser Lys Glu Ile
        35                  40                  45

Glu Ala Phe Gly Gly Gln Ala Leu Thr Phe Gly Gly Asp Val Ser Lys
    50                  55                  60

Glu Glu Asp Val Glu Ala Met Ile Lys Thr Ala Val Asp Ala Trp Gly
65                  70                  75                  80

Thr Val Asp Ile Leu Val Asn Asn Ala Gly Ile Thr Arg Asp Gly Leu
                85                  90                  95

Leu Met Arg Met Lys Lys Ser Gln Trp Gln Glu Val Ile Asp Leu Asn
            100                 105                 110
```

```
Leu Thr Gly Val Phe Leu Cys Thr Gln Ala Ala Ala Lys Ile Met Met
            115                 120                 125

Lys Lys Lys Lys Gly Arg Ile Ile Asn Ile Ala Ser Val Val Gly Leu
130                 135                 140

Val Gly
145

<210> SEQ ID NO 46
<211> LENGTH: 146
<212> TYPE: PRT
<213> ORGANISM: Bacillus subtilis

<400> SEQUENCE: 46

Leu Asn Asp Lys Thr Ala Ile Val Thr Gly Ala Ser Arg Gly Ile Gly
1               5                   10                  15

Arg Ser Ile Ala Leu Ala Leu Ala Lys Ser Gly Ala Asn Val Val Val
            20                  25                  30

Asn Tyr Ser Gly Asn Glu Ala Lys Ala Asn Glu Val Val Asp Glu Ile
        35                  40                  45

Lys Ser Met Gly Arg Lys Ala Ile Ala Val Lys Ala Asp Val Ser Asn
    50                  55                  60

Pro Glu Asp Val Gln Asn Met Ile Lys Glu Thr Leu Ser Val Phe Ser
65                  70                  75                  80

Thr Ile Asp Ile Leu Val Asn Asn Ala Gly Ile Thr Arg Asp Asn Leu
                85                  90                  95

Ile Met Arg Met Lys Glu Asp Glu Trp Asp Asp Val Ile Asn Ile Asn
            100                 105                 110

Leu Lys Gly Val Phe Asn Cys Thr Lys Ala Val Thr Arg Gln Met Met
        115                 120                 125

Lys Gln Arg Ser Gly Arg Ile Ile Asn Val Ser Ser Ile Val Gly Val
    130                 135                 140

Ser Gly
145

<210> SEQ ID NO 47
<211> LENGTH: 142
<212> TYPE: PRT
<213> ORGANISM: Salmonella Typhimurium

<400> SEQUENCE: 47

Phe Glu Gly Lys Ile Ala Leu Val Thr Gly Ala Ser Arg Gly Ile Gly
1               5                   10                  15

Arg Ala Ile Ala Glu Thr Leu Val Ala Arg Gly Ala Lys Val Ile Gly
            20                  25                  30

Thr Ala Thr Ser Glu Asn Gly Ala Lys Asn Ile Ser Asp Tyr Leu Gly
        35                  40                  45

Ala Asn Gly Lys Gly Leu Met Leu Asn Val Thr Asp Pro Ala Ser Ile
    50                  55                  60

Glu Ser Val Leu Glu Asn Ile Arg Ala Glu Phe Gly Glu Val Asp Ile
65                  70                  75                  80

Leu Val Asn Asn Ala Gly Ile Thr Arg Asp Asn Leu Leu Met Arg Met
                85                  90                  95

Lys Asp Asp Glu Trp Asn Asp Ile Ile Glu Thr Asn Leu Ser Ser Val
            100                 105                 110

Phe Arg Leu Ser Lys Ala Val Met Arg Ala Met Met Lys Lys Arg Cys
        115                 120                 125
```

```
Gly Arg Ile Ile Thr Ile Gly Ser Val Val Gly Thr Met Gly
    130                 135                 140
```

<210> SEQ ID NO 48
<211> LENGTH: 146
<212> TYPE: PRT
<213> ORGANISM: Deinococcus radiodurans

<400> SEQUENCE: 48

```
Ala Pro Ala Arg Val Ala Leu Val Thr Gly Ser Ser Arg Gly Leu Gly
1               5                   10                  15

Arg Ala Met Ala Leu Arg Leu Ala Gln Asp Gly Phe Thr Val Ala Val
                20                  25                  30

His Tyr Gly Arg Gly Glu Ala Glu Ala Gln Gln Val Ala Ala Asp Ile
            35                  40                  45

Arg Ala Ala Gly Gly Ala Ala Gln Val Phe Gly Ala Asp Leu Ser Gln
        50                  55                  60

Pro Ala Asn Ala Gly Thr Leu Val Glu Asp Val Ile Ala Ala Leu Gly
65                  70                  75                  80

Arg Leu Asp Val Leu Val Asn Asn Ala Gly Ile Thr Arg Asp Gly Leu
                85                  90                  95

Ala Ile Arg Met Lys Asp Glu Asp Trp Asp Ala Val Leu Gln Thr Asn
            100                 105                 110

Leu Ser Ser Ala Phe Ala Ala Cys Arg Ala Ala Leu Lys His Met Met
        115                 120                 125

Lys Asn Arg Ser Gly Arg Ile Val Asn Val Ser Ser Val Val Ala Leu
130                 135                 140

Ala Gly
145
```

<210> SEQ ID NO 49
<211> LENGTH: 144
<212> TYPE: PRT
<213> ORGANISM: Artificial sequence
<220> FEATURE:
<223> OTHER INFORMATION: Peptide encoded by 0.4kb PCR product in Fig. 3

<400> SEQUENCE: 49

```
Leu Met Lys Gln Thr Ala Leu Val Thr Gly Ala Ser Gly Gly Ile Gly
1               5                   10                  15

Gln Ser Ile Ser Glu Val Leu Ala Lys Asn Gly Tyr Asp Val Leu Leu
                20                  25                  30

His Tyr His Ser Asn Lys Glu Ala Ala Asn Arg Leu Ala Glu Arg Leu
            35                  40                  45

Ser Ala Ser Phe Gly Val Lys Ala Ser Ala Ile Gln Ala Asp Leu Ser
        50                  55                  60

Ser Pro Asp Gly Ala Glu Thr Phe Ser Arg Ser Val Lys Gln Pro Val
65                  70                  75                  80

Asp Ala Leu Ile Leu Asn Ser Gly Lys Ser His Phe Gly Leu Ile Thr
                85                  90                  95

Asp Val Thr Asp Asp Thr Ala Arg Glu Met Val Gln Leu His Val Thr
            100                 105                 110

Ser Pro Phe Leu Leu Val Arg Asn Leu Val Pro Gly Met Ile Arg Lys
        115                 120                 125

Lys Cys Gly Gly Ile Val Ala Ile Gly Ser Val Trp Arg Glu Ser Leu
130                 135                 140
```

CLONING AND BASE SEQUENCE DETERMINATION OF NOVEL ITURIN BIOSYNTHESIS GENE FROM ANTAGONISTIC MICROORGANISM *BACILLUS SUBTILIS* AND CHARACTERISTICS OF THE GENE

CROSS REFERENCE TO RELATED APPLICATION

This application is a national stage application under 35 U.S.C. 371 of PCT Application No. PCT/KR2011/008027, having an international filing date of Oct. 26, 2011, which designated the United States, which PCT application claimed the benefit of South Korea Patent Application No. 10-2010-0109724, filed Nov. 5, 2010, both of which are incorporated by reference in their entirety.

BACKGROUND OF THE INVENTION

1. Field of the Invention

The present disclosure relates to novel iturin biosynthesis genes, and more particularly, to novel iturin biosynthesis genes derived from *Bacillus subtilis* subsp. *krictiensis* ATCC 55079 and uses thereof.

2. Description of the Related Art

Biological control is a means of controlling pathogenic microorganisms that cause disease injuries in plants through the use of other microorganisms that have antagonistic actions. Most representative biopesticides have been primarily used for controlling various plant pathogens, insects harming crops, insect pests such as mites, nematodes, and weeds through direct or indirect use of microorganisms themselves. Studies on this biological control started in early 1990s, and since then, many efforts have been made to inhibit plant pathogens by using various kinds of bacteria and fungi. However, since the soil ecosystems are complex and complicated interactions are associated between plants and microorganisms, the results of studies were very unsatisfying. Recently, interactions between plants and microorganisms have been gradually identified and outstanding results have been reported thanks to developments in biotechnology, such as molecular biology. Currently, about 40 kinds of biological control agents have been developed all around the world (H. D. Burges, Formulation of microbial biopesticides, Kluwer Academic Publisher, Dordrecht, The Netherlands, p. 187-202, 1998) and 25 kinds of biological control agents are registered and commercially available only in the U.S. (B. B. McSpadden Gardener, et al., Plant Health Progress [Internet], May 10, 2002 [cited Aug. 13, 2010].

Registered products are mainly for the control of soil borne plant diseases by *Fusarium, Pythium, Rhizoctonia*, and *Sclerotinia (Phytophthora)*, but, these products have not yet captured a large share of the market. So far, one of the most successful examples of biological control is the control of crown gall, a disease of roots in fruit trees, caused by *Agrobacterium tumefaciens* (A. Kerr, Plant Dis., 64: 25-30, 1980). Controlling this plant disease cannot be carried out with chemosynthetic pesticides. However, it has been known that an antibiotic agrocin produced by *Agrobacterium* radiobacter inhibits the invasion of *A. tumefaciens*, and then, several products that improved *A. radiobacter* by using genetic engineering techniques have been developed and thought to have a considerable worldwide market share (names of products: Nogall, Norbac, Galltrol-A, etc.). Another successful example is the study on the control of root rots of wheat using *Pseudomonas fluorescens*, and research teams at the USDA and Washington State University succeeded in isolating *P. fluorescens* which exhibits strong antagonistic activity against *Gaeumannomyces graminis* var. *tritici* causing the root rots of wheat from soil through 10-year researches (D. M. Weller, Annu. Rev. Phytopathol., 26: 379-407, 1988; D. M. Weller, et al., Can. J. Plant Pathol., 8: 328-334, 1986; R. J. Cook, Can. J. Plant. Pathol., 14: 76-85, 1992). When wheat seeds were treated with this antagonistic microorganism and sown, the yield of wheat increased by 10 to 20% and it was concluded that this effect was caused by phenazine antibiotics (L. S. Thomashow, et al., Appl. Environ. Microbiol., 56: 908-912, 1990; C. Keel, et al., Mol. Plant-Microbe Interact., 5: 4-13, 1992) and 2,4-diacetyl phloroglucinol antibiotic produced by *Pseudomonas* (C. Keel, et al., Mol. Plant-Microbe Interact., 5: 4-13, 1992). To overcome the differences in control activities depending on application time and region, revealed through a field experiment over 8 years, research teams introduced genetic engineering techniques to maximize the gene expression of *Pseudomonas* sp. related with the production of phenazine antibiotics and succeeded in overcoming the irregularity of the control effect of root rots of wheat (M. H. Ryder, et al., Improving plant productivity with *Rhizobacteria*, CSIRO Divisions of soils, Adelaide, South Australia, p. 247-249, 1994).

*Bacillus subtilis (B. subtilis)* has been received attention of many researchers due to not only many kinds of antibiotics but also its characteristic to produce various enzymes, and along with *Saccharomyces cerevisiae (S. cerevisiae)*, and *Lactobacillus* sp., it is recognized as a harmless strain to a human body and the environment by the U.S. Food and Drug Administration. Examples of formulations of microbial pesticides developed by using *B. subtilis* include Epic, Kodiak, Companion, HiStick, Serenade, etc. and these are largely widely used for seed treatment or post-harvest application, and for protecting putrefaction of vegetables and the like (B. B. McSpadden Gardener, et al., Plant Health Progress [Internet], May 10, 2002 [cited Aug. 13, 2010]. Especially, Serenade which was registered in early 2,000s by AgraQuest Co. has been produced by using *B. subtilis* QST713 and is registered as a fungicide and a bactericide in 25 countries, and currently, various products depending on their uses are commercially available. In addition, a research team at the USDA found that iturin antibiotics produced by *B. subtilis* inhibited *Monilinia fructicola*, the pathogen of peach brown rot, and attempted a study to develop *B. subtilis* as a preservative during storage of tree fruits (R. C. Gueldner, et al., J. Agric. Food Chem., 36: 366-370, 1988).

Besides, a research team lead by Dr. Pusey at the USDA found that *B. subtilis* has an inhibitory effect on many plant diseases (P. L. Pusey, et al., Pesticide Sci., 27: 133-140, 1989) and Phae et al. also isolated *B. subtilis* NB22 having a wide inhibitory effect on plant pathogens from decomposed soil for compost and proved that its active components are iturin-based materials (C. G. Phae, et al., J. Ferment. Bioeng., 69: 1-7, 1990). Like these, iturin, a cyclic peptide antibiotic, has long been widely used as a biological control agent, but, study on iturin biosynthesis genes at the molecular level has hardly been made, except for one published in J. Ferment. Bioeng. by a Japanese research team in 1990.

The complete genome sequence of *B. subtilis* 168 strain having a gene responsible for biosynthesis of surfactin, another cyclic peptide other than iturin was published in 1997 (Kunst, F., et al., Nature, 390: 249-256, 1997), and the result of study on a gene responsible for biosynthesis of mycosubtilin from *B. subtilis* ATCC 6633 was reported by a German research team in late 1990s (E. H. Duitman, et al., Proc. Natl. Acad. Sci., 96: 13294-13299, 1999). Since then, cloning, base sequence, and characteristics of iturin A gene from *B. subtilis* RB14 was published by a Japanese research team in 2000s (K. Tsuge, et al., J. Bacteriol., 183: 6265-6273, 2001). Furthermore, a German research team found that *B. amyloliquefaciens* FZB42 which promotes plant growth and suppresses plant pathogens at the same time produced cyclic peptides, surfactin, fengycin, and bacillomycin D as secondary metabolites, and investigated and reported genetic structures and functional characteristics of produced secondary metabolites at the molecular level (A. Koumoutsi, et al., J. Bacteriol., 186: 1084-1096, 2004). Besides, the above German research team reported that *B. amyloliquefaciens* FZB42 produces polyketide-based antibiotics, macrolactin, bacillaene, and difficidin, in addition to the above three cyclic peptides (Chen, et al., Nature Biotechnol., 25: 1007-1014, 2007). Likewise, while reports on various cyclic peptide antibiotics have been made intermittently, there is hardly a report on various kinds of iturin biosynthesis genes.

Thus, the present inventors cloned iturin biosynthesis genes from *B. subtilis* subsp. *krictiensis* ATCC 55079 (S. H. Bok, et al., U.S. Pat. No. 5,155,041, 1992. 10. 13) which is effective for various plant pathogens isolated from domestic soils and produces six kinds of iturins (iturin A to F) and obtained the U.S. patent in 1992, identified iturin biosynthesis genes by determining base sequences of the genes, analyzed their characteristics, and found that the above iturin biosynthesis genes are novel iturin biosynthesis genes that show many differences in base sequences, compared to conventional iturin genes, thereby leading to completion of the present invention.

SUMMARY OF THE INVENTION

One object of the present invention is to provide novel iturin biosynthesis genes, proteins encoded by the genes, and uses thereof.

In order to achieve the objects, the present invention provides an iturin biosynthesis gene having nucleotide sequence of SEQ ID NO:6 or an iturin biosynthesis gene having 95% or more sequence identity to the gene.

The present invention also provides an iturin biosynthesis gene having nucleotide sequences of SEQ ID NO:6 and SEQ ID NO:5.

Furthermore, the present invention provides an iturin biosynthesis gene having nucleotide sequences of SEQ ID NO:6 and SEQ ID NO:3.

The present invention also provides an iturin biosynthesis gene having nucleotide sequences of SEQ ID NO:6 and SEQ ID NO:7.

Furthermore, the present invention provides an iturin biosynthesis gene having nucleotide sequences of SEQ ID NO:6 and SEQ ID NO:8.

The present invention also provides an iturin biosynthesis gene having nucleotide sequences of SEQ ID NO:6, SEQ ID NO:3, and SEQ ID NO:7.

Furthermore, the present invention provides an iturin biosynthesis gene having nucleotide sequences of SEQ ID NO:6, SEQ ID NO:3, and SEQ ID NO:8.

The present invention also provides an iturin biosynthesis gene having nucleotide sequences of SEQ ID NO:6, SEQ ID NO:7, and SEQ ID NO:8.

Furthermore, the present invention provides an iturin biosynthesis gene having nucleotide sequence of SEQ ID NO:1.

The present invention also provides an iturin protein encoded by the gene in accordance with the present invention.

Furthermore, the present invention provides a vector comprising nucleotide sequence of the gene in accordance with the present invention.

The present invention also provides a transformant transformed with the vector comprising nucleotide sequence of the gene in accordance with the present invention.

Furthermore, the present invention provides iturin protein produced by the transformant in accordance with the present invention.

The present invention also provides a biological control agent comprising the transformant producing the iturin protein in accordance with the present invention or its culture medium.

Furthermore, the present invention provides the transformant of the present invention or its culture medium for use as a biological control agent, or the iturin protein produced by the transformant of the present invention for use as a biological control agent.

Hereinafter, the present invention will be described in detail.

The present invention provides an iturin biosynthesis gene having nucleotide sequence of SEQ ID NO:6 or an iturin biosynthesis gene having 95% or more sequence identity to the gene, or iturin protein encoded by the gene.

In the iturin biosynthesis gene, the nucleotide sequence of SEQ ID NO:6 may comprise ORF 3 of the iturin biosynthesis gene, and the protein encoded by the iturin gene may be, but not limited to, conventionally known iturin biosynthesis protein.

In a specific example of the present invention, first, the present inventors used *B. subtilis* 168, which is known that produces surfactin, but does not produce iturin, to identify the novel iturin biosynthesis gene. Surfactin and iturin are cyclic lipopeptide antibiotics composed of seven amino acids and a fatty acid. They are different from each other only in amino acid composition and sequences, and are known to be very similar in their molecular weights. Since surfactin gene is as large enough to be 32 kb in size, the size of iturin gene is thought to be similar to that. It is also assumed that the biosynthetic pathways of these two antibiotics are not distinct from the beginning, but the same pathway is utilized up to established steps, and then, two antibiotics are synthesized using separate biosynthetic pathways. Since some *B. subtilis* strains are known that produce both iturin and surfactin, the present inventors assumed that each gene is less likely to exist separately in consideration of the size of two genes. That is, cyclization of peptides and acylation process of connecting peptides and fatty acids during the biosynthetic process of two antibiotics are assumed to utilize the same pathway for biosynthesis of surfactin and iturin, considering each gene size. On the basis of these assumptions, the present inventors obtained surfactin biosynthetic genes from the database of *B. subtilis* 168 which was used in the *Bacillus* genome project and tried the cloning of iturin biosynthetic genes of *B. subtilis* subsp. *krictiensis* with a DNA homology based method. In a specific example of the present invention, PCR and electrophoresis were conducted using the chromosomal DNAs of B. subtilis 168 and *B. subtilis* subsp. *krictiensis* as the template. Among gene products obtained from *B. subtilis* subsp. *krictiensis*, about 1.8 kb of a DNA fragment, the same size with the gene product from *B. subtilis* 168, was obtained (FIG. 1).

Also in a specific example of the present invention, when the amino acid sequence of the DNA fragment obtained from *B. subtilis* subsp. *krictiensis* was compared to amino acid sequences of other peptide biosynthesis genes using NCBI database, it showed 82 to 85% homology with three different surfactin biosynthesis genes and 80% homology with lichenysin biosynthesis gene produced by *B. licheniformis*.

Also in a specific example of the present invention, to clone genes responsible for acylation process of connecting peptides and fatty acids, PCR was conducted using designed 20 primers and about 0.4 kb of a DNA fragment was obtained and the sequence was determined (FIG. 3). As a result of NCBI database search to compare amino acids, this gene product had 56 to 83% homology with acyl carrier protein reductases derived from other microorganisms (FIG. 4). Especially, it showed 83% homology with acyl carrier protein reductases derived from other *B. subtilis* and it was thought to be usable for genomic library screening of *B. subtilis* subsp. *krictiensis*.

Also in a specific example of the present invention, to clone the iturin biosynthetic genes from genomic library of *B. subtilis* subsp. *krictiensis*, the genomic DNAs of *B. subtilis* subsp. *krictiensis* were partially digested with Sau3A. Then, to 30 kb of a DNA fragment was inserted into the cosmid vector pLAFR3 and *E. coli* HB101 was transformed with the vector to construct the genomic library. Colony hybridization and Southern hybridization were conducted using the constructed genomic library of *B. subtilis* subsp. *krictiensis* and 1.8 kb of peptide biosynthesis gene, which was already cloned in Example <3-1> as a probe. Consequently, two clones that showed homology with the probe DNA at 27 kb and 32 kb positions were observed and named as pJJ815 and pJJ121, respectively (FIG. 5).

Also in a specific example of the present invention, a restriction enzyme map was constructed by digesting cosmid clones with various kinds of restriction enzymes and leaving out the regions which were overlapped each other. Base sequences of some fragments were investigated. As a result, some fragment of pJJ121 showed 57 to 90% homology with surfactin synthetase I, tyrocidine synthetase II, gramicidine S synthetase I, and peptide synthetase 2. From the result, the present inventors assumed that two cosmid clones include some genes related with peptide synthesis of iturin biosynthetic process.

Also in a specific example of the present invention, Southern hybridization was conducted at 50° C. and 65° C. using chromosomal DNAs of *B. subtilis* subsp. *krictiensis* and *B. subtilis* 168 to determine whether the genes in the cosmid clones are responsible for iturin or surfactin biosynthesis. Six EcoRI fragments which were obtained by digesting cosmid clones pJJ121 and pJJ815 with EcoRI were subcloned and the fragments were prepared as probe DNAs. Consequently, at 65° C., while *B. subtilis* subsp. *krictiensis* showed homologies with all probe DNAs of six EcoRI fragments, *B. subtilis* 168 did not show homology with any probe DNAs of six EcoRI fragments. The result of Southern hybridization at 50° C. was the same as above, but, *B. subtilis* 168 showed only weak homology for pJJ121E3 fragment. Accordingly, the genes in the cosmid clones hardly showed similarity with surfactin biosynthesis genes and it was assumed that the genes are likely to be responsible for iturin biosynthesis (FIG. 7 and FIG. 8).

In a specific example of the present invention, bidirectional sequence was determined with EcoRI fragments cloned from those two cosmid clones to obtain 21,253 bp. However, the present inventors found that some genes were missing. To further obtain the missing sequence, the present inventors obtained the genes through a genomic library screening and determined sequence to obtain a total of 37,682 bp of sequence. Seven ORFs which were assumed to be responsible for iturin biosynthesis were found within the sequence (FIG. 9). When each of seven ORFs which were assumed to be responsible for iturin biosynthesis of cosmid clones was compared with other cyclic lipopeptide biosynthetic genes, they showed 76 to 86% similarity to surfactin genes derived from *B. subtilis*, but they showed 92 to 100% similarity to surfactin genes derived from *B. amyloliquefaciens*. Especially, ORF 2-1 (543 bp), ORF 2-2 (9,927 bp), and ORF 3 (10,757 bp) which were assumed to be directly engaged in iturin biosynthesis showed 92 to 98% similarity to surfactin genes derived from *B. amyloliquefaciens*, respectively (Table 1). While ORF 2-1 showed 94% similarity to *B. amyloliquefaciens* FZB42 of which number starts with CP000560.1 among strains listed in Table 1, it showed 98% similarity to the entire sequence (37,682 bp). However, since the strain was reported to produce cyclic peptides, surfactin, fengycin, and bacillomycin D (Chen, et al., Nature Biotechnol., 25: 1007-1014, 2007), but not iturin, the present inventors assumed that ORF 2-1, ORF 2-2, and ORF 3 of the cosmid clones were novel iturin biosynthesis genes.

In a specific example of the present invention, antifungal activities of iturin and surfactin were examined against three kinds of test microorganisms, the rice blast fungus *Magnaporthe grisea*, the fungus causing athlete's foot *Trichophyton mentagrophytes*, and the fungus causing wilt disease of the family Solanaceae *Fusarium oxysporum*. Consequently, as shown in FIG. 10, standard compounds iturin A and surfactin showed antifungal activities against *Magnaporthe grisea* and *Trichophyton mentagrophytes*. Iturin showed antifungal activity against *Fusarium oxysporum*, whereas surfactin did not show antifungal activity against *Fusarium oxysporum* (FIG. 10).

Also in a specific example of the present invention, when antifungal activity was examined using the supernatant of culture broth of *Bacillus* producing iturin or surfactin, *B. subtilis* subsp. *krictiensis* producing iturin showed antifungal activities against *Magnaporthe grisea*, *Trichophyton mentagrophytes*, and *Fusarium oxysporum*, just like the examination result for antifungal activities using standard compounds. On the other hand, *B. subtilis* JH642 and *B. subtilis* 168 which do not produce antibiotics did not showed antifungal activities against the above test microorganisms. *B. subtilis* C9 which is assumed to produce both surfactin and iturin showed antifungal activities against *Fusarium oxysporum* against which iturin showed antifungal activity. Based on these results, the present inventors decided to use *Fusarium oxysporum* as a test microorganism for selecting iturin mutants (FIG. 11).

Also in a specific example of the present invention, the present inventors transformed fragments of cosmid clones into *B. subtilis* subsp. *krictiensis* (FIG. 12), and then observed antifungal activity against *Fusarium oxysporum*. Consequently, pBT6 fragment (including ORF 2-2 and ORF 3) showed the strongest antifungal activity against *Fusarium oxysporum* in the transformed *B. subtilis* subsp. *krictiensis* (FIG. 13).

Also in a specific example of the present invention, to confirm that among fragments of cosmid clones responsible for iturin biosynthesis, pBT6 is the region related to iturin biosynthesis, pJJ121E2 fragment containing pBT6 fragment was cloned into pTZ18 vector, and p121E3 vector having a spectinomycin-resistant gene was digested with BamHI and XbaI, and a ClaI site was attached thereto by PCR, and then, the fragment was digested with ClaI. Again, the ClaI-digested spectinomycin-resistant gene-containing fragment was inserted into the ClaI site of the pTZ18 vector into which pJJ121E2 fragment was inserted, and a SalI site was removed to prepare pJJ121E2-1 vector. Then, *B. subtilis* subsp. *krictiensis* was transformed with pJJ121E2-1 vector (*B. subtilis* subsp. *krictiensis* mutant-10) and whether the ability for iturin biosynthesis is lost or not was examined (FIG. 14). Consequently, *B. subtilis* subsp. *krictiensis* showed a strong antifungal activity against *Fusarium oxysporum*, whereas *B. subtilis* subsp. *krictiensis* mutant-10 showed significantly decreased antifungal activity (FIG. 15). In addition, as shown in FIG. 16, it was confirmed that the spectinomycin-resistant gene was inserted into the chromosome of *B. subtilis* subsp. *krictiensis* mutant-10 strain through Southern hybridization (FIG. 16).

Also in a specific example of the present invention, metabolites of *B. subtilis* subsp. *krictiensis* and *B. subtilis* subsp. *krictiensis* mutant-10 strain were analyzed by HPLC. Consequently, peaks observed in both *B. subtilis* subsp. *krictiensis* and the commercially available standard compound iturin A were identical, whereas the peak of iturin A was not observed in *B. subtilis* subsp. *krictiensis* mutant-10 strain (FIG. 17). The molecular weights for these peaks were determined by LC-Mass, and consequently, it was confirmed that peaks which were observed in *B. subtilis* subsp. *krictiensis*, but not in *B. subtilis* subsp. *krictiensis* mutant-10 corresponded exactly to iturins A to F (FIG. 18 to FIG. 20).

That is, the present inventors cloned iturin biosynthesis genes derived from *B. subtilis* subsp. *krictiensis*, analyzed the cloned gene sequences, and confirmed that these are novel iturin biosynthetic genes of which sequences are different from those of the previously known cyclic lipopeptide biosynthetic genes.

The present invention also provides an iturin biosynthesis gene having nucleotide sequences of SEQ ID NO:6 and SEQ ID NO:5, or iturin protein encoded by the iturin biosynthesis gene.

Furthermore, the present invention provides an iturin biosynthesis gene having nucleotide sequences of SEQ ID NO:6 and SEQ ID NO:3, or iturin protein encoded by the iturin biosynthesis gene.

The present invention also provides an iturin biosynthesis gene having nucleotide sequences of SEQ ID NO:6 and SEQ ID NO:7, or iturin protein encoded by the iturin biosynthesis gene.

Furthermore, the present invention provides an iturin biosynthesis gene having nucleotide sequences of SEQ ID NO:6 and SEQ ID NO:8, or iturin protein encoded by the iturin biosynthesis gene.

In the iturin biosynthesis gene, the nucleotide sequence of SEQ ID NO:6 may comprise ORF 3 of the iturin biosynthesis gene, the nucleotide sequence of SEQ ID NO:3 may comprise ORF 2 of the iturin biosynthesis gene, and the nucleotide sequence of SEQ ID NO:5 may comprise ORF 2-2, one part of ORF 2 of the iturin biosynthesis gene, but the present invention is not limited to such. In addition, the protein encoded by the iturin biosynthesis gene having nucleotide sequence of SEQ ID NO:6 may have nucleotide sequence of SEQ ID NO:14, the protein encoded by the iturin biosynthesis gene having nucleotide sequence of SEQ ID NO:3 may have nucleotide sequence of SEQ ID NO:11, and the protein encoded by the iturin biosynthesis gene having nucleotide sequence of SEQ ID NO:5 may have nucleotide sequence of SEQ ID NO:13, but the present invention is not limited to such.

Also, in the iturin biosynthesis gene, the nucleotide sequence of SEQ ID NO:7 may comprise ORF 4 of the iturin biosynthesis gene, and the nucleotide sequence of SEQ ID NO:8 may comprise ORF 5 of the iturin biosynthesis gene, but the present invention is not limited to such. In addition, the protein encoded by the iturin biosynthesis gene having nucleotide sequence of SEQ ID NO:7 may have nucleotide sequence of SEQ ID NO:15, and the protein encoded by the iturin biosynthesis gene having nucleotide sequence of SEQ ID NO:8 may have nucleotide sequence of SEQ ID NO:16, but the present invention is not limited to such.

The nucleotide sequence of SEQ ID NO:3 is characterized by the entire nucleotide sequence of ORF 2 of the iturin biosynthesis gene, and in order to determine a specific region encoding the iturin biosynthesis gene, the present inventors divided ORF 2 region into ORF 2-1 (SEQ ID NO:4) and ORF 2-2 (SEQ ID NO:5) to use in Examples.

In a specific example, when the iturin biosynthetic genes were compared to amino acids of other cyclic lipopeptide biosynthetic genes, there was a significant difference in the size of the entire iturin gene. Thus, the present inventors prepared fragments including ORFs which compose the iturin biosynthesis gene and experimented to identify regions responsible for iturin biosynthesis protein. Consequently, the present inventors confirmed that when the vector comprising nucleotide sequences of ORF 2-2 and ORF 3 was used, antifungal activity of iturin protein was elevated, thereby identifying the gene responsible for iturin biosynthesis.

The present invention also provides an iturin biosynthesis gene having nucleotide sequences of SEQ ID NO:6, SEQ ID NO:3, and SEQ ID NO:7, or iturin protein encoded by the iturin biosynthesis gene.

Furthermore, the present invention provides an iturin biosynthesis gene having nucleotide sequences of SEQ ID NO:6, SEQ ID NO:3, and SEQ ID NO:8, or iturin protein encoded by the iturin biosynthesis gene.

The present invention also provides an iturin biosynthesis gene having nucleotide sequences of SEQ ID NO:6, SEQ ID NO:7, and SEQ ID NO:8, or iturin protein encoded by the iturin biosynthesis gene.

The nucleotide sequence of SEQ ID NO:6 of the iturin biosynthesis gene may comprise ORF 3 of the iturin biosynthesis gene, the nucleotide sequence of SEQ ID NO:3 may comprise ORF 2 of the iturin biosynthesis gene, the nucleotide sequence of SEQ ID NO:7 may comprise ORF 4 of the iturin biosynthesis gene, and the nucleotide sequence of SEQ ID NO:8 may comprise ORF 5 of the iturin biosynthesis gene. But the present invention is not limited to such and any nucleotide sequence which can produce iturin proteins in iturin biosynthesis genes may be included.

For the protein encoded by the iturin biosynthesis gene, the protein encoded by the iturin biosynthesis gene having nucleotide sequence of SEQ ID NO:6 may have nucleotide sequence of SEQ ID NO:14, the protein encoded by the iturin biosynthesis gene having nucleotide sequence of SEQ ID NO:3 may have nucleotide sequence of SEQ ID NO:11, the protein encoded by the iturin biosynthesis gene having nucleotide sequence of SEQ ID NO:7 may have nucleotide sequence of SEQ ID NO:15, and the protein encoded by the iturin biosynthesis gene having nucleotide sequence of SEQ ID NO:8 may have nucleotide sequence of SEQ ID NO:16. But the present invention is not limited to such and any nucleotide sequence which can produce iturin proteins in iturin biosynthesis genes may be included.

Furthermore, the present invention provides an iturin biosynthesis gene having nucleotide sequence of SEQ ID NO:1, or iturin protein encoded by the iturin biosynthesis gene.

In the iturin biosynthesis gene, the nucleotide sequence of SEQ ID NO:1 may comprise seven nucleotide sequences of ORFs 1 to 6 included in the iturin biosynthesis gene shown in FIG. 9, but the present invention is not limited to such.

In a specific example, the nucleotide sequence exhibited a significant difference, compared to conventional genes responsible for iturin biosynthesis, and thereby, the present inventors found that the nucleotide sequence is the novel iturin biosynthesis gene. Among ORFs composing the iturin biosynthesis gene, antifungal activity of the transformant comprising the fragment which comprises a part of ORF 2 (ORF 2-2) and ORF 3 was the most increased. Antifungal activity of transformant comprising the fragment which comprises other ORFs was confirmed.

Therefore, the present inventors identified the novel iturin biosynthesis gene having the nucleotide sequence of SEQ ID NO:1.

Furthermore, the present invention provides a vector comprising nucleotide sequence of the iturin biosynthesis gene in accordance with the present invention.

The nucleotide sequence of iturin biosynthesis gene which is included in the vector may comprise the iturin biosynthesis gene having nucleotide sequence of SEQ ID NO:1, preferably the gene having nucleotide sequences of SEQ ID NO:6, SEQ ID NO:3, and SEQ ID NO:7, the gene having nucleotide sequences of SEQ ID NO:6, SEQ ID NO:3, and SEQ ID NO:8, or the gene having nucleotide sequences of SEQ ID NO:6, SEQ ID NO:7, and SEQ ID NO:8, preferably the gene having nucleotide sequences of SEQ ID NO:6 and SEQ ID NO:5, the gene having nucleotide sequences of SEQ ID NO:6 and SEQ ID NO:3, the gene having nucleotide sequences of SEQ ID NO:6 and SEQ ID NO:7, or the gene having nucleotide sequences of SEQ ID NO:6 and SEQ ID NO:8, and more preferably, the gene having nucleotide sequence of SEQ ID NO:6, or the iturin biosynthesis gene having 95% or more sequence identity to the gene having nucleotide sequence of SEQ ID NO:6. But, the present invention is not limited to such.

The present invention also provides a transformant transformed with the vector comprising nucleotide sequence of the iturin biosynthesis gene in accordance with the present invention.

Furthermore, the present invention provides iturin protein produced by the transformant in accordance with the present invention.

*Bacillus subtilis, Saccharomyces cerevisiae,* and *Bacillus amyloliquefaciens* may be used for the transformant, but the present invention is not limited to such. In addition, methods for introducing the recombinant vector into the strain may be heat-shock method, electroporation method, and preferably Spizizen method, but they are not limited to such. Known techniques may be used for introduction.

In the iturin protein encoded by the iturin biosynthesis gene in accordance with the present invention, iturin proteins may be encoded by the vector comprising the gene or the transformant, but the present invention is not limited to such.

In a specific example, it was confirmed that antifungal activity of the strain which was transformed with the vector comprising nucleotide sequences in accordance with the present invention was increased. Therefore, culture broth of the transformed strain may be used as a biological control agent and such transformant itself may be efficiently used as a biological control agent. By using the transformant itself, it may be possible to reduce processes, transportation, and storage that are required for obtainment of iturin proteins.

The present invention also provides a biological control agent comprising the transformant producing the iturin in accordance with the present invention or its culture broth.

Furthermore, the present invention provides the transformant of the present invention or its culture broth for use as a biological control agent, or the iturin protein produced by the transformant of the present invention for use as a biological control agent.

The iturin protein, the transformant producing iturin protein, and its culture broth in accordance with the present invention may have control effect against rice blast pathogen *Magnaporthe grisea,* wilt pathogen *Fusarium oxysporum,* gray mold rot pathogen *Botrytis cinerea,* barley powdery mildew pathogen *Erysiphe graminis* f. sp. *hordei,* tomato leaf mold pathogen *Fulvia fulva,* anthracnose pathogen *Colletotrichum gloeosporioides,* Ginseng root rot pathogen *Cylindrocarpon destructans,* the pathogen of damping-off of ginseng *Rhizoctonia solani,* the pathogen of *Alternaria* leaf spot of green onions *Alternaria porri,* the pathogen of *Alternaria* leaf spot of apples *Alternaria mali,* the pathogen of *Alternaria* blight of ginseng *Alternaria panax,* the pathogen of damping-off of ginseng *Pythium* sp. or *Salmonella typhimurium,* and preferably against rice blast pathogen *Magnaporthe grisea* and wilt pathogen *Fusarium oxysporum,* but the present invention is not limited to such.

In a specific example, the present inventors transformed *B. subtilis* subsp. *krictiensis* with the fragments of cosmid clones and observed antifungal activity against *Fusarium oxysporum.* As a result, the present inventors observed that the pBT6 fragment-transformed *B. subtilis* subsp. *krictiensis* showed remarkably increased antifungal activity, compared to untransformed control *B. subtilis* subsp. *krictiensis.*

Therefore, the iturin protein encoded by novel iturin biosynthesis genes identified in the present invention, the transformant producing thereof, and culture broth thereof may be used effectively as biological control agents.

As stated above, through gene cloning, base sequence determination, and antifungal activity examination, the present inventors identified iturin biosynthesis genes from *B. subtilis* strain producing six kinds of iturins described in the present invention. In addition, through mutants and instrumental analyses, the present inventors reconfirmed that metabolites are iturins and confirmed that the genes are novel genes which are different from the genes reported up to date. Based on these, it is considered that with the use of iturin biosynthesis genes, strains may be modified to antifungal activity-enhanced strains to use as a biological control agent. On the other hand, it is considered that the gene may be transformed into bacteria showing other biological control activities, and thus, be applied to novel strain development.

BRIEF DESCRIPTION OF THE DRAWINGS

The above and other objects, features and other advantages of the present invention will be more clearly understood from the following detailed description taken in conjunction with the accompanying drawings, in which.

Lane 1: 1 kb ladder;

Lane 2: PCR products obtained from *B. subtilis* 168 strain by using SrfB7 and SrfB8 primers (products of surfactin gene);

Lane 3: PCR products obtained from *B. subtilis* subsp. *krictiensis* strain by using SrfB7 and SrfBB primers (products of putative iturin gene);

Lane 4: PCR products obtained from *B. subtilis* 168 strain by using SrfB9 and SrfB10 primers (products of surfactin gene); and Lane 5: PCR products obtained from *B. subtilis* subsp. *krictiensis* strain by using SrfB9 and SrfB10 primers (products of putative iturin gene).

Figure 2:
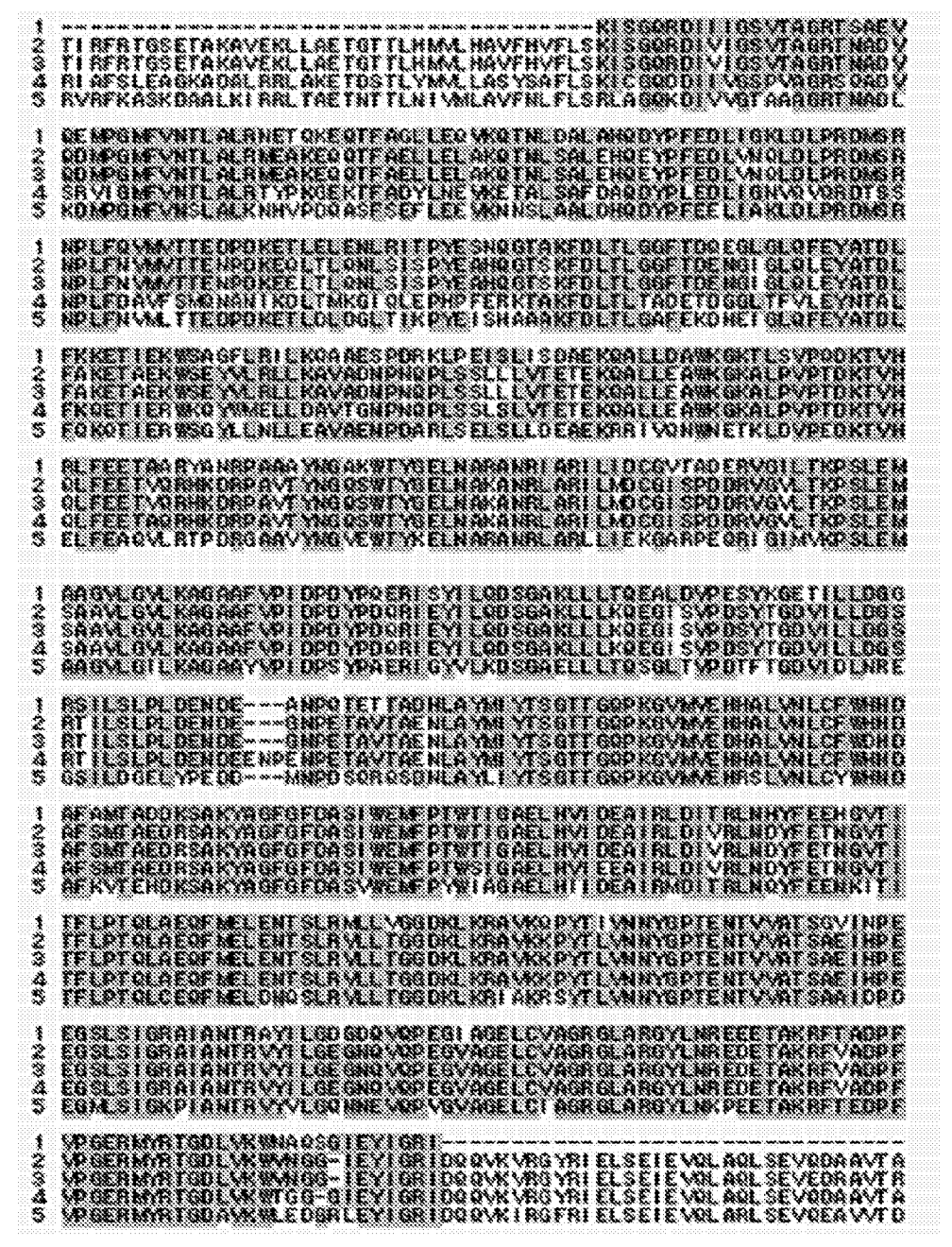

FIG. 2 is a figure showing comparative analysis of the amino acid sequence obtained from *B. subtilis* subsp. *kric*-

*tiensis* strain by using SrfB9 and SrfB10 primers with the amino acid sequence of surfactin biosynthesis gene and the amino acid sequence of lichenysin biosynthesis gene using CLUSTAL W:

1: amino acid sequence of the PCR product obtained from *B. subtilis* subsp. *krictiensis* strain by using SrfB9 and SrfB10 primers (amino acid sequence of product of putative iturin gene) (SEQ ID NO:38);

2, 3, 4: amino acid sequence of three different domains of the surfactin biosynthesis gene (SEQ ID NO:39, SEQ ID NO:40, SEQ ID NO:41 respectively); and 5: amino acid sequence of the lichenysin biosynthesis gene (SEQ ID NO:42).

FIG. 3 is a figure showing nucleotide and peptide sequences of 0.4 kb PCR product obtained from *B. subtilis* subsp. *krictiensis* strain (SEQ ID NO:43 and SEQ ID NO:44, respectively) by using SrfA5 and SrfA6 primers.

FIG. 4 is a figure showing comparative analysis of the amino acid sequence of PCR product obtained from *B. subtilis* subsp. *krictiensis* strain by using SrfA5 and SrfA6 primers with amino acid sequences of other strains using CLUSTAL W:

1. amino acid sequence of an acyl carrier protein reductase of *Cuphea lanceolata* plant (SEQ ID NO:45);

2: amino acid sequence of an acyl carrier protein reductase of *Bacillus subtilis* strain (SEQ ID NO:46);

3. amino acid sequence of an acyl carrier protein reductase of *Salmonella typhimurium* strain (SEQ ID NO:47);

4: amino acid sequence of an acyl carrier protein reductase of *Deinococcus radiodurans* strain (SEQ ID NO:48); and 5: amino acid sequence of PCR product obtained from *B. subtilis* subsp. *krictiensis* strain (SEQ ID NO:49) using SrfA5 and SrfA6 primers.

FIG. 5 is a figure showing the result of genomic library screening of *B. subtilis* subsp. *krictiensis:*

FIG. 5A is a figure showing the result of colony hybridization;

FIG. 5B is the result of agarose electrophoresis after digesting the DNAs of cosmid clones obtained by colony hybridization with EcoRI; and FIG. 5C is a figure showing the result of Southern hybridization, in which two clones exhibited homology with radioisotope-labeled probe DNA.

Figure 6:
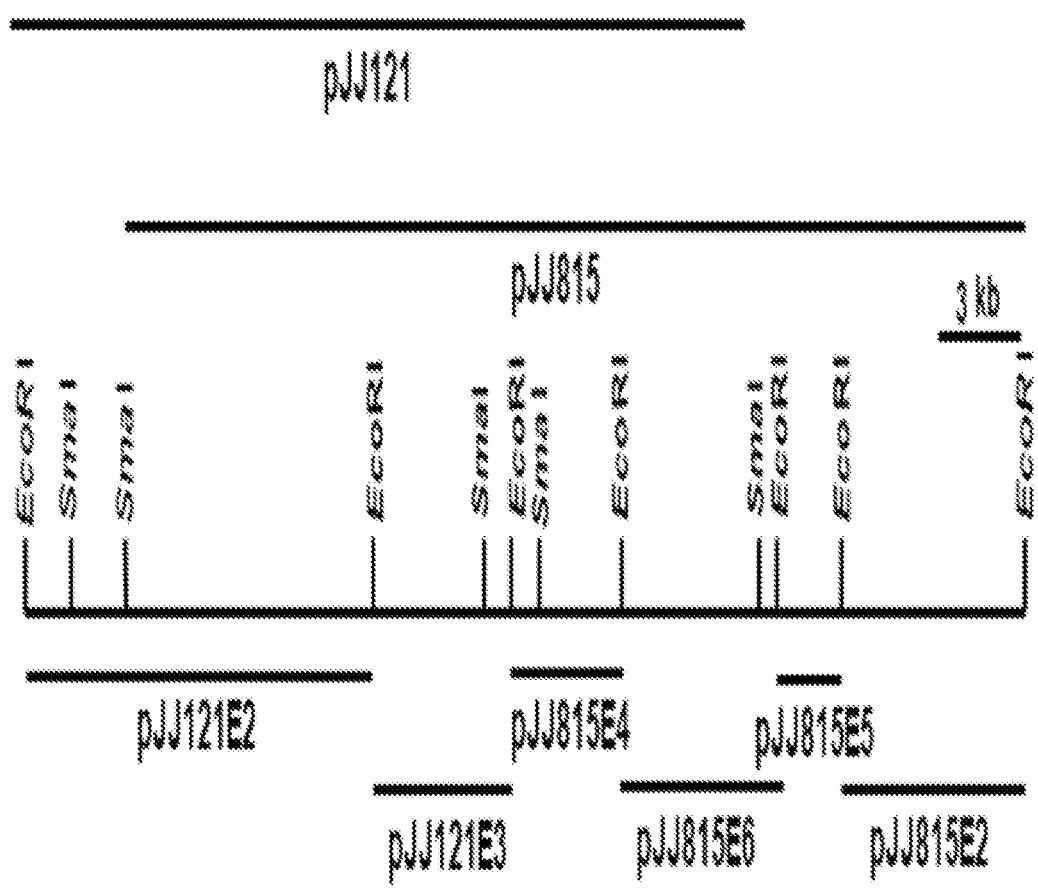

FIG. 6 is a restriction enzyme map of cosmid clones obtained by genomic library screening.

FIG. 7A to FIG. 7F are figures showing the results of hybridization at 65° C. of EcoRI-digested fragments of pJJ815 and pJJ121 clones obtained by genomic library screening from *B. subtilis* subsp. *krictiensis* and *B. subtilis* 168 strain:

Lane 1: lambda DNA digested with HindIII;
Lane 2: genomic DNA of *B. subtilis* subsp. *krictiensis;*
Lane 3: genomic DNA of *B. subtilis* 168; and
Lane 4: probe DNA.

FIG. 8A to FIG. 5F are figures showing the results of hybridization at 50° C. of EcoRI-digested fragments of pJJ815 and pJJ121 clones obtained by genomic library screening from *B. subtilis* subsp. *krictiensis* and *B. subtilis* 168:

Lane 1: lambda DNA digested with HindIII;
Lane 2: genomic DNA of *B. subtilis* subsp. *krictiensis;*
Lane 3: genomic DNA of *B. subtilis* 168; and
Lane 4: probe DNA.

Figure 9:
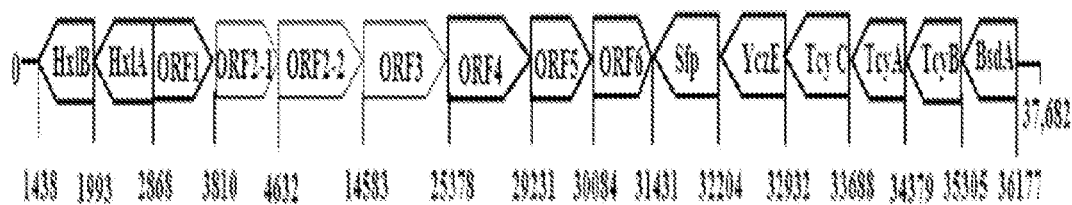

FIG. 9 shows genetic organization of iturin biosynthesis gene obtained by genomic library screening from *B. subtilis* subsp. *krictiensis* strain:

ORF1: transcriptional regulator;
ORF2-1: Itu A-1;
ORF2-2: Itu A-2;
ORF3: Itu B;
ORF4: Itu C;
ORF5: Itu D; and
OFR6: asparate transaminase-like protein.

Figure 10:
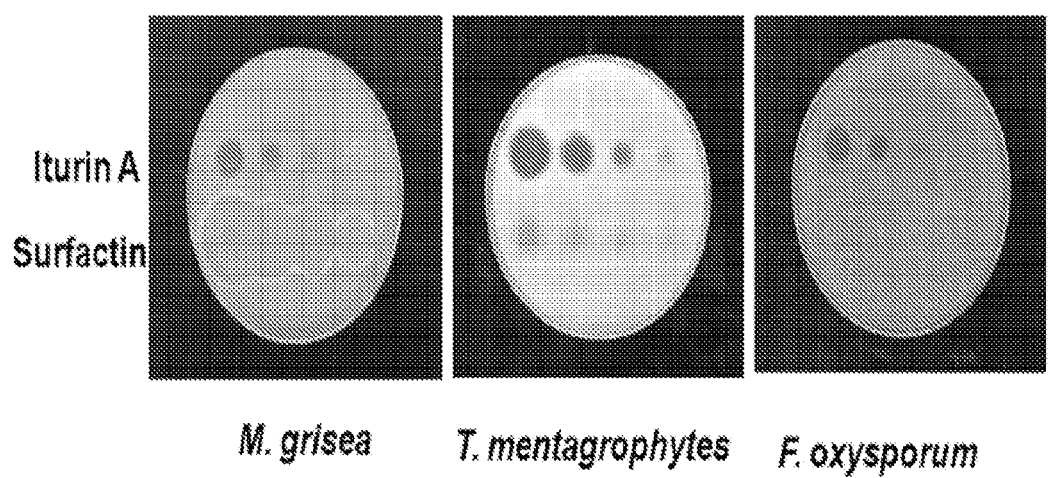

FIG. 10 is a figure showing comparison of antifungal activity of standard compounds, iturin and surfactin.

Figure 11:
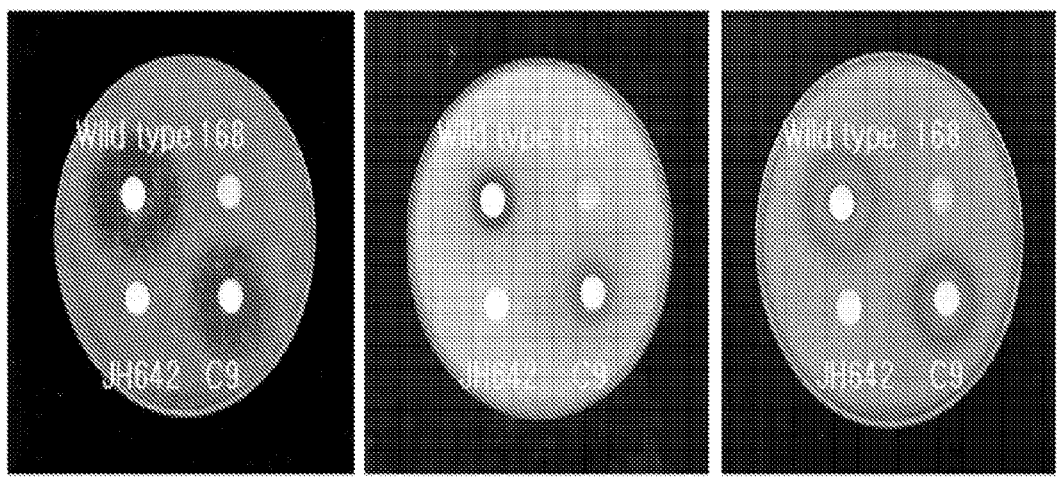

FIG. 11 is a figure showing comparison of antifungal activity of *B. subtilis* subsp. *krictiensis, B. subtilis* 168, *B. subtilis* JH642, and *B. subtilis* C9 against three kinds of test microorganisms:

Wild type: *B. subtilis* subsp. *krictiensis* producing iturin;
*B. subtilis* 168: *B. subtilis* strain having surfactin gene but not producing surfactin;
*B. subtilis* JH642: *B. subtilis* strain producing neither iturin nor surfactin; and
*B. subtilis* C9: putative *B. subtilis* strain producing both surfactin and iturin.

Figure 12:
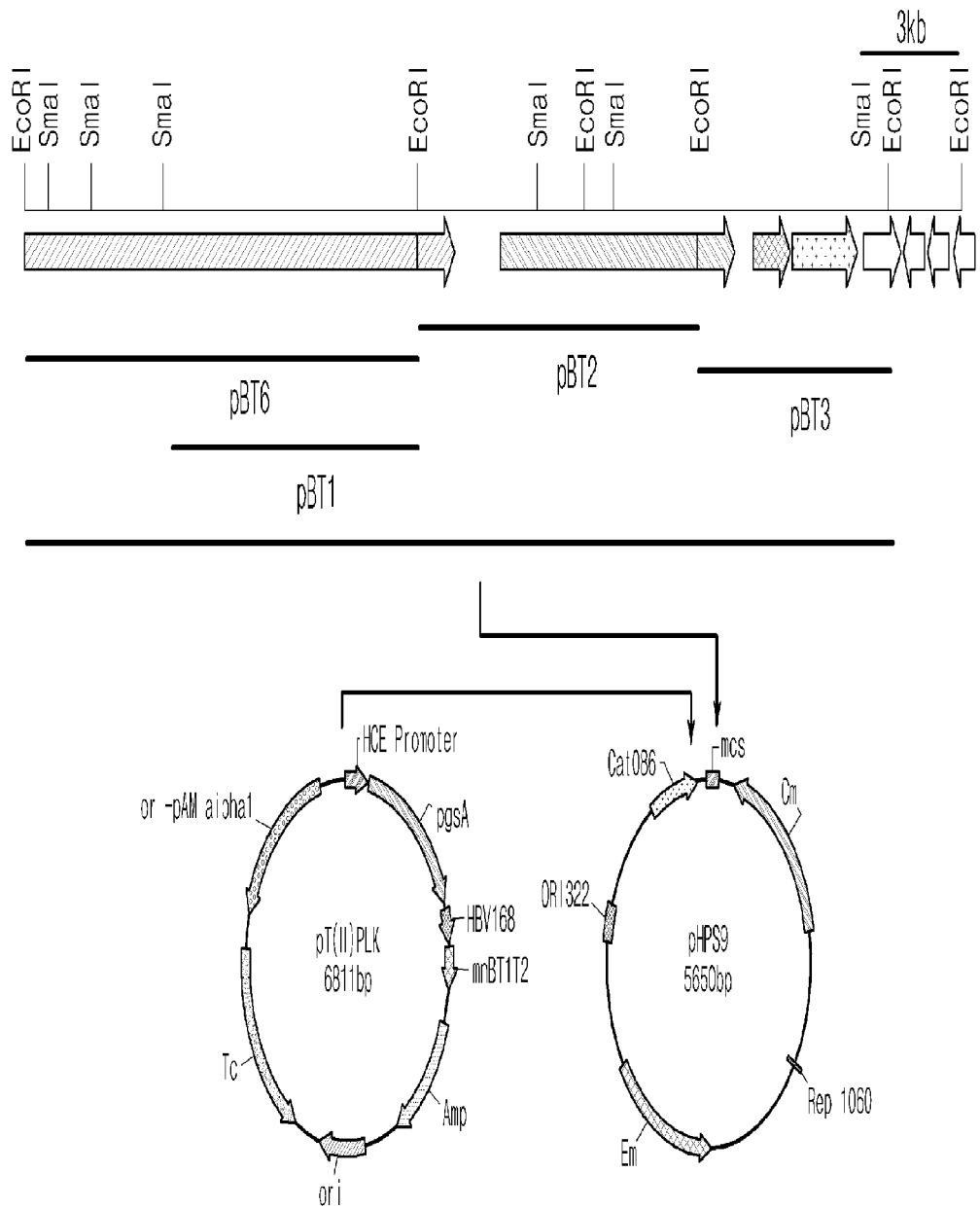

FIG. 12 shows EcoRI fragments of cosmid clones and construction of the vector comprising the fragments.

Figure 13:
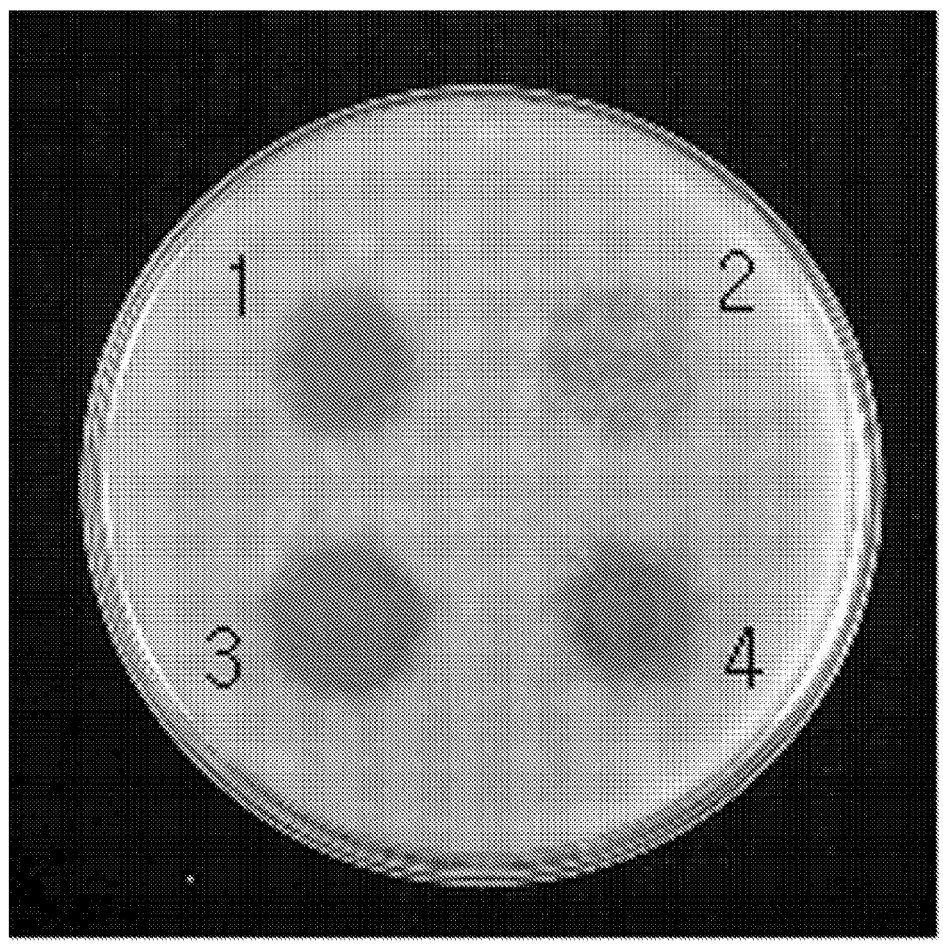

FIG. 13 is a figure showing comparison of antifungal activity of *B. subtilis* subsp. *krictiensis* transformants containing various EcoRI fragments derived from cosmid clones:

1: pBT1 fragments; fragments of cosmid pJJ121 digested with SmaI and EcoRI
2: pBT3 fragments; EcoRI fragments of cosmid pJJ815
3: pBT6 fragments; EcoRI fragments of cosmid pJJ121
4: untransformed *B. subtilis* subsp. *krictiensis* strain.

Figure 14:
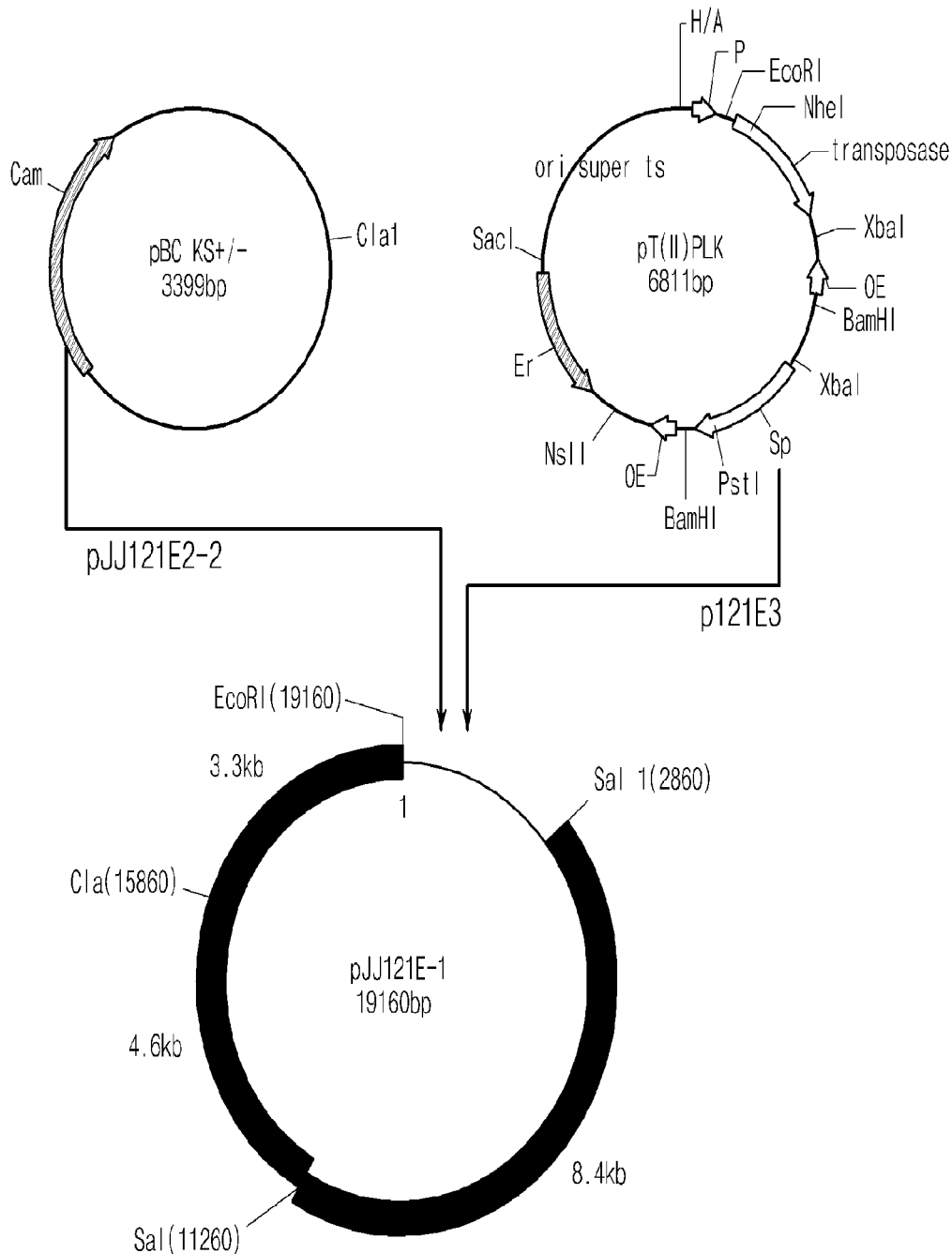

FIG. 14 is a schematic diagram of construction of a vector for preparing an iturin-less mutant.

Figure 15:
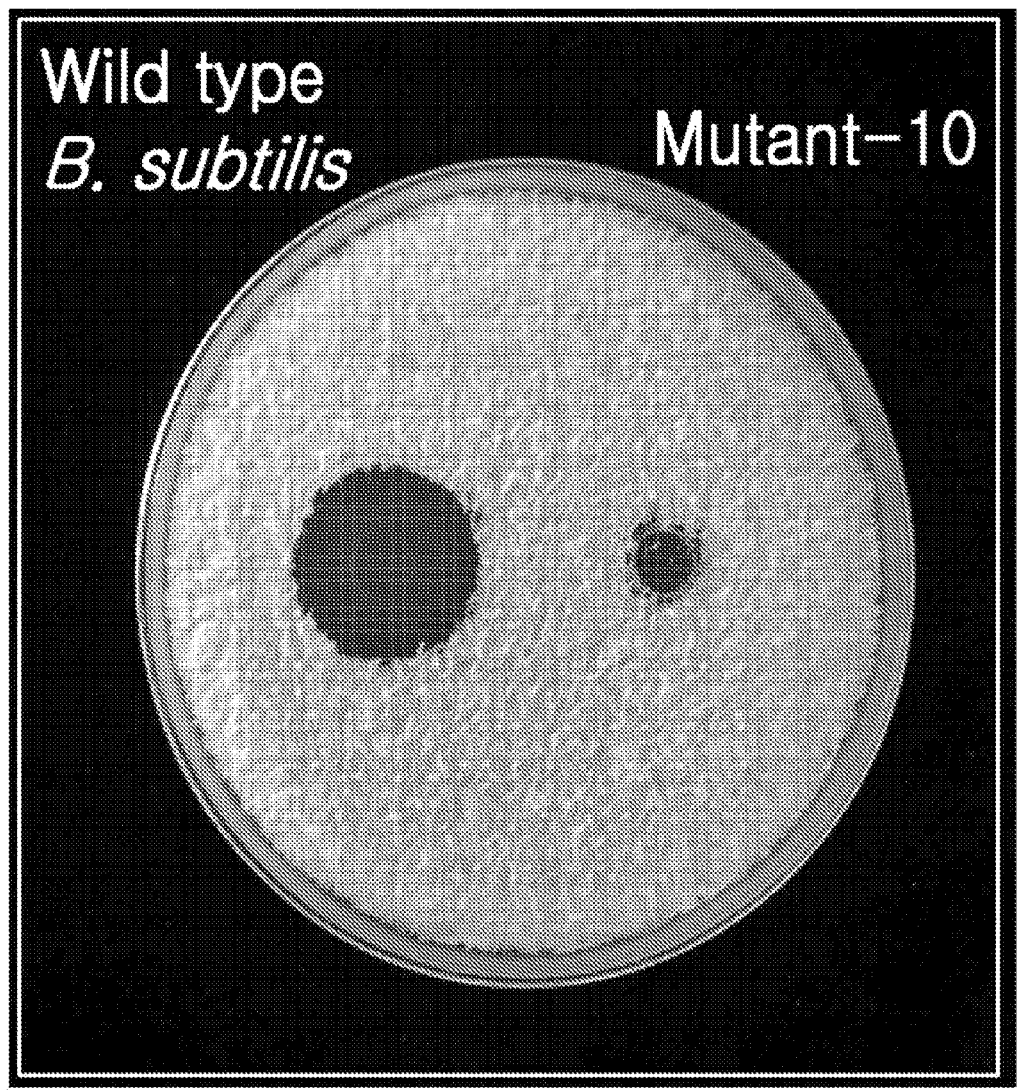

FIG. 15 is a figure showing comparison of antifungal activity of *B. subtilis* subsp. *krictiensis* producing iturin and the iturin-less mutant against *Fusarium oxysporum*.

Figure 16:
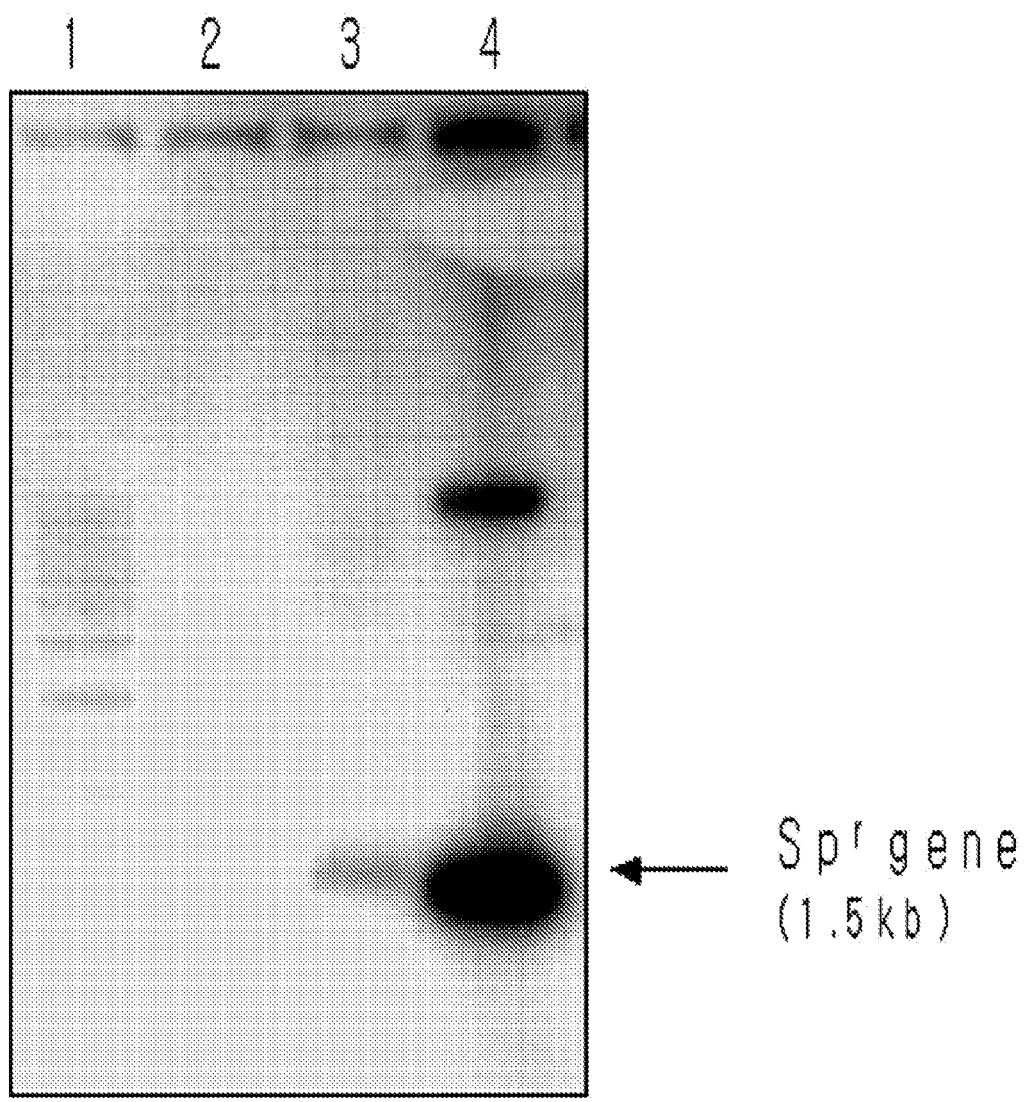

FIG. 16 shows the result of Southern hybridization for examining whether spectinomycin which was inserted within the mutant was inserted into chromosomes or not:

Lane 1: 1 kb ladder;
Lane 2: fragments of genomic DNA of B, subtilis subsp. *krictiensis* strain digested with ClaI;
Lane 3: fragments of genomic DNA of *B. subtilis* subsp. *krictiensis* mutant-10 strain digested with ClaI; and
Lane 4: p121E3 vector digested with BamHI and XbaI.

Figure 17:
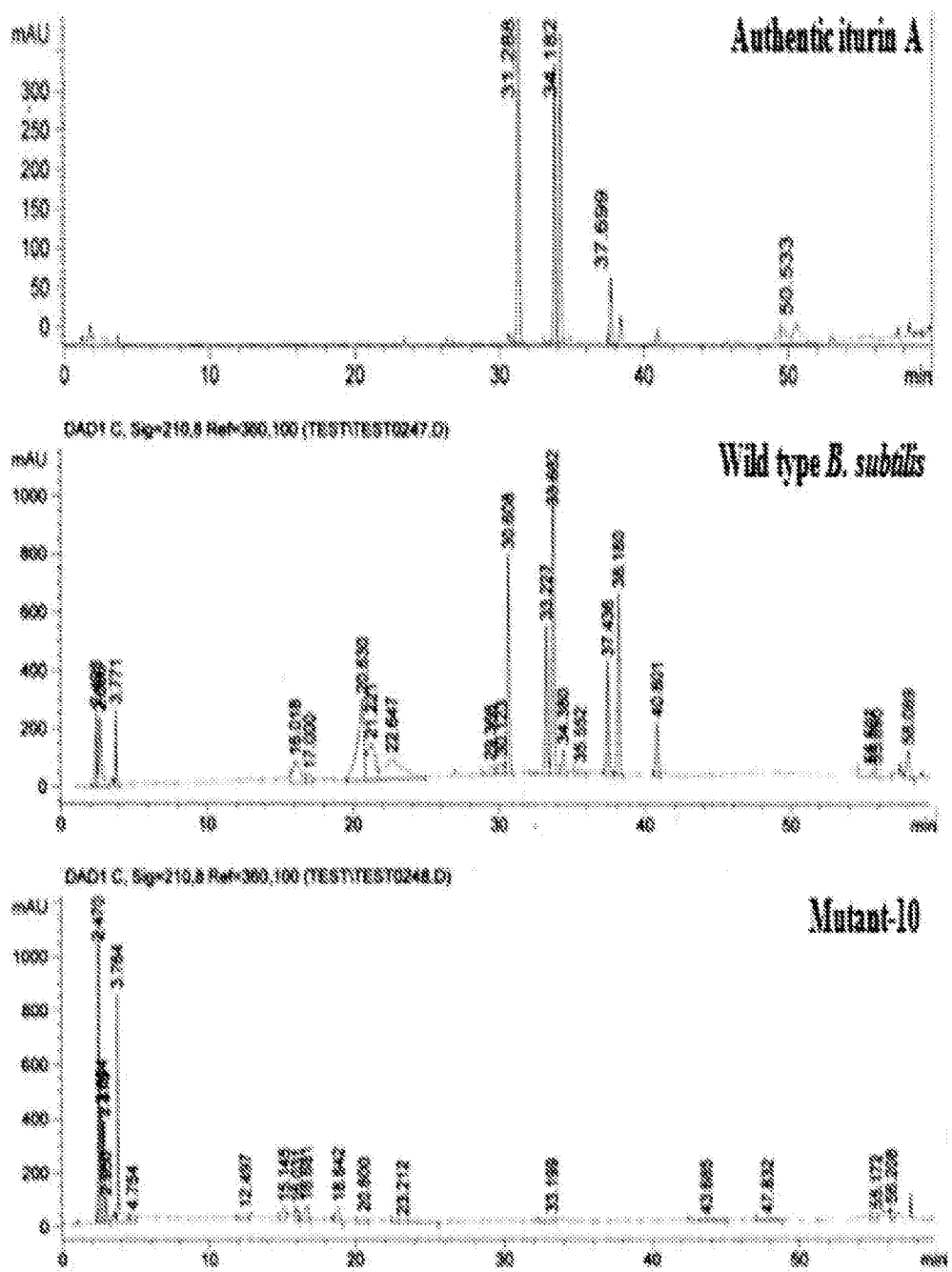

FIG. 17 is a HPLC chromatogram for examining whether iturin was produced or not from *B. subtilis* subsp. *krictiensis* and the iturin-less mutant.

Figure 18:
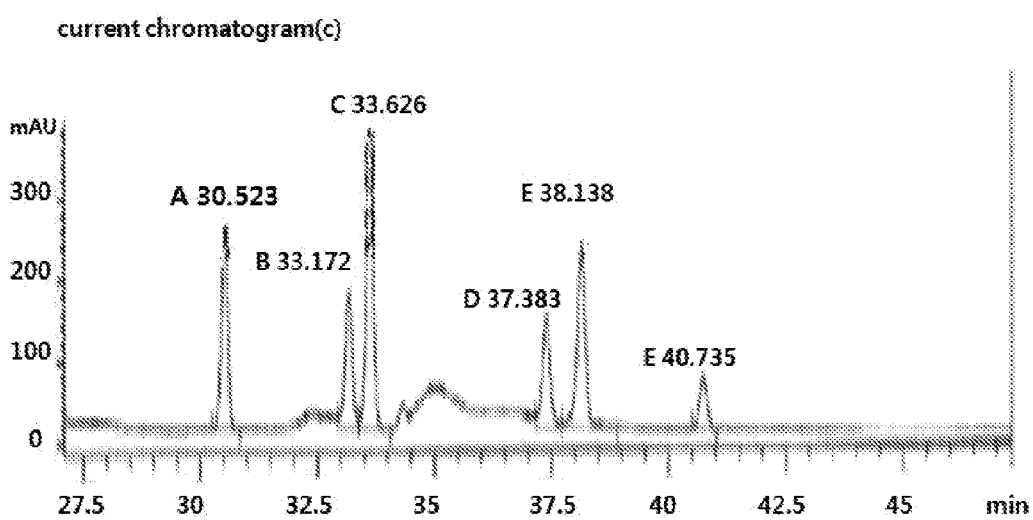

FIG. 18 is HPLC chromatograms for analyzing six kinds of iturins produced by *B. subtilis* subsp. *krictiensis:*

A: Iturin A;
B: Iturin B;
C: Iturin C;
D: Iturin D;
E: Iturin E; and
F: Iturin F.

Figure 19A:
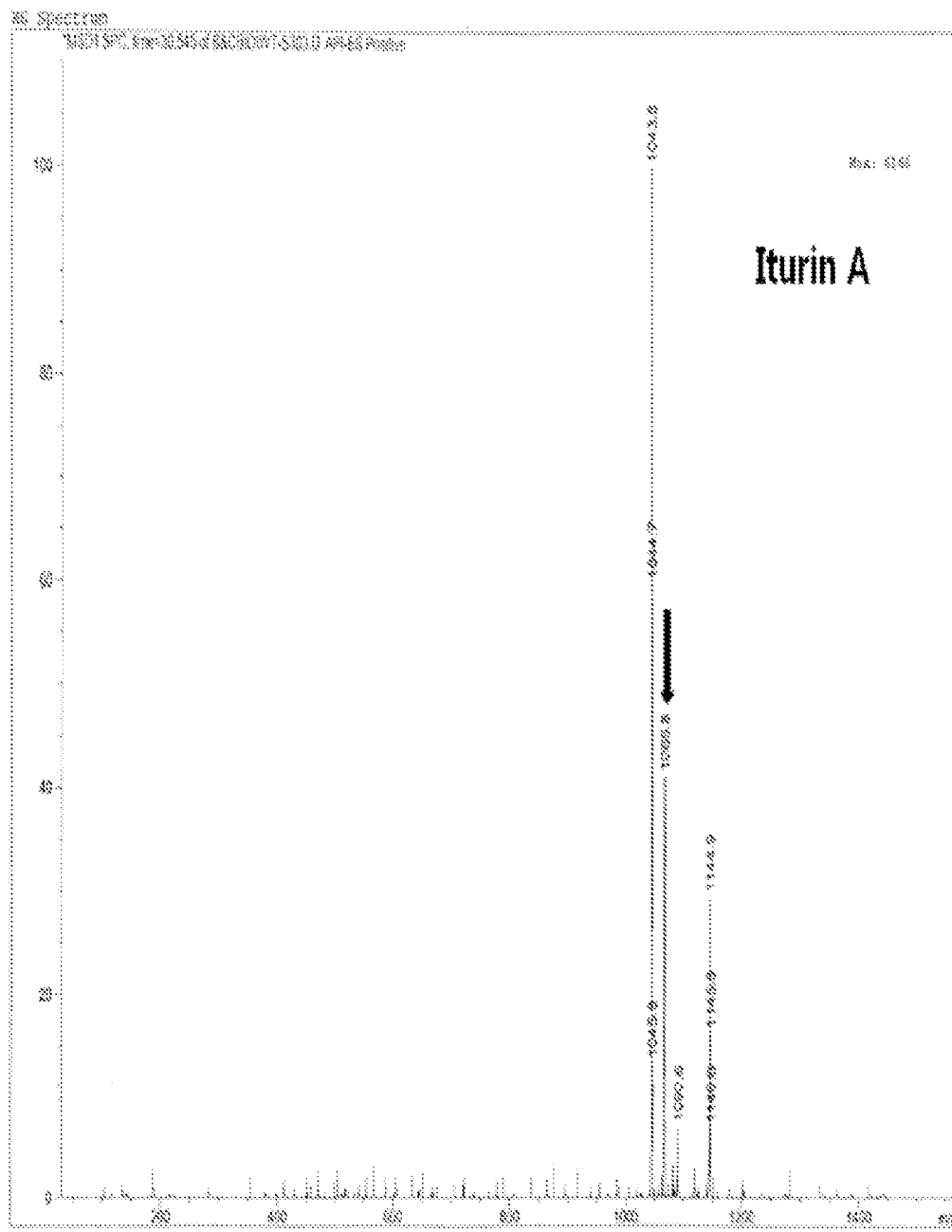
Figure 19B:
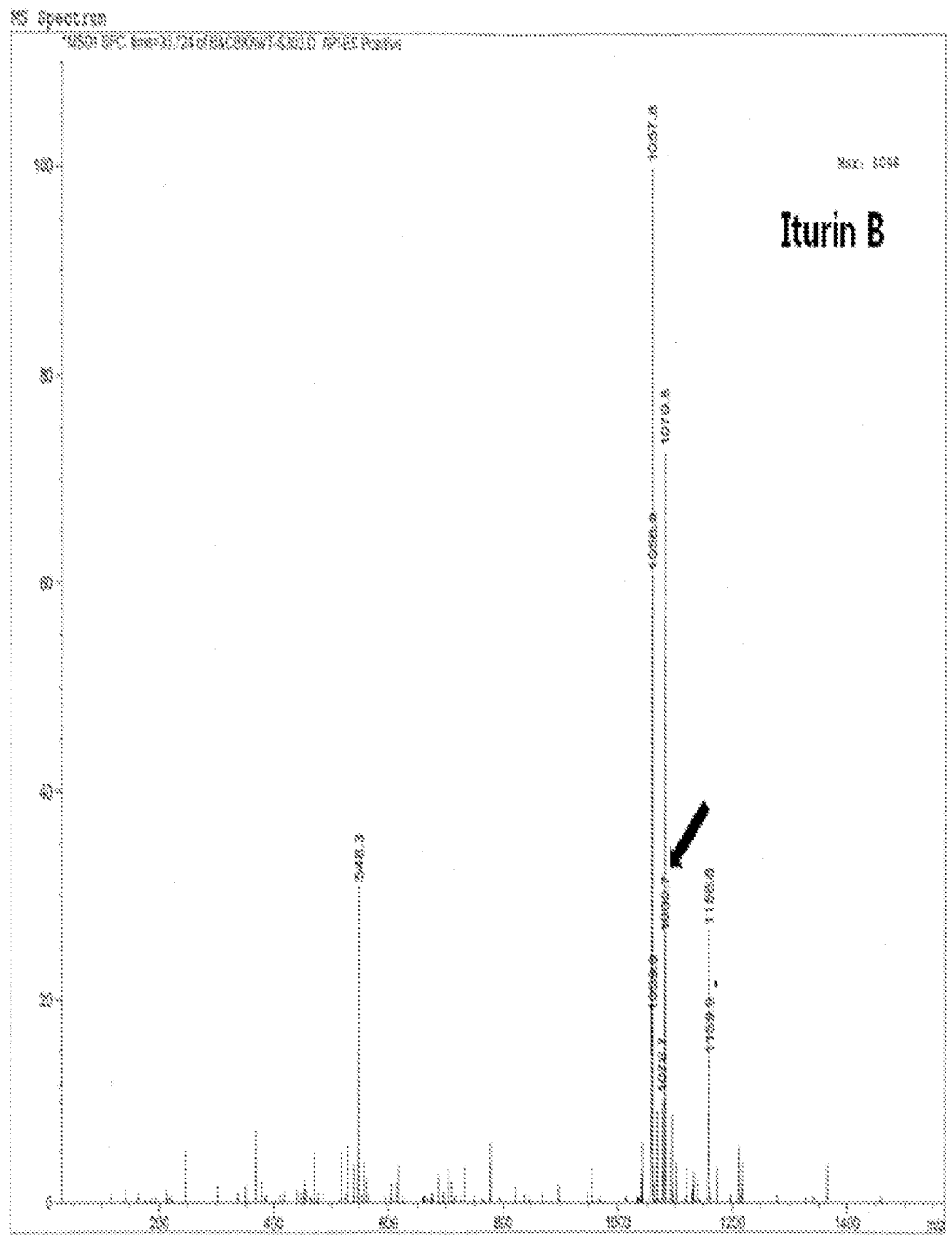
Figure 19C:
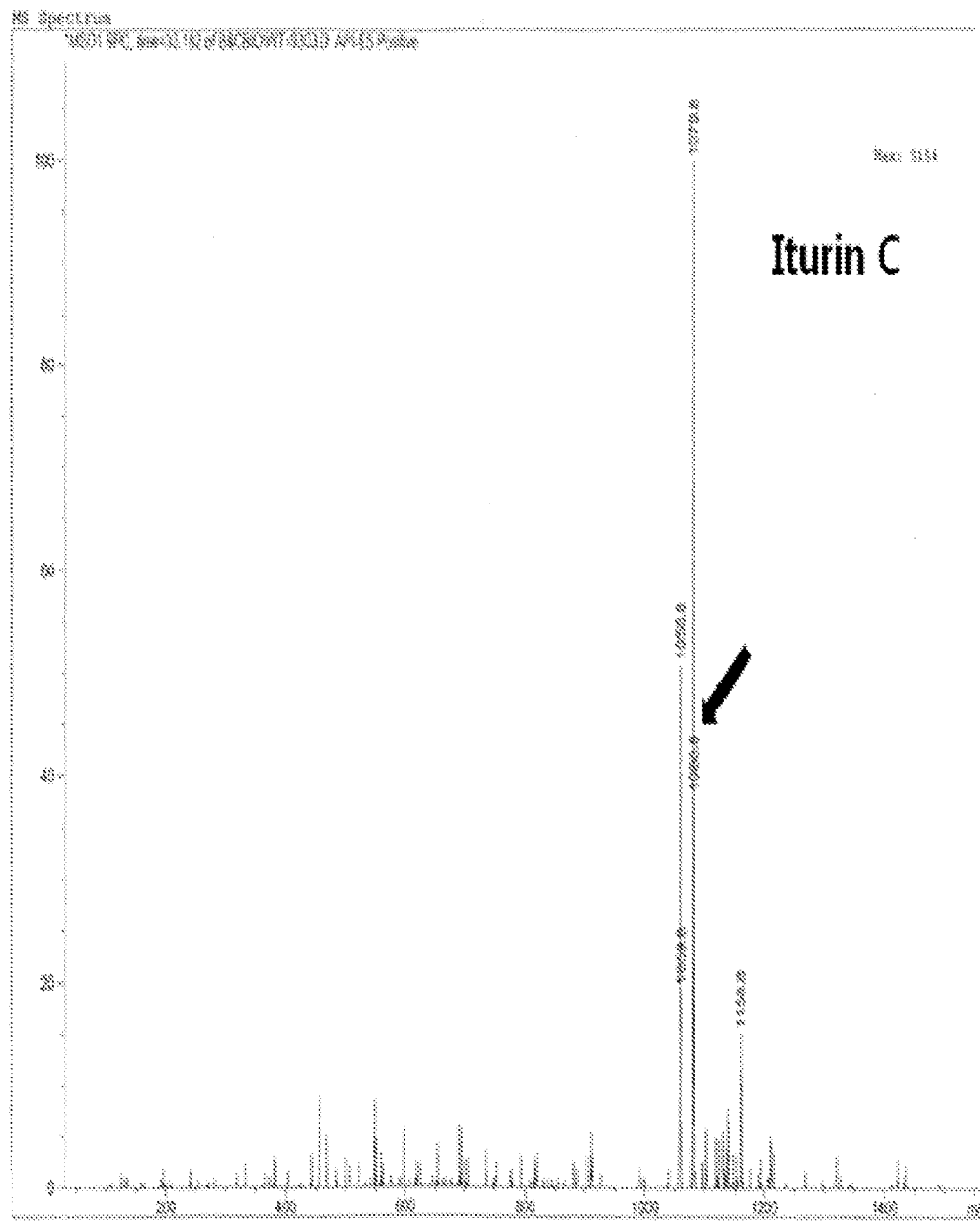

FIGS. 19A-C respectively show the result of LC-Mass analysis for examining whether iturin A, B, and C among six iturins were produced from *B. subtilis* subsp. *krictiensis*.

Figure 20A:
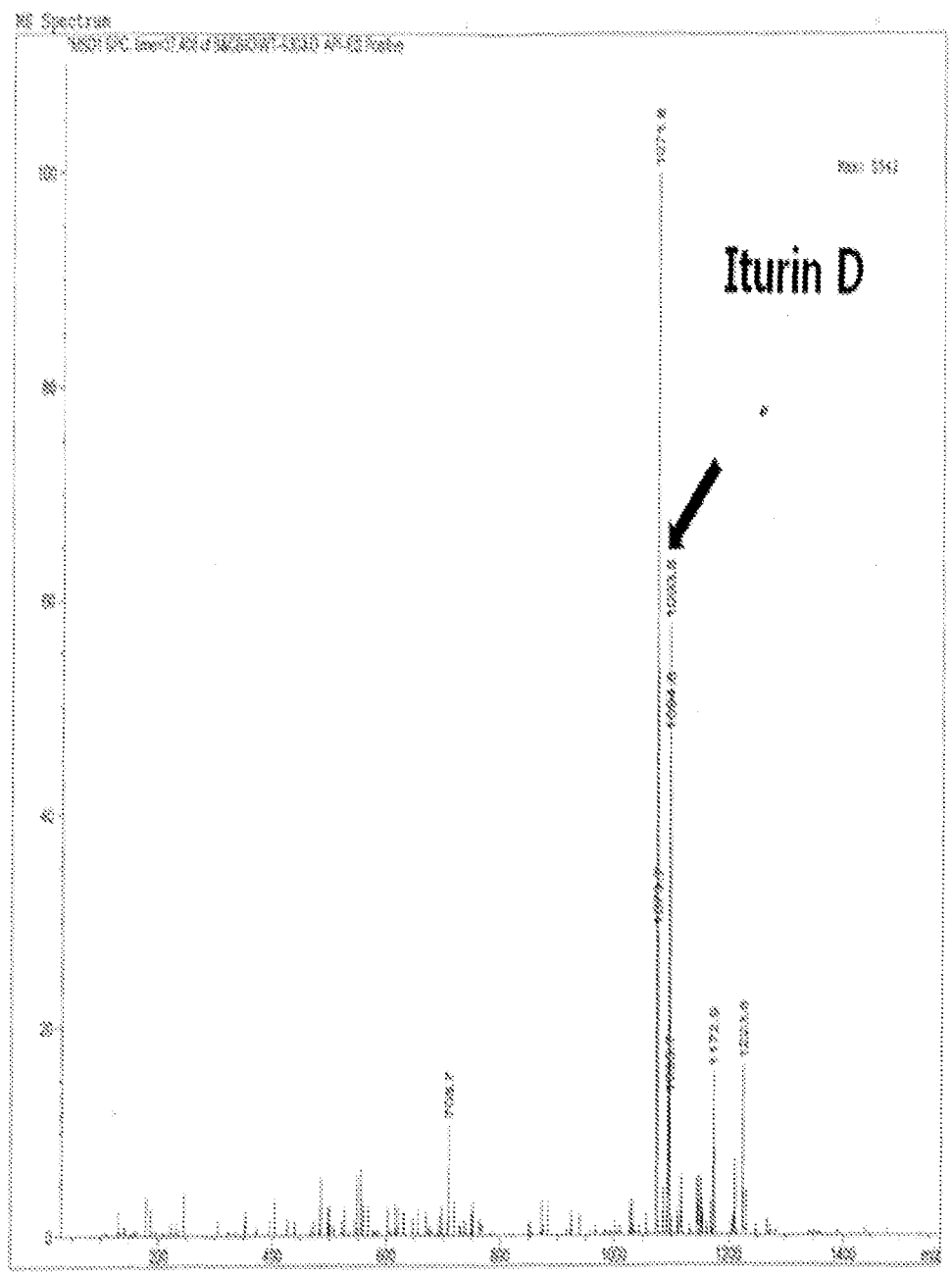
Figure 20B:
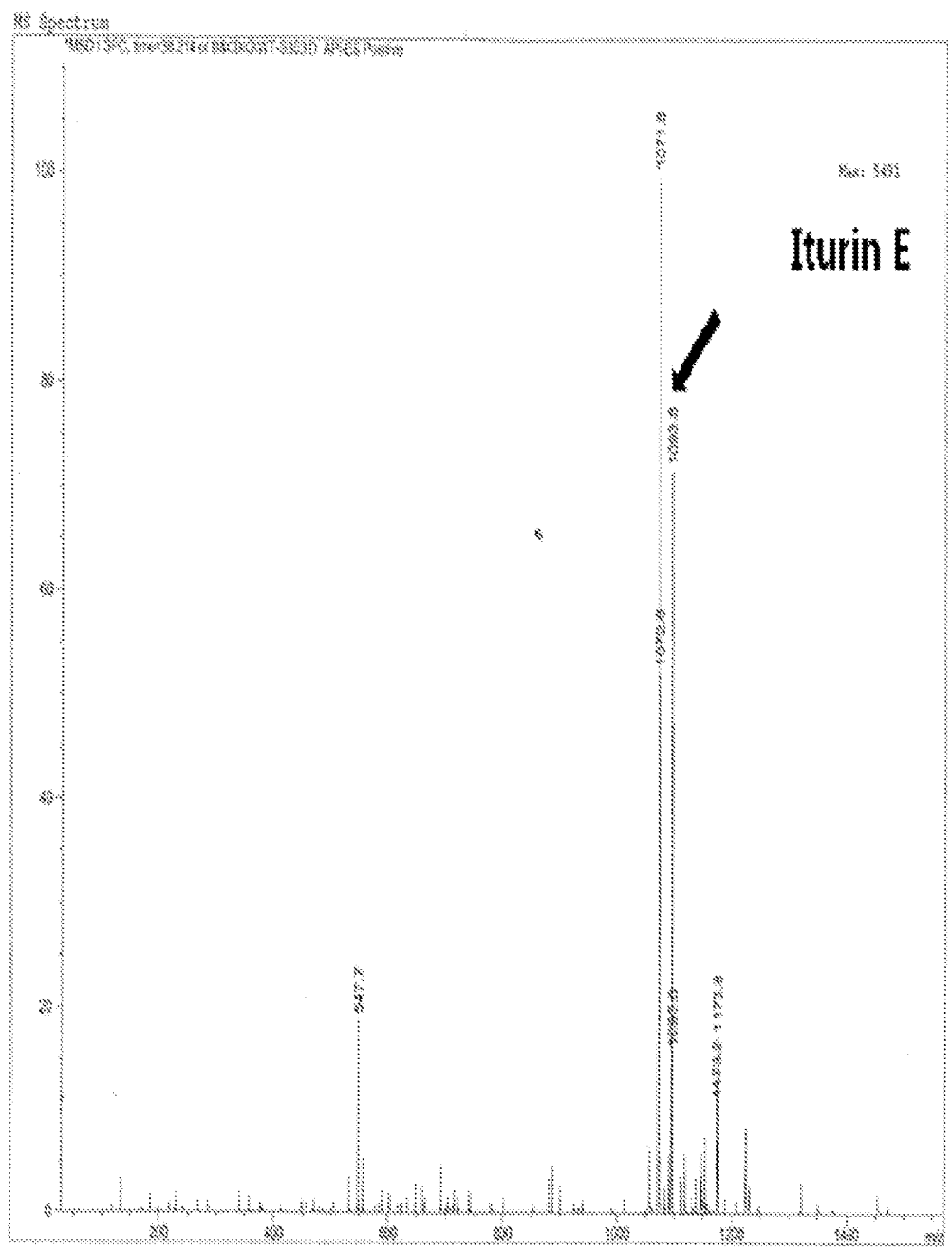
Figure 20C:
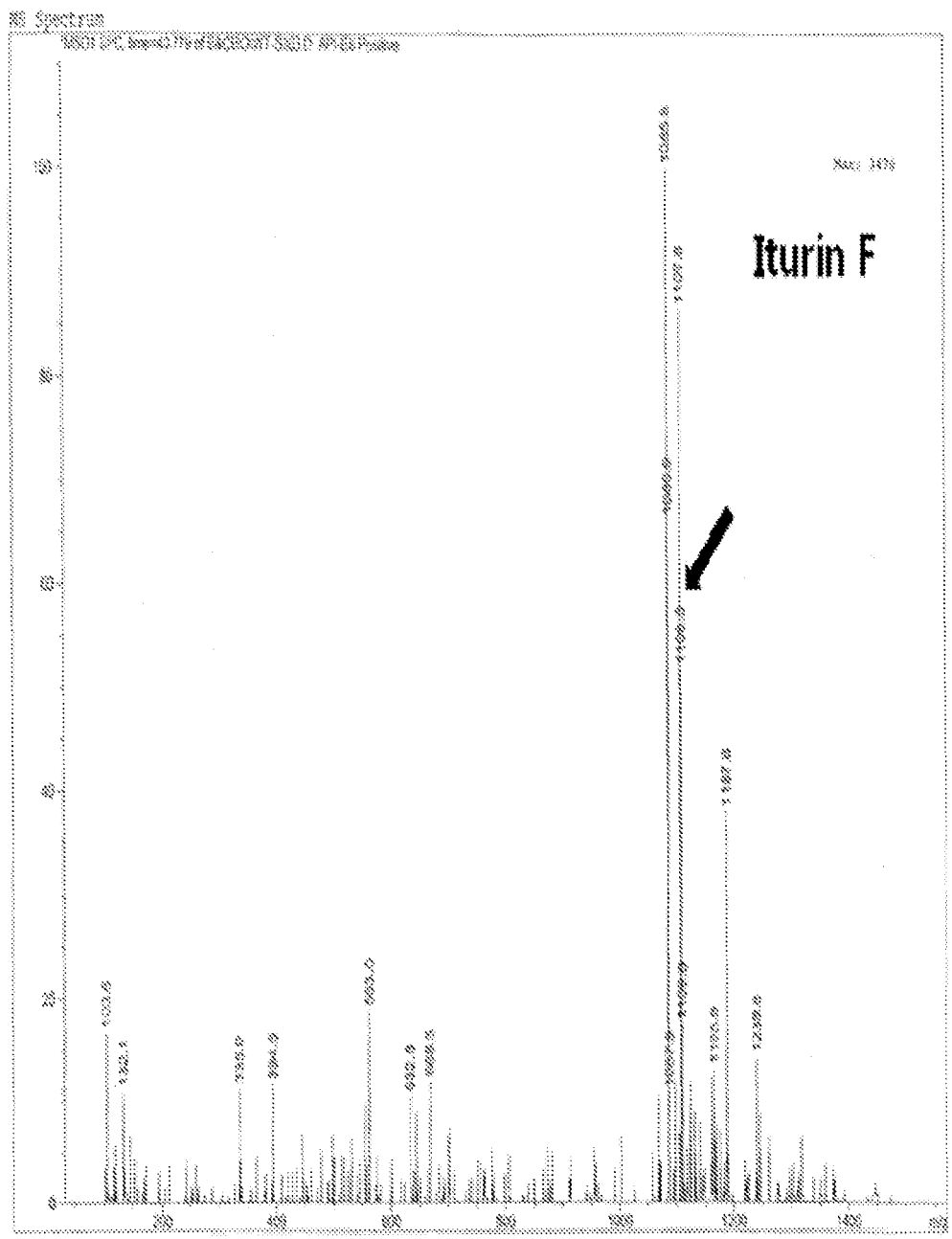

FIGS. 20A-C respectively show the result of LC-Mass analysis for examining whether iturin D, E, and F among six iturins were produced from *B. subtilis* subsp. *krictiensis*.

DESCRIPTION OF THE PREFERRED EMBODIMENTS

Hereinafter, the present invention will be described in more detail with reference to examples.

However, the following examples and experimental examples are provided for illustrative purposes only, and the scope of the present invention is not limited thereto.

Example 1

Culture of Bacillus Strains

B. subtilis subsp. krictiensis ATCC 55079 was a strain isolated by the present inventors, and the strain was described in U.S. patent. The strain was also deposited in American Type Culture Collection (ATCC). B. subtilis 168, B. subtilis JH642, and B. subtilis C9 used in examples of the present invention were provided from Bio-Chemical Research Center at Korea Research Institute of Bioscience and Biotechnology.

Bacillus subtilis and E. coli were cultured in an LB medium (Bacto-tryptone 10 g, Bacto-yeast extract 5 g, sodium chloride 10 g/L). For a medium of Bacillus subtilis strains for producing active materials, a complex medium (sucrose 30 g, soytone 10 g, yeast extract 5 g, $K_2HPO_4$ 0.5 g, $MgSO_4$ 2 g, $MnCl_2$ 4 mg, $CaCl_2$ 5 mg, $FeSO_4 \cdot 7H_2O$ 25 mg, pH 7.0/L) was used.

For transformation, Spizizen's medium (50% glucose 10 mL, 2% casein hydrolysate 10 mL, 10% yeast extract 10 mL, 1 M $MgCl_2$ 2.25 mL, $KH_2PO_4$ 6 g, $K_2HPO_4$ 14 g, $(NH_4)_2SO_4$ 2 g, Sodium citrate 1 g, $MgSO_4$ 0.2 g/L) was used.

Example 2

Construction of Genomic Library of B. subtilis Subsp. krictiensis

<2-1> Extraction of Chromosomal DNA from B. subtilis subsp. krictiensis

Since surfactin and iturin, which are cyclic lipopeptide antibiotics, are similar in molecular weights and different from each other only in amino acid composition and sequences, and surfactin gene is as large enough to be 32 kb in size, the present inventors thought that the size of iturin gene is similar to that of surfactin gene, and assumed that these two antibiotics are synthesized using the same biosynthetic pathway up to some steps, and then, from the established step, two antibiotics are synthesized using different biosynthetic pathways.

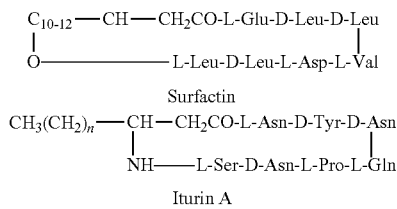

Especially, cyclization of peptides and acylation process of connecting peptides and fatty acids during the biosynthetic process of two antibiotics are assumed to utilize the same pathway for biosynthesis of surfactin and iturin. Various kinds of primers were designed from nucleotide sequence of B. subtilis 168 which is known to produce surfactin, and PCR was conducted. By conducting PCR with the chromosomal DNAs of B. subtilis 168 strain and B. subtilis subsp. krictiensis strain as the template, a 1.8 kb PCR product which was produced from both two strains was obtained. The sequence of the gene product was determined and whether the gene product is associated with a peptide synthetase or not was examined. Then, the present inventors tried to clone iturin biosynthetic genes by colony hybridization and Southern hybridization.

First, in order to extract DNAs from B. subtilis subsp. krictiensis and B. subtilis 168, each single colony of two strains was inoculated into 250 mL of LB medium, and cultured at 30° C., 250 rpm, until late logarithmic phase ($A_{600nm}$=1.0-2.0), and then centrifuged (8,000×g, 10 min, RT). The pellets were washed with 100 mL of lysis buffer [100 mM Tris-HCl, 1 mM EDTA, 10% SDS, pH 8.0] and suspended into 40 mL of lysis buffer. 100 mg of lysozyme was added thereto, and stationary culture was performed for 10 min. After stationary culture, 3 mL of 20% SDS was added thereto, and culture was performed for min. Then, 40 mL of TE-saturated phenol was added and mixed. A DNA layer was separated by centrifugation (10,000×g, 10 min, 4° C.). The DNA layer was extracted with phenol/chloroform and was isolated. 0.1 volume of 3 M sodium acetate (pH 5.2) and 2.5 volume of cooled ethanol were added to precipitate DNAs. DNAs were washed with 70% ethanol and air-dried to obtain DNA pellets. The obtained DNA pellets were dissolved in TE buffer.

<2-2> Partial Digestion

In order to determine the partial digestion condition, 10 μg of isolated DNA and buffer solution were mixed and adjusted to 150 μL, and then, 15 μL aliquots were dispensed into nine eppendorf tubes, and a 30 μL aliquot was dispensed into No. 1 tube and allowed to stand in ice. 4 unit of restriction enzyme was added to No. 1 tube and mixed well, and then, a 15 μL aliquot was transferred into No. 2 tube and mixed well. Again, a 15 μL aliquot was sequentially transferred and mixed well into each tube until No. 8 tube. No. 9 tube was used as untreated. No. 1 to No. 8 tubes were cultured at 30° C. for 1 hr, and the reaction was stopped by adding EDTA to a final concentration of 20 mM. 3 μL of gel-loading dye was added to each tube and the amount of Sau3A to obtain 20 to 30 kb DNA was determined by performing electrophoresis on 0.5% agarose gel. The cosmid vector pLAFR3 was digested with BamHI and treated with phosphatase.

<2-3> Construction of Genomic Library of B. subtilis subsp. krictiensis in E. coli To clone the iturin biosynthetic gene from genomic library of B. subtilis subsp. krictiensis strain, the chromosomal DNA of B. subtilis subsp. krictiensis strain extracted in Example <2-1> was partially digested with Sau3A. Then, 20 to 30 kb DNA fragments were inserted into cosmid vector pLAFR3 (obtained from Department of Applied Biology and Chemistry, College of Agriculture and Life Science, Seoul National University). E. coli HB101 was transformed with the DNA fragment-inserted cosmid vector pLAFR3 to construct the genomic library.

Example 3

Screening of Iturin Biosynthesis Gene from B. subtilis subsp. krictiensis

<3-1> Preparation of DNA Probe

Since iturin and surfactin genes are similar in their molecular weights, and their seven peptides form a cyclic ring, and it was reported that the size of surfactin gene is as large enough to be 32 kb in size, the present inventors assumed that iturin biosynthesis gene is equal to surfactin gene in size. Since some B. subtilis strains are reported that produce both iturin and surfactin, cyclization of peptides and acylation process of connecting fatty acids are assumed to utilize the same pathway for biosynthesis, considering each gene size. On the basis of these assumptions, primers were prepared using DNA base sequence information of surfactin gene. PCR with primer pair for surfactin gene were conducted using the genomic DNAs obtained in Example <2-1> from B. subtilis 168 having surfactin gene and B. subtilis subsp. krictiensis producing iturin as the template. PCR condition was 30 cycles at 94° C. for 30 sec, 50° C. for 30 sec, 72° C. for 60 sec; and 72° C. for 5 min. The used primers are as follows:

```
SrfA1 (SEQ ID NO: 18):
5'-CGG GAA AGC GCT GGG GAA TAA CCG C-3';

SrfA2 (SEQ ID NO: 19):
5'-CCT TCA AAG CTT TGA ACA GGT GGT C-3';

SrfA3 (SEQ ID NO: 20):
5'-CTC GCT TGG CGG AGA TTC CAT CAA AG-3';

SrfA4 (SEQ ID NO: 21):
5'-GTT CTG TCT CTT CAG CAG TCA GCG AG-3';

SrfA5 (SEQ ID NO: 22):
5'-GCG ATT GAT TAT GCG CTT GTT GAG-3';

SrfA6 (SEQ ID NO: 23):
5'-TCG GCA CAT ACG CTG ATT GAA CTG C-3';

SrfA7 (SEQ ID NO: 24):
5'-GGG TAA AGG ATC GCC TCA ATC GTT-3';

SrfA8 (SEQ ID NO: 25):
5'-CGA AAT AGG CTA TCT CGC ACT CAG-3';

SrfA9 (SEQ ID NO: 26):
5'-TTC AGA ATA GGG CTT ATC AAG CA-3';

SrfA10 (SEQ ID NO: 27):
5'-GCT GTG TTG CCG CCT TTA TCT TTG A-3';

SrfB1 (SEQ ID NO: 28):
5'-ATG TCT CAG ATG CAT GGA GC-3';

SrfB2 (SEQ ID NO: 29):
5'-CTG GCA ACT AAT AGG CTG AC-3';

SrfB3 (SEQ ID NO: 30):
5'-ATT GAA GCT TGT GCC GCC TG-3';

SrfB4 (SEQ ID NO: 31):
5'-TCC TTT AAA GCT TTG CAC AG-3';

SrfB5 (SEQ ID NO: 32):
5'-GAA ACA GCA GCG ATT ATG AAC GAC-3';

SrfB6 (SEQ ID NO: 33):
5'-AGA CAT CGA GCC AGT ATT CCT CAT C-3';

SrfB7 (SEQ ID NO: 34):
5'-ATT TCG AGC GGC CAG CTG AAC G-3';

SrfB8 (SEQ ID NO: 35):
5'-TTT CAT CCG GCG CCG TAT AGG TTT-3';

SrfB9 (SEQ ID NO: 36):
5'- GCA AAA TTT CCG GAC AGC GGG ATA T-3';
and

SrfB10 (SEQ ID NO: 37):
5'- TCG ATC CGG CCG ATG TAT TCA AT-3'.
```

Figure 1:
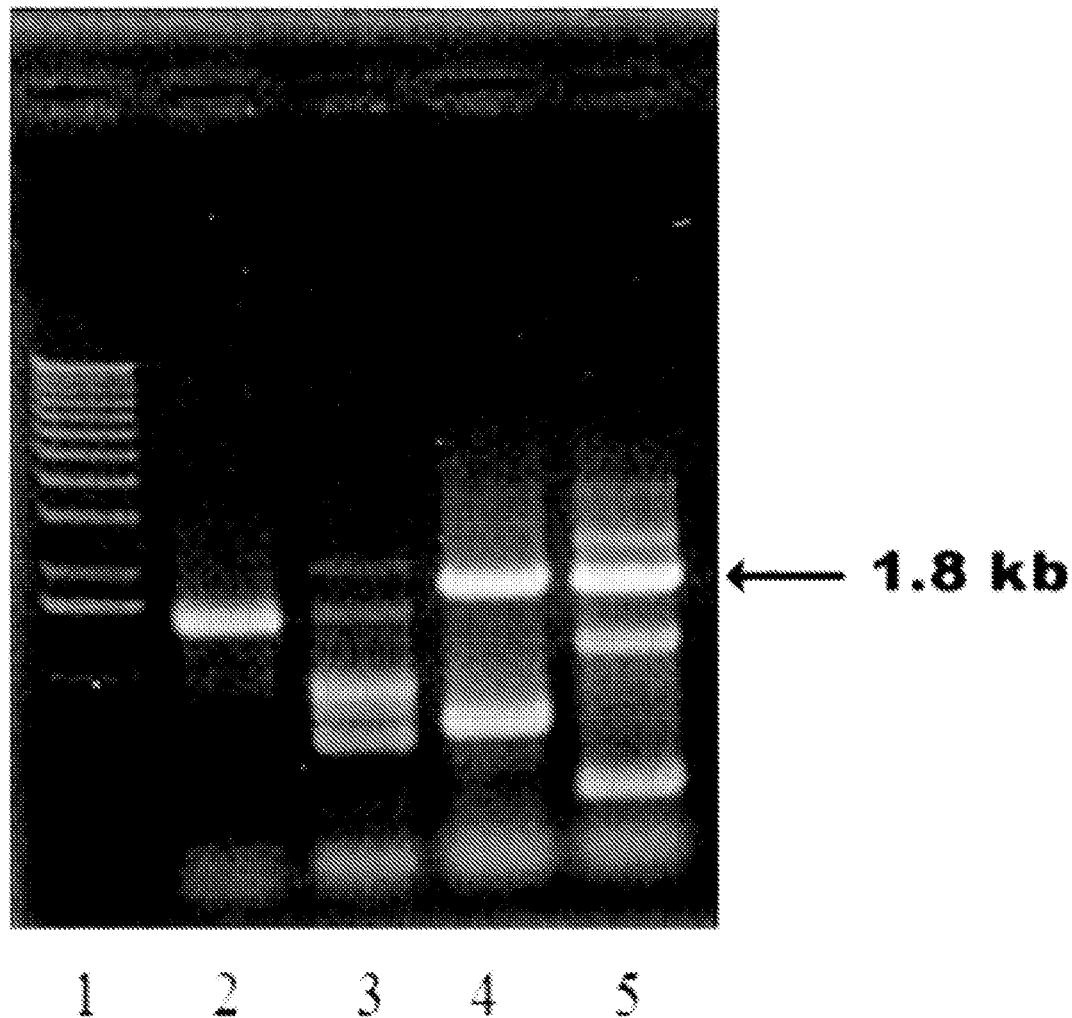
FIG. 1 is an electrophoresis photo for verifying PCR products obtained from *B. subtilis* subsp. *krictiensis* ATCC 55079 and *B. subtilis* 168 strain.

Electrophoresis of PCR products was conducted, and each gene product obtained from *B. subtilis* 168 and *B. subtilis* subsp. *krictiensis* was investigated. When PCR was conducted using SrfB9 and SrfB10 primer pair, about 1.8 kb of a DNA fragment, which has the same size as gene products of *B. subtilis* 168, derived from *B. subtilis* subsp. *krictiensis* was observed (FIG. 1). The present inventors used the DNA fragment as the probe for screening the genomic library constructed in Example 2.

<3-2> Sequence Comparison Between the Screened Iturin Biosynthesis Gene and Peptide Biosynthesis Genes Amino acid sequence of the putative probe for iturin biosynthesis gene obtained from *B. subtilis* subsp. *krictiensis* in Example <3-1> was compared to amino acid sequences of other peptide biosynthesis genes.

Amino acid sequences of surfactin and lichenysin biosynthesis genes obtained by using NCBI database were compared by using CLUSTAL W program, and as shown in FIG. 2, the amino acid sequence obtained from *B. subtilis* subsp. *krictiensis* showed 82 to 85% homology with three different surfactin biosynthesis genes and 80% homology with the lichenysin biosynthesis gene from *B. licheniformis* (FIG. 2).

<3-3> Screening of Genes Responsible for Acylation Process of Peptides and Fatty Acids of Iturin To clone the genes responsible for acylation process of connecting peptides and fatty acids, PCR with 20 primers designed in Example <3-1> were performed to obtain about 0.4 kb DNA fragment. Then, nucleotide sequence for the DNA fragment was analyzed.

Nucleotide and peptide sequences of 0.4 kb PCR product obtained from *B. subtilis* subsp. *krictiensis* strain by using SrfA 5 and SrfA 6 primers were shown in FIG. 3.

To comparatively analyze amino acids shown in FIG. 3, the NCBI database was searched. Consequently, this gene product showed 56 to 83% homology with acyl carrier protein reductase derived from other microorganisms, and especially, it showed 83% homology with acyl carrier protein derived from other *B. subtilis* (FIG. 4).

<3-4> Screening of Iturin Biosynthesis Genes Using Colony Hybridization

To search for iturin biosynthesis genes, colony hybridization was performed using the genomic library of *B. subtilis* subsp. *krictiensis* constructed in Example <2-3>.

To use the 1.8 kb DNA fragment obtained from *B. subtilis* subsp. *krictiensis* in Example <3-1> as a probe for colony hybridization, the 1.8 kb DNA fragment was boiled at 100° C. for min for denaturation and cooled rapidly in ice. Reaction solution was prepared with 5 µL of a labeling buffer (5×), 2 µL of dNTP mixed solution, 7 µL of denatured DNA template, 2 µL of BSA (10 mg/mL), 5 µL of $^{32}$P-CTP, 1 µL of Klenow enzyme, and 3 µL of D.W. and allowed to react with the 1.8 kb DNA fragment at 37° C. for 1 hr. Then, the reaction was stopped with 0.5 M EDTA. 2.5 µL of 3 N NaOH was added thereto, allowed to react again at 37° C. for 1 hr, and then, the reactant was used as a probe.

First, the genomic library of *B. subtilis* subsp. *krictiensis* constructed in <Example 2> was spread to produce 100 to 200 colonies per plate onto LB plate medium to which tetracycline was added to a final concentration of 10 µg and cultured overnight at 37° C. until the colony size becomes about 1 mm in diameter. Colonies were transferred to a nylon membrane, and the membrane was cultured in 10% SDS for 5 min, a denaturing solution [0.5 N NaOH, 1.5 M NaCl] for 5 min, and a neutralizing solution [1.5 N NaCl, 0.5 M Tris-HCl, pH 7.4] for 5 min, and then washed with 2×SSC solution [20×SSC solution was 10-fold diluted to use; 20×SSC solution consists of 0.15 M NaCl, 0.01 M sodium citrate, and 0.001 M EDTA.] and dried, and then baked in a vacuum oven at 80° C. for 1 to 2 hrs. Then, the membrane was treated with a prehydridization solution [1 mM EDTA, 250 mM Na$_2$HPO$_4$, 1% casein hydrolysate, 7% SDS, pH 7.4] and allowed to react at 80° C. for 2 hrs. Labeled probe mix [14 µL of template DNA, 5 µL of 5× labeling buffer solution (Promega), 1 µL of dNTP (ATP, TTP, GTP), 1 µL of Klenow enzyme, 2 µL of $^{32}$P-dCTP] was added to the membrane and allowed to react for overnight. After reaction, the membrane was washed with washing solutions [Washing solution I: 20×SSC 10 mL, 10% SDS 1 mL, distilled water 89 mL; Washing solution II: 20×SSC 10 mL, 10% SDS 10 mL, distilled water 80 mL; Washing solution III: 20×SSC 0.5 mL, 10% SDS 1 mL, distilled water 98.5 mL], and exposed to X-ray film. Then, the exposed positive colonies were selected.

Consequently, as shown in FIG. 5A, it was observed that colonies showing homology with the DNA fragment obtained from *B. subtilis* subsp. *krictiensis* appeared (FIG. 5A).

<3-5> Screening of Iturin Biosynthesis Genes Using Southern Hybridization

To clone iturin biosynthesis genes from genomic library of wild type *B. subtilis* subsp. *krictiensis*, the genomic DNA of wild type *B. subtilis* was partially digested with Sau3A to obtain DNA fragments with various sizes. Among them, various kinds of DNA fragments with 20 to 30 kb were inserted into cosmid vector pLAFR3 to construct the genomic library in *E. coli* HB01. Then, the obtained various kinds of colonies were digested with EcoRI and each clone was analyzed using Southern hybridization.

As shown in FIG. 5B, clones digested with EcoRI restriction enzyme were electrophoresed on 0.7% agarose gel, and dyed with ethidium bromide, and allowed to react with Solution I [Tris-HCl 100 mM, NaCl 150 mM, pH 7.5] for 15 min, and then allowed to react with Solution II [Tris-HCl 100 mM, NaCl 150 mM, blocking reagent 0.5%, pH 7.5] for 30 min. After reaction, the gel was allowed to react with Solution III [Tris-HCl 100 mM, NaCl 100 mM/L, $MgCl_2$ 100 mM, pH 9.5] for 30 min, and a nylon membrane was put on the gel, and DNA fragments were transferred to the membrane. The DNA fragments-transferred membrane was dried and hybridization was performed. During hybridization, the membrane was washed with a hybridization buffer solution containing no probe [1 mM EDTA, 250 mM $Na_2HPO_4$, 1% casein hydrolysate, 7% SDS, pH 7.4] for 2 hrs, and then washed twice with each solution, in order of Solution I, Solution II, and Solution III, 15 mL per each wash and solution was removed. Then, labeled probe mix [14 μL of template DNA, 5 μL of 5× labeling buffer solution (Promega), 1 μL of dNTP (ATP, TTP, GTP), 1 μL of Klenow enzyme, 2 μL of $^{32}$P-dCTP] was added to the membrane and allowed to react for overnight. After reaction, probe DNA was removed and the membrane was dried, put on a X-ray film, allowed to stand at −70° C. for overnight, and the X-ray film was developed (FIG. 5C).

Consequently, as shown in FIG. 5B and FIG. 5C, it was confirmed that sequence of the DNA probe obtained from *B. subtilis* subsp. *krictiensis* existed in two lanes, and these two clones were named as pJJ815 and pJJ121, respectively.

Example 4

Construction of Restriction Enzyme Map of pJJ815 and pJJ121 Clones

Restriction enzyme map of pJJ815 and pJJ121 clones obtained in <Example 3> was constructed. When the above two clones were digested with SmaI and EcoRI, and their restriction enzyme maps were constructed, the clone pJJ121 was divided into pJJ121E2 (the part of ORF 2-2 to ORF 3, 8,020~2,3480 bp in SEQ ID NO:1), pJJ121E3 (the part of ORF 3~ORF 4), pJ815E4 (the part of ORF 4), pJJ815E6 (the part of ORF 4~yczE, 29,167 bp~32,819 bp in SEQ ID NO:1) and the clone pJJ815 was divided into pJJ121E2, pJJ121E3, pJJ815E4, pJJ815E6, pJJ815E5, pJJ815E2 (the part of yczE~ycyA) (FIG. 9).

Example 5

Southern Hybridization Using the Clones pJJ815 and pJJ121

To examine whether the cosmid clones pJJ815 and pJJ121 obtained by screening the genomic library of *B. subtilis* subsp. *krictiensis* are genes associated with iturin biosynthesis or not, the cosmid clones pJJ815 and pJJ121 were digested with EcoRI and genomic Southern hybridization was performed using *B. subtilis* 168 which is known to produce surfactin and *B. subtilis* subsp. *krictiensis*.

<5-1> Construction of Probes Required for Southern Hybridization

To perform genomic Southern hybridization, six fragments (pJJ121E2, pJJ121E3, pJJ815E4, pJJ815E5, pJJ815E6, and pJJ815E2) by digesting the clones with EcoRI were constructed as probes. Specifically, six fragments obtained by cloning cosmid clones pJJ121 and pJJ815 stated in Example <2-3> in *E. coli* HB101 and digesting with EcoRI were used as probes and each fragment was labeled with $^{32}$P-dCTP isotope by the same method described in Example <3-4> and used for hybridization experiment.

<5-2> Southern Hybridization Reaction Depending on Temperature

Using six fragments (pJJ121E2, pJJ121E3, pJJ815E4, pJJ815E5, pJJ815E6, and pJJ815E2) prepared in Example <5-1> as probes, Southern hybridization was performed with chromosomal DNAs of *B. subtilis* subsp. *krictiensis* and *B. subtilis* 168. In addition, Southern hybridization was performed at 50° C. and 65° C. to examine the effect of Southern hybridization temperature on the reaction.

First, clones in which genomic DNAs of *B. subtilis* subsp. *krictiensis* and *B. subtilis* 168 were digested with EcoRI were electrophoresed on 0.7% agarose gel, and dyed with ethidium bromide, and allowed to react with Solution I [Tris-HCl 100 mM, NaCl 150 mM, pH 7.5] for 15 min, and then allowed to react with Solution II [Tris-HCl 100 mM, NaCl 150 mM, blocking reagent 0.5%, pH 7.5] for 30 min. After reaction, the gel was allowed to react with Solution III [Tris-HCl 100 mM, NaCl 100 mM/L, $MgCl_2$ 100 mM, pH 9.5] for 30 min, and a nylon membrane was put on the gel, and DNA fragments were transferred to the membrane. The DNA fragments-transferred membrane was dried and hybridization was performed. During hybridization reaction, the membrane was washed with a hybridization buffer solution containing no probe [1 mM EDTA, 250 mM $Na_2HPO_4$, 1% casein hydrolysate, 7% SDS, pH 7.4] for 2 hrs, and then washed twice with each solution, in order of Solution I, Solution II, and Solution III, 15 mL per each wash and solution was removed. Then, each $^{32}$P-dCTP isotope-labeled probe DNA was added to the membrane and allowed to react for overnight. After reaction, probe DNA was removed and the membrane was dried, put on a X-ray film, allowed to stand at −70° C. for overnight, and the X-ray film was developed.

As shown in FIG. 7, when Southern hybridization was performed at 65° C., it was observed that the probe DNA sequences existed in *B. subtilis* subsp. *krictiensis*. However, no of six EcoRI fragments used as probes existed in the genomic DNA of *B. subtilis* 168 containing the surfactin biosynthesis gene (FIG. 7).

In addition, when Southern hybridization was performed at 50° C., genomic DNA of *B. subtilis* 168 showed only weak homology for pJJ121E3 fragment probe, but it showed the same results for other fragments as in Southern hybridization at 65° C. (FIG. 8). Therefore, from the results of FIG. 7 and FIG. 8, it was concluded that temperature did not affect Southern hybridization reaction. In addition, the above results taken together, six EcoRI fragments hardly showed any similarities with the surfactin biosynthesis gene isolated from *B. subtilis* 168, except pJJ121E3 fragment which exhibited weak response at 50° C., whereas they showed similarities in *B. subtilis* subsp. *krictiensis*, suggesting that six fragments (pJJ121E2, pJJ121E3, pJJ815E4, pJJ815E5, pJJ815E6, and pJJ815E2) which were obtained by digesting cosmid clones pJJ815 and pJJ121 are likely to be genes responsible for iturin biosynthesis.

Example 6

Nucleotide Sequence Determination and Characterization of Iturin Biosynthesis Genes Clones pJJ815 and pJJ121

<6-1> Nucleotide Sequence Determination of Iturin Biosynthesis Genes (pJJ815 and pJJ121)

Bidirectional sequence was determined with EcoRI fragments cloned from the cosmid clones pJJ815 and pJJ121 to obtain 21,253 bp and to further obtain some missing gene nucleotide sequence, the present inventors obtained the genes through a genomic library screening and determined sequence to obtain a total of 37,682 bp of sequence and seven ORFs which are associated with iturin biosynthesis were found within the sequence (FIG. 9).

ORF 1 includes the nucleotide sequence at positions 2868 to 3219 of SEQ ID NO:1 (SEQ ID NO:2), ORF 2-1 includes the nucleotide sequence at positions 3810 to 4353 of SEQ ID NO:1 (SEQ ID NO:4), and ORF 2-2 includes the nucleotide sequence at positions 4632 to 14559 of SEQ ID NO:1 (SEQ ID NO:5). ORF 3 includes the nucleotide sequence at positions 14583 to 25341 of SEQ ID NO:1 (SEQ ID NO:6), ORF 4 includes the nucleotide sequence at positions 25378 to 29209 of SEQ ID NO:1 (SEQ ID NO:7), ORF 5 includes the nucleotide sequence at positions 29231 to 29960 of SEQ ID NO:1 (SEQ ID NO:8), and ORF 6 includes the nucleotide sequence at positions 30084 to 31392 of SEQ ID NO:1 (SEQ ID NO:9).

<6-2> Comparison of Nucleotide Sequences Between Iturin Biosynthesis Gene ORF and Cyclic Peptide Biosynthesis Genes Each of seven ORFs which were assumed to be responsible for iturin biosynthesis was compared with other cyclic lipopeptide biosynthetic genes.

Consequently, ORFs showed 76 to 86% similarity to surfactin genes derived from *B. subtilis*, but they showed 92 to 100% similarity to surfactin genes derived from *B. amyloliquefaciens*. Especially, ORF 2-1 (543 bp), ORF 2-2 (9,927 bp), and ORF 3 (10,757 bp) which were assumed to be directly engaged in iturin biosynthesis showed 92 to 98% similarity to surfactin genes derived from *B. amyloliquefaciens*, respectively (Table 1).

However, among these *B. amyloliquefaciens* strains, *B. amyloliquefaciens* FZB42 which shows 98% similarity is known that produce cyclic peptides surfactin, fengycin, and bacillomycin D (Chen, et al., Nature Biotechnol., 25: 1007-1014, 2007), but it has been reported that *B. amyloliquefaciens* FZB42 does not produce iturin. Accordingly, the present inventors compared homology of entire genes between *B. subtilis* subsp. *krictiensis* with *B. amyloliquefaciens* FZB42.

Consequently, when the entire gene sequences of the above two strains were compared, they showed 98% homology, however, considering the entire size of the gene, 37,682 bp, two strains showed 2% difference, that is about 753 bp or more, and especially, *B. amyloliquefaciens* FZB42 has already been reported not to produce iturin (J. Bacteriol., 186: 1084-1096, 2004; Nature Biotechnol., 25: 1007-1014, 2007). Therefore, there is a great difference between *B. amyloliquefaciens* FZB42 and *B. subtilis* subsp. *krictiensis* producing iturin.

Especially, though *B. amyloliquefaciens* FZB42 showed 92%, 98%, and 98% homology with ORF 2-1, ORF 2-2, and ORF-3, respectively, which are assumed to play a key role in iturin synthesis, there is a great difference in cyclic lipopeptide antibiotics produced by *B. amyloliquefaciens* FZB42 and *B. subtilis* subsp. *krictiensis*, suggesting that iturin and surfactin are likely to share significant part of the biosynthesis pathways.

In addition, the iturin biosynthesis genes derived from *B. subtilis* subsp. *krictiensis* showed 41% similarity with iturin A gene published in 2001 by the Japanese research team (K. Tsuge, et al., J. Bacteriol., 183: 6265-6273, 2001) and they showed 40% similarity with iturin A gene published by the German research team. Therefore, it was thought that the iturin biosynthesis genes derived from *B. subtilis* are likely to be novel genes.

TABLE 1

| ORFs | Significant alignment | Max. Identity (%) |
|---|---|---|
| ORF1 | (CBI41437) transcriptional regulator [*Bacillus amyloliquefaciens*] | 97 |
| | (YP01419994) transcriptional regulator [*Bacillus amyloliquefaciens*] | 96 |
| ORF2-1 | (CP00560) surfactin synthetase AA [*Bacillus amyloliquefaciens*] | 94 |
| | (FN597644) surfactin synthetase AA [*Bacillus subtilis*] | 92 |
| ORF2-2 | (CP000560) surfactin synthetases AA, AB [*Bacillus amyloliquefaciens*] | 97 |
| | (AJ575642) surfactin synthetases AA, AB [*Bacillus amyloliquefaciens*] | 97 |
| | (FN597644) surfactin synthetases AA, AB [*Bacillus amyloliquefaciens*] | 93 |
| ORF3 | (YP0141996) surfactin synthetase AB [*Bacillus amyloliquefaciens*] | 98 |
| | (CBI41439) surfactin synthetase AB [*Bacillus amyloliquefaciens*] | 95 |
| | (ZP06875171) surfactin synthetase AB [*Bacillus subtilis*] | 76 |
| ORF4 | (YP01419998) surfactin synthetase AC [*Bacillus amyloliquefaciens*] | 96 |
| | (ZP06875172) surfactin synthetase [*Bacillus subtilis*] | 86 |
| ORF5 | (AC099323) surfactin synthetase AD [*Bacillus amyloliquefaciens*] | 100 |
| | (YP0141999) surfactin synthetase AD [*Bacillus amyloliquefaciens*] | 99 |
| ORF6 | (ACX10665) aspartate transaminase-like protein [*Bacillus amyloliquefaciens*] | 99 |
| | (CAE02535) amino transferase [*Bacillus amyloliquefaciens*] | 99 |

The following Table 2 showed the comparative results of the entire nucleotide sequence, 37,682 bp, of the iturin biosynthesis gene and other strains including *B. subtilis* subsp. *krictiensis*, using Blast N.

Example 7

Preparation of Assay Plates

<7-1> Preparation of Plate for *Magnaporthe grisea*

For preparation of spore suspension, the rice blast pathogen *Magnaporthe grisea* was slant-cultured on a potato dextrose agar medium for 12 to 15 days, and 5 mL of distilled water was added thereto, and then spores were suspended with a Pasteur pipette, allowed to stand for an appropriate time, and the absorbance of the supernatant at 550 nm wavelength was adjusted to 1.5. The bioassay plate for *Magnaporthe grisea* was used an overlaid plate. First, rice leaf extract was added with 0.15% sucrose and 1.5% agar, and sterilized, and mixed with citrate phosphate buffer (pH 5.0) at a ratio of 1:1. 25 mL of the mixture was dispensed into each plate. After the dispensed medium was hardened, rice extract was added again with 0.15% sucrose and 1.5% agar, and sterilized, and mixed with citrate phosphate buffer (pH 5.0) at a ratio of 1:1, and maintained at 45° C. to make the overlaid medium. 5 mL of the prepared spore suspension was added to and mixed well with 50 mL of the sterilized overlaid medium, and then, each 5 to 10 mL of the mixture was overlaid onto the previously solidified base layer depending on the plate size to make a bioassay plate.

<7-2> Preparation of Plate for *Trichophyton mentagrophytes*

Mycelium slant-cultured in Sabouraud's dextrose agar medium for 10 to 14 days were used, and Sabouraud's dextrose agar was used as a basic medium for the plate for *Trichophyton mentagrophytes*. The fungus causing athlete's foot *Trichophyton mentagrophytes* was inoculated into Sabouraud's dextrose broth, shaking-cultured for 2 to 3 days, and homogenized with a sterilized waring blender. The absorbance of inoculum at 550 nm wavelength was adjusted to 1.5. 5 mL of inoculum was added to and mixed well with 50 mL of the Sabouraud's dextrose agar which was sterilized and adjusted to 50° C., and then each 5 to mL of the mixture was overlaid onto a base layer wherein Sabouraud's dextrose agar was dispensed and solidified in advance depending on the plate size to make a bioassay plate.

<7-3> Preparation of Plate for *Fusarium oxysporum*

*Fusarium oxysporum* grown on a potato dextrose agar medium was inoculated into a potato dextrose broth, shaking-cultured for 2 to 3 days, and homogenized with a sterilized waring blender. The absorbance of inoculum at 550 nm wavelength was adjusted to 1.5. 10 mL of inoculum was added to and mixed uniformly with 50 mL of the potato dextrose agar which was sterilized and adjusted to 50° C., and then each 5 to 10 mL of the mixture was overlaid onto a base layer wherein a potato dextrose agar was dispensed and solidified in advance depending on the plate size to make a bioassay plate.

Example 8

Measurement of Antifungal Activity of *Bacillus*

<8-1> Measurement of Antifungal Activity by Standard Compounds

To assay whether iturin is produced or not from iturin-producing strains obtained through mutation or recombination of them, it should depend on instrumental analysis, but it requires time and efforts. Accordingly, the present inventors tried to establish a simple method of examining whether iturin is produced or not in a laboratory. First, in order to compare antifungal activities between *B. subtilis* subsp. *krictiensis* producing iturin and *B. subtilis* 168 containing surfactin genes, the present inventors purchased standard compounds, surfactin and iturin A from Sigma Co. and Wako Co. For test microorganisms, three kinds of microorganism, the rice blast fungus *Magnaporthe grisea*, the fungus causing athlete's foot *Trichophyton mentagrophytes*, and the fungus causing wilt disease of the family Solanaceae *Fusarium oxysporum* were used to investigate antifungal activity of standard compounds, iturin A and surfactin.

Four different concentrations of surfactin or iturin A were prepared by two-fold serial dilution on the *Magnaporthe grisea* plate, *Trichophyton mentagrophytes* plate, and *Fusarium oxysporum* plate prepared in Example 7, and the range of surfactin or iturin A concentration was 1.56 to 12.56 µg/mL against the rice blast fungus, 3.12 to 25 µg/mL against the fungus causing athlete's foot, and 6.25 to 50 µg/mL against the fungus causing wilt disease of the family Solanaceae. 100 µL of each compound of four different concentrations was dispensed to sterilized cups (external diameter 6.6 mm, height 8.6 mm, stainless, Fisher Co.) placed onto the plates containing test microorganisms and the test microorganisms were cultured at 25° C. for 1 to 3 days. Growth inhibition of test microorganisms was observed to investigate antifungal activity.

Consequently, iturin A showed strong antifungal activities against *Magnaporthe grisea* and *Trichophyton mentagrophytes*, whereas surfactin showed weaker than iturin A, but slight inhibitory activities against them. There was a difference in antifungal activities between iturin A and surfactin, but there was no significant difference in antifungal spectrum. However, while iturin A showed a strong antifungal activity against the test microorganism *Fusarium oxysporum*, surfactin did not show antifungal activity. Two compounds showed obvious difference in antifungal activity against *Fusarium oxysporum* (FIG. 10).

<8-2> Measurement of Antifungal Activity by the Supernatant of Culture Broth of *Bacillus*

Since analysis of iturin production or selection of iturin-less mutants, using wild type *B. subtilis* through instrumental analysis requires great time and efforts, the present inventors tried to develop a simple bioassay system using test microorganisms. First, when antifungal activity was examined using authentic iturin and surfactin, the present inventors found that only iturin showed antifungal activity against *Fusarium* strain. Then, the present inventors used various kinds of *B. subtilis* strains associated with iturin and surfactin production kept in the relevant laboratory and Bio-Chemical Research Center at Korea Research Institute of Bioscience and Biotechnology to examine antifungal activity. In order to use strains as various as possible, the present inventors collected strains that are known to produce iturin and surfactin from various researchers and in this context, *B. subtilis* C9 was also collected and used. *Bacillus* strains were liquid-cultured and their antifungal activities against three test microorganisms were investigated.

*B. subtilis* subsp. *krictiensis* producing iturin and *B. subtilis* JH642 producing neither iturin nor surfactin were used as control. *B. subtilis* 168 which has a surfactin gene but does not produce surfactin due to natural mutation of sfp gene and *B. subtilis* C9 which is assumed to produce both surfactin and iturin were used.

Single colonies of the above *Bacillus* strains grown freshly in LB agar medium were collected and inoculated into a complex medium for producing bioactive substances [sucrose 30 g, soytone 10 g, yeast extract 5 g, $K_2HPO_4$ 0.5 g, $MgSO_4$ 2 g, $MnCl_2$ 4 mg, $CaCl_2$ 5 mg, $FeSO_4.7H_2O$ 25 mg, pH 7.0, distilled water 1 L] and cultured at 30° C., 200 rpm, for 48 hr. The culture broth was centrifuged at 8,000×g, for 10 min to remove bacterial cell. 100 µL of supernatant filtered through a 0.2 µm membrane filter was added to a paper disk. The paper disks were placed on the bioassay plates prepared in <Example 7>, and cultured at 25° C. for 1 to 3 days. Growth inhibition of test microorganisms (*Magnaporthe grisea*, *Trichophyton mentagrophytes*, and *Fusarium oxysporum*) was investigated.

Consequently, as shown in FIG. 11, *B. subtilis* subsp. *krictiensis* strain showed strong antifungal activities against all the test microorganisms, *Magnaporthe grisea*, *Trichophyton mentagrophytes*, and *Fusarium oxysporum*, just like the examination result of using the standard compound iturin A.

However, *B. subtilis* JH642 and *B. subtilis* 168 in which sfp gene is naturally mutated did not showed antifungal activities against three test microorganisms. But, *B. subtilis* C9 strain showed antifungal activities against three test microorganisms. Accordingly, the present inventors assumed that the antifungal activity of *B. subtilis* C9 shown in the above result was due to the production of iturin, in addition to surfactin. Based on these results, the present inventors used *Fusarium oxysporum* as a test microorganism for selecting iturin mutants (FIG. 11).

Example 9

Measurement of Antifungal Activity of Transformed *B. subtilis* subsp. *krictiensis* Mutants <9-1> Transformation of *B. subtilis* subsp. *krictiensis*

Each of four fragments (pBT6, pBT1, pBT2 and pBT3, FIG. 12) which were obtained by digesting DNA fragments of cosmid clones pJJ121 and pJJ815 obtained from *B. subtilis* subsp. *krictiensis* in Example <2-2> with EcoRI and the fragment of HCE promoter of pT(II)PLK digested with NdeI were cloned into *Bacillus-E. coli* shuttle vector, pHPS9 (provided from Bio-Chemical Research Center at Korea Research Institute of Bioscience and Biotechnology) and introduced to *B. subtilis* subsp. *krictiensis*. The strain was spread onto a plate containing chloramphenicol antibiotic (5 µg/mL) and colonies were selected as mutant strains.

Specifically, a single colony of *Bacillus subtilis* subsp. *krictiensis* cultured freshly in LB agar medium was inoculated into 2 mL of Spizizen's medium (50% glucose 10 mL, 2% casein hydrolysate 10 mL, 10% yeast extract 10 mL, 1M $MgCl_2$ 2.25 mL, $KH_2PO_4$ 6 g, $K_2HPO_4$ 14 g, $(NH_4)_2SO_4$ 2 g, Sodium citrate 1 g, $MgSO_4$ 0.2 g, distilled water 1 L) and cultured at 37° C., 200 rpm, for 16 to 18 hr. Again, the inoculum was inoculated into fresh medium to achieve 1% and cultured under the same condition. When the absorbance of culture broth at 580 nm wavelength was 1.0, 0.5 mL of the culture broth and about 1 µg of DNA (pBT6, pBT1, pBT2, and pBT3) were mixed and shaking-cultured for 1 hr. After shaking culture, an aliquot of culture broth was spread onto a plate containing 5 µg/mL of chloramphenicol and incubated at 37° C. for 24 hr.

Mutants containing fragments pBT6, pBT1, pBT2 and pBT3 were named as *B. subtilis* subsp. *krictiensis* (pBT6), *B. subtilis* subsp. *krictiensis* (pBT1), *B. subtilis* subsp. *krictiensis* (pBT2) and *B. subtilis* subsp. *krictiensis* (pBT3), respectively (FIG. 10).

<9-2> Measurement of Antifungal Activity of *B. subtilis* subsp. *krictiensis*

The present inventors tried to measure antifungal activities of *B. subtilis* subsp. *krictiensis* which was not transformed as control, grown freshly in LB agar medium, and *B. subtilis* subsp. *krictiensis* strains (pBT1, pBT3, and pBT6) in which fragments containing ORFs prepared in Example <8-1> were transformed.

Single colonies of *B. subtilis* subsp. *krictiensis* strains (pBT1, pBT3, and pBT6) were collected, inoculated into a complex medium for producing bioactive substances [sucrose 30 g, soytone 10 g, yeast extract 5 g, $K_2HPO_4$ 0.5 g, $MgSO_4$ 2 g, $MnCl_2$ 4 mg, $CaCl_2$ 5 mg, $FeSO_4.7H_2O$ 25 mg, pH 7.0, distilled water 1 L], and cultured at 30° C., 200 rpm, for 48 hrs. The culture medium was centrifuged at 8,000×g, for 10 min to remove bacterial cell. 100 µL of the supernatant filtered through a 0.2 µm membrane filter was added to a paper disk (thick, diameter 8 mm, Toyo Roshi Co.). The paper disks were placed on the bioassay plates prepared in <Example 7>, and incubated at 25° C. for 1 to 3 days. Growth inhibition of the test microorganism *Fusarium oxysporum* was investigated.

Consequently, as shown in FIG. 13, it was observed that the antifungal activity of *B. subtilis* subsp. *krictiensis* (pBT6) containing the clone pBT6 was increased two to three-fold over untransformed control *B. subtilis* subsp. *krictiensis*. In addition, it was observed that the potency of antifungal activities of transformed strains was increased in order of pBT3, pBT1, and pBT6. These results corresponded with the above result that surfactin did not show the antifungal activity, but iturin showed the antifungal activity against *Fusarium oxysporum*. That is, since the antifungal activity of *B. subtilis* subsp. *krictiensis* (pBT6) was increased due to transformation of the clone pBT6, compared to control *B. subtilis* subsp. *krictiensis*, the present inventors assumed that the clone pBT6 included the iturin biosynthesis gene (FIG. 13).

Example 10

Preparation of Iturin-Less Mutants and Assay of Antifungal Activity

<10-1> Preparation of Iturin-Less Mutants

In order to confirm again that iturin biosynthesis genes exist in the cosmid clone pJJ121E2, the present inventors tried to prepare an iturin-less mutant by inserting genes into the chromosome through homologous recombination using mini-Tn100. First, the clone pJJ121E2-2, in which pJJ121 fragment digested with EcoRI was inserted into the vector pBC KS(+/−) (Stratagene), was digested with EcoRI and cloned into the vector pTZ18 (Promega), and the SalI site was removed.

In addition, from the clone p121E3 (FIG. 14) in which pIC333 vector was contained in a ClaI site of this vector, the spectinomycin gene-containing region was digested with BamHI and XbaI, and a ClaI site was attached thereto by PCR based on the nucleotide sequence of pTZ18 vector, and then, the fragment was digested with ClaI and the spectinomycin gene was inserted to prepare pJJ121E2-1 vector. Then, *B. subtilis* subsp. *krictiensis* strain was transformed with pJJ121E2-1 vector. Since the spectinomycin gene region containing mini-Tn100 which was inserted into *B. subtilis* subsp. *krictiensis* does not have *Bacillus* replication origin, cloning could not be done any more, but only gene insertion was done through homologous recombination of similar parts and host chromosome. Accordingly, chromosomal insertion mutants were selected from a spectinomycin-containing medium.

Specifically, 7,940 bp from 16,430 bp to 24,370 bp of ORF 3 was inserted in *B. subtilis* mutant-10, and it was thought that iturin biosynthesis did not occur since among the inserted region, spectinomycin was inserted in the ClaI site, 21,046 bp. In order to improve the efficiency of transformation, the SalI site of pJJ121E2-1 vector was digested and removed. The lost region of ORF 3 which was inserted in *B. subtilis* mutant-10 was the SalI-EcoRI-SalI site, as described in FIG. 14. The EcoRI-SalI site was derived from pJJ121E2 fragment. The lost nucleotide sequences were 8.41 kb (8,020~16,430 bp) and the SalI site (33 bp) derived from the vector, on the left of the EcoRI site, and the total size was 8.443 kb.

<10-2> Measurement of Antifungal Activity of *B. subtilis* Mutant-10

The mutant selected from the spectinomycin-containing medium was named as *B. subtilis* mutant-10. In order to examine antifungal activity, an aliquot of the culture broth of *B. subtilis* subsp. *krictiensis* or the culture broth of *B. subtilis* mutant-10 was loaded onto the plate for the test microorganism *Fusarium oxysporum* by the same method as <Example 9> for examining antifungal activities.

Consequently, *B. subtilis* mutant-10 which lost the function of iturin biosynthesis gene showed so weak antifungal activity to be barely detectable, whereas *B. subtilis* subsp. *krictiensis* showed strong antifungal activity. It seemed certain that the obtained gene would be an iturin biosynthesis gene and it was confirmed that the gene was directly associated with the antifungal activity exhibited by *B. subtilis* subsp. *krictiensis* (FIG. 15).

<10-3> Confirmation of Spectinomycin Gene Insertion Using Southern Hybridization In order to confirm whether the spectinomycin gene was inserted into the chromosome of *B. subtilis* mutant-10 prepared in Example <9-1> or not, the spectinomycin-containing fragment, which was obtained by digesting the clone p121E3 containing pIC333 vector with mini-Tn10 by BamHI and XbaI, was labeled with $^{32}$P isotope to prepare a probe, and Southern hybridization was conducted. Genomic DNAs were extracted from *B. subtilis* subsp, *krictiensis* and *B. subtilis* mutant-10 and digested with ClaI. Southern hybridization was conducted using the genomic DNAs of *B. subtilis* subsp. *krictiensis* and iturin-less mutant-10 digested with ClaI and the probe wherein the spectinomycin fragment which contained the spectinomycin gene derived from the clone p121E3 by digesting with BamHI and XbaI, was labeled with isotope.

Consequently, as shown in FIG. 16, it was confirmed that the spectinomycin gene existed in the 1.5 kb position of the fragment, in which the clone p121E3 containing the spectinomycin gene was digested with BamHI and XbaI, used as the probe. It was confirmed that the spectinomycin gene existed in the same position as the spectinomycin fragment derived from the clone p121E3 also in *B. subtilis* mutant-10. On the other hand, the spectinomycin gene did not exist in *B. subtilis* subsp. *krictiensis* (FIG. 16). From these results, it was confirmed that the reason *B. subtilis* mutant-10 did not show antifungal activity in Example <10-2> was that the spectinomycin gene was inserted into the chromosome, so that iturin was not produced.

Example 11

Metabolite Analysis of *B. subtilis* Subsp. *krictiensis* and *B. subtilis* Mutant-10

<11-1> Metabolite Analysis by HPLC

The present inventors investigated whether there was a difference in iturin antibiotic production between the culture broth of *B. subtilis* subsp. *krictiensis* and the culture broth of *B. subtilis* mutant-10. The culture broth of *B. subtilis* subsp. *krictiensis* and the culture broth of *B. subtilis* mutant-10 were developed by thin-layer chromatography (TLC) with solvent condition of $CHC_3/MeOH/D.W.=75/25/5$. Corresponding regions of each spot from the *B. subtilis* subsp. *krictiensis* and *B. subtilis* mutant-10 were collected and separated by high performance liquid chromatography (HPLC). Iturin production between *B. subtilis* subsp. *krictiensis* and *B. subtilis* mutant-10 was compared and commercially available standard compound iturin A was used as a control.

Consequently, HPLC chromatogram of *B. subtilis* subsp. *krictiensis* and HPLC chromatogram of standard compound iturin A showed considerably similar peak pattern, whereas peaks corresponding iturin A were not observed in *B. subtilis* mutant-10 (FIG. 17). It was confirmed that the reason *B. subtilis* mutant-10 did not show antifungal activity against the test microorganism *Fusarium oxysporum* in Example <10-2> was that the spectinomycin gene was inserted into the chromosome, so that iturin was not synthesized.

<11-2> Metabolite Analysis by LC-Mass

In order to investigate whether chromatogram from *B. subtilis* subsp. *krictiensis* observed by HPLC means six kinds of iturins, iturin A to F, the molecular weight of these peaks were determined by LC-Mass. As a result of HPLC analysis, through the chromatogram, it was confirmed that six kinds of iturins, iturin A to F were produced from *B. subtilis* subsp. *krictiensis* (FIG. 18). When the molecular weights of the produced iturin compounds A to F were determined as $[M+Na]^+$ using Mass spectrometry, peaks corresponding to the molecular weights of iturin A to F (A: 1043, B: 1057, C: 1057, D: 1071, E: 1071, F: 1085) were detected. From the LC-Mass result, peaks which were present in *B. subtilis* subsp. *krictiensis*, but were not present in *B. subtilis* mutant-10 corresponded precisely with iturins A to F (FIG. 19 and FIG. 20), and thus, it was reconfirmed that *B. subtilis* mutant-10 did not show the antifungal activity on the bioassay plate against *F. oxysporum* because of the inhibition of production of iturin compounds.

The above results taken together, ORF 2-1, ORF 2-2, and ORF 3 verified in this study showed 74 to 98% similarity with surfactin genes. However, real product encoded by the genes was not surfactin but iturin, and these genes showed low similarity, 41%, with other iturin A biosynthesis genes that have been known until now. Accordingly, the iturin biosynthesis genes of *B. subtilis* subsp. *krictiensis* used in this experiment are thought to be novel genes which are different from the genes reported up to date.

What is claimed is:

1. A vector comprising the nucleotide sequence of SEQ ID NO:6.

2. The vector of claim 1 further comprising one or more nucleotide sequences selected from the group consisting of SEQ ID NO:3, SEQ ID NO:5, SEQ ID NO:7, and SEQ ID NO:8.

3. The vector of claim 2, wherein the vector comprises the nucleotide sequences of SEQ ID NO:6 and SEQ ID NO:5.

4. The vector of claim 2, wherein the vector comprises the nucleotide sequence of SEQ ID NO:1.

5. A transformant transformed with the vector of claim 1.

6. A biological control agent comprising the transformant of claim 5 for producing iturin or a culture medium of the transformant.

* * * * *